United States Patent
Renner et al.

(10) Patent No.: US 6,524,792 B1
(45) Date of Patent: *Feb. 25, 2003

(54) EXPRESSION CLONING PROCESSES FOR THE DISCOVERY, CHARACTERIZATION AND ISOLATION OF GENES ENCODING POLYPEPTIDES WITH A PREDETERMINED PROPERTY

(75) Inventors: Wolfgang A. Renner, Zürich (CH); Georg H. Orberger, Schönfliess (CH); Daniel Koller, Riniken (CH); James E. Bailey, Zürich (CH)

(73) Assignee: Cytos Biotechnology, Zurich-Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/193,707

(22) Filed: Nov. 17, 1998

Related U.S. Application Data

(63) Continuation-in-part of application No. 08/972,218, filed on Nov. 17, 1997, now Pat. No. 6,197,502.

(51) Int. Cl.$^7$ .......................... C12Q 1/68; C12P 19/34; C07H 21/02; C12N 1/20
(52) U.S. Cl. ....................... 435/6; 435/91.2; 435/320.1; 435/252.1; 536/22.1; 536/23.1; 536/24.3; 536/24.31; 536/24.32; 536/24.33
(58) Field of Search ....................... 435/6, 252.1, 91.2, 435/320.1; 536/22.1, 23.1, 24.3, 24.31, 24.32, 24.33

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,195 A | 1/1989 | Burgess et al. | |
| 4,946,778 A | 8/1990 | Ladner et al. | |
| 4,965,188 A | 10/1990 | Mullis et al. | |
| 5,091,309 A | 2/1992 | Schlesinger et al. | 435/69.1 |
| 5,217,879 A | 6/1993 | Huang et al. | 435/69.1 |
| 5,536,637 A | 7/1996 | Jacobs | |
| 5,738,985 A | 4/1998 | Miles et al. | |
| 5,766,602 A | 6/1998 | Xiong et al. | 424/218.1 |
| 5,783,431 A * | 7/1998 | Peterson et al. | 435/172.3 |
| 5,792,462 A * | 8/1998 | Johnston et al. | 424/199.1 |
| 5,811,234 A | 9/1998 | Roninson et al. | |

FOREIGN PATENT DOCUMENTS

| | | |
|---|---|---|
| WO | WO 92/07071 | 4/1992 |
| WO | WO 94/23041 | 10/1994 |

OTHER PUBLICATIONS

Onishi et al, "Applications of retrovirus mediated expression cloning", Exp. Hematol. 24:324–329, Jan. 1996.*
Sambrook, J. et al., "Molecular Cloning: A Laboratory Manual. 2$^{nd}$ Edition," pp. 16.68–16.72, Cold Spring Harbor Laboratory Press (1989).
D'Andrea, A., et al., "Expression Cloning of the Murine Erythropoietin Receptor," *Cell* 57:277–285 (1989).
Sims, J.E., et al., "cDNA Expression Cloning of the IL–1 Receptor, a Member of the Immunoglobulin Superfamily," *Science* 241:585–589 (1988).
Xiong, C., et al., "Sindbis Virus: An Efficint, Broad Host Range Vector for Gene Expression in Animal Cells," *Science* 243:1188–1191 (1989).
Arias et al., 1983, "Sequence Analysis of Two Mutants of Sindbis Virus Defective in the Intracellular Transport of Their Glycoproteins," *J. Mol. Biol.* 168:87–102.
Bargmann et al., 1986, "Multiple Independent Activations of the neu Oncogene by a Point Mutation Altering the Transmembrane Domain of p185," *Cell* 45:649–657.
Bordonaro et al., 1994, "An Improved T1/A Ribonuclease Protection Assay," *BioTechniques* 16:428–430.
Bredenbeek et al., 1993, "Sindbis Virus Expression Vectors: Packaging of RNA Replicons by Using Defective Helper RNAs," *J. Virol.* 67:6439–6446.
Butler, 1981, "The Amplified ELISA: Principles of and Applications for the Comparative Quantitation of Class and Subclass Antibodies and the Distribution of Antibodies and Antigens in Biochemical Separates," *Meth. Enzymol.* 73:482–523.
Carleton and Brown, 1996, "Events in the Endoplasmic Reticulum Abrogate the Temperature Sensitivity of Sindbis Virus Mutant ts23," *J. Virol.* 70:952–959.
Collins and Lopez Rivas, 1993, "The control of apoptosis in mammalian cells," *TIBS* 18:307–309.
Condreay et al., 1988, "Effect of Actinomycin D and Cycloheximide on Replication of Sindbis Virus in *Aedes albopictus* (Mosquito) Cells," *J. Virol.* 62:2629–2635.
Cote et al., 1983, "Generation of human monoclonal antibodies reactive with cellular antigens," *Proc. Natl. Acad. Sci. U.S.A.* 80:2026–2030.
Frolov et al., 1994, "Comparison of the Effects of Sindbis Virus and Sindbis Virus Replicons on Host Cell Protein Synthesis and Cytopathogenicity in BHK Cells," *J. Virol* 68:1721–1727.
Frolov et al., 1996, "Alphavirus–based expression vectors: Strategies and applications," *Proc. Natl. Acad. Sci. U.S.A.* 93:11371–11377.

(List continued on next page.)

*Primary Examiner*—Jeffrey Fredman
(74) *Attorney, Agent, or Firm*—Sterne, Kessler, Goldstein & Fox, P.L.L.C.

(57) ABSTRACT

The present invention is directed to a method for detection, characterization and isolation of nucleic acids encoding proteins of a desired property, such as a particular cellular localization. The invention further provides for rapid expression of such proteins or glycoproteins in mammalian cells and for facilitated purification of the novel secreted proteins or glycoproteins. Further, the invention provides for radioactive labelling of the novel proteins or glycoproteins, for rapid identification of sites of binding including animals and for rapid production of infective viral vectors for use in gene transfer.

63 Claims, 37 Drawing Sheets

OTHER PUBLICATIONS

Hahn et al., 1992, "Infectious Sindbis virus transient expression vectors for studying antigen processing and presentation," *Proc. Natl. Acad. Sci. U.S.A.* 89:2679–2683.

Hirschberg and Snider, 1987, "Topography of Glycosylation in the Rough Endoplasmic Reticulum and Golgi Apparatus," *Ann. Rev. Biochem.* 56:63–87.

Huse et al., 1989, "Generation of a Large Combinatorial Library of the Immunoglobulin Repertoire in Phage Lambda," *Science* 246:1275–1281.

Kitamura et al., 1995, "Efficient screening of retroviral cDNA expression libraries," *Proc. Natl. Acad.Sci. U.S.A.* 92:9146–9150.

Kohler and Milstein, 1975, "Continuous cultures of fused cells secreting antibody of predefined specificity," *Nature* 256:495–497.

Kosbor and Roder, 1983, "The production of monoclonal antibodies from human lymphocytes," *Immunology Today* 4:72–79.

Lauffenburger et al., 1996, "Engineering Dynamics of Growth Factors and Other Therapeutic Ligands," *Biotechnology and Bioengineering* 52:61–80.

Liljeström and Garoff, 1991, "A New Generation of Animal Cell Expression Vectors Based on the Semliki Forest Virus Replicon," *Bio/Technology* 9:1356–1361.

Lindqvist et al., 1986, "Sindbis Virus Mutant ts20 of Complementation Group E Contains a Lesion in Glycoprotein E2," *Virology* 151:10–20.

Ma et al., 1996, "Comparison of ethanol plasma–protein precipitation with plasma ultrafiltration and trichloroacetic acid protein precipitation for the measurement of unbound platinum concentrations," *Cancer Chemother. Pharmacol.* 38:391–394.

Mahal et al., 1997, "Engineering Chemical Reactivity on Cell Surfaces Through Oligosaccharide Biosynthesis," *Science* 276:1125–1128.

Martin et al., 1994, "Dicing with death: dissecting the components of the apoptosis machinery," *TIBS* 19:26–30.

Merrifield, 1963, "Solid Phase Peptide Synthesis. I. The Synthesis of a Tetrapeptide," *J. Am. Chem. Soc.* 85:2149–2154.

Morrison et al., 1984, "Chimeric human antibody molecules: Mouse antigen–binding domains with human constant region domains," *Proc. Natl. Acad. Sci. U.S.A.* 81:6851–6855.

Nagata et al., 1980, "The structure of one of the eight or more distinct chromosomal genes for human interferon–=," *Nature* 287:401–408.

Neuberger et al., 1984, "Recombinant antibodies possessing novel effector functions," *Nature* 312:604–608.

Nobori et al., 1992, "A Polymerase Chain Reaction–Based Method for Isolation of Gene–Specific Sequences from the Interferon–α Gene Cluster," *Analyt. Biochem.* 205:42–46.

Okayama et al., 1987, "High efficiency cloning of full length cDNA; Construction and screening of cDNA expression libraries for mammalian cells," *Methods in Enzymology* 154:3–28.

Rademacher et al., 1988, "Glycobiology," *Ann. Rev. Biochem.* 57:785–838.

Schlesinger and Schlesinger, 1990, "Replication of Togaviridae and Flaviviridae," *In: Virology*, Fields, et al, eds. Raven Press, Ltd., New York. Chapter 25, pp. 697–704.

Slamon et al., 1989, "Studies of the HER–2/neu Proto–oncogene in Human Breast and Ovarian Cancer," *Science* 244:707–712.

Strauss and Strauss, 1994, "The Alphaviruses: Gene Expression, Replication and Evolution," *Microbiolgical Reviews* 58:491–562.

Taira et al., 1989, "Human Diabetes Associated with a Deletion of the Tyrosine Kinase Domain of the Insulin Receptor," *Science* 245:63–66.

Takeda et al., 1985, "Construction of chimaeric processed immunoglobulin genes containing mouse variable and human constant region sequences," *Nature* 314:452–454.

Ullrich et al., 1985, "Human insulin receptor and its relationship to the tyrosine kinase family of oncogenes," *Nature* 313:756–761.

Voller et al., 1978, "Enzyme immunoassays with special reference to ELISA techniques," *J. Clin. Pathol.* 31:507–520.

Watson et al., 1991, "A Mutant CHO–K1 Strain with Resistance to *Pseudomonas* Exotoxin A and Alphaviruses Fails to Cleave Sindbis Virus Glycoprotein PE2," *J. Virol.* 65:2332–2339.

Weinberg, 1994, "Oncogenes and Tumor Suppressor Genes," *CA Cancer J. Clin.* 44:160–170.

Wels et al., 1995, "Biotechnological and gene therapeutic strategies in cancer treatment," *Gene* 159:73–80.

Xu et al., 1996, "Use of 1,2,4–dithiazolidine–3,5–dione (DtsNH) and 3–ethoxy–1,2,4–dithiazoline–5–one (EDITH) for synthesis of phosphorothioate–containing oligodeoxyribonucleotides," *Nucleic Acids Res* 24:1602–1607.

Zav'yalov and Zav'yalova, 1997, "Interferons α/β and their receptors: place in the hierarchy of cytokines," *APMIS* 105:161–186.

Zawel and Reinberg, 1995, "Common Themes in Assembly and Function of Eukaryotic Transcription Complexes," *Annu. Rev. Biochem.* 64:533–561.

Zipkin, 1997, "Rigel: Steering by a Retroviral Star," *Biocentury* (reprint).

* cited by examiner pSinRep 5
ATTGACGGCGTAGTACACACTATTGAATCAAACAGCCGACCAATTGCACTACCATCACAATGGAGAAGCCAGTAGTAAAC
GTAGACGTAGACCCCCAGAGTCCGTTTGTCGTGCAACTGCAAAAAAGCTTCCCGCAATTTGAGGTAGTAGCACAGCAGGT
CACTCCAAATGACCATGCTAATGCCAGAGCATTTTCGCATCTGGCCAGTAAACTAATCGAGCTGGAGGTTCCTACCACAG
CGACGATCTTGGACATAGGCAGCGCACCGGCTCGTAGAATGTTTTCCGAGCACCAGTATCATTGTGTCTGCCCCATGCGT
AGTCCAGAAGACCCGGACCGCATGATGAAATACGCCAGTAAACTGGCGGAAAAAGCGTGCAAGATTACAAACAAGAACTT
GCATGAGAAGATTAAGGATCTCCGGACCGTACTTGATACGCCGGATGCTGAAACACCATCGCTCTGCTTTCACAACGATG
TTACCTGCAACATGCGTGCCGAATATTCCGTCATGCAGGACGTGTATATCAACGCTCCCGGAACTATCTATCATCAGGCT
ATGAAAGGCGTGCGGACCCTGTACTGGATTGGCTTCGACACCACCCAGTTCATGTTCTCGGCTATGGCAGGTTCGTACCC
TGCGTACAACACCAACTGGGCCGACGAGAAAGTCCTTGAAGCGCGTAACATCGGACTTTGCAGCACAAAGCTGAGTGAAG
GTAGGACAGGAAAATTGTCGATAATGAGGAAGAAGGAGTTGAAGCCCGGGTCGCGGGTTTATTTCTCCGTAGGATCGACA
CTTTATCCAGAACACAGAGCCAGCTTGCAGAGCTGGCATCTTCCATCGGTGTTCCACTTGAATGGAAAGCAGTCGTACAC
TTGCCGCTGTGATACAGTGGTGAGTTGCGAAGGCTACGTAGTGAAGAAAATCACCATCAGTCCCGGGATCACGGGAGAAA
CCGTGGGATACGCGGTTACACACAATAGCGAGGGCTTCTTGCTATGCAAAGTTACTGACACAGTAAAAGGAGAACGGGTA
TCGTTCCCTGTGTGCACGTACATCCCGGCCACCATATGCGATCAGATGACTGGTATAATGGCCACGGATATATCACCTGA
CGATGCACAAAAACTTCTGGTTGGGCTCAACCAGCGAATTGTCATTAACGGTAGGACTAACAGGAACACCAACACCATGC
AAAATTACCTTCTGCCGATCATAGCACAAGGGTTCAGCAAATGGGCTAAGGAGCGCAAGGATGATCTTGATAACGAGAAA
ATGCTGGGTACTAGAGAACGCAAGCTTACGTATGGCTGCTTGTGGGCGTTTCGCACTAAGAAAGTACATTCGTTTTATCG
CCCACCTGGAACGCAGACCTGCGTAAAAGTCCCAGCCTCTTTTAGCGCTTTTCCCATGTCGTCCGTATGGACGACCTCTT
TGCCCATGTCGCTGAGGCAGAAATTGAAACTGGCATTGCAACCAAAGAAGGAGGAAAAACTGCTGCAGGTCTCGGAGGAA
TTAGTCATGGAGGCCAAGGCTGCTTTTGAGGATGCTCAGGAGGAAGCCAGAGCGGAGAAGCTCCGAGAAGCACTTCCACC
ATTAGTGGCAGACAAAGGCATCGAGGCAGCCGCAGAAGTTGTCTGCGAAGTGGAGGGGCTCCAGGCGGACATCGGAGCAG
CATTAGTTGAAACCCCGCGCGGTCACGTAAGGATAATACCTCAAGCAAATGACCGTATGATCGGACAGTATATCGTTGTC
TCGCCAAACTCTGTGCTGAAGAATGCCAAACTCGCACCAGCGCACCCGCTAGCAGATCAGGTTAAGATCATAACACACTC
CGGAAGATCAGGAAGGTACGCGGTCGAACCATACGACGCTAAAGTACTGATGCCAGCAGGAGGTGCCCGTACCATGGCCAG
AATTCCTAGCACTGAGTGAGAGCGCCACGTTAGTGTACAACGAAAGAGAGTTTGTGAACCGCAAACTATACCACATTGCC
ATGCATGGCCCCGCCAAGAATACAGAAGAGGAGCAGTACAAGGTTACAAAGGCAGAGCTTGCAGAAACAGAGTACGTGTT
TGACGTGGACAAGAAGCGTTGCGTTAAGAAGGAAGAAGCCTCAGGTCTGGTCCTCTCGGGAGAACTGACCAACCCTCCCT
ATCATGAGCTAGCTCTGGAGGGACTGAAGACCCGACCTGCGGTCCCGTACAAGGTCGAAACAATAGGAGTGATAGGCACA
CCGGGGTCGGGCAAGTCAGCTATTATCAAGTCAACTGTCACGGCACGAGATCTTGTTACCAGCGGAAAGAAAGAAAATTG
TCGCGAAATTGAGGCCGACGTGCTAAGACTGAGGGGTATGCAGATTACGTCGAAGACAGTAGATTCGGTTATGCTCAACG
GATGCCACAAAGCCGTAGAAGTGCTGTACGTTGACGAAGCGTTCGCGTGCCACGCAGGAGCACTACTTGCCTTGATTGCT
ATCGTCAGGCCCCGCAAGAAGGTAGTACTATGCGGAGACCCCATGCAATGCGGATTCTTCAACATGATGCAACTAAAGGT
ACATTTCAATCACCCTGAAAAAGACATATGCACCAAGACATTCTACAAGTATATCTCCCGGCGTTGCACACAGCCAGTTA
CAGCTATTGTATCGACACTGCATTACGATGGAAAGATGAAAACCACGAACCCGTGCAAGAAGAACATTGAAATCGATATT
ACAGGGGCCACAAAGCCGAAGCCAGGGGATATCATCCTGACATGTTTCCGCGGGTGGGTTAAGCAATTGCAAATCGACTA
TCCCGGACATGAAGTAATGACAGCCGCGGCCTCACAAGGGCTAACCAGAAAAGGAGTGTATGCCGTCCGGCAAAAAGTCA
ATGAAAACCCACTGTACGCGATCACATCAGAGCATGTGAACGTGTTGCTCACCCGCACTGAGGACAGGCTAGTGTGGAAA
ACCTTGCAGGGCGACCCATGGATTAAGCAGCCCACTAACATACCTAAAGGAAACTTTCAGGCTACTATAGAGGACTGGGA
AGCTGAACACAAGGGAATAATTGCTGCAATAAACAGCCCCACTCCCCGTGCCAATCCGTTCAGCTGCAAGACCAACGTTT
GCTGGGCGAAAGCATTGGAACCGATACTAGCCACGGCCGGTATCGTACTTACCGGTTGCCAGTGGAGCCGAACTGTTCCA
CAGTTTGCGGATGACAAACCACATTCGGCCATTTACGCCTTAGACGTAATTTGCATTAAGTTTTTCGGCATGGACTTGAC
AAGCGGACTGTTTTCTAAACAGAGCATCCCACTAACGTACCATCCCGCCGATTCAGCGAGGCCGGTAGCTCATTGGGACA
ACAGCCCAGGAACCCGCAAGTATGGGTACGATCACGCCATTGCCGCCGAACTCTCCCGTAGATTTCCGGTGTTCCAGCTA
GCTGGGAAGGGCACACAACTTGATTTGCAGACGGGGAGAACCAGAGTTATCTCTGCACAGCATAACCTGGTCCCGGTGAA
CCGCAATCTTCCTCACGCCCTTAGTCCCCGAGTACAAGGAGAAGCAACCCGGCCCGGTCAAAAAATTCTTGAACCAGTTCA

FIG. 11A

```
AACACCACTCAGTACTTGTGGTATCAGAGGAAAAAATTGAAGCTCCCCGTAAGAGAATCGAATGGATCGCCCCGATTGGC
ATAGCCGGTGCAGATAAGAACTACAACCTGGCTTTCGGGTTTCCGCCCGCAGGCACGGTACGACCTGGTGTTCATCAACAT
TGGAACTAAATACAGAAACCACCACTTTCAGCAGTGCCGAAGACCATGCGGCGACCTTAAAAACCCTTTCGCGTTCGGCCC
TGAATTGCCTTAACCCAGGAGGCACCCTCGTGGTGAAGTCCTATGGCTACGCCGACCGCAACAGTGAGGACGTAGTCACC
GCTCTTGCCAGAAAGTTTGTCAGGGTGTCTGCAGCGAGACCAGATTGTGTCTCAAGCAATACAGAAATGTACCTGATTTT
CCGACAACTAGACAACAGCCGTACACGGCAATTCACCCCGCACCATCTGAATTGCGTGATTTCGTCCGTGTATGAGGGTA
CAAGAGATGGAGTTGGAGCCGCGCCGTCATACCGCACCAAAAGGGAGAATATTGCTGACTGTCAAGAGGAAGCAGTTGTC
AACGCAGCCAATCCGCTGGGTAGACCAGGCGAAGGAGTCTGCCCGTGCCATCTATAAACGTTGGCCCGACCAGTTTTACCGA
TTCAGCCACGGAGACAGGCACCGCAAGAATGACTGTGTGCCTAGGAAAGAAAGTGATCCACGCGGTCGGCCCTGATTTCC
GGAAGCACCCAGAAGCAGAAGCCTTGAAATTGCTACAAAACGCCTACCATGCAGTGGCAGACTTAGTAAATGAACATAAC
ATCAAGTCTGTCGCCATTCCACTGCTATCTACAGGCATTTACGCAGCCGGAAAAGACCGCCTTGAAGTATCACTTAACTG
CTTGACAACCGCGCTAGACAGAACTGACGCGGACGTAACCATCTATTGCCTGGATAAGAAGTGGAAGGAAAGAATCGACG
CGGCACTCCAACTTAAGGAGTCTGTAACAGAGCTGAAGGATGAAGATATGGAGATCGACGATGAGTTAGTATGGATTCAT
CCAGACAGTTGCTTGAAGGGAAGAAAGGGATTCAGTACTACAAAAGGAAAATTGTATTCGTACTTCGAAGGCACCAAATT
CCATCAAGCAGCAAAAGACATGGCGGAGATAAAGGTCCTGTTCCCTAATGACCAGGAAAGTAATGAACAACTGTGTGCCT
ACATATTGGGTGAGACCATGGAAGCAATCCGCGAAAAGTGCCCGGTCGACCATAACCCGTCGTCTAGCCCGCCCAAAACG
TTGCCCGTGCCTTTGCATGTATGCCATGACGCCAGAAAGGGTCCACAGACTTAGAAGCAATAACCGTCAAAGAAGTTACAGT
ATGCTCCTCCACCCCCCTTCCTAAGCACAAAATTAAGAATGTTCAGAAGGTTCAGTGCACGAAAGTAGTCCTGTTTAATC
CGCACACTCCCGCATTCGTTCCCGCCCGTAAGTACATAGAAGTGCCAGAACAGCCTACCGCTCCTCCTGCACAGGCCGAG
GAGGCCCCCGAAGTTGTAGCGACACCGTCACCATCTACAGCTGATAACACCTCGCTTGATGTCACAGACATCTCACTGGA
TATGGATGACAGTAGCGAAGGCTCACTTTTTTCGAGCTTTAGCGGATCGGACAACTCTATTACTAGTATGGACAGTTGGT
CGTCAGGACCTAGTTCACTAGAGATAGTAGACCGAAGGCAGGTGGTGGTGGCTGACGTTCATGCCCGTCCAAGAGCCTGCC
CCTATTCCACCGCCAAGGCTAAAGAAGATGGCCCGCCTGGCAGCGGCAAGAAAAGAGCCCACTCCACCGGCAAGCAATAG
CTCTGAGTCCCTCCACCTCTCTTTTGGTGGGGTATCCATGTCCCTCGGATCAATTTTCGACGGAGAGACGGCCCGCCAGG
CAGCGGTACAACCCCTGGCAACAGGCCCCACGGATGTGCCTATGTCTTTCGGATCGTTTTCCGACGGAGAGATTGATGAG
CTGAGCCGCAGAGTAACTGAGTCCGAACCCGTCCTGTTTGGATCATTTGAACCGGGCGAAGTGAACTCAATTATATCGTC
CCGATCAGCCGTATCTTTTCCACTACGCAAGCAGAGACGTAGACGCAGGAGCAGGAGGACTGAATACTGACTAACCGGGG
TAGGTGGGTACATATTTTCGACGGACACAGGCCCTGGGCACTTGCAAAAGAAGTCCGTTCTGCAGAACCAGCTTACAGAA
CCGACCTTGGAGCGCAATGTCCTGGAAAGAATTCATGCCCCGGTGCTCGACACGTCGAAAGAGGAACAACTCAAACTCAG
GTACCAGATGATGCCCACCGAAGCCAACAAAAGTAGGTACCAGTCTCGTAAAGTAGAAAATCAGAAAGCCATAACCACTG
AGCGACTACTGTCAGGACTACGACTGTATAACTCTGCCACAGATCAGCCAGAATGCTATAAGATCACCTATCCGAAACCA
TTGTACTCCAGTAGCCGTACCGGCGAACTACTCCGATCCACAGTTCGCTGTAGCTGTCTGTAACAACTATCTGCATGAGAA
CTATCCGACAGTAGCATCTTATCAGATTACTGACGAGTACGATGCTTACTTGGATATGGTAGACGGGACAGTCGCCTGCC
TGGATACTGCAACCTTCTGCCCCGCTAAGCTTAGAAGTTACCCGAAAAAACATGAGTATAGAGCCCCGAATATCCGCAGT
GCGGTTCCATCAGCGATGCAGAACACGCTACAAAATGTGCTCATTGCCGCAACTAAAAGAAATTGCAACGTCACGCAGAT
GCGTGAACTGCCAACACTGGACTCAGCGACATTCAATGTCGAATGCTTTCGAAAATATGCATGTAATGACGAGTATTGGG
AGGAGTTCGCTCGGAAGCCAATTAGGATTACCACTGAGTTTGTCACCGCATATGTAGCTAGACTGAAAGGCCCTAAGGCC
GCCGCACTATTTGCAAAGACGTATAATTTGGTCCCATTGCAAGAAGTGCCTATGGATAGATTCGTCATGGACATGAAAAG
AGACGTGAAAGTTACACCAGGCACGAAACACACAGAAGAAAGACCGAAAGTACAAGTGATACAAGCCGCAGAACCCCTGG
CGACTGCTTACTTATGCGGGATTCACCGGGAATTAGTGCGTAGGCTTACGGCCGTCTTGCTTCCAAACATTCACACGCTT
TTTGACATGTCGGCCGGAGGATTTTGATGCAATCATAGCAGAACACTTCAAGCAAGGCGACCCGGTACTGGAGACGGATAT
CGCATCATTCGACAAAAGCCAAGACGACGCTATGGCGTTAACCGGTCTGATGATCTTGGAGGACCTGGGTGTGGATCAAC
CACTACTCGACTTGATCGAGTGCGCCTTTGGAGAAATATCATCCACCCATCTACCTACGGGTACTCGTTTTAAATTCGGG
GCGATGATGAAATCCGGAATGTTCCTCACACTTTTTGTCAACACAGTTTTGAATGTCGTTATCGCCAGCAGAGTACTAGA
AGAGCGGCTTAAAAACGTCCAGATGTGCAGCGTTCATTGGCGACGACAACATCATACATGGAGTAGTATCTGACAAAGAAA
```

FIG. 11B

```
TGGCTGAGAGGTGCGCCACCTGGCTCAACATGGAGGTTAAGATCATCGACGCAGTCATCGGTGAGAGACCACCTTACTTC
TGCCGGCGGATTTATCTTGCAAGATTCGGTTACTTCCACAGCGTGCCGCGTGGCGGATCCCCTGAAAAGGCTGTTTAAGTT
GGGTAAACCGCTCCCAGCCGACGACGAGCAAGACGAAGACAGAAGACGCGCTCTGCTAGATGAAACAAAGGCCGTGGTTTA
GAGTAGGTATAACAGGCACTTTAGCAGTGGCCGTGACGACCCGGTATGAGGTAGACAATATTACACCTGTCCTACTGGCA
TTGAGAACTTTTGCCCAGAGCAAAAGAGCATTCCAAGCCATCAGAGGGGAAATAAAGCATCTCTACGGTGGTCCTAAATA
GTCAGCATAGTACATTTCATCTGACTAATACTACAACACCACCACCtctagaCGCGTAGAtctcacgtgagcatgcaggc
cttgggCCCAATGATCCGACCAGCAAAACTCGATGTACTTCCGAGGAACTGATGTGCATAATGCATCAGGCTGGTACATT
AGATCCCCGCTTACCGCGGGCAATATAGCAACACTAAAAACTCGATGTACTTCCGAGGAAGCGCAGTgCATAATGCTGCG
CaGTGTTGCCACATAACCACTATATTAACCATTTATCTAGCGGACGCCAAAAACTCAATGTATTTCTGAGGAAGCGTGGT
GCATAATGCCACGCAGCGTCTGCATAACTTTTATTATTTCTTTTATTAATCAACAAAATTTTGTTTTTAACATTTCAAAA
AAAAAAAAAAAAAAAAAAAAAAAAAAAAAAAAAAAAGGGAATTCctcgattaattaagcggccgctcgaGGGGAATTAATTCT
TGAAGACGAAAGGGCCAGGTGGCACTTTTCGGGGAAATGTGCGCGGAACCCCTATTTGTTTATTTTTCTAAATACATTCA
AATATGTATCCGCTCATGAGACAATAACCCTGATAAATGCTTCAATAATATTGAAAAAGGAAGAGTATGAGTATTCAACA
TTTCCGTGTCGCCCTTATTCCCTTTTTTGCGGCATTTTGCCTTCCTGTTTTTGCTCACCCAGAAACGCTGGTGAAAGTAA
AAGATGCTGAAGATCAGTTGGGTGCACGAGTGGGTTACATCGAACTGGATCTCAACAGCGGTAAGATCCTTGAGAGTTTT
CGCCCCGAAGAACGTTTTCCAATGATGAGCACTTTTAAAGTTCTGCTATGTGGCGCGGTATTATCCCGTGTTGACGCCGG
GCAAGAGCAACTCGGTCGCCGCATACACTATTCTCAGAATGACTTGGTTGAGTACTCACCAGTCACAGAAAAGCATCTTA
CGGATGGCATGACAGTAAGAGAATTATGCAGTGCTGCCATAACCATGAGTGATAACACTGCGGCCAACTTACTTCTGACA
ACGATCGGAGGACCGAAGGAGCTAACCGCTTTTTTGCACAACATGGGGGATCATGTAACTCGCCTTGATCGTTGGGAACC
GGAGCTGAATGAAGCCATACCAAACGACGAGCGTGACACCACGATGCCTGtAGCAATGGCAACAACGTTGCGCAAACTAT
TAACTGGCGAACTACTTACTCTAGCTTCCCGGCAACAATTAATAGACTGGATGGAGGCGGATAAAGTTGCAGGACCACTT
CTGCGCTCGGCCCTTCCGGCTGGCTGGTTTATTGCTGATAAATCTGGAGCCGGTGAGCGTGGGTCTCGCGGTATCATTGC
AGCACTGGGGCCAGATGGTAAGCCCTCCCGTATCGTAGTTATCTACACGACGGGGAGTCAGGCAACTATGGATGAACGAA
ATAGACAGATCGCTGAGATAGGTGCCTCACTGATTAAGCATTGGTAACTGTCAGACCAAGTTTACTCATATATACTTTAG
ATTGATTTAAAACTTCATTTTTAATTTAAAAGGATCTAGGTGAAGATCCTTTTTGATAATCTCATGACCAAAATCCCTTA
ACGTGAGTTTTCGTTCCACTGAGCGTCAGACCCCGTAGAAAAGATCAAAGGATCTTCTTGAGATCCTTTTTTTCTGCGCG
TAATCTGCTGCTTGCAAACAAAAAAACCACCGCTACCAGCGGTGGTTTGTTTGCCGGATCAAGAGCTACCAACTCTTTTT
CCGAAGGTAACTGGCTTCAGCAGAGCGCAGATACCAAATACTGTCCTTCTAGTGTAGCCGTAGTTAGGCCACCACTTCAA
GAACTCTGTAGCACCGCCTACATACCTCGCTCTGCTAATCCTGTTACCAGTGGCTGCTGCCAGTGGCGATAAGTCGTGTC
TTACCGGGTTGGACTCAAGACGATAGTTACCGGATAAGGCGCAGCGGTCGGGCTGAACGGGGGGTTCGTGCACACAGCCC
AGCTTGGAGCGAACGACCTACACCGAACTGAGATACCTACAGCGTGAGCATTGAGAAAGCGCCACGCTTCCCGAAGGGAG
AAAGGCGGACAGGTATCCGGTAAGCGGCAGGGTCGGAACAGGAGAGCGCACGAGGGAGCTTCCAGGGGGAAACGCCTGGT
ATCTTTATAGTCCTGTCGGGTTTCGCCACCTCTGACTTGAGCGTCGATTTTTGTGATGCTCGTCAGGGGGCGGAGCCTA
TGGAAAAACGCCAGCAACGCGAGCTCgtatggacatattgtcgttagaacgcggctacaattaatacataaccttatgta
tcatacacatacgatttaggggacactatag
```

FIG. 11C pSinRep 5 EPO
ATTGACGGCGTAGTACACACTATTGAATCAAACAGCCGACCAATTGCACTACCATCACAATGGAGAAGCCAGTAGTAAAC
GTAGACGTAGACCCCCAGAGTCCGTTTGTCGTGCAACTGCAAAAAAGCTTCCCGCAATTTGAGGTAGTAGCACAGCAGGT
CACTCCAAATGACCATGCTAATGCCAGAGCATTTTCGCATCTGGCCAGTAAACTAATCGAGCTGGAGGTTCCTACCACAG
CGACGATCTTGGACATAGGCAGCGCACCGGCTCGTAGAATGTTTTCCGAGCACCAGTATCATTGTGTCTGCCCCATGCGT
AGTCCAGAAGACCCGGACCGCATGATGAAATACGCCAGTAAACTGGCGGAAAAAGCGTGCAAGATTACAAACAAGAACTT
GCATGAGAAGATTAAGGATCTCCCGGACCGTACTTGATACGCCGGATGCTGAAACACCATCGCTCTGCTTTCACAACGATG
TTACCTGCAACATGCGTGCCCGAATATTCCGTCATGCAGGACGTGTATATCAACGCTCCCGGAACTATCTATCATCAGGCT
ATGAAAGGCGTGCCGGACCCTGTACTGGATTGGCTTCGACACCACCCAGTTCATGTTCTCGGCTATGGCAGGTTCGTACCC
TGCCGTACAACACCAACTGGGCCGACGAGAAAGTCCTTGAAGCGCGTAACATCGGACTTTGCAGCACAAAGCTGAGTGAAG
GTAGGACAGGAAAATTGTCGATAATGAGGAAGAAGGAGTTGAAGCCCGGGTCGCGGGTTTATTTCTCCGTAGGATCGACA
CTTTATCCAGAACACAGAGCCAGCTTGCAGAGCTGGCATCTTCCATCGGTGTTCCACTTGAATGGAAAGCAGTCGTACAC
TTGCCGCTGTGATACAGTGGTGAGTTGCCGAAGGCTACGTAGTGAAGAAAATCACCATCAGTCCCGGGATCACGGGAGAAA
CCGTGGGATACGCGGTTACACACAATAGCCGAGGGCTTCTTGCTATGCAAAGTTACTGACACAGTAAAAGGAGAACGGGTA
TCGTTCCCTGTGTGCACGTACATCCCGGCCACCATATGCGATCAGATGACTGGTATAATGGCCACGGATATATCACCTGA
CGATGCACAAAAACTTCTGGTTGGGCTCAACCAGCGAATTGTCATTAACGGTAGGACTAACAGGAACACCAACACCATGC
AAAATTACCTTCTGCCGATCATAGCACAAGGGTTCAGCAAATGGGCTAAGGAGCGCAAGGATGATCTTGATAACGAGAAA
ATGCTGGGTACTAGAGAACGCAAGCTTACGTATGGCTGCTTGTGGGCGTTTCGCACTAAGAAAGTACATTCGTTTTATCG
CCCACCTGGAACGCAGACCTGCGTAAAAGTCCCAGCCTCTTTTAGCGCTTTTCCCATGTCGTCCGTATGGACGACCTCTT
TGCCCATGTCGCTGAGGCAGAAATTGAAACTGGCATTGCAACCAAAGAAGGAGGAAAAACTGCTGCAGGTCTCGGAGGAA
TTAGTCATGGAGGCCAAGGCTGCTTTTGAGGATGCTCAGGAGGAAGCCAGAGCGGAGAAGCTCCGAGAAGCACTTCCACC
ATTAGTGGCAGACAAAGGCATCGAGGCAGCCGCAGAAGTTGTCTGCGAAGTGGAGGGGCTCCAGGCGGACATCGGAGCAG
CATTAGTTGAAACCCCGCGCGGTCACGTAAGGATAATACCTCAAGCAAATGACCGTATGATCGGACAGTATATCGTTGTC
TCGCCAAACTCTGTGCTGAAGAATGCCAAACTCGCACCAGCGCACCCGCTAGCAGATCAGGTTAAGATCATAACACACTC
CGGAAGATCAGGAAGGTACGCGGTCGAACCATACGACGCTAAAGTACTGATGCCAGCAGGAGGTGCCGTACCATGGCCAG
AATTCCTAGCACTGAGTGAGAGCGCCACGTTAGTGTACAACGAAAGAGAGTTTGTGAACCGCAAACTATACCACATTGCC
ATGCATGGCCCCGCCAAGAATACAGAAGAGGAGCAGTACAAGGTTACAAAGGCAGAGCTTGCAGAAACACAGTACGTGTT
TGACGTGGACAAGAAGCGTTGCGTTAAGAAGGAAGAAGCCTCAGGTCTGGTCCTCTCGGGAGAACTGACCAACCCTCCCT
ATCATGAGCTAGCTCTGGAGGGACTGAAGACCCGACCTGCGGTCCCGTACAAGGTCGAAACAATAGGAGTGATAGGCACA
CCGGGGTCGGGCAAGTCAGCTATTATCAAGTCAACTGTCACGGCACGAGATCTTGTTACCAGCGGAAAGAAAGAAAATTG
TCGCGAAATTGAGGCCGACGTGCTAAGACTGAGGGGTATGCAGATTACGTCGAAGACAGTAGATTCGGTTATGCTCAACG
GATGCCACAAAGCCGTAGAAGTGCTGTACGTTGACGAAGCGTTCGCGTGCCACGCAGGAGCACTACTTGCCTTGATTGCT
ATCGTCAGGCCCCGCAAGAAGGTAGTACTATGCGGAGACCCCATGCAATGCGGATTCTTCAACATGATGCAACTAAAGGT
ACATTTCAATCACCCTGAAAAAGACATATGCACCAAGACATTCTACAAGTATATCTCCCGGCGTTGCACACAGCCAGTTA
CAGCTATTGTATCGACACTGCATTACGATGGAAAGATGAAAACCACGAACCCGTGCAAGAAGAACATTGAAATCGATATT
ACAGGGGCCACAAAGCCGAAGCCAGGGGATATCATCCTGACATGTTTCCGCGGGTGGGTTAAGCAATTGCAAATCGACTA
TCCCGGACATGAAGTAATGACAGCCGCGGCCTCACAAGGGCTAACCAGAAAAGGAGTGTATGCCGTCCGGCAAAAAGTCA
ATGAAAACCCACTGTACGCGATCACATCAGAGCATGTGAACGTGTTGCTCACCCGCACTGAGGACAGGCTAGTGTGGAAA
ACCTTGCAGGGCGACCCATGGATTAAGCAGCCCACTAACATACCTAAAGGAAACTTTCAGGCTACTATAGAGGACTGGGA
AGCTGAACACAAGGGAATAATTGCTGCAATAAACAGCCCCACTCCCCGTGCCAATCCGTTCAGCTGCAAGACCAACGTTT
GCTGGGCGAAAGCATTGGAACCGATACTAGCCACGGCCGGTATCGTACTTACCGGTTGCCAGTGGAGCGAACTGTTCCCA
CAGTTTGCGGATGACAAACCACATTCGGCCCATTTACGCCTTAGACGTAATTTGCATTAAGTTTTTCGGCATGGACTTGAC
AAGCGGACTGTTTTCTAAACAGAGCATCCCACTAACGTACCATCCCGCCGATTCAGCGAGGCCGGTAGCTCATTGGGACA
ACAGCCCAGGAACCCGCAAGTATGGGTACGATCACGCCATTGCCGCCGAACTCTCCCGTAGATTTCCGGTGTTCCAGCTA
GCTGGGAAGGGCACACAACTTGATTTGCAGACGGGGAGAACCAGAGTTATCTCTGCACAGCATAACCTGGTCCCGGTGAA
CCGCAATCTTCCTCACGCCTTAGTCCCCGAGTACAAGGAGAAGCAACCCGGCCCGGTCAAAAAATTCTTGAACCAGTTCA

FIG. 11D

```
AACACCACTCAGTACTTGTGGTATCAGAGGAAAAAATTGAAGCTCCCCGTAAGAGAATCGAATGGATCGCCCCGATTGGC
ATAGCCCGGTGCAGATAAGAACTACAACCTGGCTTTCGGGTTTCCGCCGCAGGCACGGTACGACCTGGTGTTCATCAACAT
TGGAACTAAATACAGAAACCACCACTTTCAGCAGTGCGAAGACCATGCGGCGACCTTAAAAACCCTTTCGCGTTCGGCCC
TGAATTGCCTTAACCCAGGAGGCACCCTCGTGGTGAAGTCCTATGGCTACGCCGACCGCAACAGTGAGGACGTAGTCACC
GCTCTTGCCAGAAAGTTTGTCAGGGTGTCTGCAGCGAGACCAGATTGTGTCTCAAGCAATACAGAAATGTACCTGATTTT
CCGACAACTAGACAACAGCCGTACACGGCAATTCACCCCGCACCATCTGAATTGCGTGATTTCGTCCGTGTATGAGGGTA
CAAGAGATGGAGTTGGAGCCGCGCCGTCATACCGCACCAAAAGGGAGAATATTGCTGACTGTCAAGAGGAAGCAGTTGTC
AACGCAGCCAATCCGCTGGGTAGACCAGGCGAAGGAGTCTGCCGTGCCATCTATAAACGTTGGCCGACCAGTTTTACCGA
TTCAGCCACGGAGACAGGCACCGCAAGAATGACTGTGTGCCTAGGAAAGAAAGTGATCCACGCGGTCGGCCCTGATTTCC
GGAAGCACCCAGAAGCAGAAGCCTTGAAATTGCTACAAAACGCCTACCATGCAGTGGCAGACTTAGTAAATGAACATAAC
ATCAAGTCTGTCGCCATTCCACTGCTATCTACAGGCATTTACGCAGCCGGAAAAGACCGCCTTGAAGTATCACTTAACTG
CTTGACAACCGCGCTAGACAGAACTGACGCGGACGTAACCATCTATTGCCTGGATAAGAAGTGGAAGGAAAGAATCGACG
CGGCACTCCAACTTAAGGAGTCTGTAACAGAGCTGAAGGATGAAGATATGGAGATCGACGATGAGTTAGTATGGATtCAT
CCAGACAGTTGCTTGAAGGGAAGAAAGGGATTCAGTACTACAAAAGGAAAATTGTATTCGTACTTCGAAGGCACCAAATT
CCATCAAGCAGCAAAAGACATGGCGGAGATAAAGGTCCTGTTCCCTAATGACCAGGAAAGTAATGAACAACTGTGTGCCT
ACATATTGGGTGAGACCATGGAAGCAATCCGCGAAAAGTGCCCGGTCGACCATAACCCGTCGTCTAGCCCGCCCAAAACG
TTGCCGTGCCTTTGCATGTATGCCATGACGCCAGAAAGGGTCCACAGACTTAGAAGCAATAACGTCAAAGAAGTTACAGT
ATGCTCCTCCACCCCCCTTCCTAAGCACAAAATTAAGAATGTTCAGAAGGTTCAGTGCACGAAAGTAGTCCTGTTTAATC
CGCACACTCCCGCATTCGTTCCCGCCCGTAAGTACATAGAAGTGCCAGAACAGCCTACCGCTCCTCCTGCACAGGCCGAG
GAGGCCCCCGAAGTTGTAGCGACACCGTCACCATCTACAGCTGATAACACCTCGCTTGATGTCACAGACATCTCACTGGA
TATGGATGACAGTAGCGAAGGCTCACTTTTTTCGAGCTTTAGCGGATCGGACAACTCTATTACTAGTATGGACAGTTGGT
CGTCAGGACCTAGTTCACTAGAGATAGTAGACCGAAGGCAGGTGGTGGTGGCTGACGTTCATGCCGTCCAAGAGCCTGCC
CCTATTCCACCGCCAAGGCTAAAGAAGATGGCCCGCCTGGCAGCGGCAAGAAAAGAGCCCACTCCACCGGCAAGCAATAG
CTCTGAGTCCCTCCACCTCTCTTTTGGTGGGGTATCCATGTCCCTCGGATCAATTTTCGACGGAGAGACGGCCCGCCAGG
CAGCGGTACAACCCCTGGCAACAGGCCCCACGGATGTGCCTATGTCTTTCGGATCGTTTTCCGACGGAGAGATTGATGAG
CTGAGCCGCAGAGTAACTGAGTCCGAACCCGTCCTGTTTGGATCATTTGAACCGGGCGAAGTGAACTCAATTATATCGTC
CCGATCAGCCCGTATCTTTTCCACTACGCAAGCAGAGACGTAGACGCAGGAGCAGGAGGACTGAATACTGACTAACCGGGG
TAGGTGGGTACATATTTTCGACGGACACAGGCCCTGGGCACTTGCAAAAGAAGTCCGTTCTGCAGAACCAGCTTACAGAA
CCGACCTTGGAGCGCAATGTCCTGGAAAGAATTCATGCCCCGGTGCTCGACACGTCGAAAGAGGAACAACTCAAACTCAG
GTACCAGATGATGCCCACCGAAGCCAACAAAAGTAGGTACCAGTCTCGTAAAGTAGAAAATCAGAAAGCCATAACCACTG
AGCGACTACTGTCAGGACTACGACTGTATAACTCTGCCACAGATCAGCCAGAATGCTATAAGATCACCTATCCGAAACCA
TTGTACTCCAGTAGCGTACCGGCGAACTACTCCGATCCACAGTTCGCTGTAGCTGTCTGTAACAACTATCTGCATGAGAA
CTATCCGACAGTAGCATCTTATCAGATTACTGACGAGTACGATGCTTACTTGGATATGGTAGACGGGACAGTCGCCTGCC
TGGATACTGCAACCTTCTGCCCCGCTAAGCTTAGAAGTTACCCGAAAAAACATGAGTATAGAGCCCCGAATATCCGCAGT
GCGGTTCCATCAGCCGATGCAGAACACGCTACAAAATGTGCTCATTGCCGCAACTAAAAGAAATTGCAACGTCACGCAGAT
GCGTGAACTGCCAACACTGGACTCAGCGACATTCAATGTCGAATGCTTTCGAAAATATGCATGTAATGACGAGTATTGGG
AGGAGTTCGCTCGGAAGCCAATTAGGATTACCACTGAGTTTGTCACCGCATATGTAGCTAGACTGAAAGGCCCTAAGGCC
GCCGCACTATTTGCAAAGACGTATAATTTGGTCCCATTGCAAGAAGTGCCTATGGATAGATTCGTCATGGACATGAAAAG
AGACGTGAAAGTTACACCAGGCACGAAACACACAGAAGAAAGACCGAAAGTACAAGTGATACAAGCCGCAGAACCCCTGG
CGACTGCTTACTTATGCGGGATTCACCGGGAATTAGTGCGTAGGCTTACGGCCGTCTTGCTTCCAAACATTCACACGCTT
TTTGACATGTCGGCGGAGGATTTTGATGCAATCATAGCAGAACACTTCAAGCAAGGCGACCCCGGTACTGGAGACGGATAT
CGCATCATTCGACAAAAGCCAAGACGACGCTATGGCGTTAACCGGTCTGATGATCTTGGAGGACCTGGGTGTGGATCAAC
CACTACTCGACTTGATCGAGTGCGCCTTTGGAGAAATATCATCCACCCATCTACCTACGGGTACTCGTTTTAAATTCGGG
GCGATGATGAAATCCGGAATGTTCCTCACACTTTTTGTCAACACAGTTTTGAATGTCGTTATCGCCAGCAGAGTACTAGA
AGAGCGGCTTAAAAACGTCCAGATGTGCAGCGTTCATTGGCGACGACAACATCATACATGGAGTAGTATCTGACAAAGAAA
```

FIG. 11E

```
TGGCTGAGAGGTGCGCCACCTGGCTCAACATGGAGGTTAAGATCATCGACGCAGTCATCGGTGAGAGACCACCTTACTTC
TGCGGCCGGATTTATCTTGCAAGATTCGGTTACTTCCACAGCGTGCCGCGTGGCGGATCCCCTGAAAAGGCTGTTTAAGTT
GGGTAAACCGCTCCCAGCCGACGACGAGCAAGACCAAGACAGAAGACGCGCTCTGCTAGATGAAACAAAGGCGTGGTTTA
GAGTAGGTATAACAGGCACTTTAGCAGTGGCCGTGACGACCCGGTATGAGGTAGACAATATTACACCTGTCCTACTGGCA
TTGAGAACTTTTGCCCAGAGCAAAAGAGCATTCCAAGCCATCAGAGGGGAAATAAAGCATCTCTACGGTGGTCCTAAATA
GTCAGCATAGTACATTTCATCTGACTAATACTACAACACCACCACCtctagaggcgcggagatgggggtgcacgaatgtc
ctgcctggctgtggcttctcctgtccctgctgtcgctccctctgggcctcccagtcctgggcgccccaccacgcctcatc
tgtgacagccgagtcctggagagggtacctcttggaggccaaggaggccgagaatatcacgacgggctgtgctgaacactg
cagcttgaatgagaatatcactgtcccagacaccaaagttaatttctatgcctggaagaggatggaggtcgggcagcagg
ccgtagaagtctggcagggcctggccctgctgtcggaagctgtcctgcggggccaggccctgttggtcaactcttcccag
ccgtgggagcccctgcagctgcatgtggataaagccgtcagtggccttcgcagcctcaccactctgcttcgggctctggg
agcccagaaggaagccatctcccctccagatgcggcctcagctgctccactccgaacaatcactgctgacactttccgca
aactcttccgagtctactccaatttcctccggggaaagctgaagctgtacacaggggaggcctgcaggacaggggacaga
tgagcatgcaggccttgggCCCAATGATCCGACCAGCAAAACTCGATGTACTTCCGAGGAACTGATGTGCATAATGCATC
AGGCTGGTACATTAGATCCCCGCTTACCGCGGGCAATATAGCAACACTAAAAACTCGATGTACTTCCGAGGAAGCGCAGT
gCATAATGCTGCGCaGTGTTGCCACATAACCACTATATTAACCATTTATCTAGCGGACGCCAAAAACTCAATGTATTTCT
GAGGAAGCGTGGTGCATAATGCCACGCAGCGTCTGCATAACTTTTATTATTTCTTTTATTAATCAACAAAATTTTGTTTT
TAACATTTCAAAAAAAAAAAAAAAAAAAAAAAAAAAAAAAAAAAAAGGGAATTCctcgattaattaagcggccgctcgaG
GGGAATTAATTCTTGAAGACGAAAGGGCCAGGTGGCACTTTTCGGGGAAATGTGCGCGGAACCCCTATTTGTTTATTTTT
CTAAATACATTCAAATATGTATCCGCTCATGAGACAATAACCCTGATAAATGCTTCAATAATATTGAAAAAGGAAGAGTA
TGAGTATTCAACATTTCCGTGTCGCCCTTATTCCCTTTTTGCGGCATTTTGCCTTCCTGTTTTTGCTCACCCAGAAACG
CTGGTGAAAGTAAAAGATGCTGAAGATCAGTTGGGTGCACGAGTGGGTTACATCGAACTGGATCTCAACAGCGGTAAGAT
CCTTGAGAGTTTTCGCCCCGAAGAACGTTTTCCAATGATGAGCACTTTTAAAGTTCTGCTATGTGGCGCGGTATTATCCC
GTGTTGACGCCGGGCAAGAGCAACTCGGTCGCCGCATACACTATTCTCAGAATGACTTGGTTGAGTACTCACCAGTCACA
GAAAAGCATCTTACGGATGGCATGACAGTAAGAGAATTATGCAGTGCTGCCATAACCATGAGTGATAACACTGCGGCCAA
CTTACTTCTGACAACGATCGGAGGACCGAAGGAGCTAACCGCTTTTTTGCACAACATGGGGGATCATGTAACTCGCCTTG
ATCGTTGGGAACCGGAGCTGAATGAAGCCATACCAAACGACGAGCGTGACACCACGATGCCTGtAGCAATGGCAACAACG
TTGCGCAAACTATTAACTGGCGAACTACTTACTCTAGCTTCCCGGCAACAATTAATAGACTGGATGGAGGCGGATAAAGT
TGCAGGACCACTTCTGCGCTCGGCCCTTCCGGCTGGCTGGTTTATTGCTGATAAATCTGGAGCCCGGTGAGCGTGGGTCTC
GCGGTATCATTGCAGCACTGGGGCCAGATGGTAAGCCCTCCCGTATCGTAGTTATCTACACGACGGGGAGTCAGGCAACT
ATGGATGAACGAAATAGACAGATCGCTGAGATAGGTGCCTCACTGATTAAGCATTGGTAACTGTCAGACCAAGTTTACTC
ATATATACTTTAGATTGATTTAAAACTTCATTTTTAATTTAAAAGGATCTAGGTGAAGATCCTTTTTGATAATCTCATGA
CCAAAATCCCTTAACGTGAGTTTTCGTTCCACTGAGCGTCAGACCCCGTAGAAAAGATCAAAGGATCTTCTTGAGATCCT
TTTTTTCTGCGCGTAATCTGCTGCTTGCAAACAAAAAAACCACCGCTACCAGCGGTGGTTTGTTTGCCGGATCAAGAGCT
ACCAACTCTTTTTCCGAAGGTAACTGGCTTCAGCAGAGCGCAGATACCAAATACTGTCCTTCTAGTGTAGCCGTAGTTAG
GCCACCACTTCAAGAACTCTGTAGCACCGCCTACATACCTCGCTCTGCTAATCCTGTTACCAGTGGCTGCTGCCAGTGGC
GATAAGTCGTGTCTTACCGGGTTGGACTCAAGACGATAGTTACCGGATAAGGCGCAGCGGTCGGGCTGAACGGGGGGTTC
GTGCACACAGCCCAGCTTGGAGCGAACGACCTACACCGAACTGAGATACCTACAGCGTGAGCATTGAGAAAGCGCCACGC
TTCCCGAAGGGAGAAAGGCCGGACAGGTATCCGGTAAGCGGCAGGGTCGGAACAGGAGAGCGCACGAGGGAGCTTCCAGGG
GGAAACGCCTGGTATCTTTATAGTCCTGTCGGGTTTCGCCACCTCTGACTTGAGCGTCGATTTTTGTGATGCTCGTCAGG
GGGGCGGAGCCTATGGAAAAACGCCAGCAACGCGAGCTCgtatggacatattgtcgttagaacgcggctacaattaatac
ataaccttatgtatcatacacatacgatttaggggacactatag
```

FIG. 11F pSinRep 5 hIL13Ralpha
ATTGACGGCGTAGTACACACTATTGAATCAAACAGCCGACCAATTGCACTACCATCACAATGGAGAAGCCAGTAGTAAAC
GTAGACGTAGACCCCCAGAGTCCGTTTGTCGTGCAACTGCAAAAAAGCTTCCCGCAATTTGAGGTAGTAGCACAGCAGGT
CACTCCAAATGACCATGCTAATGCCAGAGCATTTTCGCATCTGGCCAGTAAACTAATCGAGCTGGAGGTTCCTACCACAG
CGACGATCTTGGACATAGGCAGCGCACCGGCTCGTAGAATGTTTTCCGAGCACCAGTATCATTGTGTCTGCCCCATGCGT
AGTCCAGAAGACCCGGACCGCATGATGAAATACGCCAGTAAACTGGCGGAAAAAGCGTGCAAGATTACAAACAAGAACTT
GCATGAGAAGATTAAGGATCTCCGGACCGTACTTGATACGCCGGATGCTGAAACACCATCGCTCTGCTTTCACAACGATG
TTACCTGCAACATGCGTGCCCGAATATTCCGTCATGCAGGACGTGTATATCAACGCTCCCGGAACTATCTATCATCAGGCT
ATGAAAGGCGTGCCGGACCCTGTACTGGATTGGCTTCGACACCACCCAGTTCATGTTCTCGGCTATGGCAGGTTCGTACCC
TGCGTACAACACCAACTGGGCCGACGAGAAAGTCCTTGAAGCGCGTAACATCGGACTTTGCAGCACAAAGCTGAGTGAAG
GTAGGACAGGAAAATTGTCGATAATGAGGAAGAAGGAGTTGAAGCCCGGGTCGCGGGTTTATTTCTCCGTAGGATCGACA
CTTTATCCAGAACACAGAGCCAGCTTGCAGAGCTGGCATCTTCCATCGGTGTTCCACTTGAATGGAAAGCAGTCGTACAC
TTGCCGCTGTGATACAGTGGTGAGTTGCGAAGGCTACGTAGTGAAGAAAATCACCATCAGTCCCGGGATCACGGGAGAAA
CCGTGGGATACGCGGTTACACACAATAGCGAGGGCTTCTTGCTATGCAAAGTTACTGACACAGTAAAAGGAGAACGGGTA
TCGTTCCCTGTGTGCACGTACATCCCGGCCACCATATGCGATCAGATGACTGGTATAATGGCCACGGATATATCACCTGA
CGATGCACAAAAACTTCTGGTTGGGCTCAACCAGCGAATTGTCATTAACGGTAGGACTAACAGGAACACCAACACCATGC
AAAATTACCTTCTGCCGATCATAGCACAAGGGTTCAGCAAATGGGCTAAGGAGCGCAAGGATGATCTTGATAACGAGAAA
ATGCTGGGTACTAGAGAACGCAAGCTTACGTATGGCTGCTTGTGGGCGTTTCGCACTAAGAAAGTACATTCGTTTTATCG
CCCACCTGGAACGCAGACCTGCGTAAAAGTCCCAGCCTCTTTTAGCGCTTTTCCCATGTCGTCCGTATGGACGACCTCTT
TGCCCATGTCGCTGAGGCAGAAATTGAAACTGGCATTGCAACCAAAGAAGGAGGAAAAACTGCTGCAGGTCTCGGAGGAA
TTAGTCATGGAGGCCAAGGCTGCTTTTGAGGATGCTCAGGAGGAAGCCAGAGCGGAGAAGCTCCGAGAAGCACTTCCACC
ATTAGTGGCAGACAAAGCATCGAGGCAGCCGCAGAAGTTGTCTGCGAAGTGGAGGGGCTCCAGGCGGACATCGGAGCAG
CATTAGTTGAAACCCCGCGCGGTCACGTAAGGATAATACCTCAAGCAAATGACCGTATGATCGGACAGTATATCCGTTGTC
TCGCCAAACTCTGTGCTGAAGAATGCCAAACTCGCACCAGCGCACCCGCTAGCAGATCAGGTTAAGATCATAACACACTC
CGGAAGATCAGGAAGGTACGCCGGTCGAACCATACGACGCTAAAGTACTGATGCCAGCAGGAGGTGCCGTACCATGGCCAG
AATTCCTAGCACTGAGTGAGAGCGCCACGTTAGTGTACAACGAAAGAGAGTTTGTGAACCGCAAACTATACCACATTGCC
ATGCATGGCCCCGCCAAGAATACAGAAGAGGAGCAGTACAAGGTTACAAAGGCAGAGCTTGCAGAAACAGAGTACGTGTT
TGACGTGGACAAGAAGCGTTGCGTTAAGAAGGAAGAAGCCTCAGGTCTGGTCCTCTCGGGAGAACTGACCAACCCTCCCT
ATCATGAGCTAGCTCTGGAGGGACTGAAGACCCGACCTGCCGGTCCCGTACAAGGTCGAAACAATAGGAGTGATAGGCACA
CCGGGGTCGGGCAAGTCAGCTATTATCAAGTCAACTGTCACGGCACGAGATCTTGTTACCAGCGGAAAGAAAGAAAATTG
TCCGCGAAATTGAGGCCGACGTGCTAAGACTGAGGGGTATGCAGATTACGTCGAAGACAGTAGATTCGGTTATGCTCAACG
GATGCCACAAAGCCGTAGAAGTGCTGTACGTTGACGAAGCGTTCGCGTGCCACGCAGGAGCACTACTTGCCTTGATTGCT
ATCGTCAGGCCCCGCAAGAAGGTAGTACTATGCGGAGACCCCATGCAATGCGGATTCTTCAACATGATGCAACTAAAAGGT
ACATTTCAATCACCCTGAAAAAGACATATGCACCAAGACATTCTACAAGTATATCTCCCGGCGTTGCACACAGCCAGTTA
CAGCTATTGTATCGACACTGCATTACGATGGAAAGATGAAAACCACGAACCCGTGCAAGAAGAACATTGAAATCGATATT
ACAGGGGCCACAAAGCCGAAGCCAGGGGATATCATCCTGACATGTTTCCGCGGGTGGGTTAAGCAATTGCAAATCGACTA
TCCCCGGACATGAAGTAATGACAGCCGCGGCCTCACAAGGGCTAACCAGAAAAGGAGTGTATGCCGTCCGGCAAAAAGTCA
ATGAAAACCCACTGTACGCGATCACATCAGAGCATGTGAACGTGTTGCTCACCCGCACTGAGGACAGGCTAGTGTGGAAA
ACCTTGCAGGGCGACCCATGGATTAAGCAGCCCACTAACATACCTAAAGGAAACTTTCAGGCTACTATAGAGGACTGGGA
AGCTGAACACAAGGGAATAATTGCTGCAATAAACAGCCCCACTCCCCGTGCCAATCCGTTCAGCTGCAAGACCAACGTTT
GCTGGGCGAAAGCATTGGAACCGATACTAGCCACGGCCGGTATCGTACTTACCGGTTGCCAGTGGAGCGAACTGTTCCCA
CAGTTTGCCGGATGACAAACCACATTCGGCCATTTACGCCTTAGACGTAATTTGCATTAAGTTTTTCGGCATGGACTTGAC
AAGCGGACTGTTTTCTAAACAGAGCATCCCACTAACGTACCATCCCGCCGATTCAGCGAGGCCGGTAGCTCATTGGGACA
ACAGCCCAGGAACCCGCAAGTATGGGTACGATCACGCCATTGCCGCCGAACTCTCCCGTAGATTTCCGGTGTTCCAGCTA
GCTGGGAAGGGCACACAACTTGATTTGCAGACGGGGAGAACCAGAGTTATCTCTGCACAGCATAACCTGGTCCCGGTGAA
CCGCAATCTTCCTCACGCCTTAGTCCCCGAGTACAAGGAGAAGCAACCCGGCCCGGTCAAAAAAATTCTTGAACCAGTTCA

FIG. 11G

```
AACACCACTCAGTACTTGTGGTATCAGAGGAAAAAATTGAAGCTCCCCGTAAGAGAATCGAATGGATCGCCCCGATTGGC
ATAGCCGGTGCAGATAAGAACTACAACCTGGCTTTCGGGTTTCCGCCGCAGGCACGGTACGACCTGGTGTTCATCAACAT
TGGAACTAAATACAGAAACCACCACTTTCAGCAGTGCCAAGACCATGCGGCGACCTTAAAAACCCTTTCGCGTTCGGCCC
TGAATTGCCTTAACCCAGGAGGCACCCTCGTGGTGAAGTCCTATGGCTACGCCGACCGCAACAGTGAGGACGTAGTCACC
GCTCTTGCCAGAAAGTTTGTCAGGGTGTCTGCAGCGAGACCAGATTGTGTCTCAAGCAATACAGAAATGTACCTGATTTT
CCGACAACTAGACAACAGCCGTACACGGCAATTCACCCCGCACCATCTGAATTGCCGTGATTTCGTCCGTGTATGAGGGTA
CAAGAGATGGAGTTGGAGCCGCGCCGTCATACCGCACCAAAAGGGAGAATATTGCTGACTGTCAAGAGGAAGCAGTTGTC
AACGCAGCCAATCCGCTGGGTAGACCAGGCGAAGGAGTCTGCCGTGCCATCTATAAACGTTGGCCGACCAGTTTTACCGA
TTCAGCCACGGAGACAGGCACCGCAAGAATGACTGTGTGCCTAGGAAAGAAAGTGATCCACGCGGTCGGCCCTGATTTCC
GGAAGCACCCAGAAGCAGAAGCCTTGAAATTGCTACAAAACGCCTACCATGCAGTGGCAGACTTAGTAAATGAACATAAC
ATCAAGTCTGTCGCCATTCCACTGCTATCTACAGGCATTTACGCAGCCGGAAAAGACCGCCTTGAAGTATCACTTAACTG
CTTGACAACCGCGCTAGACAGAACTGACGCGGACGTAACCATCTATTGCCTGGATAAGAAGTGGAAGGAAAGAATCGACG
CGGCACTCCAACTTAAGGAGTCTCTAACAGAGCTGAAGGATGAAGATATGGAGATCGACGATGAGTTAGTATGGATtCAT
CCAGACAGTTGCTTGAAGGGAAGAAAGGGATTCAGTACTACAAAAGGAAAATTGTATTCGTACTTCGAAGGCACCAAATT
CCATCAAGCAGCAAAAGACATGGCCGGAGATAAAGGTCCTGTTCCCTAATGACCAGGAAAGTAATGAACAACTGTGTGCCT
ACATATTGGGTGAGACCATGGAAGCAATCCGCGAAAAGTGCCCGGTCGACCATAACCCGTCGTCTAGCCCGCCCAAAACG
TTGCCGTGCCTTTGCATGTATGCCATGACGCCAGAAAGGGTCCACAGACTTAGAAGCAATAACGTCAAAGAAGTTACAGT
ATGCTCCTCCACCCCCCTTCCTAAGCACAAAATTAAGAATGTTCAGAAGGTTCAGTGCACGAAAGTAGTCCTGTTTAATC
CGCACACTCCCGCATTCGTTCCCGCCCGTAAGTACATAGAAGTGCCAGAACAGCCTACCGCTCCTCCTGCACAGGCCGAG
GAGGCCCCCGAAGTTGTAGCGACACCGTCACCATCTACAGCTGATAACACCTCGCTTGATGTCACAGACATCTCACTGGA
TATGGATGACAGTAGCCGAAGGCTCACTTTTTTCGAGCTTTAGCCGGATCGGACAACTCTATTACTAGTATGGACAGTTGGT
CGTCAGGACCTAGTTCACTAGAGATAGTAGACCGAAGGCAGGTGGTGGTGGCTGACGTTCATGCCGTCCAAGAGCCTGCC
CCTATTCCACCGCCAAGGCTAAAGAAGATGGCCCGCCTGGCAGCGGCAAGAAAAGAGCCCACTCCACCGGCAAGCAATAG
CTCTGAGTCCCTCCACCTCTCTTTTGGTGGGGTATCCATGTCCCTCGGATCAATTTTCGACGGAGAGACGGCCCGCCAGG
CAGCGGTACAACCCCTGGCAACAGGCCCCACGGATGTGCCTATGTCTTTCGGATCGTTTTCCGACGGAGAGATTGATGAG
CTGAGCCGCAGAGTAACTGAGTCCGAACCCGTCCTGTTTGGATCATTTGAACCGGGCGAAGTGAACTCAATTATATCGTC
CCGATCAGCCGTATCTTTTCCACTACGCAAGCAGAGACGTAGACGCAGGAGCAGGAGGACTGAATACTGACTAACCGGGG
TAGGTGGGTACATATTTTCGACGGACACAGGCCCTGGGCACTTGCAAAAGAAGTCCGTTCTGCAGAACCAGCTTACAGAA
CCGACCTTGGAGCGCAATGTCCTGGAAAGAATTCATGCCCCGGTGCTCGACACGTCGAAAGAGGAACAACTCAAACTCAG
GTACCAGATGATGCCCACCGAAGCCAACAAAAGTAGGTACCAGTCTCGTAAAGTAGAAAATCAGAAAGCCATAACCACTG
AGCGACTACTGTCAGGACTACGACTGTATAACTCTGCCACAGATCAGCCAGAATGCTATAAGATCACCTATCCGAAACCA
TTGTACTCCAGTAGCGTACCGGCGAACTACTCCGATCCACAGTTCGCTGTAGCTGTCTGTAACAACTATCTGCATGAGAA
CTATCCGACAGTAGCATCTTATCAGATTACTGACGAGTACGATGCTTACTTGGATATGGTAGACGGGACAGTCGCCTGCC
TGGATACTGCAACCTTCTGCCCCGCTAAGCTTAGAAGTTACCCGAAAAAACATGAGTATAGAGCCCCGAATATCCGCAGT
GCCGGTTCCATCAGCGATGCAGAACACGCTACAAAATGTGCTCATTGCCGCAACTAAAAGAAATTGCAACGTCACGCAGAT
GCGTGAACTGCCAACACTGGACTCAGCGACATTCAATGTCGAATGCTTTCGAAAATATGCATGTAATGACGAGTATTGGG
AGGAGTTCGCTCGGAAGCCAATTAGGATTACCACTGAGTTTGTCACCGCATATGTAGCTAGACTGAAAGGCCCTAAGGCC
GCCCGCACTATTTGCAAAGACGTATAATTTGGTCCCATTGCAAGAAGTGCCTATGGATAGATTCGTCATGGACATGAAAAG
AGACGTGAAAGTTACACCAGGCACGAAACACACAGAAGAAAGACCGAAAGTACAAGTGATACAAGCCGCAGAACCCCTGG
CGACTGCTTACTTATGCGGGATTCACCGGGAATTAGTGCGTAGGCTTACGGCCGTCTTGCTTCCAAACATTCACACGCTT
TTTGACATGTCGGCGGAGGATTTTGATGCAATCATAGCAGAACACTTCAAGCAAGGCGACCCGGTACTGGAGACGGATAT
CGCATCATTCGACAAAAGCCAAGACGACGCTATGGCGTTAACCGGTCTGATGATCTTGGAGGACCTGGGTGTGGATCAAC
CACTACTCGACTTGATCGAGTGCGCCTTTGGAGAAATATCATCCACCCATCTACCTACGGGTACTCGTTTTAAATTCGGG
GCGATGATGAAATCCGGAATGTTCCTCACACTTTTTGTCAACACAGTTTTGAATGTCGTTATCGCCAGCAGAGTACTAGA
AGAGCGGCTTAAAAACGTCCAGATGTGCAGCCGTTCATTGGCGACGACAACATCATACATGGAGTAGTATCTGACAAAGAAA
```

FIG. 11H

TGGCTGAGAGGTGCGCCACCTGGCTCAACATGGAGGTTAAGATCATCGACGCAGTCATCGGTGAGAGACCACCTTACTTC
TGCGGCCGGATTTATCTTGCAAGATTCGGTTACTTCCACAGCCGTGCCGCGTGGCGGATCCCCTGAAAAGGCTGTTTAAGTT
GGGTAAACCGCTCCCAGCCGACGACGAGCAAGACGAAGACAGAAGACGCGCTCTGCTAGATGAAACAAAGGCGTGGTTTA
GAGTAGGTATAACAGGCACTTTAGCAGTGGCCGTGACGACCCGGTATGAGGTAGACAATATTACACCTGTCCTACTGGCA
TTGAGAACTTTTGCCCAGAGCAAAAGAGCATTCCAAGCCATCAGAGGGGAAATAAAGCATCTCTACGGTGGTCCTAAATA
GTCAGCATAGTACATTTCATCTGACTAATACTACAACACCACCACCtctagatcagcccggccgggctccgggcgagag
gctgcatggagtggccggcgcggctctgcgggctgtgggcgctgctgctctgcgccggcggcggggggcggggcgggggc
gccgcgcctacggaaactcagccacctgtgacaaatttgagtgtctctgttgaaaacctctgcacagtaatatggacatg
gaatccacccggagggagccagctcaaattgtagtctatggtatttagtcattttggcgacaaacaagataagaaaatag
ctccggaaactcgtcgttcaatagaagtacccctgaatgagaggatttgtctgcaagtggggtcccagtgtagcaccaat
gagagtgagaagcctagcattttggttgaaaaatgcatctcacccccagaaggtgatcctgagtctgctgtgactgagct
tcaatgcatttggcacaacctgagctacatgaagtgttcttggctccctggaaggaataccagtcccgacactaactata
ctctctactattggcacagaagcctggaaaaaattcatcaatgtgaaaacatctttagagaaggccaatactttggttgt
tcctttgatctgaccaaagtgaaggattccagttttgaacaacacagtgtccaaataatggtcaaggataatgcaggaaa
aattaaaaccatccttcaatatagtgcctttaacttcccgtgtgaaacctgatcctccacatattaaaaacctctccttcc
acaatgatgacctatatgtgcaatgggagaatccacagaatttattagcagatgcctattttatgaagtagaagtcaat
aacagccaaactgagacacataatgtttttctacgtccaagaggctaaatgtgagaatccagaatttgagagaaatgtgga
gaatacatcttgtttcatggtccctggtgttcttcctgatactttgaacacagtcagaataagagtcaaaacaaataagt
tatgctatgaggatgacaaactctggagtaattggagccaagaaatgagtataggtaagaagcgcaattccacactctac
ataaccatgttactcattgttccagtcatcgtcgcaggtgcaatcatagtactcctgctttacctaaaaaggctcaagat
tattatattcccctccaattcctgatcctggcaagatttttaaagaaatgtttggagaccagaatgatgatactctgcact
ggaagaagtacgacatctatgagaagcaaaccaaggggaaaccgactctgtagtgctgatagaaaacctgaagaaagcc
tctcagtgatggagataatttatttttttaccttcactgtgaccttgagaagattcttcccattctccatttgttatctggg
aacttattaaatggaaactgaaactactgcaccatttaaaaacaggcagctcataagagccacaggtctttatgttgagt
cgcgcaccgaaaaactaaaaataatgggcgctttggagaagagtgtggagtcattctcattgaattataaaagccagcag
gcttcaaactaggggacaaagcaaaaagtgatgatagtggtggagttaatcttatcaagagttgtgacaacttcctgagg
gatctatacttgctttgtgttctttgtgtcaacatgaacaaatttttatttgtaggggaactcatttggggtgcaaatgct
aatgtcaaacttgagtcacaaagaacatgtagaaaacaaaatggataaaatctgatatgtattgtttgggatcctattga
accatgtttgtggctattaaaactcttttaacagtctgggctgggtccggtggctcacgcctgtaatcccagcaatttgg
gagtccgaggcgggcggatcactcgagctgcaggcatgcaagcttggcactggccgtcgttttacaacgtcgtgactggg
aaaaccctggcgttacccaacttaatcgccttgcagcacatcccccttcgccagccttgggCCCAATGATCCGACCAGC
AAAACTCGATGTACTTCCGAGGAACTGATGTGCATAATGCATCAGGCTGGTACATTAGATCCCCGCTTACCGCGGGCAAT
ATAGCAACACTAAAAACTCGATGTACTTCCGAGGAAGCGCAGTgCATAATGCTGCCGaGTGTTGCCACATAACCACTATA
TTAACCATTTATCTAGCGGACGCCAAAAACTCAATGTATTTCTGAGGAAGCGTGGTGCATAATGCCACGCAGCGTCTGCA
TAACTTTTATTATTTCTTTTATTAATCAACAAAATTTTGTTTTTAACATTTCAAAAAAAAAAAAAAAAAAAAAAAAAAAA
AAAAAAAAAGGGAATTCCtcgattaattaagcggccgctcgaGGGGAATTAATTCTTGAAGACGAAAGGGCCAGGTGGCA
CTTTTCGGGGAAATGTGCGCGGAACCCCTATTTGTTTATTTTTCTAAATACATTCAAATATGTATCCGCTCATGAGACAA
TAACCCTGATAAATGCTTCAATAATATTGAAAAAGGAAGAGTATGAGTATTCAACATTTCCGTGTCGCCCTTATTCCCTT
TTTTGCGGCATTTTGCCTTCCTGTTTTTGCTCACCCAGAAACGCTGGTGAAAGTAAAAGATGCTGAAGATCAGTTGGGTG
CACGAGTGGGTTACATCGAACTGGATCTCAACAGCGGTAAGATCCTTGAGAGTTTTCGCCCCGAAGAACGTTTTCCAATG
ATGAGCACTTTTAAAGTTCTGCTATGTGGCGCGGTATTATCCCGTGTTGACGCCGGGCAAGAGCAACTCGGTCGCCGCAT

FIG. 11I

```
ACACTATTCTCAGAATGACTTGGTTGAGTACTCACCAGTCACAGAAAAGCATCTTACGGATGGCATGACAGTAAGAGAAT
TATGCAGTGCTGCCATAACCATGAGTGATAACACTGCGGCCAACTTACTTCTGACAACGATCGGAGGACCGAAGGAGCTA
ACCGCTTTTTTGCACAACATGGGGGATCATGTAACTCGCCTTGATCGTTGGGAACCGGAGCTGAATGAAGCCATACCAAA
CGACGAGCGTGACACCACGATGCCTGTAGCAATGGCAACAACGTTGCGCAAACTATTAACTGGCGAACTACTTACTCTAG
CTTCCCGGCAACAATTAATAGACTGGATGGAGGCGGATAAAGTTGCAGGACCACTTCTGCGCTCGGCCCTTCCGGCTGGC
TGGTTTATTGCTGATAAATCTGGAGCCGGTGAGCGTGGGTCTCGCGGTATCATTGCAGCACTGGGGCCAGATGGTAAGCC
CTCCCGTATCGTAGTTATCTACACCACGGGGAGTCAGGCAACTATGGATGAACGAAATAGACAGATCGCTGAGATAGGTG
CCTCACTGATTAAGCATTGGTAACTGTCAGACCAAGTTTACTCATATATACTTTAGATTGATTTAAAACTTCATTTTTAA
TTTAAAAGGATCTAGGTGAAGATCCTTTTTGATAATCTCATGACCAAAATCCCTTAACGTGAGTTTTCGTTCCACTGAGC
GTCAGACCCCGTAGAAAAGATCAAAGGATCTTCTTGAGATCCTTTTTTTCTGCGCGTAATCTGCTGCTTGCAAACAAAAA
AACCACCGCTACCAGCGGTGGTTTGTTTGCCGGATCAAGAGCTACCAACTCTTTTTCCGAAGGTAACTGGCTTCAGCAGA
GCGCAGATACCAAATACTGTCCTTCTAGTGTAGCCGTAGTTAGGCCACCACTTCAAGAACTCTGTAGCACCGCCTACATA
CCTCGCTCTGCTAATCCTGTTACCAGTGGCTGCTGCCAGTGGCGATAAGTCGTGTCTTACCGGGTTGGACTCAAGACGAT
AGTTACCGGATAAGGCGCAGCGGTCGGGCTGAACGGGGGGTTCGTGCACACAGCCCAGCTTGGAGCGAACGACCTACACC
GAACTGAGATACCTACAGCGTGAGCATTGAGAAAGCGCCACGCTTCCCGAAGGGAGAAAGGCGGACAGGTATCCGGTAAG
CGGCAGGGTCGGAACAGGAGAGCGCACGAGGGAGCTTCCAGGGGGAAACGCCTGGTATCTTTATAGTCCTGTCGGGTTTC
GCCACCTCTGACTTGAGCGTCGATTTTTGTGATGCTCGTCAGGGGGCGGAGCCTATGGAAAAACGCCAGCAACGCGAGC
Tcgtatggacatattgtcgttagaacgcggctacaattaatacataaccttatgtatcatacacatacgatttaggggac
actatag
```

FIG. 11J pDH-EB
GGATATAGTGGTGAGTATCCCCGCCTGTCACGCGGGAGACCGGGGTTCGGTTCCCCGACGGGGAGCCAAACAGCCGACCA
ATTGCACTACCATCACAATGGAGAAGCCAGTAGTAAACGTAGACGTAGACCCCCAGAGTCCGTTTGTCGTGCAACTGCAA
AAAAGCTTCCCGCAATTTGAGGTAGTAGCACAGCAGGTCACTCCAAATGACCATGCTAATGCCAGAGCATTTTCGCATCT
GGCCAGTAAACTAATCGAGCTGGAGGTTCCTACCACAGCGACGATCTTGGACATAGGCAGCGCACCGGCTCGTAGAATGT
TTTCCGAGCACCAGTATCATTGTGTCTGCCCCATGCGTAGTCCAGAAGACCCGGACCGCATGATGAAATACGCCAGTAAA
CTGGCGGAAAAAGCGTGCAAGATTACAAACAAGAACTTGCATGAGAAGATTAAGGATCTCCGGACCGTACTTGATACGCC
GGATGCTGAAACACCATCGCTCTGCTTTCACAACGATGTTACCTGCAACATGCGTGCCGAATATTCCGTCATGCAGGACG
TGTATATCAACGCTCCCGGAACTATCTATCATCAGGCTATGAAAGCCGTGCGGACCCTGTACTGGATTGGCTTCGACACC
ACCCAGTTCATGTTCTCGGCTATGGCAGGTTCGTACCCTGCGTACAACACCAACTGGGCCGACGAGAAAGTCCTTGAAGC
GCGTAACATCGGACTTTGCAGCACAAAGCTGAGTGAAGGTAGGACAGGAAAATTGTCGATAATGAGGAAGAAGGAGTTGA
AGCCCGGGTCGCGGGTTTATTTCTCCGTAGGATCGACACTTTATCCAGAACACAGAGCCAGCTTGCAGAGCTGGCATCTT
CCATCGGTGTTCCACTTGAATGGAAAGCAGTCGTACACTTGCCGCTGTGATACAGTGGTGAGTTGCGAAGGCTACGTAGT
GAAGAAAATCACCATCAGTCCCGGGATCACGGGAGAAACCGTGGGATACGCGGTTACACACAATAGCGAGGGCTTCTTGC
TATGCAAAGTTACTGACACAGTAAAAGGAGAACGGGTATCGTTCCCTGTGTGCACGTACATCCCCGGCCACCATATGCGAT
CAGATGACTGGTATAATGGCCACGGATATATCACCTGACGATGCACAAAAACTTCTGGTTGGGCTCAACCAGCGAATTGT
CATTAACGGTAGGACTAACAGGAACACCAACACCATGCAAAATTACCTTCTGCCGATCATAGCACAAGGGTTCAGCAAAT
GGGCTAAGGAGCGCAAGGATGATCTTGATAACGAGAAAATGCTGGGTACTAGAGAACGCAAGCTTACGTATGGCTGCTTG
TGGGCCGTTTCGCACTAAGAAAGTACATTCGTTTTATCGCCCACCTGGAACGCAGACCTGCGTAAAAGTCCCAGCCTCTTT
TAGCCGATCCCCTGAAAAGGCTGTTTAAGTTGGGTAAACCGCTCCCAGCCGACGACGAGCAAGACGAAGACAGAAGACGCG
CTCTGCTAGATGAAACAAAGGCGTGGTTTAGAGTAGGTATAACAGGCACTTTAGCAGTGGCCGTGACGACCCGGTATGAG
GTAGACAATATTACACCTGTCCTACTGGCATTGAGAACTTTTGCCCAGAGCAAAAGAGCATTCCAAGCCATCAGAGGGGA
AATAAAGCATCTCTACGGTGGTCCTAAATAGTCAGCATAGTACATTTCATCTGACTAATACTACAACACCACCACCATGA
ATAGAGGATTCTTTAACATGCTCGGCCGCCGCCCCTTCCCGGCCCCACTGCCATGTGGAGGCCGCGGAGAAGGAGGCAG
GCGGCCCCGATGCCTGCCCGCAACGGGCTGGCTTCTCAAATCCAGCAACTGACCACAGCCGTCAGTGCCCTAGTCATTGG
ACAGGCAACTAGACCTCAACCCCCACGTCCACGCCCGCCACCGCGCCAGAAGAAGCAGGCGCCCAAGCAACCACCGAAGC
CGAACAAACCAAAAACGCAGGAGAAGAAGAAGAAGCAACCTGCAAAACCCAAACCCGGAAAGAGACAGCGCATGGCACTT
AAGTTGGAGGCCGACAGATTGTTCGACGTCAAGAACGAGGACGGAGATGTCATCGGGCACGCACTGGCCATGGAAGGAAA
GGTAATGAAACCTCTGCACGTGAAAGGAACCATCGACCACCCTGTGCTATCAAAGCTCAAATTTACCAAGTCGTCAGCAT
ACGACATGGAGTTCGCACAGTTGCCAGTCAACATGAGAAGTGAGGCATTCACCTACACCAGTGAACACCCCGAAGGATTC
TATAACTGGCACCACGGAGCGGTGCAGTATAGTGGAGGTAGATTTACCATCCCTCGCGGAGTAGGAGGCAGAGGAGACAG
CGGTCGTCCGATCATGGATAACTCCGGTCGGGTTGTCGCGATAGTCCTCGGTGGCGCTGATGAAGGAACACGAACTGCCC
TTTCGGTCGTCACCTGGAATAGTAAAGGGAAGACAATTAAGACGACCCCGGAAGGGACAGAAGAGTGGTCCGCAGCACCA
CTGGTCACGGCAATGTGTTTGCTCGGAAATGTGAGCTTCCCATGCGACCGCCCGCCCACATGCTATACCCGCGAACCTTC
CAGAGCCCTCGACATCCTTGAAGAGAACGTGAACCATGAGGCCTACGATACCCTGCTCAATGCCATATTGCCGGTGCGGAT
CGTCTGGCAGAAGCAAAAGAAGCGTCATTGACGACTTTACCCTGACCAGCCCCTACTTGGGCACATGCTCGTACTGCCAC
CATACTGTACCGTGCTTCAGCCCTGTTAAGATCGAGCAGGTCTGGGACGAAGCGGACGATAACACCATACGCATACAGAC
TTCCGCCCAGTTTGGATACGACCAAAGCGGAGCAGCAAGCGCAAACAAGTACCGCTACATGTCGCTTAAGCAGGATCACA
CCGTTAAAGAAGGCACCATGGATGACATCAAGATTAGCACCTCAGGACCGTGTAGAAGGCTTAGCTACAAAGGATACTTT
CTCCTCGCAAAATGCCCTCCAGGGGACAGCGTAACGGTTAGCATAGTGAGTAGCAACTCAGCAACGTCATGTACACTGGC
CCGCAAGATAAAACCAAAATTCGTGGGACGGGAAAAATATGATCTACCTCCCGTTCACGGTAAAAAAATTCCTTGCACAG
TGTACGACCGTCTGAAAGAAACAACTGCAGGCTACATCACTATGCACAGGCCGAGACCGCACGCTTATACATCCTACCTG
GAAGAATCATCAGGGAAAGTTTACGCAAAGCCGCCATCTGGGAAGAACATTACGTATGAGTGCAAGTGCCGGCGACTACAA
GACCGGAACCGTTTCGACCCGCACCGAAATCACTGGTTGCACCGCCATCAAGCAGTGCGTCGCCCTATAAGAGCGACCAAA
CGAAGTGGGTCTTCAACTCACCGGACTTGATCAGACATGACGACCACACGGCCCAAGGGAAATTGCATTTGCCTTTCAAG
TTGATCCCGAGTACCTGCATGGTCCCTGTTGCCCACGCGCCGAATGTAATACATGGCTTTAAACACATCAGCCTCCAATT

FIG. 11K

```
AGATACAGACCACTTGACATTGCTCACCACCAGGAGACTAGGGGCAAACCCGGAACCAACCACTGAATGGATCGTCGGAA
AGACGGTCAGAAACTTCACCGTCGACCGAGATGGCCTGGAATACATATGGGGAAATCATGAGCCAGTGAGGGTCTATGCC
CAAGAGTCAGCACCAGGAGACCCTCACGGATGGCCACACGAAATAGTACAGCATTACTACCATCGCCATCCTGTGTACAC
CATCTTAGCCGTCGCATCAGCTACCGTGGCGATGATGATTGGCCGTAACTGTTGCAGTGTTATGTGCCTGTAAAGCGCGCC
GTGAGTGCCTGACGCCATACGCCCTGGCCCCAAACGCCGTAATCCCAACTTCGCTGGCACTCTTGTGCTGCCGTTAGGTCG
GCCAATGCTGAAACGTTCACCGAGACCATGAGTTACTTGTGGTCGAACAGTCAGCCGTTCTTCTGGGTCCAGTTGTGCAT
ACCTTTGGCCGCTTTCATCGTTCTAATGCGCTGCTGCTCCTGCTGCCTGCCTTTTTTAGTGGTTGCCGGCGCCTACCTGG
CGAAGGTAGACGCCTACGAACATGCGACCACTGTTCCAAATGTGCCACAGATACCGTATAAGGCACTTGTTGAAAGGGCA
GGGTATGCCCCGCTCAATTTGGAGATCACTGTCATGTCCTCGGAGGTTTTGCCTTCCACCAACCAAGAGTACATTACCTG
CAAATTCACCACTGTGGTCCCCTCCCCAAAAATCAAATGCTGCCGGCTCCTTGGAATGTCAGCCGGCCGCTCATGCAGACT
ATACCTGCAAGGTCTTCGGAGGGGTCTACCCCTTTATGTGGGGAGGAGCGCAATGTTTTTGCGACAGTGAGAACAGCCAG
ATGAGTGAGGCGTACGTCGAATTGTCAGCAGATTGCGCGTCTGACCACGCGCAGGCGATTAAGGTGCACACTGCCGCGAT
GAAAGTAGGACTGCGTATTGTGTACGGGAACACTACCAGTTTCCTAGATGTGTACGTGAACGGAGTCACACCAGGAACGT
CTAAAGACTTGAAAGTCATAGCTGGACCAATTTCAGCATCGTTTACGCCATTCGATCATAAGGTCGTTATCCATCGCGGC
CTGGTGTACAACTATGACTTCCCGGAATATGGAGCGATGAAACCAGGAGCGTTTGGAGACATTCAAGCTACCTCCTTGAC
TAGCAAGGATCTCATCGCCAGCACAGACATTAGGCTACTCAAGCCTTCCGCCAAGAACGTGCATGTCCCGTACACGCAGG
CCTCATCAGGATTTGAGATGTGGAAAAACAACTCAGGCCGCCCACTGCAGGAAACCGCACCTTTCGGGTGTAAGATTGCA
GTAAATCCGCTCCGAGCGGTGGACTGTTCATACGGGAACATTCCCATTTCTATTGACATCCCGAACGCTGCCTTTATCAG
GACATCAGATGCACCACTGGTCTCAACAGTCAAATGTGAAGTCAGTGAGTGCACTTATTCAGCAGACTTCGGCGGGATGG
CCACCCTGCAGTATGTATCCGACCGCGAAGGTCAATGCCCCGTACATTCGCATTCGAGCACAGCAACTCTCCAAGAGTCG
ACAGTACATGTCCTGGAGAAAGGAGCGGTGACAGTACACTTTAGCACCGCGAGTCCACAGGCGAACTTTATCGTATCGCT
GTGTGGGAAGAAGACAACATGCAATGCAGAATGTAAACCACCAGCTGACCATATCCGTGAGCACCCCGCACAAAAATGACC
AAGAATTTCAAGCCGCCATCTCAAAAACATCATGGAGTTGGCTGTTTGCCCTTTTCGGCGGCGCCTCGTCGCTATTAATT
ATAGGACTTATGATTTTTGCTTGCAGCATGATGCTGACTAGCACACGAAGATGACCGCTACGCCCCAATGATCCGACCAG
CAAAACTCGATGTACTTCCGAGGAACTGATGTGCATAATGCATCAGGCTGGTACATTAGATCCCCGCTTACCGCGGGCAA
TATAGCAACACTAAAAACTCGATGTACTTCCGAGGAAGCGCAGTgCATAATGCTGCGCaGTGTTGCCACATAACCACTAT
ATTAACCATTTATCTAGCGGACGCCAAAAACTCAATGTATTTCTGAGGAAGCGTGGTGCATAATGCCACGCAGCCGTCTGC
ATAACTTTTATTATTTCTTTTATTAATCAACAAAATTTTGTTTTTAACATTTCAAAAAAAAAAAAAAAAAAAAAAAAAAAA
AAAAAAAAAAGGGAATTCctcGAGGGGAATTAATTCTTGAAGACGAAAGGGCCTCGTGATACGCCTATTTTTATAGGTTA
ATGTCATGATAATAATGGTTTCTTAGACGTCAGGTGGCACTTTTCGGGGAAATGTGCGCGGAACCCCTATTTGTTTATTT
TTCTAAATACATTCAAATATGTATCCGCTCATGAGACAATAACCCTGATAAATGCTTCAATAATATTGAAAAAGGAAGAG
TATGAGTATTCAACATTTCCGTGTCGCCCTTATTCCCTTTTTTGCGGCATTTTGCCTTCCTGTTTTTGCTCACCCAGAAA
CGCTGGTGAAAGTAAAAGATGCTGAAGATCAGTTGGGTGCACGAGTGGGTTACATCGAACTGGATCTCAACAGCGGTAAG
ATCCTTGAGAGTTTTCGCCCCGAAGAACGTTTTCCAATGATGAGCACTTTTAAAGTTCTGCTATGTGGCGCGGTATTATC
CCGTGTTGACGCCGGGCAAGAGCAACTCGGTCGCCGCATACACTATTCTCAGAATGACTTGGTTGAGTACTCACCAGTCA
CAGAAAAGCATCTTACGGATGGCATGACAGTAAGAGAATTATGCAGTGCTGCCATAACCATGAGTGATAACACTGCGGCC
AACTTACTTCTGACAACGATCGGAGGACCGAAGGAGCTAACCGCTTTTTTGCACAACATGGGGGATCATGTAACTCGCCT
TGATCGTTGGGAACCGGAGCTGAATGAAGCCATACCAAACGACGAGCGTGACACCACGATGCCTGTAGCAATGGCAACAA
CGTTGCGCAAACTATTAACTGGCGAACTACTTACTCTAGCTTCCCGGCAACAATTAATAGACTGGATGGAGGCGGATAAA
GTTGCAGGACCACTTCTGCGCTCGGCCCTTCCGGCTGGCTGGTTTATTGCTGATAAATCTGGAGCCGGTGAGCGTGGGTC
TCGCGGTATCATTGCAGCACTGGGGCCAGATGGTAAGCCCTCCCGTATCGTAGTTATCTACACGACGGGGAGTCAGGCAA
CTATGGATGAACGAAATAGACAGATCGCTGAGATAGGTGCCTCACTGATTAAGCATTGGTAACTGTCAGACCAAGTTTAC
TCATATATACTTTAGATTGATTTAAAACTTCATTTTTAATTTAAAAGGATCTAGGTGAAGATCCTTTTTGATAATCTCAT
GACCAAAATCCCTTAACGTGAGTTTTCGTTCCACTGAGCGTCAGACCCCGTAGAAAAGATCAAAGGATCTTCTTGAGATC
```

FIG. 11L

```
CTTTTTTTTCTGCGCGTAATCTGCTGCTTGCAAACAAAAAAAACCACCGCTACCAGCGGTGGTTTGTTTGCCGGATCAAGAG
CTACCAACTCTTTTTCCGAAGGTAACTGGCTTCAGCAGAGCGCAGATACCAAATACTGTCCTTCTAGTGTAGCCGTAGTT
AGGCCACCACTTCAAGAACTCTGTAGCACCGCCTACATACCTCGCTCTGCTAATCCTGTTACCAGTGGCTGCTGCCAGTG
GCGATAAGTCGTGTCTTACCGGGTTGGACTCAAGACGATAGTTACCGGATAAGGCGCAGCGGTCGGGCTGAACGGGGGGT
TCGTGCACACAGCCCAGCTTGGAGCGAACGACCTACACCGAACTGAGATACCTACAGCGTGAGCATTGAGAAAGCGCCAC
GCTTCCCGAAGGGAGAAAGGCGGACAGGTATCCGGTAAGCGGCAGGGTCGGAACAGGAGAGCGCACGAGGGAGCTTCCAG
GGGGAAACGCCTGGTATCTTTATAGTCCTGTCGGGTTTCGCCACCTCTGACTTGAGCGTCGATTTTTGTGATGCTCGTCA
GGGGGGCGGAGCCTATGGAAAAACGCCAGCAACGCGAGCTCGGATCTGGCTAGCGATGACCCTGCTGATTGGTTCGCTGA
CCATTTCCGGGTGCGGGACGGCGTTACCAGAAACTCAGAAGGTTCGTCCAACCAAACCGACTCTGACGGCAGTTTACGAG
AGAGATGATAGGGTCTGCATCAGTAAGCCAGATGCTACACAATTAGGCTTGTACATATTGTCCTTAGAACGCCGGCTACAA
TTAATACATAACCTTATGTATCATACACATACGATTTAGGTGACACTATA
```

FIG. 11M

Nucleotide sequence of pTE5'2J
ATTGACGGCGTAGTACACACTATTGAATCAAACAGCCGACCAATTGCACTACCATCACAATGGAGAAGCCAGTAGTAAAC
GTAGACGTAGACCCCCAGAGTCCGTTTGTCGTGCAACTGCAAAAAAGCTTCCCGCAATTTGAGGTAGTAGCACAGCAGGT
CACTCCAAATGACCATGCTAATGCCAGAGCATTTTCGCATCTGGCCAGTAAACTAATCGAGCTGGAGGTTCCTACCACAG
CGACGATCTTGGACATAGGCAGCGCACCGGCTCGTAGAATGTTTTCCGAGCACCAGTATCATTGTGTCTGCCCCATGCGT
AGTCCAGAAGACCCGGACCGCATGATGAAATACGCCAGTAAACTGGCGGAAAAAGCGTGCAAGATTACAAACAAGAACTT
GCATGAGAAGATTAAGGATCTCCGGACCGTACTTGATACGCCGGATGCTGAAACACCATCGCTCTGCTTTCACAACGATG
TTACCTGCAACATGCGTGCCGAATATTCCGTCATGCAGGACGTGTATATCAACGCTCCCGGAACTATCTATCATCAGGCT
ATGAAAGCCGTGCGGACCCTGTACTGGATTGGCTTCGACACCACCCAGTTCATGTTCTCGGCTATGGCAGGTTCGTACCC
TGCGTACAACACCAACTGGGCCGACGAGAAAGTCCTTGAAGCGCGTAACATCGGACTTTGCAGCACAAAGCTGAGTGAAG
GTAGGACAGGAAAATTGTCGATAATGAGGAAGAAGGAGTTGAAGCCCGGGTCGCGGGTTTATTTCTCCGTAGGATCGACA
CTTTATCCAGAACACAGAGCCAGCTTGCAGAGCTGGCATCTTCCATCGGTGTTCCACTTGAATGGAAAGCAGTCGTACAC
TTGCCGCTGTGATACAGTGGTGAGTTGCGAAGGCTACGTAGTGAAGAAAATCACCATCAGTCCCGGGATCACGGGAGAAA
CCGTGGGATACGCGGTTACACACAATAGCGAGGGCTTCTTGCTATGCAAAGTTACTGACACAGTAAAAGGAGAACGGGTA
TCGTTCCCTGTGTGCACGTACATCCCGGCCACCATATGCGATCAGATGACTGGTATAATGGCCACGGATATATCACCTGA
CGATGCACAAAAACTTCTGGTTGGGCTCAACCAGCGAATTGTCATTAACGGTAGGACTAACAGGAACACCAACACCATGC
AAAATTACCTTCTGCCGATCATAGCACAAGGGTTCAGCAAATGGGCTAAGGAGCGCAAGGATGATCTTGATAACGAGAAA
ATGCTGGGTACTAGAGAACGCAAGCTTACGTATGGCTGCTTGTGGGCGTTTCGCACTAAGAAAGTACATTCGTTTTATCG
CCCACCTGGAACGCAGACCTGCGTAAAAGTCCCAGCCTCTTTTAGCGCTTTTCCCATGTCGTCCGTATGGACGACCTCTT
TGCCCATGTCGCTGAGGCAGAAATTGAAACTGGCATTGCAACCAAAGAAGGAGGAAAAACTGCTGCAGGTCTCGGAGGAA
TTAGTCATGGAGGCCAAGGCTGCTTTTGAGGATGCTCAGGAGGAAGCCAGAGCGGAGAAGCTCCGAGAAGCACTTCCACC
ATTAGTGGCAGACAAAGGCATCGAGGCAGCCGCAGAAGTTGTCTGCGAAGTGGAGGGGCTCCAGGCGGACATCGGAGCAG
CATTAGTTGAAACCCCGCGCGGTCACGTAAGGATAATACCTCAAGCAAATGACCGTATGATCGGACAGTATATCGTTGTC
TCGCCAAACTCTGTGCTGAAGAATGCCAAACTCGCACCAGCGCACCCGCTAGCAGATCAGGTTAAGATCATAACACACTC
CGGAAGATCAGGAAGGTACGCGGTCGAACCATACGACGCTAAAGTACTGATGCCAGCAGGAGGTGCCCGTACCATGGCCAG
AATTCCTAGCACTGAGTGAGAGCGCCACGTTAGTGTACAACGAAAGAGAGTTTGTGAACCGCAAACTATACCACATTGCC
ATGCATGGCCCCGCCAAGAATACAGAAGAGGAGCAGTACAAGGTTACAAAGGCAGAGCTTGCAGAAACAGAGTACGTGTT
TGACGTGGACAAGAAGCGTTGCGTTAAGAAGGAAGAAGCCTCAGGTCTGGTCCTCTCGGGAGAACTGACCAACCCTCCCT
ATCATGAGCTAGCTCTGGAGGGACTGAAGACCCGACCTGCGGTCCCGTACAAGGTCGAAACAATAGGAGTGATAGGCACA
CCGGGGTCGGGCAAGTCAGCTATTATCAAGTCAACTGTCACGGCACGAGATCTTGTTACCAGCGGAAAGAAAGAAAATTG
TCGCGAAATTGAGGCCGACGTGCTAAGACTGAGGGGTATGCAGATTACGTCGAAGACAGTAGATTCGGTTATGCTCAACG
GATGCCACAAAGCCGTAGAAGTGCTGTACGTTGACGAAGCGTTCGCGTGCCACGCAGGAGCACTACTTGCCCTTGATTGCT
ATCGTCAGGCCCCGCAAGAAGGTAGTACTATGCGGAGACCCCATGCAATGCGGATTCTTCAACATGATGCAACTAAAGGT
ACATTTCAATCACCCTGAAAAAGACATATGCACCAAGACATTCTACAAGTATATCTCCCGGCGTTGCACACAGCCAGTTA
CAGCTATTGTATCGACACTGCATTACGATGGAAAGATGAAAACCACGAACCCGTGCAAGAAGAACATTGAAATCGATATT
ACAGGGGCCACAAAGCCGAAGCCAGGGGATATCATCCTGACATGTTTCCGCGGGTGGGTTAAGCAATTGCAAATCGACTA
TCCCGGACATGAAGTAATGACAGCCGCGGCCTCACAAGGGCTAACCAGAAAAGGAGTGTATGCCCGTCCGGCAAAAAGTCA
ATGAAAACCCACTGTACGCGATCACATCAGAGCATGTGAACGTGTTGCTCACCCGCACTGAGGACAGGCTAGTGTGGAAA
ACCTTGCAGGGCGACCCATGGATTAAGCAGCCCACTAACATACCTAAAGGAAACTTTCAGGCTACTATAGAGGACTGGGA
AGCTGAACACAAGGGAATAATTGCTGCAATAAACAGCCCCACTCCCCGTGCCAATCCGTTCAGCTGCAAGACCAACGTTT
GCTGGGCGAAAGCATTGGAACCGATACTAGCCACGGCCGGTATCGTACTTACCGGTTGCCAGTGGAGCGAACTGTTCCCA
CAGTTTGCGGATGACAAACCACATTCGGCCATTTACGCCTTAGACGTAATTTGCATTAAGTTTTTCGGCATGGACTTGAC
AAGCGGACTGTTTTCTAAACAGAGCATCCCACTAACGTACCATCCCGCCGATTCAGCGAGGCCGGTAGCTCATTGGGACA
ACAGCCCAGGAACCCGCAAGTATGGGTACGATCACGCCATTGCCGCCGAACTCTCCCGTAGATTTCCGGTGTTCCAGCTA
GCTGGGAAGGGCACACAACTTGATTTGCAGACGGGGAGAACCAGAGTTATCTCTGCACAGCATAACCTGGTCCCGGTGAA
CCGCAATCTTCCTCACGCCTTAGTCCCCGAGTACAAGGAGAAGCAACCCGGCCCGGTCAAAAAATTCTTGAACCAGTTCA

FIG. 12A

```
AACACCACTCAGTACTTGTGGTATCAGAGGAAAAAATTGAAGCTCCCCGTAAGAGAATCGAATGGATCGCCCCGATTGGC
ATAGCCGGTGCAGATAAGAACTACAACCTGGCTTTCGGGTTTCCGCCCGCAGGCACGGTACGACCTGGTGTTCATCAACAT
TGGAACTAAATACAGAAACCACCACTTTCAGCAGTGCGAAGACCATGCGGCGACCTTAAAAACCCTTTCGCGTTCGGCCC
TGAATTGCCTTAACCCAGGAGGCACCCTCGTGGTGAAGTCCTATGGCTACGCCGACCGCAACAGTGAGGACGTAGTCACC
GCTCTTGCCAGAAAGTTTGTCAGGGTGTCTGCAGCGAGACCAGATTGTGTCTCAAGCAATACAGAAATGTACCTGATTTT
CCGACAACTAGACAACAGCCGTACACGGCAATTCACCCCGCACCATCTGAATTGCCTGATTTCGTCCGTGTATGAGGGTA
CAAGAGATGGACTTGGAGCCGCGCCGTCATACCGCACCAAAAGGGAGAATATTGCTGACTGTCAAGAGGAAGCAGTTGTC
AACGCAGCCAATCCGCTGGGTAGACCAGGCGAAGGAGTCTGCCGTGCCATCTATAAACGTTGGCCGACCAGTTTTACCGA
TTCAGCCACGGAGACAGGCACCGCAAGAATGACTGTGTGCCTAGGAAAGAAAGTGATCCACGCGGTCGGCCCTGATTTCC
GGAAGCACCCAGAAGCAGAAGCCTTGAAATTGCTACAAAACGCCTACCATGCAGTGGCAGACTTAGTAAATGAACATAAC
ATCAAGTCTGTCGCCATTCCACTGCTATCTACAGGCATTTACGCAGCCGGAAAAGACCGCCTTGAAGTATCACTTAACTG
CTTGACAACCGCGCTAGACAGAACTGACGCGGACGTAACCATCTATTGCCTGGATAAGAAGTGGAAGGAAAGAATCGACG
CGGCACTCCAACTTAAGGAGTCTGTAACAGAGCTGAAGGATGAAGATATGGAGATCGACGATGAGTTAGTATGGATLCAT
CCAGACAGTTGCTTGAAGGGAAGAAAGGGATTCAGTACTACAAAAGGAAAATTGTATTCGTACTTCGAAGGCACCAAATT
CCATCAAGCAGCAAAAGACATGGCGGAGATAAAGGTCCTGTTCCCTAATGACCAGGAAAGTAATGAACAACTGTGTGCCT
ACATATTGGGTGAGACCATGGAAGCAATCCGCGAAAAGTGCCCGGTCGACCATAACCCGTCGTCTAGCCCGCCCAAAACG
TTGCCGTGCCTTTGCATGTATGCCATGACGCCAGAAAGGGTCCACAGACTTAGAAGCAATAACGTCAAAGAAGTTACAGT
ATGCTCCTCCACCCCCCTTCCTAAGCACAAAATTAAGAATGTTCAGAAGGTTCAGTGCACGAAAGTAGTCCTGTTTAATC
CGCACACTCCCGCATTCGTTCCCGCCCGTAAGTACATAGAAGTGCCAGAACAGCCTACCGCTCCTCCTGCACAGGCCGAG
GAGGCCCCCGAAGTTGTAGCGACACCGTCACCATCTACAGCTGATAACACCTCGCTTGATGTCACAGACATCTCACTGGA
TATGGATGACAGTAGCGAAGGCTCACTTTTTTCGAGCTTTAGCGGATCGGACAACTCTATTACTAGTATGGACAGTTGGT
CGTCAGGACCTAGTTCACTAGAGATAGTAGACCGAAGGCAGGTGGTGGTGGCTGACGTTCATGCCGTCCAAGAGCCTGCC
CCTATTCCACCGCCAAGGCTAAAGAAGATGGCCCGCCTGGCAGCGGCAAGAAAAGAGCCCACTCCACCGGCAAGCAATAG
CTCTGAGTCCCTCCACCTCTCTTTTGGTGGGGTATCCATGTCCCTCGGATCAATTTTCGACGGAGAGACGGCCCGCCAGG
CAGCGGTACAACCCCTGGCAACAGGCCCCACGGATGTGCCTATGTCTTTCGGATCGTTTTCCGACGGAGAGATTGATGAG
CTGAGCCGCAGAGTAACTGAGTCCGAACCCGTCCTGTTTGGATCATTTGAACCGGGCGAAGTGAACTCAATTATATCGTC
CCGATCAGCCGTATCTTTTCCACTACGCAAGCAGAGACGTAGACGCAGGAGCAGGAGGACTGAATACTGACTAACCGGGG
TAGGTGGGTACATATTTTCGACGGACACAGGCCCTGGGCACTTGCAAAAGAAGTCCGTTCTGCAGAACCAGCTTACAGAA
CCGACCTTGGAGCGCAATGTCCTGGAAAGAATTCATGCCCCGGTGCTCGACACGTCGAAAGAGGAACAACTCAAACTCAG
GTACCAGATGATGCCCACCGAAGCCAACAAAAGTAGGTACCAGTCTCGTAAAGTAGAAAATCAGAAAGCCATAACCACTG
AGCGACTACTGTCAGGACTACGACTGTATAACTCTGCCACAGATCAGCCAGAATGCTATAAGATCACCTATCCGAAACCA
TTGTACTCCAGTAGCGTACCGGCGAACTACTCCGATCCACAGTTCGCTGTAGCTGTCTGTAACAACTATCTGCATGAGAA
CTATCCGACAGTAGCATCTTATCAGATTACTGACGAGTACGATGCTTACTTGGATATGGTAGACGGGACAGTCGCCTGCC
TGGATACTGCAACCTTCTGCCCCGCTAAGCTTAGAAGTTACCCGAAAAAACATGAGTATAGAGCCCCGAATATCCGCAGT
GCGGTTCCATCAGCCGATGCAGAACACGCTACAAAATGTGCTCATTGCCCGCAACTAAAAGAAATTGCAACGTCACGCAGAT
GCGTGAACTGCCAACACTGGACTCAGCGACATTCAATGTCGAATGCTTTCGAAAATATGCATGTAATGACGAGTATTGGG
AGGAGTTCGCTCGGAAGCCAATTAGGATTACCACTGAGTTTGTCACCGCATATGTAGCTAGACTGAAAGGCCCTAAGGCC
GCCGCACTATTTGCAAAGACGTATAATTTGGTCCCATTGCAAGAAGTGCCTATGGATAGATTCGTCATGGACATGAAAAG
AGACGTGAAAGTTACACCAGGCACGAAACACACAGAAGAAAGACCGAAAGTACAAGTGATACAAGCCGCAGAACCCCTGG
CGACTGCTTACTTATGCGGGATTCACCGGGAATTAGTGCGTAGGCTTACGGCCGTCTTGCTTCCAAACATTCACACGCTT
TTTGACATGTCGGCGGAGGATTTTGATGCAATCATAGCAGAACACTTCAAGCAAGGCGACCCGGTACTGGAGACGGATAT
CGCATCATTCGACAAAAGCCAAGACGACGCTATGGCGTTAACCGGTCTGATGATCTTGGAGGACCTGGGTGTGGATCAAC
CACTACTCGACTTGATCGAGTGCGCCTTTGGAGAAATATCATCCACCCATCTACCTACGGGTACTCGTTTTAAATTCGGG
GCGATGATGAAATCCGGAATGTTCCTCACACTTTTTGTCAACACAGTTTTGAATGTCGTTATCGCCAGCAGAGTACTAGA
```

FIG. 12B

```
AGAGCGGCTTAAAACGTCCAGATGTGCAGCCGTTCATTGGCGACGACAACATCATACATGGAGTAGTATCTGACAAAGAAA
TGGCTGAGAGGTGCGCCACCTGGCTCAACATGGAGGTTAAGATCATCGACGCAGTCATCGGTGAGAGACCACCTTACTTC
TGCGGCGGATTTATCTTGCAAGATTCGGTTACTTCCACAGCGTGCCGCGTGGCGGATCCCCTGAAAAGGCTGTTTAAGTT
GGGTAAACCGCTCCCAGCCGACGACGAGCAAGACGAAGACAGAAGACGCGCTCTGCTAGATGAAACAAAGGCGTGGTTTA
GAGTAGGTATAACAGGCACTTTAGCAGTGGCCGTGACGACCGGTATGAGGTAGACAATATTACACCTGTCCTACTGGCA
TTGAGAACTTTTGCCCAGAGCAAAAGAGCATTCCAAGCCATCAGAGGGGAAATAAAGCATCTCTACGGTGGTCCTAAATA
GTCAGCATAGTACATTTCATCTGACTAATACTACAACACCACCACCtctagaccatggggtaccgagctcgaattcgCCT
CGTCGCTATTAATTATAGGACTTATGATTTTTGCTTGCAGCATGATGCTGACTAGCACACGAAGATGACgggcccAGGTA
GACAATATTACACCTGTCCTACTGGCATTGAGAACTTTTGCCCAGAGCAAAAGAGCATTCCAAGCCATCAGAGGGGAAAT
AAAGCATCTCTACGGTGGTCCTAAATAGTCAGCATAGTACATTTCATCTGACTAATACTACAACACCACCACCATGAATA
GAGGATTCTTTAACATGCTCGGCCGCCGCCCCTTCCCGGCCCCCACTGCCATGTGGAGGCCGCGGAGAAGGAGGCAGGCG
GCCCCGATGCCTGCCCGCAACGGGCTGGCTTCTCAAATCCAGCAACTGACCACAGCCGTCAGTGCCCTAGTCATTGGACA
GGCAACTAGACCTCAACCCCCACGTCCACGCCCGCCACCGCGCCAGAAGAAGCAGGCGCCCAAGCAACCACCGAAGCCGA
AGAAACCAAAAACGCAGGAGAAGAAGAAGAAGCAACCTGCAAAACCCAAACCCGGAAAGAGACAGCGCATGGCACTTAAG
TTGGAGGCCGACAGATTGTTCGACGTCAAGAACGAGGACGGAGATGTCATCGGGCACGCACTGGCCATGGAAGGAAAGGT
AATGAAACCTCTGCACGTGAAAGGAACCATCGACCACCCTGTGCTATCAAAGCTCAAATTTACCAAGTCGTCAGCATACG
ACATGGAGTTCGCACAGTTGCCAGTCAACATGAGAAGTGAGGCATTCACCTACACCAGTGAACACCCCGAAGGATTCTAT
AACTGGCACCACGGAGCGGTGCAGTATAGTGGAGGTAGATTTACCATCCCTCGCGGAGTAGGAGGCAGAGGAGACAGCGG
TCGTCCGATCATGGATAACTCCGGTCGGGTTGTCGCGATAGTCCTCGGTGGCGCTGATGAAGGAACACGAACTGCCCTTT
CGGTCGTCACCTGGAATAGTAAAGGGAAGACAATTAAGACGACCCCGGAAGGGACAGAAGAGTGGTCCGCAGCACCACTG
GTCACGGCAATGTGTTTGCTCGGAAATGTGAGCTTCCCATGCGACCGCCCGCCCACATGCTATACCCGCGAACCTTCCAG
AGCCCTCGACATCCTTGAAGAGAACGTGAACCATGAGGCCTACGATACCCTGCTCAATGCCATATTGCGGTGCCGGATCGT
CTGGCAGAAGCAAAAGAAGCGTCATcGACGACTTTACCCTGACCAGCCCCTACTTGGGCACATGCTCGTACTGCCACCAT
ACTGaACCGTGCTTCAGCCCTGTTAAGATCGAGCAGGTCTGGGACGAAGCGGACGATAACACCATACGCATACAGACTTC
CGCCCAGTTTGGATACGACCAtAGCGGAGCAGCAAGCGCAAACAAGTACCGCTACATGTCGCTTAAGCAGGATCACACCG
TTAAAGAAGGCACCATGGATGACATCAAGATTAGCACCTCAGGACCGTGTAGAAGGCTTAGCTACAAAGGATACTTTCTC
CTCGCAAAATGCCCTCCAGGGGACAGCGTAACGGTTAGCATAGTGAGTAGCAACTCAGCAACGTCATGTACACTGGCCCG
CAAGATAAAACCAAAATTCGTGGGACGGGAAAAATATGATCTACCTCCCGTTCACGGTAAAAAAAATTCCTTGCACAGTGT
ACGACCGTCTGAAAGAAACAACTGCAGGCTACATCACTATGCACAGGCCGgGACCGCACGCTTATACATCCTACCTGGAA
GAATCATCAGGGAAAGTTTACGCAAAGCCGCCATCTGGGAAGAACATTACGTATGAGTGCAAGTGCCGGCGACTACAAGAC
CGGAACCGTTTCGACCCCGCACCGAAATCACTGGTTGCACCGCCATCAAGCAGTGCGTCGCCTATAAGAGCGACCAAACGA
AGTGGGTCTTCAACTCACCGGACTTGATCAGACATGACGACCACACGGCCCAAGGGAAATTGCATTTGCCCTTTCAAGTTG
ATCCCGAGTACCTGCATGGTCCCTGTTGCCCACGCGCCGAATGTAATACATGGCTTTAAACACATCAGCCTCCAATTAGA
TACAGACCACTTGACATTGCTCACCACCAGGAGACTAGGGGCAAAACCCGGAACCAACCACTGAATGGATCGTCGGAAAGA
CGGTCAGAAACTTCACCGTCGACCGAGATGGCCTGGAATACATATGGGGAAATCATGAGCCAGTGAGGGTCTATGCCCAA
GAGTCAGCACCAGGAGACCCTCACGGATGGCCACACGAAATAGTACAGCATTACTACCATCGCCATCCTGTGTACACCAT
CTTAGCCGTCGCATCAGCTACCGTGGCGATGATGATTGGCCGTAACTGTTGCAGTGTTATGTGCCTGTAAAGCGCGCCGTG
AGTGCCTGACGCCATACGCCCTGGCCCCAAACGCCGTAATCCCAACTTCGCTGGCACTCTTGTGCTGCGTTAGGTCGGCC
AATGCTGAAACGTTCACCGAGACCATGAGTTACTTGTGGTCGAACAGTCAGCCGTTCTTCTGGGTCCAGTTGTGCATACC
TTTGGCCGCTTTCATCGTTCTAATGCGCTGCTGCTCCTGCTGCCTGCCTTTTTTAGTGGTTGCCGGCGCCTACCTGGCGA
AGGTAGACGCCTACGAACATGCGACCACTGTTCCAAATGTGCCACAGATACCGTATAAGGCACTTGTTGAAAGGGCAGGG
TATGCCCCGCTCAATTTGGAGATCACTGTCATGTCCTCGGAGGTTTTGCCTTCCACCAACCAAGAGTACATTACCTGCAA
ATTCACCACTGTGGTCCCCTCCCCAAAAATCAAATGCTGCCGGCTCCTTGGAATGTCAGCCGGCCGCTCATGCAGACTATA
CCTGCAAGGTCTTCGGAGGGGTCTACCCCCTTTATGTGGGGAGGAGCGCAATGTTTTTGCGACAGTGAGAACAGCCAGATG
```

FIG. 12C

```
AGTGAGGCGTACGTCGAATTGTCAGCAGATTGCGCGTCTGACCACGCGCAGGCGATTAAGGTGCACACTGCCGCGATGAA
AGTAGGACTGCGTATTGTGTACGGGAACACTACCAGTTTCCTAGATGTGTACGTGAACGGAGTCACACCAGGAACGTCTA
AAGACTTGAAAGTCATAGCTGGACCAATTTCAGCATCaTTTACGCCATTCGATCATAAGGTCGTTATCCATCGCGGCCTG
GTGTACAACTATGACTTCCCGGAATATGGAGCGATGAAACCAGGAGCGTTTGGAGACATTCAAGCTACCTCCTTGACTAG
CAAGGATCTCATCGCCAGCACAGACATTAGGCTACTCAAGCCTTCCGCCAAGAATGTGCATGTCCCGTACACGCAGGCCg
CATCAGGATTTGAGATGTGGAAAAACAACTCAGGCCGCCCAtTGCAGGAAACCGCACCTTTCGGGTGTAAGATTGCAGTA
AATCCGCTCCGAGCGGTGGACTGTTCATACGGGAACATTCCCATTTCTATTGACATCCCGAACGCTGCCTTTATCAGGAC
ATCAGATGCACCACTGGTCTCAACAGTCAAATGTGAAGTCAGTGAGTGCACTTATTCAGCAGACTTCGaCGGGATGGCCA
CCCTGCAGTATGTATCCGACCGCGAAGGTCAATGCCCCGTACATTCGCATTCGAGCACAGCAACTCTCCAAGAGTCGACA
GTACATGTCCTGGAGAAAGGAGCGGTGACAGTACACTTTAGCACCGCGAGTCCACAGGCGAACTTTATCGTATCGCTGTG
TGGGAAGAAGACAACATGCAATGCAGAATGTAAACCACCAGCTGACCATATCGTGAGCACCCCGCACAAAAATGACCAAG
AATTTCAAGCCGCCATCTCAAAAACATCATGGAGTTGGCTGTTTGCCCTTTTCGGCGGCGCCTCGTCGCTATTAATTATA
GGACTTATGATTTTTGCTTGCAGCATGATGCTGACTAGCACACGAAGATGACCGCTACGCCCCAATGATCCGACCAGCAA
AACTCGATGTACTTCCGAGGAACTGATGTGCATAATGCATCAGGCTGGTACATTAGATCCCCGCTTACCGCGGGCAATAT
AGCAACACTAAAAACTCGATGTACTTCCGAGGAAGCGCAGTgCATAATGCTGCGCaGTGTTGCCCACATAACCACTATATT
AACCATTTATCTAGCGGACGCCAAAAACTCAATGTATTTCTGAGGAAGCGTGGTGCATAATGCCACGCAGCGTCTGCATA
ACTTTTATTATTTCTTTTATTAATCAACAAAATTTTGTTTTTAACATTTCAAAAAAAAAAAAAAAAAAAAAAAAAAAAAA
AAAAAAAGGGAATTCctcGAGGGGAATTAATTCTTGAAGACGAAAGGGCCAGGTGGCACTTTTCGGGGAAATGTGCGCGG
AACCCCTATTTGTTTATTTTTCTAAATACATTCAAATATGTATCCGCTCATGAGACAATAACCCTGATAAATGCTTCAAT
AATATTGAAAAAGGAAGAGTATGAGTATTCAACATTTCCGTGTCGCCCTTATTCCCTTTTTTGCGGCATTTTGCCTTCCT
GTTTTTGCTCACCCAGAAACGCTGGTGAAAGTAAAAGATGCTGAAGATCAGTTGGGTGCACGAGTGGGTTACATCGAACT
GGATCTCAACAGCGGTAAGATCCTTGAGAGTTTTCGCCCCGAAGAACGTTTTCCAATGATGAGCACTTTTAAAGTTCTGC
TATGTGGCGCGGTATTATCCCGTGTTGACGCCGGGCAAGAGCAACTCGGTCGCCGCATACACTATTCTCAGAATGACTTG
GTTGAGTACTCACCAGTCACAGAAAAGCATCTTACGGATGGCATGACAGTAAGAGAATTATGCAGTGCTGCCATAACCAT
GAGTGATAACACTGCGGCCAACTTACTTCTGACAACGATCGGAGGACCGAAGGAGCTAACCGCTTTTTTGCACAACATGG
GGGATCATGTAACTCGCCTTGATCGTTGGGAACCGGAGCTGAATGAAGCCATACCAAACGACGAGCGTGACACCACGATG
CCTGtAGCAATGGCAACAACGTTGCGCAAACTATTAACTGGCGAACTACTTACTCTAGCTTCCCGGCAACAATTAATAGA
CTGGATGGAGGCGGATAAAGTTGCAGGACCACTTCTGCGCTCGGCCCTTCCGGCTGGCTGGTTTATTGCTGATAAATCTG
GAGCCGGTGAGCGTGGGTCTCGCGGTATCATTGCAGCACTGGGGCCAGATGGTAAGCCCTCCCGTATCGTAGTTATCTAC
ACGACGGGAGTCAGGCAACTATGGATGAACGAAATAGACAGATCGCTGAGATAGGTGCCTCACTGATTAAGCATTGGTA
ACTGTCAGACCAAGTTTACTCATATATACTTTAGATTGATTTAAAACTTCATTTTTAATTTAAAAGGATCTAGGTGAAGA
TCCTTTTTGATAATCTCATGACCAAAATCCCTTAACGTGAGTTTTCGTTCCACTGAGCGTCAGACCCCGTAGAAAAGATC
AAAGGATCTTCTTGAGATCCTTTTTTTCTGCGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCTTCAGCAGAGCGCAGATACCAAATACTGTCC
TTCTAGTGTAGCCGTAGTTAGGCCACCACTTCAAGAACTCTGTAGCACCGCCTACATACCTCGCTCTGCTAATCCTGTTA
CCAGTGGCTGCTGCCAGTGGCGATAAGTCGTGTCTTACCGGGTTGGACTCAAGACGATAGTTACCGGATAAGGCGCAGCG
GTCGGGCTGAACGGGGGGTTCGTGCACACAGCCCAGCTTGGAGCCGAACGACCTACACCGAACTGAGATACCTACAGCGTG
AGCATTGAGAAAGCGCCACGCTTCCCGAAGGGAGAAAGGCGGACAGGTATCCGGTAAGCGGCAGGGTCGGAACAGGAGAG
CGCACGAGGGAGCTTCCAGGGGAAACGCCTGGTATCTTTATAGTCCTGTCGGGTTTCGCCACCTCTGACTTGAGCGTCG
ATTTTTGTGATGCTCGTCAGGGGGCGGAGCCTATGGAAAAACGCCAGCAACGCGAGCTCgtatggacatattgtcgtta
gaacgcggctacaattaatacataaccttatgtatcatacacatacgatttaggggacactatag
```

FIG. 12D

Nucleotide sequence of 987 BB neo
CTGACGCGCCCTGTAGCGGCGCATTAAGCGCGGCGGGTGTGGTGGTTACGCGCAGCGTGACCGCTACACTTGCCAGCGCC
CTAGCGCCCGCTCCTTTCGCTTTCTTCCCTTCCTTTCTCGCCACGTTCGCCGGCTTTCCCCGTCAAGCTCTAAATCGGGG
GCTCCCTTTAGGGTTCCGATTTAGTGCTTTACGGCACCTCGACCCCAAAAAACTTGATTAGGGTGATGGTTCACGTAGTG
GGCCATCGCCCTGATAGACGGTTTTTCGCCCTTTGACGTTGGAGTCCACGTTCTTTAATAGTGGACTCTTGTTCCAAACT
GGAACAACACTCAACCCTATCTCGGTCTATTCTTTTGATTTATAAGGGATTTTGCCGATTTCGGCCTATTGGTTAAAAAA
TGAGCTGATTTAACAAAAATTTAACGCGAATTTTAACAAAATATTAACGCTTACAATTTCCATTCGCCATTCAGGCTGCG
CAACTGTTGGGAAGGGCGATCGGTGCGGGCCTCTTCGCTATTACGCCAGCTGGCGAAAGGGGGATGTGCTGCAAGGCGAT
TAAGTTGGGTAACGCCAGGGTTTTCCCAGTCACGACGTTGTAAAACGACGGCCAGTGAgcgcgcaattaaccctcactaa
agggaacaaaagctggctagtgGATCCAGTCTTATGCAATACTCTTGTAGTCTTGCAACATGGTAACGATGAGTTAGCAA
CATGCCTTACAAGGAGAGAAAAAGCACCGTGCATGCCGATTGGTGGAAGTAAGGTGGTACGATCGTGCCTTATTAGGAAG
GCAACAGACGGGTCTGACATGGATTGGACGAACCACTGAATTCCGCATTGCAGAGATATTGTATTTAAGTGCCCTACCTc
gataccgTCGAGATATAGTGGTGAGTATCCCCGCCTGTCACGCGGGAGACCGGGGTTCGGTTCCCCGACGGGGAGCCAAA
CAGCCGACCAATTGCACTACCATCACAATGGAGAAGCCAGTAGTAAACGTAGACGTAGACCCCCAGAGTCCGTTTGTCGT
GCAACTGCAAAAAAGCTTCCCGCAATTTGAGGTAGTAGCACAGCAGGTCACTCCAAATGACCATGCTAATGCCAGAGCAT
TTTCGCATCTGGCCAGTAAACTAATCGAGCTGGAGGTTCCTACCACAGCGACGATCTTGGACATAGGCAGCGCACCGGCT
CGTAGAATGTTTTCCGAGCACCAGTATCATTGTGTCTGCCCCATGCGTAGTCCAGAAGACCCGGACCGCATGATGAAATA
CGCCAGTAAACTGGCGGAAAAAGCGTGCAAGATTACAAACAAGAACTTGCATGAGAAGATTAAGGATCTCCGGGATCCCC
TGAAAAGGCTGTTTAAGTTGGGTAAACCGCTCCCAGCCGACGACGAGCAAGACGAAGACAGAAGACGCGCTCTGCTAGAT
GAAACAAAGGCGTGGTTTAGAGTAGGTATAACAGGCACTTTAGCAGTGGCCGTGACGACCCGGTATGAGGTAGACAATAT
TACACCTGTCCTACTGGCATTGAGAACTTTTGCCCAGAGCAAAAGAGCATTCCAAGCCATCAGAGGGGAAATAAAGCATC
TCTACGGTGGTCCTAAATAGTCAGCATAGTACATTTCATCTGACTAATACTACAACACCACCACCATGAATAGAGGATTC
TTTAACATGCTCGGCCGCCGCCCCTTCCCGGCCCCCACTGCCATGTGGAGGCCGCGGAGAAGGAGGCAGGCGGCCCCGAT
GCCTGCCCGCAACGGGCTGGCTTCTCAAATCCAGCAACTGACCACAGCCGTCAGTGCCCTAGTCATTGGACAGGCAACTA
GACCTCAACCCCCACGTCCACGCCCGCCACCGCGCCAGAAGAAGCAGGCGCCCAAGCAACCACCGAAGCCGAAGAAACCA
AAAACGCAGGAGAAGAAGAAGAAGCAACCTGCAAAACCCAAACCCGGAAAGAGACAGCGCATGGCACTTAAGTTGGAGGC
CGACAGATTGTTCGACGTCAAGAACGAGGACGGAGATGTCATCGGGCACGCACTGGCCATGGAAGGAAAGGTAATGAAAC
CTCTGCACGTGAAAGGAACCATCGACCACCCTGTGCTATCAAAGCTCAAATTTACCAAGTCGTCAGCATACGACATGGAG
TTCGCACAGTTGCCAGTCAACATGAGAAGTGAGGCATTCACCTACACCAGTGAACACCCCGAAGGATTCTATAACTGGCA
CCACGGAGCGGTGCAGTATAGTGGAGGTAGATTTACCATCCCTCGCGGAGTAGGAGGCAGAGGAGACAGCGGTCGTCCGA
TCATGGATAACTCCGGTCGGGTTGTCGCGATAGTCCTCGGTGGCGCTGATGAAGGAACACGAACTGCCCTTTCGGTCGTC
ACCTGGAATAGTAAAGGGAAGACAATTAAGACGACCCCGGAAGGGACAGAAGAGTGGTCCGCAGCACCACTGGTCACGGC
AATGTGTTTGCTCGGAAATGTGAGCTTCCCATGCGACCGCCCGCCCACATGCTATACCCGCGAACCTTCCAGAGCCCTCG
ACATCCTTGAAGAGAACGTGAACCATGAGGCCTACGATACCCTGCTCAATGCCATATTGCGGTGCGGATCGTCTGGCAGA
AGCAAAAGAAGCGTCATTGACGACTTTACCCTGACCAGCCCCTACTTGGGCACATGCTCGTACTGCCACCATACTGTACC
GTGCTTCAGCCCTGTTAAGATCGAGCAGGTCTGGGACGAAGCGGACGATAACACCATACGCATACAGACTTCCGCCCAGT
TTGGATACGACCAAAGCGGAGCAGCAAGCGCAAACAAGTACCGCTACATGTCGCTTAAGCAGGATCACACCGTTAAAGAA
GGCACCATGGATGACATCAAGATTAGCACCTCAGGACCGTGTAGAAGGCTTAGCTACAAAGGATACTTTCTCCTCGCAAA
ATGCCCTCCAGGGGACAGCGTAACCGGTTAGCATAGTGAGTAGCAACTCAGCAACGTCATGTACACTGGCCCGCAAGATAA
AACCAAAATTCGTGGGACCGGAAAAATATGATCTACCTCCCGTTCACGGTAAAAAAATTCCTTGCACAGTGTACGACCGT
CTGAAAGAAACAACTGCAGGCTACATCACTATGCACAGGCCGAGACCGCACGCTTATACATCCTACCTGGAAGAATCATC
AGGGAAAGTTTACGCAAAGCCGCCATCTGGGAAGAACATTACGTATGAGTGCAAGTGCGGCGACTACAAGACCGGAACCG
TTTCGACCCGCACCGAAATCACTGGTTGCACCGCCATCAAGCAGTGCGTCGCCTATAAGAGCGACCAAACGAAGTGGGTC
TTCAACTCACCGGACTTGATCAGACATGACGACCACACGGCCCAAGGGAAATTGCATTTGCCTTTCAAGTTGATCCCGAG
TACCTGCATGGTCCCTGTTGCCCACGCGCCGAATGTAATACATGGCTTTAAACACATCAGCCTCCAATTAGATACAGACC

FIG. 13A

```
ACTTGACATTGCTCACCACCAGGAGACTAGGGGCAAACCCGGAACCAACCACTGAATGGATCGTCGGAAAGACGGTCAGA
AACTTCACCGTCGACCGAGATGGCCTGGAATACATATGGGGAAATCATGAGCCAGTGAGGGTCTATGCCCAAGAGTCAGC
ACCAGGAGACCCTCACGGATGGCCACACGAAATAGTACAGCATTACTACCATCGCCATCCTGTGTACACCATCTTAGCCG
TCGCATCAGCTACCGTGGCGATGATGATTGGCGTAACTGTTGCAGTGTTATGTGCCTGTAAAGCGCGCCGTGAGTGCCTG
ACGCCATACGCCCTGGCCCCAAACGCCGTAATCCCAACTTCGCTGGCACTCTTGTGCTGCGTTAGGTCGGCCAATGCTGA
AACGTTCACCGAGACCATGAGTTACTTGTGGTCGAACAGTCAGCCGTTCTTCTGGGTCCAGTTGTGCATACCTTTGGCCG
CTTTCATCGTTCTAATGCGCTGCTGCTCCTGCTGCCTGCCTTTTTTAGTGGTTGCCGGCGCCTACCTGGCGAAGGTAGAC
GCCTACGAACATGCGACCACTGTTCCAAATGTGCCACAGATACCGTATAAGGCACTTGTTGAAAGGGCAGGGTATGCCCC
GCTCAATTTGGAGATCACTGTCATGTCCTCGGAGGTTTTGCCTTCCACCAACCAAGAGTACATTACCTGCAAATTCACCA
CTGTGGTCCCCTCCCCAAAAATCAAATGCTGCGGCTCCTTGGAATGTCAGCCGGCCGCTCATGCAGACTATACCTGCAAG
GTCTTCGGAGGGGTCTACCCCTTTATGTGGGGAGGAGCGCAATGTTTTTGCCGACAGTGAGAACAGCCAGATGAGTGAGGC
GTACGTCGAATTGTCAGCAGATTGCCGCGTCTGACCACGCGCAGGCGATTAAGGTGCACACTGCCGCGATGAAAGTAGGAC
TGCGTATTGTGTACGGGAACACTACCAGTTTCCTAGATGTGTACGTGAACGGAGTCACACCAGGAACGTCTAAAGACTTG
AAAGTCATAGCTGGACCAATTTCAGCATCGTTTACGCCATTCGATCATAAGGTCGTTATCCATCGCGGCCTGGTGTACAA
CTATGACTTCCCGGAATATGGAGCGATGAAACCAGGAGCGTTTGGAGACATTCAAGCTACCTCCTTGACTAGCAAGGATC
TCATCGCCAGCACAGACATTAGGCTACTCAAGCCTTCCGCCAAGAACGTGCATGTCCCGTACACGCAGGCCTCATCAGGA
TTTGAGATGTGGAAAAACAACTCAGGCCGCCCACTGCAGGAAACCGCACCTTTCGGGTGTAAGATTGCAGTAAATCCGCT
CCGAGCGGTGGACTGTTCATACGGGAACATTCCCATTTCTATTGACATCCCGAACGCTGCCTTTATCAGGACATCAGATG
CACCACTGGTCTCAACAGTCAAATGTGAAGTCAGTGAGTGCACTTATTCAGCAGACTTCGGCGGGATGGCCACCCTGCAG
TATGTATCCGACCGCGAAGGTCAATGCCCCGTACATTCGCATTCGAGCACAGCAACTCTCCAAGAGTCGACAGTACATGT
CCTGGAGAAAGGAGCGGTGACAGTACACTTTAGCACCGCGAGTCCACAGGCGAACTTTATCGTATCGCTGTGTGGGAAGA
AGACAACATGCAATGCAGAATGTAAACCACCAGCTGACCATATCGTGAGCACCCCGCACAAAAATGACCAAGAATTTCAA
GCCGCCATCTCAAAAACATCATGGAGTTGGCTGTTTGCCCTTTTCGGCGGCGCCTCGTCGCTATTAATTATAGGACTTAT
GATTTTTGCTTGCAGCATGATGCTGACTAGCACACGAAGATGACCGCTACGCCCCAATGATCCGACCAGCAAAACTCGAT
GTACTTCCGAGGAACTGATGTGCATAActagagGaATTCCGCCCCTCTCCCTCCCCCCCCCCCTAACGTTACTGGCCGAAG
CCGCTTGGAATAAGGCCGGTGTGCCGTTTGTCTATATGTTATTTTCCACCATATTGCCGTCTTTTGGCAATGTGAGGGCCC
GGAAACCTGGCCCTGTCTTCTTGACGAGCATTCCTAGGGGTCTTTCCCCTCTCGCCAAAGGAATGCAAGGTCTGTTGAAT
GTCGTGAAGGAAGCAGTTCCTCTGGAAGCTTCTTGAAGACAAACAACGTCTGTAGCGACCCTTTGCAGGCAGCGGAACCC
CCCACCTGGCGACAGGTGCCTCTGCGGCCAAAAAGCCACGTGTATAAGATACACCTGCAAAGGCGGCACAACCCCAGTGCC
ACGTTGTGAGTTGGATAGTTGTGGAAAGAGTCAAATGGCTCTCCTCAAGCGTATTCAACAAGGGGCTGAAGGATGCCCAG
AAGGTACCCCATTGTATGGGATCTGATCTGGGGCCTCGGTGCACATGCTTTACATGTGTTTAGTCGAGGTTAAAAAACGT
CTAGGCCCCCCGAACCACGGGGACGTGGTTTTCCTTTGAAAAACACGATGATAAGCTTGCCACAACCATGgctgaacAAG
ATGGATTGCACGCAGGTTCTCCGGCCGCTTGGGTGGAGAGGCTATTCGGCTATGACTGGGCACAACAGACAATCGGCTGC
TCTGATGCCGCCGTGTTCCGGCTGTCAGCGCAGGGGCGCCCGGTTCTTTTTGTCAAGACCGACCTGTCCGGTGCCCTGAA
TGAACTGCAGGACGAGGCAGCGCGGCTATCGTGGCTGGCCACGACGGGCGTTCCTTGCGCAGCTGTGCTCGACGTTGTCA
CTGAAGCGGGAAGGGACTGGCTGCTATTGGGCGAAGTGCCGGGGCAGGATCTCCTGTCATCTCACCTTGCTCCTGCCGAG
AAAGTATCCATCATGGCTGATGCAATGCGGCGGCTGCATACGCTTGATCCGGCTACCTGCCCATTCGACCACCAAGCGAA
ACATCGCATCGAGCGAGCACGTACTCGGATGGAAGCCGGTCTTGTCGATCAGGATGATCTGGACGAAGAGCATCAGGGGC
TCGCGCCAGCCGAACTGTTCGCCAGGCTCAAGGCGCGCATGCCCGACGGCGAGGATCTCGTCGTGACCCATGGCGATGCC
TGCTTGCCGAATATCATGGTGGAAAATGGCCGCTTTTCTGGATTCATCGACTGTGGCCGGCTGGGTGTGGCGGACCGCTA
TCAGGACATAGCGTTGGCTACCCGTGATATTGCTGAAGAGCTTGGCGGCGAATGGGCTGACCGCTTCCTCGTGCTTTACG
GTATCGCCGCTCCCGATTCGCAGCGCATCGCCTTCTATCGCCTTCTTGACGAGttcttctgagcgggatcggctagTCAG
GCTGGTACATTAGATCCCCGCTTACCGCGGGCAATATAGCAACACTAAAAACTCGATGTACTTCCGAGGAAGCGCAGTgC
```

FIG. 13B

```
ATAATGCTGCGCaGTGTTGCCACATAACCACTATATTAACCATTTATCTAGCGGACGCCAAAAACTCAATGTATTTCTGA
GGAAGCGTGGTGCATAATGCCACGCAGCGTCTGCATAACTTTTATTATTTCTTTTATTAATCAACAAAATTTTGTTTTTA
ACATTTCAAAAAAAAAAAAAAAAAAAAAAAAAAAAAAAAAAAAAAAAAAGGGAATTCCCAACTTGTTTATTGCAGCTTATAATGG
TTACAAATAAAGCAATAGCATCACAAATTTCACAAATAAAGCATTTTTTTCACTGCATTCTAGTTGTGGTTTGTCCAAAC
TCATCAATGTATCTTATCATGTCTGGATCCGTCGAGACGCCTccaattcgccctatagtgagtcgtattacgcgcgcTTG
GCGTAATCATGGTCATAGCTGTTTCCTGTGTGAAATTGTTATCCGCTCACAATTCCACACAACATACGAGCCGGAAGCAT
AAAGTGTAAAGCCTGGGGTGCCTAATGAGTGAGCTAACTCACATTAATTGCGTTGCGCTCACTGCCCGCTTTCCAGTCGG
GAAACCTGTCGTGCCAGCTGCATTAATGAATCGGCCAACGCGCGGGGAGAGGCGGTTTGCGTATTGGGCGCTCTTCCGCT
TCCTCGCTCACTGACTCGCTGCGCTCGGTCGTTCGGCTGCGGCGAGCGGTATCAGCTCACTCAAAGGCGGTAATACGGTT
ATCCACAGAATCAGGGGATAACGCAGGAAAGAACATGTGAGCAAAAGGCCAGCAAAAGGCCAGGAACCGTAAAAAGGCCG
CGTTGCTGGCGTTTTTCCATAGGCTCCGCCCCCCTGACGAGCATCACAAAAATCGACGCTCAAGTCAGAGGTGGCGAAAC
CCGACAGGACTATAAAGATACCAGGCGTTTCCCCCTGGAAGCTCCCTCGTGCGCTCTCCTGTTCCGACCCTGCCGCTTAC
CGGATACCTGTCCGCCTTTCTCCCTTCGGGAAGCGTGGCGCTTTCTCAATGCTCACGCTGTAGGTATCTCAGTTCGGTGT
AGGTCGTTCGCTCCAAGCTGGGCTGTGTGCACGAACCCCCCGTTCAGCCCGACCGCTGCGCCTTATCCGGTAACTATCGT
CTTGAGTCCAACCCGGTAAGACACGACTTATCGCCACTGGCAGCAGCCACTGGTAACAGGATTAGCAGAGCGAGGTATGT
AGGCGGTGCTACAGAGTTCTTGAAGTGGTGGCCTAACTACGGCTACACTAGAAGGACAGTATTTGGTATCTGCGCTCTGC
TGAAGCCAGTTACCTTCGGAAAAAGAGTTGGTAGCTCTTGATCCGGCAAACAAACCACCGCTGGTAGCGGTGGTTTTTTT
GTTTGCAAGCAGCAGATTACGCGCAGAAAAAAAGGATCTCAAGAAGATCCTTTGATCTTTTCTACGGGGTCTGACGCTCA
GTGGAACGAAAACTCACGTTAAGGGATTTTGGTCATGAGATTATCAAAAAGGATCTTCACCTAGATCCTTTTAAATTAAA
AATGAAGTTTTAAATCAATCTAAAGTATATATGAGTAAACTTGGTCTGACAGTTACCAATGCTTAATCAGTGAGGCACCT
ATCTCAGCGATCTGTCTATTTCGTTCATCCATAGTTGCCTGACTCCCCGTCGTGTAGATAACTACGATACGGGAGGGCTT
ACCATCTGGCCCCAGTGCTGCAATGATACCGCGAGACCCACGCTCACCGGCTCCAGATTTATCAGCAATAAACCAGCCAG
CCGGAAGGGCCGAGCGCAGAAGTGGTCCTGCAACTTTATCCGCCTCCATCCAGTCTATTAATTGTTGCCGGGAAGCTAGA
GTAAGTAGTTCGCCAGTTAATAGTTTGCGCAACGTTGTTGCCATTGCTACAGGCATCGTGGTGTCACGCTCGTCGTTTGG
TATGGCTTCATTCAGCTCCGGTTCCCAACGATCAAGGCGAGTTACATGATCCCCCATGTTGTGCAAAAAAGCGGTTAGCT
CCTTCGGTCCTCCGATCGTTGTCAGAAGTAAGTTGGCCGCAGTGTTATCACTCATGGTTATGGCAGCACTGCATAATTCT
CTTACTGTCATGCCATCCGTAAGATGCTTTTCTGTGACTGGTGAGTACTCAACCAAGTCATTCTGAGAATAGTGTATGCG
GCGACCGAGTTGCTCTTGCCCGGCGTCAATACGGGATAATACCGCGCCACATAGCAGAACTTTAAAAGTGCTCATCATTG
GAAAACGTTCTTCGGGGCGAAAACTCTCAAGGATCTTACCGCTGTTGAGATCCAGTTCGATGTAACCCACTCGTGCACCC
AACTGATCTTCAGCATCTTTTACTTTCACCAGCGTTTCTGGGTGAGCAAAAACAGGAAGGCAAAATGCCGCAAAAAAGGG
AATAAGGGCGACACGGAAATGTTGAATACTCATACTCTTCCTTTTTCAATATTATTGAAGCATTTATCAGGGTTATTGTC
TCATGAGCGGATACATATTTGAATGTATTTAGAAAAATAAACAAATAGGGGTTCCGCGCACATTTCCCCGAAAAGTGCCA
C
```

FIG. 13C

Nucleotide sequence of CAT

CTAGAGATCTGCAGGTCGACGGATCCCCCGAGATTTTCAGGAGCTAAGGAAGCTAAAATGGAGAAAAAAATC
ACTGGATATACCACCGTTGATATATCCCAATGGCATCGTAAAGAACATTTTGAGGCATTTCAGTCAGTTGCT
CAATGTAACTATAACCAGACCGTTCAGCTGGATATTACGGCCTTTTTAAAGACCGTAAAGAAAAATAAGCAC
AAGTTTTATCCGGCCTTTATTCACATTCTTGCCCGCCTGATGAATGCTCATCCGGAATTCCGTATGGCAATG
AAAGACGGTGAGCTGGTGATATGGGATAGTGTTCACCCTTGTTACACCGTTTTCCATGAGCAAACTGAAACG
TTTTCATCGCTCTGGAGTGAATACCACGACGATTTCCGGCAGTTTCTACACATATATTCGCAAGATGTGGCG
TGTTACGGTGAAAACCTGGCCTATTTCCCTAAAGGGTTTATTGAGAATATGTTTTTCGTCTCAGCCAATCCC
TGGGTGAGTTTCACCAGTTTTGATTTAAACGTGGCCAATATGGACAACTTCTTCGCCCCCCGTTTTCACCATG
GGCAAATATTATACGCAAGGCGACAAGGTGCTGATGCCGCTGGCGATTCAGGTTCATCATGCCGTCTGTGAT
GGCTTCCATGTCGGCAGAATGCTTAATGAATTACAACAGTACTGCGATGAGTGGCAGGGCGGGGCGTAATTT
TTTTAAGGCAGTTATTGGTGCCTCGA

FIG. 14

Nucleotide sequence of XbaI ApaI fragment of synthetic erythropoietin tctagaggcgcggagatgggggtgcacgaatgtcctgcctggctgtggcttctcctgtccctgctgtcgctc
cctctgggcctcccagtcctgggcgccccaccacgcctcatctgtgacagccgagtcctggagaggtacctc
ttggaggccaaggaggccgagaatatcacgacgggctgtgctgaacactgcagcttgaatgagadtatcact
gtcccagacaccaaagttaatttctatgcctggaagaggatggaggtcgggcagcaggccgtagaagtctgg
cagggcctggccctgctgtcggaagctgtcctgcggggccaggccctgttggtcaactcttcccagccgtgg
gagccctgcagctgcatgtggataaagccgtcagtggccttcgcagcctcaccactctgcttcgggctctg
ggagcccagaaggaagccatctcccctccagatgcggcctcagctgctccactccgaacaatcactgctgac
actttccgcaaactcttccgagtctactccaatttcctccggggaaagctgaagctgtacacaggggaggcc
tgcaggacaggggacagatgagcatgcaggccttgggCCC

FIG. 15

SEQUENCE LISTING

<160> NUMBER OF SEQ ID NOS: 18

<210> SEQ ID NO 1
<211> LENGTH: 13905
<212> TYPE: DNA
<213> ORGANISM: Alphavirus, Sindbis virus

<400> SEQUENCE: 1

```
attgacggcg tagtacacac tattgaatca aacagccgac caattgcact accatcacaa        60
tggagaagcc agtagtaaac gtagacgtag accccagag tccgtttgtc gtgcaactgc        120
aaaaaagctt cccgcaattt gaggtagtag cacagcaggt cactccaaat gaccatgcta       180
atgccagagc attttcgcat ctggccagta aactaatcga gctggaggtt cctaccacag       240
cgacgatctt ggacataggc agcgcaccgg ctcgtagaat gttttccgag caccagtatc       300
attgtgtctg ccccatgcgt agtccagaag acccggaccg catgatgaaa tacgccagta       360
aactggcgga aaaagcgtgc aagattacaa acaagaactt gcatgagaag attaaggatc       420
tccggaccgt acttgatacg ccggatgctg aaacaccatc gctctgcttt cacaacgatg       480
ttacctgcaa catgcgtgcc gaatattccg tcatgcagga cgtgtatatc aacgctcccg       540
gaactatcta tcatcaggct atgaaaggcg tgcggaccct gtactggatt ggcttcgaca       600
ccacccagtt catgttctcg gctatggcag gttcgtaccc tgcgtacaac accaactggg       660
ccgacgagaa agtccttgaa gcgcgtaaca tcggactttg cagcacaaag ctgagtgaag       720
gtaggacagg aaaattgtcg ataatgagga agaaggagtt gaagcccggg tcgcgggttt       780
atttctccgt aggatcgaca ctttatccag aacacagagc cagcttgcag agctggcatc       840
ttccatcggt gttccacttg aatggaaagc agtcgtacac ttgccgctgt gatacagtgg       900
tgagttgcga aggctacgta gtgaagaaaa tcaccatcag tcccgggatc acgggagaaa       960
ccgtgggata cgcggttaca cacaatagcg agggcttctt gctatgcaaa gttactgaca       1020
cagtaaaagg agaacgggta tcgttccctg tgtgcacgta catcccggcc accatatgcg      1080
atcagatgac tggtataatg gccacggata tatccctga cgatgcacaa aaacttctgg      1140
```

-continued

```
ttgggctcaa ccagcgaatt gtcattaacg gtaggactaa caggaacacc aacaccatgc    1200
aaaattacct tctgccgatc atagcacaag ggttcagcaa atgggctaag gagcgcaagg    1260
atgatcttga taacgagaaa atgctgggta ctagagaacg caagcttacg tatggctgct    1320
tgtgggcgtt tcgcactaag aaagtacatt cgttttatcg cccacctgga acgcagacct    1380
gcgtaaaagt cccagcctct tttagcgctt ttcccatgtc gtccgtatgg acgacctctt    1440
tgcccatgtc gctgaggcag aaattgaaac tggcattgca accaaagaag gaggaaaaac    1500
tgctgcaggt ctcggaggaa ttagtcatgg aggccaaggc tgcttttgag gatgctcagg    1560
aggaagccag agcggagaag ctccgagaag cacttccacc attagtggca gacaaaggca    1620
tcgaggcagc cgcagaagtt gtctgcgaag tggaggggct ccaggcggac atcggagcag    1680
cattagttga accccgcgc ggtcacgtaa ggataatacc tcaagcaaat gaccgtatga    1740
tcggacagta tatcgttgtc tcgccaaact ctgtgctgaa gaatgccaaa ctcgcaccag    1800
cgcacccgct agcagatcag gttaagatca taacacactc cggaagatca ggaaggtacg    1860
cggtcgaacc atacgacgct aaagtactga tgccagcagg aggtgccgta ccatggccag    1920
aattcctagc actgagtgag agcgccacgt tagtgtacaa cgaaagagag tttgtgaacc    1980
gcaaactata ccacattgcc atgcatggcc ccgccaagaa tacagaagag gagcagtaca    2040
aggttacaaa ggcagagctt gcagaaacag agtacgtgtt tgacgtggac aagaagcgtt    2100
gcgttaagaa ggaagaagcc tcaggtctgg tcctctcggg agaactgacc aaccctccct    2160
atcatgagct agctctggag ggactgaaga cccgacctgc ggtcccgtac aaggtcgaaa    2220
caataggagt gataggcaca ccggggtcgg gcaagtcagc tattatcaag tcaactgtca    2280
cggcacgaga tcttgttacc agcggaaaga agaaaaattg tcgcgaaatt gaggccgacg    2340
tgctaagact gaggggtatg cagattacgt cgaagacagt agattcggtt atgctcaacg    2400
gatgccacaa agccgtagaa gtgctgtacg ttgacgaagc gttcgcgtgc acgcaggag    2460 cactacttgc cttgattgct atcgtcaggc cccgcaagaa ggtagtacta tgcggagacc    2520
ccatgcaatg cggattcttc aacatgatgc aactaaaggt acatttcaat cacctgaaa    2580 aagacatatg caccaagaca ttctacaagt atatctcccg gcgttgcaca cagccagtta    2640
cagctattgt atcgacactg cattacgatg aaagatgaa aaccacgaac ccgtgcaaga    2700
agaacattga atcgatatt acaggggcca caaagccgaa gccaggggat atcatcctga    2760
catgtttccg cggtgggtt aagcaattgc aaatcgacta tcccggacat gaagtaatga    2820
cagccgcggc ctcacaaggg ctaaccagaa aaggagtgta tgccgtccgg caaaaagtca    2880
atgaaaaccc actgtacgcg atcacatcag agcatgtgaa cgtgttgctc acccgcactg    2940
aggacaggct agtgtggaaa accttgcagg gcgacccatg gattaagcag cccactaaca    3000
tacctaaagg aaactttcag gctactatag aggactggga agctgaacac aagggaataa    3060
ttgctgcaat aaaacagccc actccccgtg ccaatccgtt cagctgcaag accaacgttt    3120
gctgggcgaa agcattggaa ccgatactag ccacggccgg tatcgtactt accggttgcc    3180
agtggagcga actgttccca cagtttgcgg atgacaaacc acattcggcc atttacgcct    3240
tagacgtaat ttgcattaag ttttttcggca tggacttgac aagcggactg ttttctaaac    3300
agagcatccc actaacgtac catcccgccg attcagcgag gccggtagct cattgggaca    3360
acagcccagg aacccgcaag tatgggtacg atcacgccat tgccgccgaa ctctcccgta    3420
gatttccggt gttccagcta gctgggaagg gcacacaact tgatttgcag acggggagaa    3480
ccagagttat ctctgcacag cataaacctgg tcccggtgaa ccgcaatctt cctcacgcct    3540
```

```
tagtccccga gtacaaggag aagcaacccg gcccggtcaa aaaattcttg aaccagttca    3600
aacaccactc agtacttgtg gtatcagagg aaaaaattga agctccccgt aagagaatcg    3660
aatggatcgc cccgattggc atagccggtg cagataagaa ctacaacctg gctttcgggt    3720
ttccgccgca ggcacggtac gacctggtgt tcatcaacat tggaactaaa tacagaaacc    3780
accactttca gcagtgcgaa gaccatgcgg cgaccttaaa aacccctttcg cgttcggccc    3840 tgaattgcct taacccagga ggcaccctcg tggtgaagtc ctatggctac gccgaccgca    3900
acagtgagga cgtagtcacc gctcttgcca gaaagtttgt cagggtgtct gcagcgagac    3960
cagattgtgt ctcaagcaat acagaaatgt acctgatttt ccgacaacta gacaacagcc    4020
gtacacggca attcaccccg caccatctga attgcgtgat ttcgtccgtg tatgagggta    4080
caagagatgg agttggagcc gcgccgtcat accgcaccaa aagggagaat attgctgact    4140
gtcaagagga agcagttgtc aacgcagcca atccgctggg tagaccaggc gaaggagtct    4200
gccgtgccat ctataaacgt tggccgacca gttttaccga ttcagccacg gagacaggca    4260
ccgcaagaat gactgtgtgc ctaggaaaga aagtgatcca cgcggtcggc cctgatttcc    4320
ggaagcaccc agaagcagaa gccttgaaat tgctacaaaa cgcctaccat gcagtggcag    4380
acttagtaaa tgaacataac atcaagtctg tcgccattcc actgctatct acaggcattt    4440
acgcagccgg aaaagaccgc cttgaagtat cacttaactg cttgacaacc gcgctagaca    4500
gaactgacgg ggacgtaacc atctattgcc tggataagaa gtggaaggaa gaatcgacg    4560 cggcactcca acttaaggag tctgtaacag agctgaagga tgaagatatg gagatcgacg    4620
atgagttagt atggattcat ccagacagtt gcttgaaggg aagaaaggga ttcagtacta    4680
caaaaggaaa attgtattcg tacttcgaag gcaccaaatt ccatcaagca gcaaaagaca    4740
tggcggagat aaaggtcctg ttccctaatg accaggaaag taatgaacaa ctgtgtgcct    4800
acatattggg tgagaccatg gaagcaatcc gcgaaaagtg cccggtcgac cataacccgt    4860
cgtctagccc gccaaaacg ttgccgtgcc tttgcatgta tgccatgacg ccagaaaggg    4920
tccacagact tagaagcaat aacgtcaaag aagttacagt atgctcctcc accccccttc    4980
ctaagcacaa aattaagaat gttcagaagg ttcagtgcac gaaagtagtc ctgtttaatc    5040
cgcacactcc cgcattcgtt cccgcccgta agtacataga agtgccagaa cagcctaccg    5100
ctcctcctgc acaggccgag gaggcccccg aagttgtagc gacaccgtca ccatctacag    5160
ctgataacac ctcgcttgat gtcacagaca tctcactgga tatggatgac agtagcgaag    5220
gctcactttt ttcgagcttt agcggatcgg acaactctat tactagtatg gacagttggt    5280
cgtcaggacc tagttcacta gagatagtag accgaaggca ggtggtggtg gctgacgttc    5340
atgccgtcca agagcctgcc cctattccac cgccaaggct aaagaagatg gcccgcctgg    5400
cagcggcaag aaaagagccc actccaccgg caagcaatag ctctgagtcc ctccacctct    5460
cttttggtgg ggtatccatg tccctcggat caattttcga cggagagacg gcccgccagg    5520
cagcggtaca acccctggca acaggccca cggatgtgcc tatgtctttc ggatcgtttt    5580
ccgacggaga gattgatgag ctgagccgca gagtaactga gtccgaaccc gtcctgtttg    5640
gatcatttga accgggcgaa gtgaactcaa ttatatcgtc ccgatcagcc gtatctttc    5700 cactacgcaa gcagagacgt agacgcagga gcaggaggac tgaatactga ctaaccgggg    5760
taggtgggta catattttcg acggacacag gccctgggca cttgcaaaag aagtccgttc    5820
tgcagaacca gcttacagaa ccgaccttgg agcgcaatgt cctggaaaga attcatgccc    5880
```

```
cggtgctcga cacgtcgaaa gaggaacaac tcaaactcag gtaccagatg atgcccaccg    5940
aagccaacaa aagtaggtac cagtctcgta aagtagaaaa tcagaaagcc ataaccactg    6000
agcgactact gtcaggacta cgactgtata actctgccac agatcagcca gaatgctata    6060
agatcaccta tccgaaacca ttgtactcca gtagcgtacc ggcgaactac tccgatccac    6120
agttcgctgt agctgtctgt aacaactatc tgcatgagaa ctatccgaca gtagcatctt    6180
atcagattac tgacgagtac gatgcttact tggatatggt agacgggaca gtcgcctgcc    6240
tggatactga accttctgc cccgctaagc ttagaagtta cccgaaaaaa catgagtata    6300
gagccccgaa tatccgcagt gcggttccat cagcgatgca gaacacgcta caaaatgtgc    6360
tcattgccgc aactaaaaga aattgcaacg tcacgcagat gcgtgaactg ccaacactgg    6420
actcagcgac attcaatgtc gaatgctttc gaaaatatgc atgtaatgac gagtattggg    6480
aggagttcgc tcggaagcca attaggatta ccactgagtt tgtcaccgca tatgtagcta    6540
gactgaaagg ccctaaggcc gccgcactat ttgcaaagac gtataatttg gtcccattgc    6600
aagaagtgcc tatggataga ttcgtcatgg acatgaaaag agacgtgaaa gttacaccag    6660
gcacgaaaca cacagaagaa agaccgaaag tacaagtgat acaagccgca gaaccctgg    6720 cgactgctta cttatgcggg attcaccggg aattagtgcg taggcttacg gccgtcttgc    6780
ttccaaacat tcacacgctt tttgacatgt cggcggagga ttttgatgca atcatagcag    6840
aacacttcaa gcaaggcgac ccggtactgg agacggatat cgcatcattc gacaaaagcc    6900
aagacgacgc tatggcgtta accggtctga tgatcttgga ggacctgggt gtggatcaac    6960
cactactcga cttgatcgag tgcgcctttg gagaaatatc atccacccat ctacctacgg    7020
gtactcgttt taaattcggg gcgatgatga atccggaat gttcctcaca ctttttgtca    7080
acacagtttt gaatgtcgtt atcgccagca gagtactaga agagcggctt aaaacgtcca    7140
gatgtgcagc gttcattggc gacgacaaca tcatacatgg agtagtatct gacaaagaaa    7200
tggctgagag gtgcgccacc tggctcaaca tggaggttaa gatcatcgac gcagtcatcg    7260
gtgagagacc accttacttc tgcggcggat ttatcttgca agattcggtt acttccacag    7320
cgtgccgcgt ggcggatccc ctgaaaaggc tgtttaagtt gggtaaaccg ctcccagccg    7380
acgacgagca agacgaagac agaagacgcg ctctgctaga tgaaacaaag gcgtggttta    7440
gagtaggtat aacaggcact ttagcagtgg ccgtgacgac ccggtatgag gtagacaata    7500
ttacacctgt cctactggca ttgagaactt tgcccagag caaaagagca ttccaagcca    7560
tcagagggga aataaagcat ctctacggtg gtcctaaata gtcagcatag tacatttcat    7620
ctgactaata ctacaacacc accacctcta gaccatgggg taccgagctc gaattcgcct    7680
cgtcgctatt aattatagga cttatgattt ttgcttgcag catgatgctg actagcacac    7740
gaagatgacg ggcccaggta gacaatatta cacctgtcct actggcattg agaactttg    7800 cccagagcaa aagagcattc caagccatca gaggggaaat aaagcatctc tacggtggtc    7860
ctaaatagtc agcatagtac atttcatctg actaatacta caacaccacc accatgaata    7920
gaggattctt taacatgctc ggccgccgcc ccttcccggc ccccactgcc atgtggaggc    7980
cgcggagaag gaggcaggcg gccccgatgc ctgcccgcaa cgggctggct tctcaaatcc    8040
agcaactgac cacagccgtc agtgccctag tcattggaca ggcaactaga cctcaacccc    8100
cacgtccacg cccgccaccg cgccagaaga agcaggcgcc caagcaacca ccgaagccga    8160
agaaaccaaa aacgcaggag aagaagaaga agcaacctgc aaaacccaaa cccggaaaga    8220
gacagcgcat ggcacttaag ttggaggccg acagattgtt cgacgtcaag aacgaggacg    8280
```

```
gagatgtcat cgggcacgca ctggccatgg aaggaaaggt aatgaaacct ctgcacgtga   8340
aaggaaccat cgaccaccct gtgctatcaa agctcaaatt taccaagtcg tcagcatacg   8400
acatggagtt cgcacagttg ccagtcaaca tgagaagtga ggcattcacc tacaccagtg   8460
aacaccccga aggattctat aactggcacc acggagcggt gcagtatagt ggaggtagat   8520
ttaccatccc tcgcggagta ggaggcagag gagacagcgg tcgtccgatc atggataact   8580
ccggtcgggt tgtcgcgata gtcctcggtg gcgctgatga aggaacacga actgcccttt   8640
cggtcgtcac ctggaatagt aaaggaagac aattaagac gaccccggaa gggacagaag    8700
agtggtccgc agcaccactg gtcacggcaa tgtgtttgct cggaaatgtg agcttcccat   8760
gcgaccgccc gcccacatgc tatacccgcg aaccttccag agccctcgac atccttgaag   8820
agaacgtgaa ccatgaggcc tacgataccc tgctcaatgc catattgcgg tgcggatcgt   8880
ctggcagaag caaaagaagc gtcatcgacg actttaccct gaccagcccc tacttgggca   8940
catgctcgta ctgccaccat actgaaccgt gcttcagccc tgttaagatc gagcaggtct   9000
gggacgaagc ggacgataac accatacgca tacagacttc cgcccagttt ggatacgacc   9060
atagcggagc agcaagcgca aacaagtacc gctacatgtc gcttaagcag gatcacaccg   9120
ttaaagaagg caccatggat gacatcaaga ttagcacctc aggaccgtgt agaaggctta   9180
gctacaaagg atactttctc ctcgcaaaat gccctccagg ggacagcgta acggttagca   9240
tagtgagtag caactcagca acgtcatgta cactggcccg caagataaaa ccaaaattcg   9300
tgggacggga aaaatatgat ctacctcccg ttcacggtaa aaaaattcct tgcacagtgt   9360
acgaccgtct gaaagaaaca actgcaggct acatcactat gcacaggccg ggaccgcacg   9420
cttatacatc ctacctggaa gaatcatcag ggaaagttta cgcaaagccg ccatctggga   9480
agaacattac gtatgagtgc aagtgcggcg actacaagac cggaaccgtt tcgacccgca   9540
ccgaaatcac tggttgcacc gccatcaagc agtgcgtcgc ctataagagc gaccaaacga   9600
agtgggtctt caactcaccg gacttgatca gacatgacga ccacacgcc caagggaaat   9660 tgcatttgcc tttcaagttg atcccgagta cctgcatggt ccctgttgcc cacgcgccga   9720
atgtaataca tggcttttaaa cacatcagcc tccaattaga tacagaccac ttgacattgc   9780
tcaccaccag gagactaggg gcaaacccgg aaccaaccac tgaatggatc gtcggaaaga   9840
cggtcagaaa cttcaccgtc gaccgagatg gcctggaata catatgggga aatcatgagc   9900
cagtgagggt ctatgcccaa gagtcagcac caggagaccc tcacggatgg ccacacgaaa   9960
tagtacagca ttactaccat cgccatcctg tgtacaccat cttagccgtc gcatcagcta   10020
ccgtggcgat gatgattggc gtaactgttg cagtgttatg tgcctgtaaa gcgcgccgtg   10080
agtgcctgac gccatacgcc ctggcccaa acgccgtaat cccaacttcg ctggcactct   10140
tgtgctgcgt taggtcggcc aatgctgaaa cgttcaccga gccatgagt tacttgtggt   10200 cgaacagtca gccgttcttc tgggtccagt tgtgcatacc tttggccgct ttcatcgttc   10260
taatgcgctg ctgctcctgc tgcctgcctt ttttagtggt tgccggcgcc tacctggcga   10320
aggtagacgc ctacgaacat gcgaccactg ttccaaatgt gccacagata ccgtataagg   10380
cacttgttga aagggcaggg tatgcccgc tcaatttgga gatcactgtc atgtcctcgg   10440
aggttttgcc ttccaccaac caagagtaca ttacctgcaa attcaccact gtggtccct   10500 ccccaaaaat caaatgctgc ggctccttgg aatgtcagcc ggccgctcat gcagactata   10560
cctgcaaggt cttcggaggg gtctaccct ttatgtgggg aggagcgcaa tgttttttgcg   10620
```

-continued

```
acagtgagaa cagccagatg agtgaggcgt acgtcgaatt gtcagcagat tgcgcgtctg   10680
accacgcgca ggcgattaag gtgcacactg ccgcgatgaa agtaggactg cgtattgtgt   10740
acgggaacac taccagtttc ctagatgtgt acgtgaacgg agtcacacca ggaacgtcta   10800
aagacttgaa agtcatagct ggaccaattt cagcatcatt tacgccattc gatcataagg   10860
tcgttatcca tcgcggcctg gtgtacaact atgacttccc ggaatatgga gcgatgaaac   10920
caggagcgtt tggagacatt caagctacct ccttgactag caaggatctc atcgccagca   10980
cagacattag gctactcaag ccttccgcca agaatgtgca tgtcccgtac acgcaggccg   11040
catcaggatt tgagatgtgg aaaaacaact caggccgccc attgcaggaa accgcacctt   11100
tcgggtgtaa gattgcagta aatccgctcc gagcggtgga ctgttcatac gggaacattc   11160
ccatttctat tgacatcccg aacgctgcct ttatcaggac atcagatgca ccactggtct   11220
caacagtcaa atgtgaagtc agtgagtgca cttattcagc agacttcgac gggatggcca   11280
ccctgcagta tgtatccgac cgcgaaggtc aatgccccgt acattcgcat tcgagcacag   11340
caactctcca agagtcgaca gtacatgtcc tggagaaagg agcggtgaca gtacactta   11400
gcaccgcgag tccacaggcg aactttatcg tatcgctgtg tgggaagaag acaacatgca   11460
atgcagaatg taaaccacca gctgaccata tcgtgagcac cccgcacaaa aatgaccaag   11520
aatttcaagc cgccatctca aaaacatcat ggagttggct gtttgccctt tcggcggcg   11580
cctcgtcgct attaattata ggacttatga ttttttgcttg cagcatgatg ctgactagca   11640
cacgaagatg accgctacgc cccaatgatc cgaccagcaa aactcgatgt acttccgagg   11700
aactgatgtg cataatgcat caggctggta cattagatcc ccgcttaccg cgggcaatat   11760
agcaacacta aaaactcgat gtacttccga ggaagcgcag tgcataatgc tgcgcagtgt   11820
tgccacataa ccactatatt aaccatttat ctagcggacg ccaaaaactc aatgtatttc   11880
tgaggaagcg tggtgcataa tgccacgcag cgtctgcata acttttatta tttcttttat   11940
taatcaacaa aattttgttt ttaacatttc aaaaaaaaaa aaaaaaaaa aaaaaaaaa   12000
aaaaaaaggg aattcctcga ggggaattaa ttcttgaaga cgaaagggcc aggtggcact   12060
tttcggggaa atgtgcgcgg aaccccatt tgtttatttt tctaaataca ttcaaatatg   12120
tatccgctca tgagacaata accctgataa atgcttcaat aatattgaaa aaggaagagt   12180
atgagtattc aacatttccg tgtcgccctt attcccttt ttgcggcatt tgccttcct   12240
gttttttgctc acccagaaac gctggtgaaa gtaaaagatg ctgaagatca gttgggtgca   12300
cgagtgggtt acatcgaact ggatctcaac agcggtaaga tccttgagag ttttcgcccc   12360
gaagaacgtt ttccaatgat gagcactttt aaagttctgc tatgtggcgc ggtattatcc   12420
cgtgttgacg ccgggcaaga gcaactcggt cgccgcatac actattctca gaatgacttg   12480
gttgagtact caccagtcac agaaaagcat cttacggatg gcatgacagt aagagaatta   12540
tgcagtgctg ccataaccat gagtgataac actgcggcca acttacttct gacaacgatc   12600
ggaggaccga aggagctaac cgcttttttg cacaacatgg gggatcatgt aactcgcctt   12660
gatcgttggg aaccggagct gaatgaagcc ataccaaacg acgagcgtga ccacgatg   12720
cctgtagcaa tggcaacaac gttgcgcaaa ctattaactg gcgaactact tactctagct   12780
tcccggcaac aattaataga ctggatggag gcggataaag ttgcaggacc acttctgcgc   12840
tcggcccttc cggctggctg gtttattgct gataaatctg gagccggtga gcgtgggtct   12900
cgcggtatca ttgcagcact ggggccagat ggtaagccct cccgtatcgt agttatctac   12960
acgacgggga gtcaggcaac tatggatgaa cgaaatagac agatcgctga gataggtgcc   13020
```

-continued

```
tcactgatta agcattggta actgtcagac caagtttact catatatact ttagattgat     13080
ttaaaacttc atttttaatt taaaaggatc taggtgaaga tccttttga taatctcatg     13140 accaaaatcc cttaacgtga gttttcgttc cactgagcgt cagacccgt agaaaagatc     13200 aaaggatctt cttgagatcc ttttttttctg cgcgtaatct gctgcttgca aacaaaaaaa     13260
ccaccgctac cagcggtggt ttgtttgccg gatcaagagc taccaactct ttttccgaag     13320
gtaactggct tcagcagagc gcagatacca atactgtcc ttctagtgta gccgtagtta     13380
ggccaccact tcaagaactc tgtagcaccg cctacatacc tcgctctgct aatcctgtta     13440
ccagtggctg ctgccagtgg cgataagtcg tgtcttaccg ggttggactc aagacgatag     13500
ttaccggata aggcgcagcg tcgggctga acggggggtt cgtgcacaca gcccagcttg     13560
gagcgaacga cctacaccga actgagatac ctacagcgtg agcattgaga aagcgccacg     13620
cttcccgaag ggagaaaggc ggacaggtat ccggtaagcg gcagggtcgg aacaggagag     13680
cgcacgaggg agcttccagg gggaaacgcc tggtatcttt atagtcctgt cgggtttcgc     13740
cacctctgac ttgagcgtcg attttttgtga tgctcgtcag ggggcggag cctatggaaa     13800 aacgccagca acgcgagctc gtatggacat attgtcgtta gaacgcggct acaattaata     13860 cataaccta tgtatcatac acatacgatt taggggacac atag                      13905
```

<210> SEQ ID NO 2
<211> LENGTH: 9521
<212> TYPE: DNA
<213> ORGANISM: Alphavirus, Sindbis Virus

<400> SEQUENCE: 2

```
ctgacgcgcc ctgtagcggc gcattaagcg cggcgggtgt ggtggttacg cgcagcgtga       60
ccgctacact tgccagcgcc ctagcgcccg ctcctttcgc tttcttccct tcctttctcg      120
ccacgttcgc cggctttccc cgtcaagctc taaatcgggg gctccctttta gggttccgat      180 ttagtgcttt acggcacctc gacccaaaa aacttgatta gggtgatggt tcacgtagtg      240
ggccatcgcc ctgatagacg gttttcgcc ctttgacgtt ggagtccacg ttctttaata      300
gtggactctt gttccaaact ggaacaacac tcaaccctat ctcggtctat tcttttgatt      360
tataagggat tttgccgatt tcggcctatt ggttaaaaaa tgagctgatt taacaaaaat      420
ttaacgcgaa ttttaacaaa atattaacgc ttacaatttc cattcgccat tcaggctgcg      480
caactgttgg gaagggcgat cggtgcgggc ctcttcgcta ttacgccagc tggcgaaagg      540
gggatgtgct gcaaggcgat taagttgggt aacgccaggg ttttcccagt cacgacgttg      600
taaaacgacg gccagtgagc gcgcaattaa ccctcactaa agggaacaaa agctggctag      660
tggatccagt cttatgcaat actcttgtag tcttgcaaca tggtaacgat gagttagcaa      720
catgccttac aaggagagaa aaagcaccgt gcatgccgat tggtggaagt aaggtggtac      780
gatcgtgcct tattaggaag gcaacagacg ggtctgacat ggattggacg aaccactgaa      840
ttccgcattg cagagatatt gtatttaagt gccctacctc gataccgtcg agatatagtg      900
gtgagtatcc ccgcctgtca cgcgggagac cggggttcgg ttccccgacg gggagccaaa      960
cagccgacca attgcactac catcacaatg gagaagccaa tagtaaacgt agacgtagac     1020
ccccagagtc cgtttgtcgt gcaactgcaa aaaagcttcc cgcaatttga ggtagtagca     1080
cagcaggtca ctccaaatga ccatgctaat gccagagcat tttcgcatct ggccagtaaa     1140
ctaatcgagc tggaggttcc taccacagcg acgatcttgg acataggcag cgcaccggct     1200
```

```
cgtagaatgt tttccgagca ccagtatcat tgtgtctgcc ccatgcgtag tccagaagac    1260
ccggaccgca tgatgaaata cgccagtaaa ctggcggaaa aagcgtgcaa gattacaaac    1320
aagaacttgc atgagaagat taaggatctc cgggatcccc tgaaaaggct gtttaagttg    1380
ggtaaaccgc tcccagccga cgacgagcaa gacgaagaca aagacgcgc tctgctagat     1440 gaaacaaagg cgtggtttag agtaggtata acaggcactt tagcagtggc cgtgacgacc    1500
cggtatgagg tagacaatat tacacctgtc ctactggcat tgagaacttt tgcccagagc    1560
aaaagagcat tccaagccat cagagggaa ataaagcatc tctacggtgg tcctaaatag     1620
tcagcatagt acatttcatc tgactaatac tacaacacca ccaccatgaa tagaggattc    1680
tttaacatgc tcggccgccg ccccttcccg gcccccactg ccatgtggag gccgcggaga    1740
aggaggcagg cggccccgat gcctgcccgc aacgggctgg cttctcaaat ccagcaactg    1800
accacagccg tcagtgccct agtcattgga caggcaacta gacctcaacc cccacgtcca    1860
cgcccgccac cgcgccagaa gaagcaggcg cccaagcaac caccgaagcc gaagaaacca    1920
aaaacgcagg agaagaagaa gaagcaacct gcaaaaccca acccggaaa gagacagcgc     1980 atggcactta agttggaggc cgacagattg ttcgacgtca agaacgagga cggagatgtc    2040
atcgggcacg cactggccat ggaaggaaag gtaatgaaac ctctgcacgt gaaaggaacc    2100
atcgaccacc ctgtgctatc aaagctcaaa tttaccaagt cgtcagcata cgacatggag    2160
ttcgcacagt tgccagtcaa catgagaagt gaggcattca cctacaccag tgaacacccc    2220
gaaggattct ataactggca ccacggagcg gtgcagtata gtggaggtag atttaccatc    2280
cctcgcggag taggaggcag aggagacagc ggtcgtccga tcatggataa ctccggtcgg    2340
gttgtcgcga tagtcctcgg tggcgctgat gaaggaacac gaactgccct ttcggtcgtc    2400
acctggaata gtaaagggaa gacaattaag acgaccccgg aagggacaga agagtggtcc    2460
gcagcaccac tggtcacggc aatgtgtttg ctcggaaatg tgagcttccc atgcgaccgc    2520
ccgcccacat gctatacccg cgaaccttcc agagccctcg acatccttga agagaacgtg    2580
aaccatgagg cctacgatac cctgctcaat gccatattgc ggtgcggatc gtctggcaga    2640
agcaaaagaa gcgtcattga cgactttacc ctgaccagcc cctacttggg cacatgctcg    2700
tactgccacc atactgtacc gtgcttcagc cctgttaaga tcgagcaggt ctgggacgaa    2760
gcggacgata acaccatacg catacagact tccgcccagt ttggatacga ccaaagcgga    2820
gcagcaagcg caaacaagta ccgctacatg tcgcttaagc aggatcacac cgttaaagaa    2880
ggcaccatgg atgacatcaa gattagcacc tcaggaccgt gtagaaggct tagctacaaa    2940
ggatactttc tcctcgcaaa atgccctcca ggggacagcg taacggttag catagtgagt    3000
agcaactcag caacgtcatg tacactggcc cgcaagataa aaccaaaatt cgtgggacgg    3060 gaaaatatg atctacctcc cgttcacggt aaaaaaattc cttgcacagt gtacgaccgt    3120
ctgaaagaaa caactgcagg ctacatcact atgcacaggc cgagaccgca cgcttataca    3180
tcctacctgg aagaatcatc agggaaagtt tacgcaaagc cgccatctgg gaagaacatt    3240
acgtatgagt gcaagtgcgg cgactacaag accggaaccg tttcgacccg caccgaaatc    3300
actggttgca ccgccatcaa gcagtgcgtc gcctataaga gcgaccaaac gaagtgggtc    3360
ttcaactcac cggacttgat cagacatgac gaccacacgg cccaagggaa attgcatttg    3420
cctttcaagt tgatcccgag tacctgcatg gtccctgttg cccacgcgcc gaatgtaata    3480
catggcttta aacacatcag cctccaatta gatacagacc acttgacatt gctcaccacc    3540
aggagactag gggcaaaccc ggaaccaacc actgaatgga tcgtcggaaa gacggtcaga    3600
```

```
aacttcaccg tcgaccgaga tggcctggaa tacatatggg gaaatcatga gccagtgagg    3660
gtctatgccc aagagtcagc accaggagac cctcacggat ggccacacga aatagtacag    3720
cattactacc atcgccatcc tgtgtacacc atcttagccg tcgcatcagc taccgtggcg    3780
atgatgattg gcgtaactgt tgcagtgtta tgtgcctgta agcgcgccg tgagtgcctg     3840 acgccatacg ccctggcccc aaacgccgta atcccaactt cgctggcact cttgtgctgc    3900
gttaggtcgg ccaatgctga aacgttcacc gagaccatga gttacttgtg gtcgaacagt    3960
cagccgttct tctgggtcca gttgtgcata cctttggccg ctttcatcgt tctaatgcgc    4020
tgctgctcct gctgcctgcc ttttttagtg gttgccggcg cctacctggc gaaggtagac    4080
gcctacgaac atgcgaccac tgttccaaat gtgccacaga taccgtataa ggcacttgtt    4140
gaaagggcag ggtatgcccc gctcaatttg gagatcactg tcatgtcctc ggaggttttg    4200
ccttccacca accaagagta cattacctgc aaattcacca ctgtggtccc ctccccaaaa    4260
atcaaatgct gcggctcctt ggaatgtcag ccggccgctc atgcagacta tacctgcaag    4320
gtcttcggag gggtctaccc ctttatgtgg ggaggagcgc aatgttttg cgacagtgag     4380 aacagccaga tgagtgaggc gtacgtcgaa ttgtcagcag attgcgcgtc tgaccacgcg    4440
caggcgatta aggtgcacac tgccgcgatg aaagtaggac tgcgtattgt gtacgggaac    4500
actaccagtt tcctagatgt gtacgtgaac ggagtcacac caggaacgtc taaagacttg    4560
aaagtcatag ctggaccaat ttcagcatcg tttacgccat tcgatcataa ggtcgttatc    4620
catcgcggcc tggtgtacaa ctatgacttc ccggaatatg gagcgatgaa accaggagcg    4680
tttgagacaa ttcaagctac ctccttgact agcaaggatc tcatcgccag cacagacatt    4740
aggctactca agccttccgc caagaacgtg catgtcccgt acacgcaggc ctcatcagga    4800
tttgagatgt ggaaaaacaa ctcaggccgc ccactgcagg aaaccgcacc tttcgggtgt    4860
aagattgcag taaatccgct ccgagcggtg gactgttcat acgggaacat tcccatttct    4920
attgacatcc cgaacgctgc ctttatcagg acatcagatg caccactggt ctcaacagtc    4980
aaatgtgaag tcagtgagtg cacttattca gcagacttcg gcgggatggc caccctgcag    5040
tatgtatccg accgcaagg tcaatgcccc gtacattcgc attcgagcac agcaactctc     5100
caagagtcga cagtacatgt cctggagaaa ggagcggtga cagtacactt tagcaccgcg    5160
agtccacagg cgaactttat cgtatcgctg tgtgggaaga agacaacatg caatgcagaa    5220
tgtaaaccac cagctgacca tatcgtgagc accccgcaca aaaatgacca agaatttcaa    5280
gccgccatct caaaaacatc atggagttgg ctgtttgccc ttttcggcgg cgcctcgtcg    5340
ctattaatta taggacttat gattttttgct tgcagcatga tgctgactag cacacgaaga    5400
tgaccgctac gccccaatga tccgaccagc aaaactcgat gtacttccga ggaactgatg    5460
tgcataacta gaggaattcc gccctctcc ctcccccccc cctaacgtta ctggccgaag     5520
ccgcttggaa taaggccggt gtgcgtttgt ctatatgtta ttttccacca tattgccgtc    5580
ttttggcaat gtgagggccc ggaaacctgg ccctgtcttc ttgacgagca ttcctagggg    5640
tctttcccct ctcgccaaag gaatgcaagg tctgttgaat gtcgtgaagg aagcagttcc    5700
tctggaagct tcttgaagac aaacaacgtc tgtagcgacc ctttgcaggc agcggaaccc    5760
cccacctggc gacaggtgcc tctgcggcca aaagccacgt gtataagata cacctgcaaa    5820
ggcggcacaa cccagtgcc acgttgtgag ttggatagtt gtggaaagag tcaaatggct     5880
ctcctcaagc gtattcaaca aggggctgaa ggatgcccag aaggtacccc attgtatggg    5940
```

-continued

```
atctgatctg gggcctcggt gcacatgctt tacatgtgtt tagtcgaggt taaaaaacgt     6000
ctaggccccc cgaaccacgg ggacgtggtt ttcctttgaa aaacacgatg ataagcttgc     6060
cacaaccatg gctgaacaag atggattgca cgcaggttct ccggccgctt gggtggagag     6120
gctattcggc tatgactggg cacaacagac aatcggctgc tctgatgccg ccgtgttccg     6180
gctgtcagcg caggggcgcc cggttctttt tgtcaagacc gacctgtccg gtgccctgaa     6240
tgaactgcag gacgaggcag cgcggctatc gtggctggcc acgacgggcg ttccttgcgc     6300
agctgtgctc gacgttgtca ctgaagcggg aagggactgg ctgctattgg gcgaagtgcc     6360
ggggcaggat ctcctgtcat ctcaccttgc tcctgccgag aaagtatcca tcatggctga     6420
tgcaatgcgg cggctgcata cgcttgatcc ggctacctgc ccattcgacc accaagcgaa     6480
acatcgcatc gagcgagcac gtactcggat ggaagccggt cttgtcgatc aggatgatct     6540
ggacgaagag catcagggc tcgcgccagc cgaactgttc gccaggctca aggcgcgcat     6600
gcccgacggc gaggatctcg tcgtgaccca tggcgatgcc tgcttgccga atatcatggt     6660
ggaaaatggc cgcttttctg gattcatcga ctgtggccgg ctgggtgtgg cggaccgcta     6720
tcaggacata gcgttggcta cccgtgatat tgctgaagag cttggcggcg aatgggctga     6780
ccgcttcctc gtgctttacg gtatcgccgc tcccgattcg cagcgcatcg ccttctatcg     6840
ccttcttgac gagttcttct gagcgggatc ggctagtcag gctggtacat tagatccccg     6900
cttaccgcgg gcaatatagc aacactaaaa actcgatgta cttccgagga agcgcagtgc     6960
ataatgctgc gcagtgttgc cacataacca ctatattaac catttatcta gcggacgcca     7020
aaaactcaat gtatttctga ggaagcgtgg tgcataatgc cacgcagcgt ctgcataact     7080
tttattattt cttttattaa tcaacaaaat tttgttttta acatttcaaa aaaaaaaaa     7140 aaaaaaaaaa aaaaaaaaa aaagggaat tcccaacttg tttattgcag cttataatgg     7200
ttacaaataa agcaatagca tcacaaattt cacaaataaa gcatttttt cactgcattc     7260 tagttgtggt ttgtccaaac tcatcaatgt atcttatcat gtctggatcc gtcgagacgc     7320
gtccaattcg ccctatagtg agtcgtatta cgcgcgcttg gcgtaatcat ggtcatagct     7380
gtttcctgtg tgaaattgtt atccgctcac aattccacac aacatacgag ccggaagcat     7440
aaagtgtaaa gcctggggtg cctaatgagt gagctaactc acattaattg cgttgcgctc     7500
actgcccgct ttccagtcgg gaaacctgtc gtgccagctg cattaatgaa tcggccaacg     7560
cgcggggaga ggcggtttgc gtattgggcg ctcttccgct tcctcgctca ctgactcgct     7620
gcgctcggtc gttcggctgc ggcgagcggt atcagctcac tcaaaggcgg taatacggtt     7680
atccacagaa tcaggggata acgcaggaaa gaacatgtga gcaaaaggcc agcaaaaggc     7740
caggaaccgt aaaaaggccg cgttgctggc gtttttccat aggctccgcc cccctgacga     7800
gcatcacaaa aatcgacgct caagtcagag gtggcgaaac ccgacaggac tataaagata     7860
ccaggcgttt ccccctggaa gctccctcgt gcgctctcct gttccgaccc tgccgcttac     7920
cggatacctg tccgcctttc tcccttcggg aagcgtggcg ctttctcaat gctcacgctg     7980
taggtatctc agttcggtgt aggtcgttcg ctccaagctg ggctgtgtgc acgaaccccc     8040
cgttcagccc gaccgctgcg ccttatccgg taactatcgt cttgagtcca acccggtaag     8100
acacgactta tcgccactgg cagcagccac tggtaacagg attagcagag cgaggtatgt     8160
aggcggtgct acagagttct tgaagtggtg gcctaactac ggctacacta aggacagt     8220 atttggtatc tgcgctctgc tgaagccagt taccttcgga aaaagagttg gtagctcttg     8280
atccggcaaa caaaccaccg ctggtagcgg tggttttttt gtttgcaagc agcagattac     8340
```

-continued

```
gcgcagaaaa aaaggatctc aagaagatcc tttgatcttt tctacggggt ctgacgctca      8400
gtggaacgaa aactcacgtt aagggatttt ggtcatgaga ttatcaaaaa ggatcttcac      8460
ctagatcctt ttaaattaaa aatgaagttt taaatcaatc taaagtatat atgagtaaac      8520
ttggtctgac agttaccaat gcttaatcag tgaggcacct atctcagcga tctgtctatt      8580
tcgttcatcc atagttgcct gactccccgt cgtgtagata actacgatac gggagggctt      8640
accatctggc cccagtgctg caatgatacc gcgagaccca cgctcaccgg ctccagattt      8700
atcagcaata accagccagc cggaagggc cgagcgcaga gtggtcctg caactttatc        8760 cgcctccatc cagtctatta attgttgccg ggaagctaga gtaagtagtt cgccagttaa      8820
tagtttgcgc aacgttgttg ccattgctac aggcatcgtg gtgtcacgct cgtcgtttgg      8880
tatggcttca ttcagctccg gttcccaacg atcaaggcga gttacatgat cccccatgtt      8940
gtgcaaaaaa gcggttagct ccttcggtcc tccgatcgtt gtcagaagta agttggccgc      9000
agtgttatca ctcatggtta tggcagcact gcataattct cttactgtca tgccatccgt      9060
aagatgcttt tctgtgactg gtgagtactc aaccaagtca ttctgagaat agtgtatgcg      9120
gcgaccgagt tgctcttgcc cggcgtcaat acgggataat accgcgccac atagcagaac      9180
tttaaaagtg ctcatcattg gaaaacgttc ttcggggcga aaactctcaa ggatcttacc      9240
gctgttgaga tccagttcga tgtaacccac tcgtgcaccc aactgatctt cagcatcttt      9300
tactttcacc agcgtttctg ggtgagcaaa aacaggaagg caaaatgccg caaaaaaggg      9360
aataagggcg acacggaaat gttgaatact catactcttc cttttcaat attattgaag       9420 catttatcag ggttattgtc tcatgagcgg atacatattt gaatgtattt agaaaaataa      9480
acaaataggg gttccgcgca catttccccg aaaagtgcca c                         9521
```

<210> SEQ ID NO 3
<211> LENGTH: 9951
<212> TYPE: DNA
<213> ORGANISM: Alphavirus, Sindbis Virus

<400> SEQUENCE: 3

```
attgacggcg tagtacacac tattgaatca aacagccgac caattgcact accatcacaa       60
tggagaagcc agtagtaaac gtagacgtag accccagag tccgtttgtc gtgcaactgc       120
aaaaaagctt cccgcaattt gaggtagtag cacagcaggt cactccaaat gaccatgcta      180
atgccagagc attttcgcat ctggccagta aactaatcga gctggaggtt cctaccacag      240
cgacgatctt ggacataggc agcgcaccgg ctcgtagaat gttttccgag caccagtatc      300
attgtgtctg ccccatgcgt agtccagaag acccggaccg catgatgaaa tacgccagta      360
aactggcgga aaagcgtgc aagattacaa caagaactt gcatgagaag attaaggatc        420
tccggaccgt acttgatacg ccggatgctg aaacaccatc gctctgcttt cacaacgatg      480
ttacctgcaa catgcgtgcc gaatattccg tcatgcagga cgtgtatatc aacgctcccg      540
gaactatcta tcatcaggct atgaaaggcg tgcggaccct gtactggatt ggcttcgaca      600
ccacccagtt catgttctcg gctatggcag gttcgtaccc tgcgtacaac accaactggg      660
ccgacgagaa agtccttgaa gcgcgtaaca tcggactttg cagcacaaag ctgagtgaag      720
gtaggacagg aaaattgtcg ataatgagga agaaggagtt gaagcccggg tcgcgggttt      780
atttctccgt aggatcgaca ctttatccag aacacagagc cagcttgcag agctggcatc      840
ttccatcggt gttccacttg aatggaaagc agtcgtacac ttgccgctgt gatacagtgg      900
```

-continued

```
tgagttgcga aggctacgta gtgaagaaaa tcaccatcag tcccgggatc acggagaaa     960 ccgtgggata cgcggttaca cacaatagcg agggcttctt gctatgcaaa gttactgaca   1020
cagtaaaagg agaacgggta tcgttccctg tgtgcacgta catcccggcc accatatgcg   1080
atcagatgac tggtataatg gccacggata tatcacctga cgatgcacaa aaacttctgg   1140
ttgggctcaa ccagcgaatt gtcattaacg gtaggactaa caggaacacc aacaccatgc   1200
aaaattacct tctgccgatc atagcacaag ggttcagcaa atgggctaag gagcgcaagg   1260
atgatcttga taacgagaaa atgctgggta ctagagaacg caagcttacg tatggctgct   1320
tgtgggcgtt tcgcactaag aaagtacatt cgttttatcg cccacctgga acgcagacct   1380
gcgtaaaagt cccagcctct tttagcgctt ttcccatgtc gtccgtatgg acgacctctt   1440
tgcccatgtc gctgaggcag aaattgaaac tggcattgca accaaagaag gaggaaaaac   1500
tgctgcaggt ctcggaggaa ttagtcatgg aggccaaggc tgcttttgag gatgctcagg   1560
aggaagccag agcggagaag ctccgagaag cacttccacc attagtggca gacaaaggca   1620
tcgaggcagc cgcagaagtt gtctgcgaag tggaggggct ccaggcggac atcggagcag   1680
cattagttga accccgcgc ggtcacgtaa ggataatacc tcaagcaaat gaccgtatga    1740
tcggacagta tatcgttgtc tcgccaaaact ctgtgctgaa gaatgccaaa ctcgcaccag   1800
cgcacccgct agcagatcag gttaagatca taacacactc cggaagatca ggaaggtacg   1860
cggtcgaacc atacgacgct aaagtactga tgccagcagg aggtgccgta ccatggccag   1920
aattcctagc actgagtgag agcgccacgt tagtgtacaa cgaaagagag tttgtgaacc   1980
gcaaactata ccacattgcc atgcatggcc ccgccaagaa tacagaagag gagcagtaca   2040
aggttacaaa ggcagagctt gcagaaacag agtacgtgtt tgacgtggac aagaagcgtt   2100
gcgttaagaa ggaagaagcc tcaggtctgg tcctctcggg agaactgacc aaccctccct   2160
atcatgagct agctctggag ggactgaaga cccgacctgc ggtcccgtac aaggtcgaaa   2220
caataggagt gataggcaca ccggggtcgg gcaagtcagc tattatcaag tcaactgtca   2280
cggcacgaga tcttgttacc agcggaaaga agaaaaattg tcgcgaaatt gaggccgacg   2340
tgctaagact gagggggtatg cagattacgt cgaagacagt agattcggtt atgctcaacg   2400
gatgccacaa agccgtagaa gtgctgtacg ttgacgaagc gttcgcgtgc cacgcaggag   2460
cactacttgc cttgattgct atcgtcaggc cccgcaagaa ggtagtacta tgcggagacc   2520
ccatgcaatg cggattcttc aacatgatgc aactaaaggt acatttcaat caccctgaaa   2580
aagacatatg caccaagaca ttctacaagt atatctcccg gcgttgcaca cagccagtta   2640
cagctattgt atcgacactg cattacgatg gaaagatgaa aaccacgaac ccgtgcaaga   2700
agaacattga atcgatatt acaggggcca caaagccgaa gccaggggat atcatcctga   2760
catgtttccg cggtgggtt aagcaattgc aaatcgacta tcccgacat gaagtaatga    2820 cagccgcggc ctcacaaggg ctaaccagaa aaggagtgta tgccgtccgg caaaaagtca   2880
atgaaaaccc actgtacgcg atcacatcag agcatgtgaa cgtgttgctc acccgcactg   2940
aggacaggct agtgtggaaa accttgcagg gcgacccatg gattaagcag cccactaaca   3000
tacctaaagg aaactttcag gctactatag aggactggga agctgaacac aagggaataa   3060
ttgctgcaat aaacagcccc actccccgtg ccaatccgtt cagctgcaag accaacgttt   3120
gctgggcgaa agcattggaa ccgatactag ccacggccgg tatcgtactt accggttgcc   3180
agtggagcga actgttccca cagtttgcgg atgacaaacc acattcggcc atttacgcct   3240
tagacgtaat ttgcattaag tttttcggca tggacttgac aagcggactg ttttctaaac   3300
```

```
agagcatccc actaacgtac catcccgccg attcagcgag gccggtagct cattgggaca   3360
acagcccagg aacccgcaag tatgggtacg atcacgccat tgccgccgaa ctctcccgta   3420
gatttccggt gttccagcta gctgggaagg gcacacaact tgatttgcag acggggagaa   3480
ccagagttat ctctgcacag cataacctgg tcccggtgaa ccgcaatctt cctcacgcct   3540 tagtcccga gtacaaggag aagcaacccg gcccggtcaa aaaattcttg aaccagttca   3600
aacaccactc agtacttgtg gtatcagagg aaaaaattga agctccccgt aagagaatcg   3660
aatggatcgc cccgattggc atagccggtg cagataagaa ctacaacctg gctttcgggt   3720
ttccgccgca ggcacggtac gacctggtgt tcatcaacat tggaactaaa tacagaaacc   3780
accactttca gcagtgcgaa gaccatgcgg cgaccttaaa aaccctttcg cgttcggccc   3840
tgaattgcct taacccagga ggcaccctcg tggtgaagtc ctatggctac gccgaccgca   3900
acagtgagga cgtagtcacc gctcttgcca gaaagtttgt cagggtgtct gcagcgagac   3960
cagattgtgt ctcaagcaat acagaaatgt acctgatttt ccgacaacta gacaacagcc   4020
gtacacggca attcaccccg caccatctga attgcgtgat ttcgtccgtg tatgagggta   4080
caagagatgg agttggagcc gcgccgtcat accgcaccaa aagggagaat attgctgact   4140
gtcaagagga agcagttgtc aacgcagcca atccgctggg tagaccaggc gaaggagtct   4200
gccgtgccat ctataaacgt tggccgacca gttttaccga ttcagccacg agacaggca   4260 ccgcaagaat gactgtgtgc ctaggaaaga agtgatcca cgcggtcggc cctgatttcc   4320
ggaagcaccc agaagcagaa gccttgaaat tgctacaaaa cgcctaccat gcagtggcag   4380
acttagtaaa tgaacataac atcaagtctg tcgccattcc actgctatct acaggcattt   4440
acgcagccgg aaaagaccgc cttgaagtat cacttaactg cttgacaacc gcgctagaca   4500
gaactgacgc ggacgtaacc atctattgcc tggataagaa gtggaaggaa agaatcgacg   4560
cggcactcca acttaaggag tctgtaacag agctgaagga tgaagatatg gagatcgacg   4620
atgagttagt atggattcat ccagacagtt gcttgaaggg aagaaaggga ttcagtacta   4680
caaaaggaaa attgtattcg tacttcgaag gcaccaaatt ccatcaagca gcaaaagaca   4740
tggcggagat aaaggtcctg ttccctaatg accaggaaag taatgaacaa ctgtgtgcct   4800
acatattggg tgagaccatg gaagcaatcc gcgaaaagtg cccggtcgac cataacccgt   4860
cgtctagccc gcccaaaacg ttgccgtgcc tttgcatgta tgccatgacg ccagaaaggg   4920
tccacagact tagaagcaat aacgtcaaag aagttacagt atgctcctcc accccccttc   4980
ctaagcacaa aattaagaat gttcagaagg ttcagtgcac gaaagtagtc ctgtttaatc   5040
cgcacactcc cgcattcgtt cccgcccgta agtacataga agtgccagaa cagcctaccg   5100
ctcctcctgc acaggccgag gaggccccg aagttgtagc gacaccgtca ccatctacag   5160
ctgataacac ctcgcttgat gtcacagaca tctcactgga tatggatgac agtagcgaag   5220
gctcactttt ttcgagcttt agcggatcgg acaactctat tactagtatg gacagttggt   5280
cgtcaggacc tagttcacta gagatagtag accgaaggca ggtggtggtg gctgacgttc   5340
atgccgtcca agagcctgcc cctattccac cgccaaggct aaagaagatg gcccgcctgg   5400
cagcggcaag aaaagagccc actccaccgg caagcaatag ctctgagtcc ctccacctct   5460
cttttggtgg ggtatccatg tccctcggat caattttcga cggagagacg gcccgccagg   5520
cagcggtaca ccccctggca acaggcccca ggatgtgcc tatgtctttc ggatcgtttt   5580
ccgacggaga gattgatgag ctgagccgca gagtaactga gtccgaaccc gtcctgtttg   5640
```

-continued

```
gatcatttga accgggcgaa gtgaactcaa ttatatcgtc ccgatcagcc gtatcttttc    5700
cactacgcaa gcagagacgt agacgcagga gcaggaggac tgaatactga ctaaccgggg    5760
taggtgggta catattttcg acggacacag gccctgggca cttgcaaaag aagtccgttc    5820
tgcagaacca gcttacagaa ccgaccttgg agcgcaatgt cctggaaaga attcatgccc    5880
cggtgctcga cacgtcgaaa gaggaacaac tcaaactcag gtaccagatg atgcccaccg    5940
aagccaacaa agtaggtac cagtctcgta aagtagaaaa tcagaaagcc ataaccactg      6000
agcgactact gtcaggacta cgactgtata actctgccac agatcagcca gaatgctata    6060
agatcaccta tccgaaacca ttgtactcca gtagcgtacc ggcgaactac tccgatccac    6120
agttcgctgt agctgtctgt aacaactatc tgcatgagaa ctatccgaca gtagcatctt    6180
atcagattac tgacgagtac gatgcttact tggatatggt agacgggaca gtcgcctgcc    6240
tggatactgc aaccttctgc cccgctaagc ttagaagtta cccgaaaaaa catgagtata    6300
gagccccgaa tatccgcagt gcggttccat cagcgatgca gaacacgcta caaaatgtgc    6360
tcattgccgc aactaaaaga aattgcaacg tcacgcagat gcgtgaactg ccaacactgg    6420
actcagcgac attcaatgtc gaatgctttc gaaaatatgc atgtaatgac gagtattggg    6480
aggagttcgc tcggaagcca attaggatta ccactgagtt tgtcaccgca tatgtagcta    6540
gactgaaagg ccctaaggcc gccgcactat ttgcaaagac gtataatttg gtcccattgc    6600
aagaagtgcc tatggataga ttcgtcatgg acatgaaaag agacgtgaaa gttacaccag    6660
gcacgaaaca cacagaagaa agaccgaaag tacaagtgat acaagccgca gaaccctgg     6720 cgactgctta cttatgcggg attcaccggg aattagtgcg taggcttacg gccgtcttgc    6780
ttccaaacat tcacacgctt tttgacatgt cggcggagga ttttgatgca atcatagcag    6840
aacacttcaa gcaaggcgac ccggtactgg agacggatat cgcatcattc gacaaaagcc    6900
aagacgacgc tatggcgtta accggtctga tgatcttgga ggacctgggt gtggatcaac    6960
cactactcga cttgatcgag tgcgcctttg gagaaatatc atccacccat ctacctacgg    7020
gtactcgttt taaattcggg gcgatgatga atccggaat gttcctcaca cttttttgtca     7080 acacagtttt gaatgtcgtt atcgccagca gagtactaga agagcggctt aaaacgtcca    7140
gatgtgcagc gttcattggc gacgacaaca tcatacatgg agtagtatct gacaaagaaa    7200
tggctgagag gtgcgccacc tggctcaaca tggaggttaa gatcatcgac gcagtcatcg    7260
gtgagagacc accttacttc tgcggcggat ttatcttgca agattcggtt acttccacag    7320
cgtgccgcgt ggcggatccc ctgaaaaggc tgtttaagtt gggtaaaccg ctcccagccg    7380
acgacgagca agacgaagac agaagacgcg ctctgctaga tgaaacaaag gcgtggttta    7440
gagtaggtat aacaggcact ttagcagtgg ccgtgacgac ccggtatgag gtagacaata    7500
ttacacctgt cctactggca ttgagaactt ttgcccagag caaaagagca ttccaagcca    7560
tcagagggga aataaagcat ctctacggtg gtcctaaata gtcagcatag tacatttcat    7620
ctgactaata ctacaacacc accacctcta gacgcgtaga tctcacgtga gcatgcaggc    7680
cttgggccca atgatccgac cagcaaaact cgatgtactt ccgaggaact gatgtgcata    7740
atgcatcagg ctggtacatt agatccccgc ttaccgcggg caatatagca acactaaaaa    7800
ctcgatgtac ttccgaggaa gcgcagtgca taatgctgcg cagtgttgcc acataaccac    7860
tatattaacc atttatctag cggacgccaa aaactcaatg tatttctgag gaagcgtggt    7920
gcataatgcc acgcagcgtc tgcataactt ttattatttc ttttattaat caacaaaatt    7980
ttgtttttaa catttcaaaa aaaaaaaaaa aaaaaaaaaa aaaaaaaaaa aaagggaatt    8040
```

```
cctcgattaa ttaagcggcc gctcgagggg aattaattct tgaagacgaa agggccaggt    8100
ggcacttttc ggggaaatgt gcgcggaacc cctatttgtt tattttttcta aatacattca    8160 aatatgtatc cgctcatgag acaataaccc tgataaatgc ttcaataata ttgaaaaagg    8220
aagagtatga gtattcaaca tttccgtgtc gcccttattc cctttttttgc ggcattttgc    8280 cttcctgttt ttgctcaccc agaaacgctg gtgaaagtaa aagatgctga agatcagttg    8340
ggtgcacgag tgggttacat cgaactggat ctcaacagcg gtaagatcct tgagagtttt    8400
cgccccgaag aacgttttcc aatgatgagc acttttaaag ttctgctatg tggcgcggta    8460
ttatcccgtg ttgacgccgg gcaagagcaa ctcggtcgcc gcatacacta ttctcagaat    8520
gacttggttg agtactcacc agtcacagaa aagcatctta cggatggcat gacagtaaga    8580
gaattatgca gtgctgccat aaccatgagt gataacactg cggccaactt acttctgaca    8640
acgatcggag gaccgaagga gctaaccgct tttttgcaca acatggggga tcatgtaact    8700
cgccttgatc gttgggaacc ggagctgaat gaagccatac caaacgacga gcgtgacacc    8760
acgatgcctg tagcaatggc aacaacgttg cgcaaactat taactggcga actacttact    8820
ctagcttccc ggcaacaatt aatagactgg atggaggcgg ataaagttgc aggaccactt    8880
ctgcgctcgg cccttccggc tggctggttt attgctgata aatctggagc cggtgagcgt    8940
gggtctcgcg gtatcattgc agcactgggg ccagatggta agccctcccg tatcgtagtt    9000
atctacacga cggggagtca ggcaactatg gatgaacgaa atagacagat cgctgagata    9060
ggtgcctcac tgattaagca ttggtaactg tcagaccaag tttactcata tatactttag    9120
attgatttaa aacttcattt ttaatttaaa aggatctagg tgaagatcct ttttgataat    9180
ctcatgacca aaatccctta acgtgagttt tcgttccact gagcgtcaga ccccgtagaa    9240
aagatcaaag gatcttcttg agatcctttt tttctgcgcg taatctgctg cttgcaaaca    9300
aaaaaaccac cgctaccagc ggtggtttgt ttgccggatc aagagctacc aactcttttt    9360
ccgaaggtaa ctggcttcag cagagcgcag ataccaaata ctgtccttct agtgtagccg    9420
tagttaggcc accacttcaa gaactctgta gcaccgccta catacctcgc tctgctaatc    9480
ctgttaccag tggctgctgc cagtggcgat aagtcgtgtc ttaccgggtt ggactcaaga    9540
cgatagttac cggataaggc gcagcggtcg ggctgaacgg ggggttcgtg cacacagccc    9600
agcttggagc gaacgaccta caccgaactg agatacctac agcgtgagca ttgagaaagc    9660
gccacgcttc ccgaagggag aaaggcggac aggtatccgg taagcggcag ggtcggaaca    9720
ggagagcgca cgagggagct tccaggggga aacgcctggt atctttatag tcctgtcggg    9780
tttcgccacc tctgacttga gcgtcgattt ttgtgatgct cgtcaggggg gcggagccta    9840
tggaaaaacg ccagcaacgc gagctcgtat ggacatattg tcgttagaac gcggctacaa    9900
ttaatacata accttatgta tcatacacat acgatttagg ggacactata g            9951
```

<210> SEQ ID NO 4  
<211> LENGTH: 10524  
<212> TYPE: DNA  
<213> ORGANISM: Homo sapien

<400> SEQUENCE: 4

```
attgacggcg tagtacacac tattgaatca acagccgac caattgcact accatcacaa      60
tggagaagcc agtagtaaac gtagacgtag acccccagag tccgtttgtc gtgcaactgc     120
aaaaaagctt cccgcaattt gaggtagtag cacagcaggt cactccaaat gaccatgcta     180
```

-continued

```
atgccagagc attttcgcat ctggccagta aactaatcga gctggaggtt cctaccacag    240
cgacgatctt ggacataggc agcgcaccgg ctcgtagaat gttttccgag caccagtatc    300
attgtgtctg ccccatgcgt agtccagaag acccggaccg catgatgaaa tacgccagta    360
aactggcgga aaaagcgtgc aagattacaa acaagaactt gcatgagaag attaaggatc    420
tccggaccgt acttgatacg ccggatgctg aaacaccatc gctctgcttt cacaacgatg    480
ttacctgcaa catgcgtgcc gaatattccg tcatgcagga cgtgtatatc aacgctcccg    540
gaactatcta tcatcaggct atgaaaggcg tgcggaccct gtactggatt ggcttcgaca    600
ccacccagtt catgttctcg gctatggcag gttcgtaccc tgcgtacaac accaactggg    660
ccgacgagaa agtccttgaa gcgcgtaaca tcggactttg cagcacaaag ctgagtgaag    720
gtaggacagg aaaattgtcg ataatgagga agaaggagtt gaagcccggg tcgcgggttt    780
atttctccgt aggatcgaca ctttatccag aacacagagc cagcttgcag agctggcatc    840
ttccatcggt gttccacttg aatggaaagc agtcgtacac ttgccgctgt gatacagtgg    900
tgagttgcga aggctacgta gtgaagaaaa tcaccatcag tcccgggatc acggagaaa     960 ccgtgggata cgcggttaca cacaatagcg agggcttctt gctatgcaaa gttactgaca    1020
cagtaaaagg agaacgggta tcgttccctg tgtgcacgta catcccggcc accatatgcg    1080
atcagatgac tggtataatg gccacggata tatcacctga cgatgcacaa aaacttctgg    1140
ttgggctcaa ccagcgaatt gtcattaacg gtaggactaa caggaacacc aacaccatgc    1200
aaaattacct tctgccgatc atagcacaag ggttcagcaa atgggctaag gagcgcaagg    1260
atgatcttga taacgagaaa atgctgggta ctagagaacg caagcttacg tatggctgct    1320
tgtgggcgtt tcgcactaag aaagtacatt cgttttatcg cccacctgga acgcagacct    1380
gcgtaaaagt cccagcctct tttagcgctt ttcccatgtc gtccgtatgg acgacctctt    1440
tgcccatgtc gctgaggcag aaattgaaac tggcattgca accaaagaag gaggaaaaac    1500
tgctgcaggt ctcggaggaa ttagtcatgg aggccaaggc tgcttttgag gatgctcagg    1560
aggaagccag agcggagaag ctccgagaag cacttccacc attagtggca gacaaaggca    1620
tcgaggcagc cgcagaagtt gtctgcgaag tggagggget ccaggcggac atcggagcag    1680
cattagttga aacccgcgc ggtcacgtaa ggataatacc tcaagcaaat gaccgtatga    1740
tcggacagta tatcgttgtc tcgccaaact ctgtgctgaa gaatgccaaa ctcgcaccag    1800
cgcacccgct agcagatcag gttaagatca taacacactc cggaagatca ggaaggtacg    1860
cggtcgaacc atacgacgct aaagtactga tgccagcagg aggtgccgta ccatggccag    1920
aattcctagc actgagtgag agcgccacgt tagtgtacaa cgaaagagag tttgtgaacc    1980
gcaaactata ccacattgcc atgcatggcc ccgccaagaa tacagaagag gagcagtaca    2040
aggttacaaa ggcagagctt gcagaaacag agtacgtgtt tgacgtggac aagaagcgtt    2100
gcgttaagaa ggaagaagcc tcaggtctgg tcctctcggg agaactgacc aaccctccct    2160
atcatgagct agctctggag ggactgaaga cccgacctgc ggtcccgtac aaggtcgaaa    2220
caataggagt gataggcaca ccggggtcgg gcaagtcagc tattatcaag tcaactgtca    2280
cggcacgaga tcttgttacc agcggaaaga agaaaaattg tcgcgaaatt gaggccgacg    2340
tgctaagact gaggggtatg cagattacgt cgaagacagt agattcggtt atgctcaacg    2400
gatgccacaa agccgtagaa gtgctgtacg ttgacgaagc gttcgcgtgc cacgcaggag    2460
cactacttgc cttgattgct atcgtcaggc cccgcaagaa ggtagtacta tgcggagacc    2520
ccatgcaatg cggattcttc aacatgatgc aactaaaggt acatttcaat cacccctgaaa   2580
```

```
aagacatatg caccaagaca ttctacaagt atatctcccg gcgttgcaca cagccagtta   2640
cagctattgt atcgacactg cattacgatg gaaagatgaa aaccacgaac ccgtgcaaga   2700
agaacattga aatcgatatt acaggggcca caaagccgaa gccagggat atcatcctga    2760 catgtttccg cgggtgggtt aagcaattgc aaatcgacta tcccggacat gaagtaatga   2820
cagccgcggc ctcacaaggg ctaaccagaa aaggagtgta tgccgtccgg caaaaagtca   2880
atgaaaaccc actgtacgcg atcacatcag agcatgtgaa cgtgttgctc acccgcactg   2940
aggacaggct agtgtggaaa accttgcagg gcgacccatg gattaagcag cccactaaca   3000
tacctaaagg aaactttcag gctactatag aggactggga agctgaacac aagggaataa   3060
ttgctgcaat aaacagcccc actccccgtg ccaatccgtt cagctgcaag accaacgttt   3120
gctgggcgaa agcattggaa ccgatactag ccacggccgg tatcgtactt accggttgcc   3180
agtggagcga actgttccca cagtttgcgg atgacaaacc acattcggcc atttacgcct   3240
tagacgtaat ttgcattaag ttttttcggca tggacttgac aagcggactg ttttctaaac   3300
agagcatccc actaacgtac catcccgccg attcagcgag gccggtagct cattgggaca   3360
acagcccagg aacccgcaag tatgggtacg atcacgccat tgccgccgaa ctctcccgta   3420
gatttccggt gttccagcta gctgggaagg gcacacaact tgatttgcag acggggagaa   3480
ccagagttat ctctgcacag cataacctgg tcccggtgaa ccgcaatctt cctcacgcct   3540
tagtccccga gtacaaggag aagcaacccg gcccggtcaa aaaattcttg aaccagttca   3600
aacaccactc agtacttgtg gtatcagagg aaaaaattga agctcccccgt aagagaatcg   3660 aatggatcgc cccgattggc atagccggtg cagataagaa ctacaacctg gctttcgggt   3720
ttccgccgca ggcacggtac gacctggtgt tcatcaacat tggaactaaa tacagaaacc   3780
accactttca gcagtgcgaa gaccatgcgg cgaccttaaa aacccttcg cgttcggccc   3840 tgaattgcct taacccagga ggcaccctcg tggtgaagtc ctatggctac gccgaccgca   3900
acagtgagga cgtagtcacc gctcttgcca gaaagtttgt cagggtgtct gcagcgagac   3960
cagattgtgt ctcaagcaat acagaaatgt acctgatttt ccgacaacta gacaacagcc   4020
gtacacggca attcaccccg caccatctga attgcgtgat ttcgtccgtg tatgagggta   4080
caagagatgg agttggagcc gcgccgtcat accgcaccaa aagggagaat attgctgact   4140
gtcaagagga agcagttgtc aacgcagcca atccgctggg tagaccaggc gaaggagtct   4200
gccgtgccat ctataaacgt tggccgacca gttttaccga ttcagccacg gagacaggca   4260
ccgcaagaat gactgtgtgc ctaggaaaga aagtgatcca cgcggtcggc cctgatttcc   4320
ggaagcaccc agaagcagaa gccttgaaat tgctacaaaa cgcctaccat gcagtggcag   4380
acttagtaaa tgaacataac atcaagtctg tcgccattcc actgctatct acaggcattt   4440
acgcagccgg aaaagaccgc cttgaagtat cacttaactg cttgacaacc gcgctagaca   4500
gaactgacgc ggacgtaacc atctattgcc tggataagaa gtggaaggaa agaatcgacg   4560
cggcactcca acttaaggag tctgtaacag agctgaagga tgaagatatg gagatcgacg   4620
atgagttagt atggattcat ccagacagtt gcttgaaggg aagaaaggga ttcagtacta   4680
caaaaggaaa attgtattcg tacttcgaag gcaccaaatt ccatcaagca gcaaaagaca   4740
tggcggagat aaaggtcctg ttccctaatg accaggaaag taatgaacaa ctgtgtgcct   4800
acatattggg tgagaccatg gaagcaatcc gcgaaaagtg cccggtcgac cataacccgt   4860
cgtctagccc gcccaaaacg ttgccgtgcc tttgcatgta tgccatgacg ccagaaaggg   4920
```

```
tccacagact tagaagcaat aacgtcaaag aagttacagt atgctcctcc accccccttc    4980
ctaagcacaa aattaagaat gttcagaagg ttcagtgcac gaaagtagtc ctgtttaatc    5040
cgcacactcc cgcattcgtt cccgcccgta agtacataga agtgccagaa cagcctaccg    5100
ctcctcctgc acaggccgag gaggcccccg aagttgtagc gacaccgtca ccatctacag    5160 ctgataaacac ctcgcttgat gtcacagaca tctcactgga tatggatgac agtagcgaag    5220
gctcactttt ttcgagcttt agcggatcgg acaactctat tactagtatg gacagttggt    5280
cgtcaggacc tagttcacta gagatagtag accgaaggca ggtggtggtg gctgacgttc    5340
atgccgtcca agagcctgcc cctattccac cgccaaggct aaagaagatg gcccgcctgg    5400
cagcggcaag aaaagagccc actccaccgg caagcaatag ctctgagtcc ctccacctct    5460
cttttggtgg ggtatccatg tccctcggat caattttcga cggagagacg gcccgccagg    5520
cagcggtaca acccctggca acaggcccca cggatgtgcc tatgtctttc ggatcgtttt    5580
ccgacggaga gattgatgag ctgagccgca gagtaactga gtccgaaccc gtcctgtttg    5640
gatcatttga accgggcgaa gtgaactcaa ttatatcgtc ccgatcagcc gtatcttttc    5700
cactacgcaa gcagagacgt agacgcagga gcaggaggac tgaatactga ctaaccgggg    5760
taggtgggta catattttcg acggacacag gccctgggca cttgcaaaag aagtccgttc    5820
tgcagaacca gcttacagaa ccgaccttgg agcgcaatgt cctggaaaga attcatgccc    5880
cggtgctcga cacgtcgaaa gaggaacaac tcaaactcag gtaccagatg atgcccaccg    5940
aagccaacaa aagtaggtac cagtctcgta agtagaaaa tcagaaagcc ataaccactg    6000
agcgactact gtcaggacta cgactgtata actctgccac agatcagcca gaatgctata    6060
agatcaccta tccgaaacca ttgtactcca gtagcgtacc ggcgaactac tccgatccac    6120
agttcgctgt agctgtctgt aacaactatc tgcatgagaa ctatccgaca gtagcatctt    6180
atcagattac tgacgagtac gatgcttact ggatatggt agacgggaca gtcgcctgcc    6240
tggatactgc aaccttctgc cccgctaagc ttagaagtta cccgaaaaaa catgagtata    6300
gagccccgaa tatccgcagt gcggttccat cagcgatgca gaacacgcta caaaatgtgc    6360
tcattgccgc aactaaaaga aattgcaacg tcacgcagat gcgtgaactg ccaacactgg    6420
actcagcgac attcaatgtc gaatgctttc gaaaatatgc atgtaatgac gagtattggg    6480
aggagttcgc tcggaagcca attaggatta ccactgagtt tgtcaccgca tatgtagcta    6540
gactgaaagg ccctaaggcc gccgcactat ttgcaaagac gtataatttg gtcccattgc    6600
aagaagtgcc tatggataga ttcgtcatgg acatgaaaag agacgtgaaa gttacaccag    6660
gcacgaaaca cacagaagaa agaccgaaag tacaagtgat acaagccgca gaaccccctgg    6720 cgactgctta cttatgcggg attcaccggg aattagtgcg taggcttacg gccgtcttgc    6780
ttccaaacat tcacacgctt tttgacatgt cggcggagga ttttgatgca atcatagcag    6840
aacacttcaa gcaaggcgac ccggtactgg agacggatat cgcatcattc gacaaaagcc    6900
aagacgacgc tatggcgtta accggtctga tgatcttgga ggacctgggt gtggatcaac    6960
cactactcga cttgatcgag tgcgcctttg gagaaatatc atccacccat ctacctacgg    7020
gtactcgttt taaattcggg gcgatgatga atccggaat gttcctcaca ctttttgtca    7080
acacagtttt gaatgtcgtt atcgccagca gagtactaga agagcggctt aaaacgtcca    7140
gatgtgcagc gttcattggc gacgacaaca tcatacatgg agtagtatct gacaaagaaa    7200
tggctgagag gtgcgccacc tggctcaaca tggaggttaa gatcatcgac gcagtcatcg    7260
gtgagagacc accttacttc tgcggcggat ttatcttgca agattcggtt acttccacag    7320
```

```
cgtgccgcgt ggcggatccc ctgaaaaggc tgtttaagtt gggtaaaccg ctcccagccg    7380
acgacgagca agacgaagac agaagacgcg ctctgctaga tgaaacaaag gcgtggttta    7440
gagtaggtat aacaggcact ttagcagtgg ccgtgacgac ccggtatgag gtagacaata    7500
ttacacctgt cctactggca ttgagaactt tgcccagag caaagagca ttccaagcca    7560 tcagagggga aataaagcat ctctacggtg gtcctaaata gtcagcatag tacatttcat    7620
ctgactaata ctacaacacc accacctcta gaggcgcgga gatggggtg cacgaatgtc    7680 ctgcctggct gtggcttctc ctgtccctgc tgtcgctccc tctgggcctc ccagtcctgg    7740
gcgccccacc acgcctcatc tgtgacagcc gagtcctgga gaggtacctc ttggaggcca    7800
aggaggccga gaatatcacg acgggctgtg ctgaacactg cagcttgaat gagaatatca    7860
ctgtcccaga caccaaagtt aatttctatg cctggaagag gatggaggtc gggcagcagg    7920
ccgtagaagt ctggcagggc ctggccctgc tgtcggaagc tgtcctgcgg ggccaggccc    7980
tgttggtcaa ctcttcccag ccgtgggagc ccctgcagct gcatgtggat aaagccgtca    8040
gtggccttcg cagcctcacc actctgcttc gggctctggg agcccagaag gaagccatct    8100
cccctccaga tgcggcctca gctgctccac tccgaacaat cactgctgac actttccgca    8160
aactcttccg agtctactcc aatttcctcc ggggaaagct gaagctgtac acaggggagg    8220
cctgcaggac aggggacaga tgagcatgca ggccttgggc ccaatgatcc gaccagcaaa    8280
actcgatgta cttccgagga actgatgtgc ataatgcatc aggctggtac attagatccc    8340
cgcttaccgc gggcaatata gcaacactaa aaactcgatg tacttccgag gaagcgcagt    8400
gcataatgct gcgcagtgtt gccacataac cactatatta accatttatc tagcggacgc    8460
caaaaactca atgtatttct gaggaagcgt ggtgcataat gccacgcagc gtctgcataa    8520
cttttattat ttcttttatt aatcaacaaa attttgtttt taacatttca aaaaaaaaa    8580 aaaaaaaaaa aaaaaaaaa aaaaaggga attcctcgat taattaagcg gccgctcgag    8640
gggaattaat tcttgaagac gaaagggcca ggtggcactt tcggggaaa tgtgcgcgga    8700 acccctattt gtttatttt ctaaatacat tcaaatatgt atccgctcat gagacaataa    8760
ccctgataaa tgcttcaata atattgaaaa aggaagagta tgagtattca acatttccgt    8820 gtcgcccta ttcccttttt tgcggcattt tgccttcctg ttttgctca cccagaaacg    8880 ctggtgaaag taaaagatgc tgaagatcag ttgggtgcac gagtgggtta catcgaactg    8940
gatctcaaca gcggtaagat ccttgagagt tttcgccccg aagaacgttt tccaatgatg    9000
agcactttta aagttctgct atgtggcgcg gtattatccc gtgttgacgc cgggcaagag    9060
caactcggtc gccgcataca ctattctcag aatgacttgg ttgagtactc accagtcaca    9120
gaaaagcatc ttacggatgg catgacagta agagaattat gcagtgctgc cataaccatg    9180
agtgataaca ctgcggccaa cttacttctg acaacgatcg gaggaccgaa ggagctaacc    9240
gcttttttgc acaacatggg ggatcatgta actcgccttg atcgttggga accggagctg    9300
aatgaagcca taccaaacga cgagcgtgac accacgatgc ctgtagcaat ggcaacaacg    9360
ttgcgcaaac tattaactgg cgaactactt actctagctt cccggcaaca attaatagac    9420
tggatggagg cggataaagt tgcaggacca cttctgcgct cggcccttcc ggctggctgg    9480
tttattgctg ataaatctgg agccggtgag cgtgggtctc gcggtatcat tgcagcactg    9540
gggccagatg gtaagccctc ccgtatcgta gttatctaca cgacggggag tcaggcaact    9600
atggatgaac gaaatagaca gatcgctgag ataggtgcct cactgattaa gcattggtaa    9660
```

-continued

| | |
|---|---|
| ctgtcagacc aagtttactc atatatactt tagattgatt taaaacttca tttttaattt | 9720 |
| aaaaggatct aggtgaagat ccttttttgat aatctcatga ccaaaatccc ttaacgtgag | 9780 |
| ttttcgttcc actgagcgtc agaccccgta gaaaagatca aaggatcttc ttgagatcct | 9840 |
| ttttttctgc gcgtaatctg ctgcttgcaa acaaaaaaac caccgctacc agcggtggtt | 9900 |
| tgtttgccgg atcaagagct accaactctt tttccgaagg taactggctt cagcagagcg | 9960 |
| cagataccaa atactgtcct tctagtgtag ccgtagttag gccaccactt caagaactct | 10020 |
| gtagcaccgc ctacatacct cgctctgcta atcctgttac cagtggctgc tgccagtggc | 10080 |
| gataagtcgt gtcttaccgg gttggactca agacgatagt taccggataa ggcgcagcgg | 10140 |
| tcgggctgaa cggggggttc gtgcacacag cccagcttgg agcgaacgac ctacaccgaa | 10200 |
| ctgagatacc tacagcgtga gcattgagaa agcgccacgc ttcccgaagg gagaaaggcg | 10260 |
| gacaggtatc cggtaagcgg cagggtcgga acaggagagc gcacgaggga gcttccaggg | 10320 |
| ggaaacgcct ggtatcttta tagtcctgtc gggtttcgcc acctctgact tgagcgtcga | 10380 |
| tttttgtgat gctcgtcagg ggggcggagc ctatggaaaa acgccagcaa cgcgagctcg | 10440 |
| tatggacata ttgtcgttag aacgcggcta caattaatac ataaccttat gtatcataca | 10500 |
| catacgattt aggggacact atag | 10524 |

<210> SEQ ID NO 5
<211> LENGTH: 11927
<212> TYPE: DNA
<213> ORGANISM: Homo sapien

<400> SEQUENCE: 5

| | |
|---|---|
| attgacggcg tagtacacac tattgaatca aacagccgac caattgcact accatcacaa | 60 |
| tggagaagcc agtagtaaac gtagacgtag accccccagag tccgtttgtc gtgcaactgc | 120 |
| aaaaaagctt cccgcaattt gaggtagtag cacagcaggt cactccaaat gaccatgcta | 180 |
| atgccagagc atttttcgcat ctggccagta aactaatcga gctggaggtt cctaccacag | 240 |
| cgacgatctt ggacataggc agcgcaccgg ctcgtagaat gttttccgag caccagtatc | 300 |
| attgtgtctg ccccatgcgt agtccagaag acccggaccg catgatgaaa tacgccagta | 360 |
| aactggcgga aaagcgtgc aagattacaa acaagaactt gcatgagaag attaaggatc | 420 |
| tccggaccgt acttgatacg ccggatgctg aaacaccatc gctctgcttt cacaacgatg | 480 |
| ttacctgcaa catgcgtgcc gaatattccg tcatgcagga cgtgtatatc aacgctcccg | 540 |
| gaactatcta tcatcaggct atgaaaggcg tgcggaccct gtactggatt ggcttcgaca | 600 |
| ccacccagtt catgttctcg gctatggcag gttcgtaccc tgcgtacaac accaactggg | 660 |
| ccgacgagaa agtccttgaa gcgcgtaaca tcggactttg cagcacaaag ctgagtgaag | 720 |
| gtaggacagg aaaattgtcg ataatgagga agaaggagtt gaagcccggg tcgcgggttt | 780 |
| atttctccgt aggatcgaca ctttatccag aacacagagc cagcttgcag agctggcatc | 840 |
| ttccatcggt gttccacttg aatggaaagc agtcgtacac ttgccgctgt gatacagtgg | 900 |
| tgagttgcga aggctacgta gtgaagaaaa tcaccatcag tcccgggatc acgggagaaa | 960 |
| ccgtgggata cgcggttaca cacaatagcg agggcttctt gctatgcaaa gttactgaca | 1020 |
| cagtaaaagg agaacgggta tcgttccctg tgtgcacgta catcccggcc accatatgcg | 1080 |
| atcagatgac tggtataatg gccacggata tatcacctga cgatgcacaa aaacttctgg | 1140 |
| ttgggctcaa ccagcgaatt gtcattaacg gtaggactaa caggaacacc aacaccatgc | 1200 |
| aaaattacct tctgccgatc atagcacaag ggttcagcaa atgggctaag gagcgcaagg | 1260 |

```
atgatcttga taacgagaaa atgctgggta ctagagaacg caagcttacg tatggctgct    1320
tgtgggcgtt tcgcactaag aaagtacatt cgttttatcg cccacctgga acgcagacct    1380
gcgtaaaagt cccagcctct tttagcgctt ttcccatgtc gtccgtatgg acgacctctt    1440
tgcccatgtc gctgaggcag aaattgaaac tggcattgca accaaagaag gaggaaaaac    1500
tgctgcaggt ctcggaggaa ttagtcatgg aggccaaggc tgcttttgag gatgctcagg    1560
aggaagccag agcggagaag ctccgagaag cacttccacc attagtggca gacaaaggca    1620
tcgaggcagc cgcagaagtt gtctgcgaag tggaggggct ccaggcggac atcggagcag    1680
cattagttga accccgcgc ggtcacgtaa ggataatacc tcaagcaaat gaccgtatga    1740
tcggacagta tatcgttgtc tcgccaaact ctgtgctgaa gaatgccaaa ctcgcaccag    1800
cgcacccgct agcagatcag gttaagatca taacacactc cggaagatca ggaaggtacg    1860
cggtcgaacc atacgacgct aaagtactga tgccagcagg aggtgccgta ccatggccag    1920
aattcctagc actgagtgag agcgccacgt tagtgtacaa cgaaagagag tttgtgaacc    1980
gcaaactata ccacattgcc atgcatggcc ccgccaagaa tacagaagag gagcagtaca    2040
aggttacaaa ggcagagctt gcagaaacag agtacgtgtt tgacgtggac aagaagcgtt    2100
gcgttaagaa ggaagaagcc tcaggtctgg tcctctcggg agaactgacc aaccctccct    2160
atcatgagct agctctggag ggactgaaga cccgacctgc ggtcccgtac aaggtcgaaa    2220
caataggagt gataggcaca ccggggtcgg gcaagtcagc tattatcaag tcaactgtca    2280
cggcacgaga tcttgttacc agcggaaaga agaaaaattg tcgcgaaatt gaggccgacg    2340
tgctaagact gagggggtatg cagattacgt cgaagacagt agattcggtt atgctcaacg    2400
gatgccacaa agccgtagaa gtgctgtacg ttgacgaagc gttcgcgtgc cacgcaggag    2460
cactacttgc cttgattgct atcgtcaggc ccgcaagaa ggtagtacta tgcggagacc    2520
ccatgcaatg cggattcttc aacatgatgc aactaaaggt acatttcaat caccctgaaa    2580
aagacatatg caccaagaca ttctacaagt atatctcccg gcgttgcaca cagccagtta    2640
cagctattgt atcgacactg cattacgatg aaagatgaa aaccacgaac ccgtgcaaga    2700
agaacattga aatcgatatt acaggggcca caaagccgaa gccagggat atcatcctga    2760 catgtttccg cggtgggtt aagcaattgc aaatcgacta tcccgacat gaagtaatga    2820 cagccgcggc ctcacaaggg ctaaccagaa aaggagtgta tgccgtccgg caaaaagtca    2880
atgaaaaccc actgtacgcg atcacatcag agcatgtgaa cgtgttgctc acccgcactg    2940
aggacaggct agtgtggaaa accttgcagg gcgacccatg gattaagcag cccactaaca    3000
tacctaaagg aaactttcag gctactatag aggactggga agctgaacac aagggaataa    3060
ttgctgcaat aaacagcccc actccccgtg ccaatccgtt cagctgcaag accaacgttt    3120
gctgggcgaa agcattggaa ccgatactag ccacggccgg tatcgtactt accggttgcc    3180
agtggagcga actgttccca cagtttgcgg atgacaaacc acattcggcc atttacgcct    3240
tagacgtaat ttgcattaag ttttttcggca tggacttgac aagcggactg ttttctaaac    3300
agagcatccc actaacgtac catcccgccg attcagcgag gccggtagct cattgggaca    3360
acagcccagg aacccgcaag tatgggtacg atcacgccat tgccgccgaa ctctcccgta    3420
gatttccggt gttccagcta gctgggaagg gcacacaact tgatttgcag acggggagaa    3480
ccagagttat tctgcacag cataacctgg tcccggtgaa ccgcaatctt cctcacgcct    3540 tagtcccga gtacaaggag aagcaacccg gcccggtcaa aaaattcttg aaccagttca    3600
aacaccactc agtacttgtg gtatcagagg aaaaaattga agctccccgt aagagaatcg    3660
```

-continued

```
aatggatcgc cccgattggc atagccggtg cagataagaa ctacaacctg gctttcgggt    3720
ttccgccgca ggcacggtac gacctggtgt tcatcaacat tggaactaaa tacagaaacc    3780
accactttca gcagtgcgaa gaccatgcgg cgaccttaaa aacccttttcg cgttcggccc   3840
tgaattgcct taacccagga ggcaccctcg tggtgaagtc ctatggctac gccgaccgca    3900
acagtgagga cgtagtcacc gctcttgcca gaaagtttgt cagggtgtct gcagcgagac    3960
cagattgtgt ctcaagcaat acagaaatgt acctgatttt ccgacaacta gacaacagcc    4020
gtacacggca attcaccccg caccatctga attgcgtgat ttcgtccgtg tatgagggta    4080
caagagatgg agttggagcc gcgccgtcat accgcaccaa aagggagaat attgctgact    4140
gtcaagagga agcagttgtc aacgcagcca atccgctggg tagaccaggc gaaggagtct    4200
gccgtgccat ctataaacgt tggccgacca gttttaccga ttcagccacg gagacaggca    4260
ccgcaagaat gactgtgtgc ctaggaaaga aagtgatcca cgcggtcggc cctgatttcc    4320
ggaagcaccc agaagcagaa gccttgaaat tgctacaaaa cgcctaccat gcagtggcag    4380
acttagtaaa tgaacataac atcaagtctg tcgccattcc actgctatct acaggcattt    4440
acgcagccgg aaaagaccgc cttgaagtat cacttaactg cttgacaacc gcgctagaca    4500
gaactgacgc ggacgtaacc atctattgcc tggataagaa gtggaaggaa agaatcgacg    4560
cggcactcca acttaaggag tctgtaacag agctgaagga tgaagatatg gagatcgacg    4620
atgagttagt atggattcat ccagacagtt gcttgaaggg aagaaaggga ttcagtacta    4680
caaaaggaaa attgtattcg tacttcgaag gcaccaaatt ccatcaagca gcaaaagaca    4740
tggcggagat aaaggtcctg ttccctaatg accaggaaag taatgaacaa ctgtgtgcct    4800
acatattggg tgagaccatg gaagcaatcc gcgaaaagtg cccggtcgac cataacccgt    4860
cgtctagccc gcccaaaacg ttgccgtgcc tttgcatgta tgccatgacg ccagaaaggg    4920
tccacagact tagaagcaat aacgtcaaag aagttacagt atgctcctcc accccccttc    4980
ctaagcacaa aattaagaat gttcagaagg ttcagtgcac gaaagtagtc ctgtttaatc    5040
cgcacactcc cgcattcgtt cccgcccgta agtacataga agtgccagaa cagcctaccg    5100
ctcctcctgc acaggccgag gaggcccccg aagttgtagc gacaccgtca ccatctacag    5160
ctgataacac ctcgcttgat gtcacagaca tctcactgga tatggatgac agtagcgaag    5220
gctcactttt ttcgagcttt agcggatcgg acaactctat tactagtatg gacagttggt    5280
cgtcaggacc tagttcacta gagatagtag accgaaggca ggtggtggtg gctgacgttc    5340
atgccgtcca agagcctgcc cctattccac cgccaaggct aaagaagatg gcccgcctgg    5400
cagcggcaag aaaagagccc actccaccgg caagcaatag ctctgagtcc ctccacctct    5460
cttttggtgg ggtatccatg tccctcggat caattttcga cggagagacg gcccgccagg    5520
cagcggtaca acccctggca acaggcccca cggatgtgcc tatgtctttc ggatcgtttt    5580
ccgacggaga gattgatgag ctgagccgca gagtaactga gtccgaaccc gtcctgtttg    5640
gatcatttga accgggcgaa gtgaactcaa ttatatcgtc ccgatcagcc gtatcttttc    5700
cactacgcaa gcagagacgt agacgcagga gcaggaggac tgaatactga ctaaccgggg    5760
taggtgggta catattttcg acggacacag gccctgggca cttgcaaaag aagtccgttc    5820
tgcagaacca gcttacagaa ccgaccttgg agcgcaatgt cctggaaaga attcatgccc    5880
cggtgctcga cacgtcgaaa gaggaacaac tcaaactcag gtaccagatg atgcccaccg    5940
aagccaacaa aagtaggtac cagtctcgta aagtagaaaa tcagaaagcc ataaccactg    6000
```

```
agcgactact gtcaggacta cgactgtata actctgccac agatcagcca gaatgctata   6060
agatcaccta tccgaaacca ttgtactcca gtagcgtacc ggcgaactac tccgatccac   6120
agttcgctgt agctgtctgt aacaactatc tgcatgagaa ctatccgaca gtagcatctt   6180
atcagattac tgacgagtac gatgcttact ggatatggt agacgggaca gtcgcctgcc    6240
tggatactgc aaccttctgc cccgctaagc ttagaagtta cccgaaaaaa catgagtata   6300
gagccccgaa tatccgcagt gcggttccat cagcgatgca gaacacgcta caaaatgtgc   6360
tcattgccgc aactaaaaga aattgcaacg tcacgcagat gcgtgaactg ccaacactgg   6420
actcagcgac attcaatgtc gaatgctttc gaaaatatgc atgtaatgac gagtattggg   6480
aggagttcgc tcggaagcca attaggatta ccactgagtt tgtcaccgca tatgtagcta   6540
gactgaaagg ccctaaggcc gccgcactat ttgcaaagac gtataatttg gtcccattgc   6600
aagaagtgcc tatggataga ttcgtcatgg acatgaaaag agacgtgaaa gttacaccag   6660
gcacgaaaca cacagaagaa agaccgaaag tacaagtgat acaagccgca gaaccctgg    6720 cgactgctta cttatgcggg attcaccggg aattagtgcg taggcttacg gccgtcttgc   6780
ttccaaacat tcacacgctt tttgacatgt cggcggagga ttttgatgca atcatagcag   6840
aacacttcaa gcaaggcgac ccggtactgg agacggatat cgcatcattc gacaaaagcc   6900
aagacgacgc tatggcgtta accggtctga tgatcttgga ggacctgggt gtggatcaac   6960
cactactcga cttgatcgag tgcgcctttg gagaaatatc atccacccat ctacctacgg   7020
gtactcgttt taaattcggg gcgatgatga atccggaat gttcctcaca cttttgtca    7080 acacagtttt gaatgtcgtt atcgccagca gagtactaga agagcggctt aaaacgtcca   7140
gatgtgcagc gttcattggc gacgacaaca tcatacatgg agtagtatct gacaaagaaa   7200
tggctgagag gtgcgccacc tggctcaaca tggaggttaa gatcatcgac gcagtcatcg   7260
gtgagagacc accttacttc tgcggcggat ttatcttgca agattcggtt acttccacag   7320
cgtgccgcgt ggcggatccc ctgaaaaggc tgtttaagtt gggtaaaccg ctcccagccg   7380
acgacgagca agacgaagac agaagacgcg ctctgctaga tgaaacaaag gcgtggttta   7440
gagtaggtat aacaggcact ttagcagtgg ccgtgacgac ccggtatgag gtagacaata   7500
ttacacctgt cctactggca ttgagaactt ttgcccagag caaaagagca ttccaagcca   7560
tcagagggga aataaagcat ctctacggtg gtcctaaata gtcagcatag tacatttcat   7620
ctgactaata ctacaacacc accctcta gatcagcccg ccgggctcc gaggcgagag      7680 gctgcatgga gtggccggcg cggctctgcg ggctgtgggc gctgctgctc tgcgccggcg   7740 gcggggcgg gggcggggc gccgcgccta cggaaactca gccacctgtg acaaatttga     7800
gtgtctctgt tgaaaacctc tgcacagtaa tatggacatg aatccaccc gagggagcca    7860 gctcaaattg tagtctatgg tattttagtc attttggcga caaacaagat aagaaaatag   7920
ctccggaaac tcgtcgttca atagaagtac ccctgaatga gaggatttgt ctgcaagtgg   7980
ggtcccagtg tagcaccaat gagagtgaga agcctagcat tttggttgaa aaatgcatct   8040
cacccccaga aggtgatcct gagtctgctg tgactgagct tcaatgcatt tggcacaacc   8100
tgagctacat gaagtgttct tggctcccctg gaaggaatac cagtcccgac actaactata   8160
ctctctacta ttggcacaga agcctggaaa aaattcatca atgtgaaaac atctttagag   8220
aaggccaata ctttggttgt tccttttgatc tgaccaaagt gaaggattcc agttttgaac   8280
aacacagtgt ccaaataatg gtcaaggata atgcaggaaa aattaaacca tccttcaata   8340
tagtgccttt aacttcccgt gtgaaacctg atcctccaca tattaaaaac ctctccttcc   8400
```

```
acaatgatga cctatatgtg caatgggaga atccacagaa ttttattagc agatgcctat   8460
tttatgaagt agaagtcaat aacagccaaa ctgagacaca taatgttttc tacgtccaag   8520
aggctaaatg tgagaatcca gaatttgaga gaaatgtgga gaatacatct tgtttcatgg   8580
tccctggtgt tcttcctgat actttgaaca cagtcagaat aagagtcaaa acaaataagt   8640
tatgctatga ggatgacaaa ctctggagta attggagcca agaaatgagt ataggtaaga   8700
agcgcaattc cacactctac ataaccatgt tactcattgt tccagtcatc gtcgcaggtg   8760
caatcatagt actcctgctt tacctaaaaa ggctcaagat tattatattc cctccaattc   8820
ctgatcctgg caagattttt aaagaaatgt ttggagacca gaatgatgat actctgcact   8880
ggaagaagta cgacatctat gagaagcaaa ccaaggagga accgactct gtagtgctga   8940 tagaaaacct gaagaaagcc tctcagtgat ggagataatt tattttttacc ttcactgtga   9000 ccttgagaag attcttccca ttctccattt gttatctggg aacttattaa atggaaactg   9060
aaactactgc accatttaaa acaggcagc tcataagagc cacaggtctt tatgttgagt   9120
cgcgcaccga aaaactaaaa ataatgggcg ctttggagaa gagtgtggag tcattctcat   9180
tgaattataa aagccagcag gcttcaaact aggggacaaa gcaaaaagtg atgatagtgg   9240
tggagttaat cttatcaaga gttgtgacaa cttcctgagg gatctatact tgctttgtgt   9300
tctttgtgtc aacatgaaca aattttattt gtaggggaac tcatttgggg tgcaaatgct   9360
aatgtcaaac ttgagtcaca aagaacatgt agaaaacaaa atggataaaa tctgatatgt   9420
attgtttggg atcctattga accatgtttg tggctattaa aactctttta acagtctggg   9480
ctgggtccgg tggctcacgc ctgtaatccc agcaatttgg gagtccgagg cgggcggatc   9540
actcgagctg caggcatgca agcttggcac tggccgtcgt tttacaacgt cgtgactggg   9600
aaaaccctgg cgttacccaa cttaatcgcc ttgcagcaca tcccccttc gccagccttg   9660 ggcccaatga tccgaccagc aaaactcgat gtacttccga ggaactgatg tgcataatgc   9720
atcaggctgg tacattagat ccccgcttac cgcgggcaat atagcaacac taaaaactcg   9780
atgtacttcc gaggaagcgc agtgcataat gctgcgcagt gttgccacat aaccactata   9840
ttaaccattt atctagcgga cgccaaaaac tcaatgtatt tctgaggaag cgtggtgcat   9900
aatgccacgc agcgtctgca taactttat tatttctttt attaatcaac aaaattttgt   9960
ttttaacatt tcaaaaaaaa aaaaaaaaa aaaaaaaaa aaaaaaaag ggaattcctc   10020 gattaattaa gcggccgctc gagggggaatt aattcttgaa gacgaaaggg ccaggtggca   10080
cttttcgggg aaatgtgcgc ggaaccccta tttgtttatt tttctaaata cattcaaata   10140
tgtatccgct catgagacaa taaccctgat aaatgcttca ataatattga aaaggaaga   10200 gtatgagtat tcaacatttc cgtgtcgccc ttattccctt ttttgcggca ttttgccttc   10260 ctgttttttgc tcacccagaa acgctggtga agtaaaaga tgctgaagat cagttgggtg   10320
cacgagtggg ttacatcgaa ctggatctca acagcggtaa gatccttgag agttttcgcc   10380
ccgaagaacg ttttccaatg atgagcactt ttaaagttct gctatgtggc gcggtattat   10440
cccgtgttga cgccgggcaa gagcaactcg gtcgccgcat acactattct cagaatgact   10500
tggttgagta ctcaccagtc acagaaaagc atcttacgga tggcatgaca gtaagagaat   10560
tatgcagtgc tgccataacc atgagtgata acactgcggc caacttactt ctgacaacga   10620
tcggaggacc gaaggagcta accgcttttt tgcacaacat ggggggatcat gtaactcgcc   10680 ttgatcgttg ggaaccggag ctgaatgaag ccataccaaa cgacgagcgt gacaccacga   10740
```

-continued

```
tgcctgtagc aatggcaaca acgttgcgca aactattaac tggcgaacta cttactctag    10800
cttcccggca acaattaata gactggatgg aggcggataa agttgcagga ccacttctgc    10860
gctcggccct tccggctggc tggtttattg ctgataaatc tggagccggt gagcgtgggt    10920
ctcgcggtat cattgcagca ctggggccag atggtaagcc ctcccgtatc gtagttatct    10980
acacgacggg gagtcaggca actatggatg aacgaaatag acagatcgct gagataggtg    11040
cctcactgat taagcattgg taactgtcag accaagttta ctcatatata ctttagattg    11100
atttaaaact tcatttttaa tttaaaagga tctaggtgaa gatccttttt gataatctca    11160
tgaccaaaat cccttaacgt gagttttcgt tccactgagc gtcagacccc gtagaaaaga    11220
tcaaaggatc ttcttgagat cctttttttc tgcgcgtaat ctgctgcttg caaacaaaaa    11280
aaccaccgct accagcggtg gtttgtttgc cggatcaaga gctaccaact cttttccga    11340 aggtaactgg cttcagcaga gcgcagatac caaatactgt ccttctagtg tagccgtagt    11400
taggccacca cttcaagaac tctgtagcac cgcctacata cctcgctctg ctaatcctgt    11460
taccagtggc tgctgccagt ggcgataagt cgtgtcttac cgggttggac tcaagacgat    11520
agttaccgga taaggcgcag cggtcgggct gaacgggggg ttcgtgcaca cagcccagct    11580
tggagcgaac gacctacacc gaactgagat acctacagcg tgagcattga gaaagcgcca    11640
cgcttcccga agggagaaag gcggacaggt atccggtaag cggcagggtc ggaacaggag    11700
agcgcacgag ggagcttcca gggggaaacg cctggtatct ttatagtcct gtcgggtttc    11760
gccacctctg acttgagcgt cgatttttgt gatgctcgtc aggggggcgg agcctatgga    11820
aaaacgccag caacgcgagc tcgtatggac atattgtcgt tagaacgcgg ctacaattaa    11880
tacataacct tatgtatcat acacatacga tttaggggac actatag          11927
```

<210> SEQ ID NO 6
<211> LENGTH: 7970
<212> TYPE: DNA
<213> ORGANISM: Alphavirus, Sindbis Virus

<400> SEQUENCE: 6

```
ggatatagtg gtgagtatcc ccgcctgtca cgcgggagac cggggttcgg ttccccgacg      60
gggagccaaa cagccgacca attgcactac catcacaatg gagaagccag tagtaaacgt     120
agacgtagac ccccagagtc cgtttgtcgt gcaactgcaa aaaagcttcc cgcaatttga     180
ggtagtagca cagcaggtca ctccaaatga ccatgctaat gccagagcat tttcgcatct     240
ggccagtaaa ctaatcgagc tggaggttcc taccacagcg acgatcttgg acataggcag     300
cgcaccggct cgtagaatgt tttccgagca ccagtatcat tgtgtctgcc ccatgcgtag     360
tccagaagac ccggaccgca tgatgaaata cgccagtaaa ctggcggaaa agcgtgcaa     420 gattacaaac aagaacttgc atgagaagat taaggatctc cggaccgtac ttgatacgcc     480
ggatgctgaa acaccatcgc tctgctttca caacgatgtt acctgcaaca tgcgtgccga     540
atattccgtc atgcaggacg tgtatatcaa cgctcccgga actatctatc atcaggctat     600
gaaaggcgtg cggaccctgt actggattgg cttcgacacc acccagttca tgttctcggc     660
tatggcaggt tcgtaccctg cgtacaacac caactgggcc gacgagaaag tccttgaagc     720
gcgtaacatc ggactttgca gcacaaagct gagtgaaggt aggacaggaa aattgtcgat     780
aatgaggaag aaggagttga agcccggggtc gcgggtttat ttctccgtag gatcgacact     840
ttatccagaa cacagagcca gcttgcagag ctggcatctt ccatcggtgt tccacttgaa     900
tggaaagcag tcgtacactt gccgctgtga tacagtggtg agttgcgaag gctacgtagt     960
```

```
gaagaaaatc accatcagtc ccgggatcac gggagaaacc gtgggatacg cggttacaca   1020
caatagcgag ggcttcttgc tatgcaaagt tactgacaca gtaaaaggag aacgggtatc   1080
gttccctgtg tgcacgtaca tcccggccac catatgcgat cagatgactg gtataatggc   1140
cacggatata tcacctgacg atgcacaaaa acttctggtt gggctcaacc agcgaattgt   1200
cattaacggt aggactaaca ggaacaccaa caccatgcaa aattaccttc tgccgatcat   1260
agcacaaggg ttcagcaaat gggctaagga gcgcaaggat gatcttgata cgagaaaat   1320 gctgggtact agagaacgca agcttacgta tggctgcttg tgggcgtttc gcactaagaa   1380
agtacattcg ttttatcgcc cacctggaac gcagacctgc gtaaaagtcc cagcctcttt   1440
tagcgatccc ctgaaaaggc tgtttaagtt gggtaaaccg ctcccagccg acgacgagca   1500
agacgaagac agaagacgcg ctctgctaga tgaaacaaag gcgtggttta gagtaggtat   1560
aacaggcact ttagcagtgg ccgtgacgac ccggtatgag gtagacaata ttacacctgt   1620
cctactggca ttgagaactt tgcccagag caaaagagca ttccaagcca tcagagggga   1680
aataaagcat ctctacggtg gtcctaaata gtcagcatag tacatttcat ctgactaata   1740
ctacaacacc accaccatga atagaggatt ctttaacatg ctcggccgcc gccccttccc   1800
ggcccccact gccatgtgga ggccgcggag aaggaggcag gcggcccga tgcctgcccg   1860 caacgggctg gcttctcaaa tccagcaact gaccacagcc gtcagtgccc tagtcattgg   1920
acaggcaact agacctcaac ccccacgtcc acgcccgcca ccgcgccaga agaagcaggc   1980
gcccaagcaa ccaccgaagc cgaagaaacc aaaaacgcag gagaagaaga agaagcaacc   2040
tgcaaaaccc aaacccggaa agagacacgc catggcactt aagttggagg ccgacagatt   2100
gttcgacgtc aagaacgagg acggagatgt catcgggcac gcactggcca tggaaggaaa   2160
ggtaatgaaa cctctgcacg tgaaaggaac catcgaccac cctgtgctat caaagctcaa   2220
atttaccaag tcgtcagcat acgacatgga gttcgcacag ttgccagtca acatgagaag   2280
tgaggcattc acctacacca gtgaacaccc cgaaggattc tataactggc accacgagc   2340 ggtgcagtat agtggaggta gatttaccat ccctcgcgga gtaggaggca gaggagacag   2400
cggtcgtccg atcatggata actccggtcg ggttgtcgcg atagtcctcg gtggcgctga   2460
tgaaggaaca cgaactgccc tttcggtcgt cacctggaat agtaaaggga agacaattaa   2520 gacgacccg gaagggacag aagagtggtc cgcagcacca ctggtcacgg caatgtgttt   2580
gctcggaaat gtgagcttcc catgcgaccg cccgcccaca tgctatacc gcgaaccttc   2640 cagagccctc gacatccttg aagagaacgt gaaccatgag gcctacgata ccctgctcaa   2700
tgccatattg cggtgcggat cgtctggcag aagcaaaaga agcgtcattg acgactttac   2760
cctgaccagc ccctacttgg gcacatgctc gtactgccac catactgtac cgtgcttcag   2820
ccctgttaag atcgagcagg tctgggacga agcggacgat aacaccatac gcatacagac   2880
ttccgcccag tttggatacg accaaagcgg agcagcaagc gcaaacaagt accgctacat   2940
gtcgcttaag caggatcaca ccgttaaaga aggcaccatg gatgacatca agattagcac   3000
ctcaggaccg tgtagaaggc ttagctacaa aggatacttt ctcctcgcaa aatgccctcc   3060
aggggacagc gtaacggtta gcatagtgag tagcaactca gcaacgtcat gtacactggc   3120
ccgcaagata aaaccaaaat tcgtgggacg ggaaaaatat gatctacctc ccgttcacgg   3180
taaaaaaatt ccttgcacag tgtacgaccg tctgaaagaa acaactgcag gctacatcac   3240
tatgcacagg ccgagaccgc acgcttatac atcctacctg gaagaatcat cagggaaagt   3300
```

```
ttacgcaaag ccgccatctg ggaagaacat tacgtatgag tgcaagtgcg gcgactacaa    3360
gaccggaacc gtttcgaccc gcaccgaaat cactggttgc accgccatca agcagtgcgt    3420
cgcctataag agcgaccaaa cgaagtgggt cttcaactca ccggacttga tcagacatga    3480
cgaccacacg gcccaaggga aattgcattt gcctttcaag ttgatcccga gtacctgcat    3540
ggtccctgtt gcccacgcgc cgaatgtaat acatggcttt aaacacatca gcctccaatt    3600
agatacagac cacttgacat tgctcaccac caggagacta ggggcaaacc cggaaccaac    3660
cactgaatgg atcgtcggaa agacggtcag aaacttcacc gtcgaccgag atggcctgga    3720
atacatatgg ggaaatcatg agccagtgag ggtctatgcc caagagtcag caccaggaga    3780
ccctcacgga tggccacacg aaatagtaca gcattactac catcgccatc ctgtgtacac    3840
catcttagcc gtcgcatcag ctaccgtggc gatgatgatt ggcgtaactg ttgcagtgtt    3900
atgtgcctgt aaagcgcgcc gtgagtgcct gacgccatac gccctggccc caaacgccgt    3960
aatcccaact cgctggcac tcttgtgctg cgttaggtcg gccaatgctg aaacgttcac    4020
cgagaccatg agttacttgt ggtcgaacag tcagccgttc ttctgggtcc agttgtgcat    4080
acctttggcc gctttcatcg ttctaatgcg ctgctgctcc tgctgcctgc ctttttagt    4140 ggttgccggc gcctacctgg cgaaggtaga cgcctacgaa catgcgacca ctgttccaaa    4200
tgtgccacag ataccgtata aggcacttgt tgaaagggca gggtatgccc cgctcaattt    4260
ggagatcact gtcatgtcct cggaggtttt gccttccacc aaccaagagt acattacctg    4320
caaattcacc actgtggtcc cctccccaaa aatcaaatgc tgcggctcct tggaatgtca    4380
gccggccgct catgcagact ataccgtcaa ggtcttcgga ggggtctacc cctttatgtg    4440
gggaggagcg caatgttttt gcgacagtga gaacagccag atgagtgagg cgtacgtcga    4500
attgtcagca gattgcgcgt ctgaccacgc gcaggcgatt aaggtgcaca ctgccgcgat    4560
gaaagtagga ctgcgtattg tgtacgggaa cactaccagt ttcctagatg tgtacgtgaa    4620
cggagtcaca ccaggaacgt ctaaagactt gaaagtcata gctggaccaa tttcagcatc    4680
gtttacgcca ttcgatcata aggtcgttat ccatcgcggc ctggtgtaca actatgactt    4740
cccggaatat ggagcgatga accaggagc gtttggagac attcaagcta cctccttgac    4800
tagcaaggat ctcatcgcca gcacagacat taggctactc aagccttccg ccaagaacgt    4860
gcatgtcccg tacacgcagg cctcatcagg atttgagatg tggaaaaaca actcaggccg    4920
cccactgcag gaaaccgcac ctttcgggtg taagattgca gtaaatccgc tccgagcggt    4980
ggactgttca tacgggaaca ttcccattc tattgacatc ccgaacgctg cctttatcag    5040
gacatcagat gcaccactgg tctcaacagt caaatgtgaa gtcagtgagt gcacttattc    5100
agcagacttc ggcgggatgg ccaccctgca gtatgtatcc gaccgcgaag gtcaatgccc    5160
cgtacattcg cattcgagca cagcaactct ccaagagtcg acagtacatg tcctggagaa    5220
aggagcggtg acagtacact ttagcaccgc gagtccacag gcgaacttta tcgtatcgct    5280
gtgtgggaag aagacaacat gcaatgcaga atgtaaacca ccagctgacc atatcgtgag    5340
caccccgcac aaaaatgacc aagaatttca agccgccatc tcaaaaacat catggagttg    5400
gctgtttgcc ctttcggcg gcgcctcgtc gctattaatt ataggactta tgattttgc    5460 ttgcagcatg atgctgacta gcacacgaag atgaccgcta cgcccaatg atccgaccag    5520 caaaactcga tgtacttccg aggaactgat gtgcataatg catcaggctg gtacattaga    5580
tccccgctta ccgcgggcaa tatagcaaca ctaaaaactc gatgtacttc cgaggaagcg    5640
cagtgcataa tgctgcgcag tgttgccaca taaccactat attaaccatt tatctagcgg    5700
```

-continued

```
acgccaaaaa ctcaatgtat ttctgaggaa gcgtggtgca taatgccacg cagcgtctgc     5760 ataacttta ttatttcttt tattaatcaa caaaattttg ttttaacat ttcaaaaaaa       5820 aaaaaaaaaa aaaaaaaaaa aaaaaaaaaa gggaattcct cgaggggaat taattcttga     5880
agacgaaagg gcctcgtgat acgcctattt ttataggtta atgtcatgat aataatggtt     5940
tcttagacgt caggtggcac ttttcgggga aatgtgcgcg gaacccctat ttgtttattt     6000
ttctaaatac attcaaatat gtatccgctc atgagacaat aaccctgata aatgcttcaa     6060
taatattgaa aaggaagag tatgagtatt caacatttcc gtgtcgccct tattcccttt      6120
tttgcggcat tttgccttcc tgtttttgct cacccagaaa cgctggtgaa agtaaaagat     6180
gctgaagatc agttgggtgc acgagtgggt tacatcgaac tggatctcaa cagcggtaag     6240
atccttgaga gttttcgccc cgaagaacgt tttccaatga tgagcacttt taaagttctg     6300
ctatgtggcg cggtattatc ccgtgttgac gccgggcaag agcaactcgg tcgccgcata     6360
cactattctc agaatgactt ggttgagtac tcaccagtca cagaaaagca tcttacggat     6420
ggcatgacag taagagaatt atgcagtgct gccataacca tgagtgataa cactgcggcc     6480
aacttacttc tgacaacgat cggaggaccg aaggagctaa ccgcttttt gcacaacatg      6540 ggggatcatg taactcgcct tgatcgttgg gaaccggagc tgaatgaagc cataccaaac     6600
gacgagcgtg acaccacgat gcctgtagca atggcaacaa cgttgcgcaa actattaact     6660
ggcgaactac ttactctagc ttcccggcaa caattaatag actggatgga ggcggataaa     6720
gttgcaggac cacttctgcg ctcggccctt ccggctggct ggtttattgc tgataaatct     6780
ggagccggtg agcgtgggtc tcgcggtatc attgcagcac tggggccaga tggtaagccc     6840
tcccgtatcg tagttatcta cacgacgggg agtcaggcaa ctatggatga acgaaataga     6900
cagatcgctg agataggtgc ctcactgatt aagcattggt aactgtcaga ccaagtttac     6960
tcatatatac tttagattga tttaaaactt catttttaat ttaaaaggat ctaggtgaag     7020 atccttttg ataatctcat gaccaaaatc ccttaacgtg agttttcgtt ccactgagcg      7080 tcagacccg tagaaaagat caaaggatct tcttgagatc ctttttttct gcgcgtaatc      7140
tgctgcttgc aaacaaaaaa accaccgcta ccagcggtgg tttgtttgcc ggatcaagag     7200
ctaccaactc tttttccgaa ggtaactggc ttcagcagag cgcagatacc aaatactgtc     7260
cttctagtgt agccgtagtt aggccaccac ttcaagaact ctgtagcacc gcctacatac     7320
ctcgctctgc taatcctgtt accagtggct gctgccagtg gcgataagtc gtgtcttacc     7380
gggttggact caagacgata gttaccggat aaggcgcagc ggtcgggctg aacggggggt     7440
tcgtgcacac agcccagctt ggagcgaacg acctacaccg aactgagata cctacagcgt     7500
gagcattgag aaagcgccac gcttcccgaa gggagaaagg cggacaggta tccggtaagc     7560
ggcagggtcg gaacaggaga gcgcacgagg gagcttccag ggggaaacgc ctggtatctt     7620
tatagtcctg tcgggtttcg ccacctctga cttgagcgtc gatttttgtg atgctcgtca     7680
ggggggcgga gcctatggaa aaacgccagc aacgcgagct cggatctggc tagcgatgac     7740
cctgctgatt ggttcgctga ccatttccgg gtgcgggacg gcgttaccag aaactcagaa     7800
ggttcgtcca accaaaccga ctctgacggc agtttacgag agagatgata gggtctgcat     7860
cagtaagcca gatgctacac aattaggctt gtacatattg tcgttagaac gcggctacaa     7920
ttaatacata accttatgta tcatacacat acgatttagg tgacactata               7970
```

<210> SEQ ID NO 7

<211> LENGTH: 660
<212> TYPE: DNA
<213> ORGANISM: Escherichia coli

<400> SEQUENCE: 7

```
atggagaaaa aaatcactgg atataccacc gttgatatat cccaatggca tcgtaaagaa      60
cattttgagg catttcagtc agttgctcaa tgtaactata accagaccgt tcagctggat     120
attacggcct ttttaaagac cgtaaagaaa aataagcaca gttttatcc ggcctttatt      180
cacattcttg cccgcctgat gaatgctcat ccggaattcc gtatggcaat gaaagacggt     240
gagctggtga tatgggatag tgttcaccct tgttacaccg ttttccatga gcaaactgaa     300
acgttttcat cgctctggag tgaataccac gacgatttcc ggcagtttct acacatatat     360
tcgcaagatg tggcgtgtta cggtgaaaac ctggcctatt tccctaaagg gtttattgag     420
aatatgtttt tcgtctcagc caatccctgg gtgagtttca ccagttttga tttaaacgtg     480
gccaatatgg acaacttctt cgcccccgtt ttcaccatgg gcaaatatta tacgcaaggc     540
gacaaggtgc tgatgccgct ggcgattcag gttcatcatg ccgtctgtga tggcttccat     600
gtcggcagaa tgcttaatga attacaacag tactgcgatg agtggcaggg cggggcgtaa     660
```

<210> SEQ ID NO 8
<211> LENGTH: 616
<212> TYPE: DNA
<213> ORGANISM: Homo sapien

<400> SEQUENCE: 8

```
tctagaggcg cggagatggg ggtgcacgaa tgtcctgcct ggctgtggct tctcctgtcc      60
ctgctgtcgc tccctctggg cctcccagtc ctgggcgccc caccacgcct catctgtgac     120
agccgagtcc tggagaggta cctcttggag gccaaggagg ccgagaatat cacgacgggc     180
tgtgctgaac actgcagctt gaatgagaat atcactgtcc cagacaccaa agttaatttc     240
tatgcctgga gaggatgga ggtcgggcag caggccgtag aagtctggca gggcctggcc      300
ctgctgtcgc aagctgtcct gcggggccag gccctgttgg tcaactcttc ccagccgtgg     360
gagcccctgc agctgcatgt ggataaagcc gtcagtggcc ttcgcagcct caccactctg     420
cttcgggctc tgggagccca gaaggaagcc atctcccctc cagatgcggc tcagctgctt     480
ccactccgaa caatcactgc tgacactttc cgcaaactct ccgagtcta ctccaatttc    540
ctccggggaa agctgaagct gtacacaggg gaggcctgca ggacagggga cagatgagca     600
tgcaggcctt gggccc                                                    616
```

<210> SEQ ID NO 9
<211> LENGTH: 11
<212> TYPE: DNA
<213> ORGANISM: Artificial Sequence
<220> FEATURE:
<223> OTHER INFORMATION: Primer

<400> SEQUENCE: 9

```
gcgcgggccc t                                                           11
```

<210> SEQ ID NO 10
<211> LENGTH: 31
<212> TYPE: DNA
<213> ORGANISM: Artificial Sequence
<220> FEATURE:
<223> OTHER INFORMATION: Primer

<400> SEQUENCE: 10

```
gcgcgggccc cgctgcgtgg cattatgcac c                              31
```

<210> SEQ ID NO 11
<211> LENGTH: 21
<212> TYPE: DNA
<213> ORGANISM: Artificial Sequence
<220> FEATURE:
<223> OTHER INFORMATION: DNA that hybridize to Sindbis structural
      protein

<400> SEQUENCE: 11

```
gcacttaagt tggaggccga c                                         21
```

<210> SEQ ID NO 12
<211> LENGTH: 25
<212> TYPE: DNA
<213> ORGANISM: Artificial Sequence
<220> FEATURE:
<223> OTHER INFORMATION: DNA that hybridize to Sindbis structural
      protein

<400> SEQUENCE: 12

```
ggcactcacg gcgcgcttta caggc                                     25
```

<210> SEQ ID NO 13
<211> LENGTH: 29
<212> TYPE: DNA
<213> ORGANISM: Artificial Sequence
<220> FEATURE:
<223> OTHER INFORMATION: DNA that hybridize to Sindbis structural
      protein

<400> SEQUENCE: 13

```
gcaatgttaa caggtctgta tctaattgg                                 29
```

<210> SEQ ID NO 14
<211> LENGTH: 29
<212> TYPE: DNA
<213> ORGANISM: Artificial Sequence
<220> FEATURE:
<223> OTHER INFORMATION: DNA that hybridize to Sindbis structural
      protein

<400> SEQUENCE: 14

```
cagacctgtt aacattgctc accaccagg                                 29
```

<210> SEQ ID NO 15
<211> LENGTH: 29
<212> TYPE: DNA
<213> ORGANISM: Artificial Sequence
<220> FEATURE:
<223> OTHER INFORMATION: DNA that hybridize to Sindbis structural
      protein

<400> SEQUENCE: 15

```
gacagcggtc gatcgatcat ggataactc                                 29
```

<210> SEQ ID NO 16
<211> LENGTH: 29
<212> TYPE: DNA
<213> ORGANISM: Artificial Sequence
<220> FEATURE:
<223> OTHER INFORMATION: DNA that hybridize to Sindbis structural
      protein

<400> SEQUENCE: 16

```
gagttatcca tgatcgatcg accgctgtc                                        29

<210> SEQ ID NO 17
<211> LENGTH: 19
<212> TYPE: DNA
<213> ORGANISM: Artificial Sequence
<220> FEATURE:
<223> OTHER INFORMATION: DNA hybridizing to subgenomic promotor region
      of Sindbis

<400> SEQUENCE: 17
ttccaagcca tcagagggg                                                   19

<210> SEQ ID NO 18
<211> LENGTH: 20
<212> TYPE: DNA
<213> ORGANISM: Artificial Sequence
<220> FEATURE:
<223> OTHER INFORMATION: DNA that hybridize to Sindbis structural
      protein

<400> SEQUENCE: 18
agattagcac ctcaggaccg                                                  20
```

EXPRESSION CLONING PROCESSES FOR THE DISCOVERY, CHARACTERIZATION AND ISOLATION OF GENES ENCODING POLYPEPTIDES WITH A PREDETERMINED PROPERTY

CROSS-REFERENCE TO RELATED APPLICATIONS

This application is a continuation-in-part of U.S. application Ser. No. 08/972,218, filed Nov. 17, 1997, now U.S. Pat. No. 6,197,502, issued on Mar. 6, 2001.

I. FIELD OF THE INVENTION

The present in invention relates, generally, to the field of expressed gene technology and expression cloning. More specifically, the present invention relates to the identification, characization, and isolation of transcribed nucleic acid sequences encoding polypeptides having a predetermined property, e.g., cellular localization, structure, enzymatic function, or affinity to other molecules, and the production of the corresponding polypeptides.

II. BACKGROUND OF THE INVENTION

General Background. Proteins are the most prominent biomolecules in living organisms; in addition to their role as structural components and catalysts, they play a crucial role in regulatory processes. Both regulation of cell proliferation and metabolic functions are largely controlled and effected by the cooperation of numerous cellular and extracellular proteins. Lehninger, A. L., 1975, "Biochemistry", Worth Publishers Inc., New York, N.Y. For example, signal transduction pathways of many kinds that affect critical physiological responses operate through proteins by way of their intermolecular interactions. Metzler, D. E., 1977, "Biochemistry", Academic Press Inc., London. Furthermore, the transcription of genes and the regulation of such transcription is dependent upon and controlled by the interdependence of numerous protein factors. Wainwright, S. D., "Control Mechanisms and Protein Synthesis", Columbia University Press, New York and London.

Proper functioning of a multicellular organism does not only depend on the interaction of biomolecules within the cell, but individual cells must also communicate appropriately. Such intercellular communication, and interaction of cells with the environment is often realized by the actions of receptors on the extracellular surface and associated intracellular signal transduction mechanisms. Poste, G., Nicholson, G. L., 1976, "The Cell Surface", Elseviere, Amsterdam. The information is communicated through the cell environment to regulate gene expression or protein activities in the cell. Secreted proteins in the extracellular environment thereby exert potent regulatory effects on certain cellular functions.

In view of the above outlined, very simplified paradigm of cell function, particular properties of a protein, including cellular localization, structure, affinity to a binding partner, or enzymatic activity under physiological conditions appear to be highly indicative of its type of function. With respect to a particular cellular localization, secreted proteins, for example, are likely to function as intercellular communicators of signals, while membrane associated receptors having an extracellular and intracellular domain most likely transmit an extracellular signal into the cell. Cytoplasmic proteins may function as intracellular signal transmitters and coordinators. Jeter, J. R., Cameron, I. L., Padilla, I. L., Padilla, G. M., Zimmerman, A. M., 1978, "Cell Cycle Regulation"; London. Nuclear proteins are likely to be involved in certain aspects of gene regulation. Zawel et al., 1995, Annu. Rev. Biochem. 64:533–561. Mature proteins found in the Golgi or the ER may have regulatory roles in the post-translational processing of protein precursors, e.g., cleavage or addition of carbohydrates. Hirschberg, 1987, C. Annu. Rev. Biochem. 56:63–87.

Membrane-Associated Proteins. For many years, the paradigm of cell function has motivated numerous drug discovery programs to focus on identifying membrane-associated proteins, in particular new receptors, and their respective functions. Porter, R. and O'Connor, M., 1970, "Molecular Properties of Drug Receptors, Ciba Foundation Symposium", J&A Churchill, London. Many examples in fact compel the conclusion that improper function of membrane receptors is a significant source of the development of serious metabolic and proliferative diseases such as cancer. For example, a certain form of Diabetes mellitus, i.e., the non-insulin-dependent diabetes (NIDDM) may be caused by mutations in the insulin receptor. Ullrich et al., 1985, Nature 313:756–761; Taira et al., 1989, Science 245:63–66. Furthermore, 30% of all mammary carcinomas are associated with amplification of the receptor tyrosine kinase HER2. Bargman et al., 1986, Cell 45:649–657; Slamon et al., 1989, Science 244:707–712. In addition to traditional drug discovery programs targeting receptors, an ambitiously pursued objective has become to identify membrane-associated receptors as possible gene therapy targets using comparative genomics, which allows. determination of changes in gene expression under, e.g., pathological conditions. Wels, et al., 1995, Gene 159(1):73–80.

Secreted Proteins. While receptors have mostly been considered as important potential therapeutic targets, secreted proteins are of particular interest as potential therapeutic agents. They often have a signalling or hormone function, and hence have a high and specific biological activity. Schoen, F. J., 1994, "Robbins Pathologic Basis of Disease",. W.B. Saunders Company, Philadelphia. For example, secreted proteins control physiological reactions such as differentiation and proliferation, blood clotting and thrombolysis, somatic growth and cell death, and immune response. Schoen, F. J., 1994, "Robbins Pathologic Basis of Disease", W. B. Saunders Company, Philadelphia.

Significant resources and research efforts have been expended for the discovery and investigation of new secreted proteins controlling biological functions. Many of such secreted proteins, including cytokines and peptide hormones, are manufactured and used as therapeutic agents. Zavyalov et al., 1997, APMIS 105(3):161–186. However, of the several thousand expected secreted proteins, only a few are currently used as therapeutic compounds. It can be expected that many of the so far undiscovered secreted proteins of the human organism are effective in correcting physiological disorders and are thus promising candidates for new drugs.

In the past, novel cytokines and hormone proteins were identified by assaying a certain cell type for its response to protein fractions or purified proteins. Lauffenburger et al., 1996, Biotechnology and Bioengineering 52(1):61–80. Other investigators have used sequence similarities on DNA level to clone novel interferons and interleukins. Nabori et al., 1992, Analyt. Biochem. 205(1):42–46. In again another approach, differential display techniques were used to compare the expression patterns of stimulated versus unstimulated cells. Nagata et al., 1980, Nature 287:401–408. All these methods may yield identification and isolation of certain secreted polypeptides.

Recently, a screening method for the identification of cDNA encoding novel secreted mammalian proteins in yeast using the invertase gene as a selection marker has been described. See, U.S. Pat. No. 5,536,637 (the "'637 Patent"). The disclosed technology relies on the concept that leader sequences of mammalian cDNAs are effective in exporting the invertase protein depleted of its leader sequence. This approach yields partial cDNAs which in turn can be used to screen a full-length cDNA library. The novel protein of interest can then be manufactured by standard, but laborious, techniques, including subcloning, transforming a recombinant host, expression, development and implementation of a purification process. Furthermore, since the assays described in the '637 Patent are performed in yeast, the glycosylation pattern of the isolated products will differ significantly from the natural product produced in mammalian cells. This difference is a major impediment in view of the fact that an extremely important feature of secreted proteins (as it is true for the extracellular domain of receptors) is their glycosylation pattern and carbohydrate composition. Rademacher et al., 1988, *Annu. Rev. Biochem.* 57:785–838.

Nuclear Proteins. In the nucleus, both replication of DNA and transcription of genes is actually implemented. Many nuclear proteins are directly involved in these processes as transcription factors, as cell cycle regulators, or both. Some nuclear proteins are responsible for turning on expression of certain metabolic proteins in response to environmental changes. Zawel et al., 1995, *Annu. Rev. Biochem.* 64:533–561. Many others are directly involved in the regulation of cell proliferation. Jeter, J. R., Cameron, I. L., Padilla, G. M., Zimmerman, A. M., 1978, *"Cell Cycle Regulation"*, London. Proteins in this latter class fall into two general categories: (1) dominant transforming genes, including oncogenes; and (2) recessive cell proliferation genes, including tumor suppressor genes and genes encoding products involved in programmed cell death ("apoptosis").

Oncogenes generally encode proteins that are associated with the promotion of cell growth. Because cell division is a crucial part of normal tissue development and continues to play an important role in tissue regeneration, properly regulated oncogene activity is essential for the survival of the organism. However, inappropriate expression or improperly controlled activation of oncogenes may drive uncontrolled cell proliferation and result in the development of severe diseases, such as cancer. Weinberg, 1994, *CA Cancer J. Clin.* 44:160–170.

Tumor suppressor genes, on the other hand, normally act as "brakes" on cell proliferation, thus opposing the activity of oncogenes. Accordingly, inactivation of tumor suppressor genes, e.g., through mutations or the removal of their growth inhibitory effects may result in the loss of growth control, and cell proliferative diseases such as cancer may develop. Weinberg, 1994, *CA Cancer J. Clin.* 44:160–170.

Related to tumor suppressor genes are genes whose product is involved in the control of apoptosis; rather than regulating proliferation of cells, they influence the survival of cells in the body. In normal cells, surveillance systems are believed to ensure that the growth regulatory mechanisms are intact; if abnormalities are detected, the surveillance system switches on a suicide program that culminates in apoptosis.

Several genes that are involved in the process of apoptosis have been described. See, for example, Collins and Lopez Rivas, 1993, *TIBS* 18:307–308; Martin et al., 1994, *TIBS* 19:26–30. Cells that are resistant to apoptosis have an advantage over normal cells, and tend to outgrow their normal counterparts and dominate the tissue. As a consequence, inactivation of genes involved in apoptosis may result in the progression of tumors, and, in fact, is an important step in tumorigenesis.

Accordingly, the identification of nuclear proteins addresses two areas of interest. First, oncogenes are prone to be valuable targets for the development of highly specific drugs for the treatment of cancer. Secondly, tumor suppressors and apoptosis inducing proteins can be useful as agents for the treatment of cancer.

Other Cellular Localizations. Also many of the remaining cellular localizations are associated with particular functions. For example, most metabolic enzymes are located in the mitochondria. Lehninger, A. L., 1975, *"Biochemistry"*, Worth Publishers Inc., New York. Thus, mitochondrial proteins could reveal targets for the treatment of metabolic diseases. The Golgi apparatus and the ER are associated with post-translational processing of proteins; such processes are valuable targets for the treatment of diseases related to protein folding and glycosylation. Rademacher et al., 1988, *Ann. Rev. Biochem.* 57:785–838.

Enzymatic Activities. A particular enzymatic activity can be indicative of a protein's function. For example, kinases are frequently involved in signal transduction processes.

Structures. Protein is also indicative of protein function. Indeed, proteins with similar structures frequently share certain functional properties. Thus, identifying proteins having a structure related to that of a known protein having a particular function of interest can reveal additional proteins having such function.

Generally, a method would be desirable which allows one to pre-sort proteins according to a property of interest, e.g., localization in the cell, affinity to binding partners, enzymatic activity, structure and the like. Such a method would allow one to generate libraries of, e.g., secreted proteins, such as cytokines, membrane associated proteins, such as receptors, nuclear proteins, such as transcription factors, mitochondrial proteins, such as respiratory proteins, and so on. Further, it would be desirable to perform screening, isolation and production of any product in mammalian cells in order to achieve the proper glycosylation pattern. Finally, the most preferred method would additionally allow one to identify and isolate proteins of interest per se rather than a partial DNA sequence.

The present invention addresses this need. The present invention provides methods and expression systems for the generation of expression libraries encoding polypeptides of a predetermined property, including but not limited to cellular localization, structure, enzymatic function, or affinity to other molecules. The methods and expression systems of the present invention allow one to identify and isolate nucleic acids encoding novel proteins of interest. The methods and expression systems furthermore provide a powerful system for the identification of thus far unelucidated receptor/ligand relationships. Since the methods provided can employed in a wide variety of host cell systems, including mammalian systems, they provide for expression products having an appropriate carbohydrate composition.

III. SUMMARY OF THE INVENTION

The present invention relates, generally, to the field of expressed gene technology and expression cloning. More specifically, the present invention relates to the identification, characterization, and isolation of transcribed nucleic acid sequences encoding polypeptides having a predetermined property, including, but not limited to, cellular localization, structure, enzymatic function, or affinity to other molecules and the production of the corresponding polypeptides.

More specifically, the invention is directed to a method for identifying nucleic acids encoding proteins with a predetermined property of interest. Such a property may include a particular cellular localization, structure, enzymatic function, or affinity to other molecules. In one embodiment of the invention, a plurality of eukaryotic host cells is provided, wherein each host cell has an expression system comprising a different member, each member comprising a recombinant nucleic acid encoding an exogenous protein operatively linked to a control element. In a second step, the eukaryotic host cells are cultured under conditions where the exogenous protein is expressed while expression of endogenous proteins of the eukaryotic host cell is suppressed. In this time window, the exogenous protein may optionally be labelled, or may be treated in a way that allows discrimination from the untreated exogenous proteins. Finally, the member or members of the expression system that encode the exogenous protein or proteins having the property of interest are identified.

In another aspect of the invention, a method for identifying a recombinant nucleic acid encoding an exogenous protein having a property of interest is achieved by providing a plurality of eukaryotic host cells, wherein each host cell has an expression system comprising a different member, and each member comprises a recombinant virus having a recombinant nucleic acid encoding an exogenous protein operatively linked to a control element. The eukaryotic host cells are cultured to express the exogenous proteins, and expression systems expressing recombinant nucleic acid encoding an exogenous protein having the property of interest are identified. Optionally, the expression systems are capable of expressing exogenous proteins while endogenous protein production of the eukaryotic host cell is suppressed. Although any kind of recombinant eukaryotic virus can be used, particularly advantageous viruses are alpha viruses. In addition, the exogenous proteins can be preferentially labelled or distinguished from endogenous proteins. The recombinant virus may be capable of directing the generation of viral particles and replicating, or the recombinant virus may lack functions required for propagation.

Also encompassed within the invention are methods for generating genetic expression libraries encoding proteins having a predetermined property of interest. In one aspect, such methods entail providing a plurality of eukaryotic host cells, wherein each host cell has an expression system comprising a different member, each member having a recombinant nucleic acid encoding an exogenous protein operatively linked to a control element, culturing the eukaryotic host cells under conditions where said exogenous protein is expressed while expression of endogenous proteins of said eukaryotic host cell is suppressed, and identifying the members that express recombinant nucleic acids encoding exogenous proteins having the property of interest. In another aspect, the methods entail providing a plurality of eukaryotic host cells, wherein each host cell has an expression system comprising a different member, each member being a recombinant virus having a recombinant nucleic acid encoding an exogenous protein operatively linked to a control element, culturing the eukaryotic host cells to express the exogenous proteins, and identifying the members that express recombinant nucleic acids encoding exogenous proteins having the property of interest. The invention further includes libraries of proteins identified using such methods. Additionally, the invention encompasses nucleic acid libraries having a population of eukaryotic expression systems with a plurality of members, each member having a recombinant nucleic acid encoding an exogenous protein operatively linked to a control element for expression in eukaryotic host cells. In one embodiment, the control element directs the expression of the exogenous proteins while expression of endogenous proteins in the eukaryotic host cells are suppressed. In yet another embodiment, the control element is derived from a eukaryotic virus.

IV. BRIEF DESCRIPTION OF THE DRAWINGS

FIG. 1 depicts an experiment in which expression systems containing either a nucleic acid encoding a secreted protein or a nucleic acid encoding an intracellular protein from a mixture of nucleic acids were identified using compartment screening. FIG. 1A is an autoradiogram of labelled proteins precipitated from the supernatants of the screened cell cultures, as described in more detail in Example 1. Lanes are as follows: lane 1-non-infected BHK 21 cells; lane 2-cells transfected with an expression system encoding an intracellular protein, pSinRep5 lacZ; lane 6-cells transfected with an expression system encoding a secreted protein (EPO), pSinRep 5 EPO; lanes 3 to 5 contain mixtures of the 2 expression systems in the ratios 90:10, 50:50, 10:90 (sinRep5 lacZ:SinRep5 EPO) showing increasing amounts of EPO. Protein mass standard is shown on the left side; the molecular weight of EPO is indicated by the arrow. FIG. 1B is an autoradiogram of the labelled proteins in the corresponding cell pellets from lanes 1 and 2 of FIG. 1A, showing the accumulation of lac Z protein in the cell pellet, and the shutdown of endogenous protein production, in cells infected with pSinRep5 lacZ.

FIG. 2 depicts separation of labelled viral particles from secreted protein, as described in more detail below in Example 2. Shut-down of endogenous protein synthesis is apparent in lanes 4 to 6 (infection with TE 5'2J CAT) and in lanes 7 to 9 (infection with TE 5'2J EPO) as compared to lanes 1 to 3 (non-infected BHK 21 cells). Removal of viral particles is demonstrated by the absence of the characteristic pattern of Sindbis structural proteins (capsid, E1 and E2). Lane 9 shows diffusion of a protein of the size of EPO through the agarose. In lanes 4 to 9 a soluble protein of viral origin can be seen. It is assumed that this protein is released by proteolytic cleavage. Labelled protein was collected at different time points: 2 h (lanes 1,4,7), 4 h (lanes 2,5,8) and 8 h (lanes 3,6,9). Protein mass standard is shown on the left side, the size of Sindbis viral glycoproteins is indicated by the upper arrow, the molecular weight of EPO is indicated by the lower arrow.

FIG. 3 demonstrates that release of viral soluble proteins is reduced by protease inhibitors. As described below in Example 3, $10^6$ BHK 21 cells in a 35 mm dish were infected with TE 5'2J CAT. Varying concentrations of the Protease inhibitor cocktail (100, 20, 10, 5, 1 µl per ml, lanes 1 to 5) were applied in the 4 mm agarose overlay. The molecular mass standard is shown on the left; the arrow indicates the expected mass of Sindbis glycoprotein E1.

FIGS. 4A–4B show identification of an expression system containing a nucleic acid encoding a protein with a predetermined enzymatic activity in a semi-solid medium screening. Confluent 35 mm dishes of BHK 21 cells were infected with 200 pfs SinRep lacZ (FIG. 4A) or a mixture of 200 pfs SinRep lacZ/20 pfu of SinRep 5 SEAP (FIG. 4B). Enzymatic activity was detected on the filters with AP staining.

Blot 1 (FIG. 4A) (containing only a lacZ expression system) is negative in SEAP activity whereas blot 2 (FIG. 4B) shows 2 distinct areas with SEAP activity (indicated by arrows).

FIGS. 5A–5D depict the pSIN vectors used to illustrate the invention. The source and construction of these vectors is described in Table I.

FIGS. 6A–6D are schematic representations of the pTE vectors used to illustrate the invention. Vectors shown are pTE (FIG. 6A); pTE CAT (FIG. 6B); pTE SEAP (FIG. 6C); and pTE EPO (FIG. 6D). The source and construction of these vectors is described in Table I.

FIGS. 7A and 7B depict approximately 20 pfu of pSinRep5 SEAP and 780 pfu pSinRep5 LacZ were mixed in 1 ml Turbodoma HP-1 and a 60 mm dish with BHK 21 cells was infected for 2 hours. An agarose blot assay was performed as described in Example 10. FIG. 7A shows the AP stained nitrocellulose membrane, blotted SEAP protein is represented by the violet spots of the developed X-ray film (FIG. 7B, the AP stained membrane exposed to the X-ray film) where the black spots represent labeled secreted protein. Coordinates (indicated by arrows x1,x2,x3 in the AP stained membrane and the corresponding arrows y1, y2, y3 in the developed X-ray film) of the spots with SEAP activity can be superimposed with the spots of labeled secreted proteins (compare x1 with y 1, x2 with y2, x3 with y3).

FIGS. 8A, 8B and 8C depict pSinRep 5 SEAP mRNA and pDHEB ts mutant mRNAs were co-electroporated into BHK 21 cells. The cell supernatant of the electroporated cells was analyzed 20 hours post-electroporation by spotting 4 µl supernatant on a nitrocellulose strip and AP staining was done as described before. All the electroporations were positive for SEAP secretion (violet spots on nitrocellulose filter) as shown in FIG. 8A. The first passage of the ts mutant viruses was tested for infectivity at 37° C. and at 30° C. The supernatants of the infected cells were tested by AP staining for the secreted product SEAP, the upper row in FIG. 8B represents the supernatant of cells incubated at 37° C., the lower row of FIG. 8B represents the supernatant of cells incubated at 30° C. The double mutant pSinRep 5 SEAP/pDHEB ts2,20 produced 20 hours post-infection a low amount of SEAP (see FIG. 8B) but virus particles were amplified and a high amount of product was detected after 48 hours post-infection, as shown in FIG. 8C.).

FIGS. 9A, 9B, 9C and 9D depict pSinRep 5 hIL13 R alpha-infected BHK 21 cells (at an moi of approximately 0.1) were analyzed by Immunofluorescence. Expressed hIL13 R alpha was detected with IL13-flag, M2 antibody and antiMouse-FITC. FIG. 9A: BHK 21 infected at an moi of 0.1 with pSinRep 5 hIL13 R alpha, analyzed and sorted with FACS; FIG. 9B: the same cells as in FIG. 9A with Immunfluorescence Microscopy; FIG. 9C: pSinRep 5 LacZ infected cells as negative control; FIG. 9D:1:100 diluted pSinRep 5 hIl13 R alpha virus in pSinRep 5 LacZ virus analyzed and sorted with FACS.

FIG. 10 depicts approximately 20 pfu of pSinRep 5 Epo/DHEB were mixed with 200 pfu of pSinRep 5 LacZ. The virus supernatant was incubated for 2 hours on 90% confluent BHK 21 cells in a 60 mm dish, before the supernatant was replaced with 3 ml of 0.8% 41° C. warm agarose in 1×HP-1 medium. Two days later, a nitrocellulose membrane was applied on the agarose and diffusion blotting was proceeded for 14 hours. Blotted EPO was detected by immuno-detection with anti-EPO antibody (rabbit) and AP-conjugated anti-rabbit antibody. The violet spots d1,d2, d3 (and the other dark spots) represent the blotted EPO derived from the underlying virus plaque representing pSinRep5 EPO virus.

FIGS. 11A–11M depict the polynucleotide sequences of pSinRep 5, pSinRep 5 EPO, pSinRep 5 hIL 13 Ralpha, and PDH-EB.

FIGS. 12A–12D depict the polynucleotide sequence of pTE5'2J (SEQ ID NO:1).

FIGS. 13A–13C depict the-polynucleotide sequence of 987 BB neo (SEQ ID NO:2).

FIG. 14 depicts the polynucleotide sequence of CAT (SEQ ID NO:7).

FIG. 15 depicts the polynucleotide sequence of the XbaI/ApaI fragment of synthetic erythropoietin (SEQ ID NO:8).

V. DEFINITIONS

Figure 1A:
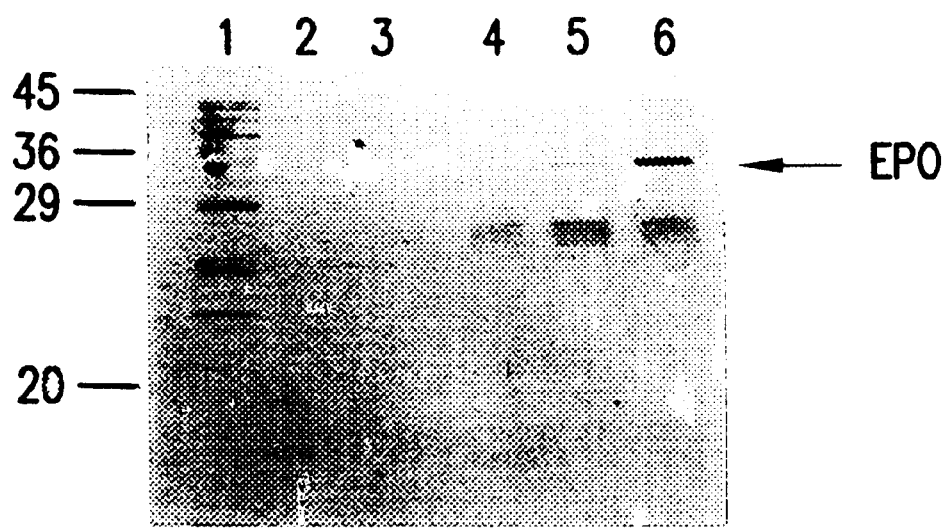

Terms used herein are in general as typically used in the art. The following terms are intended to have the following general meanings as they are used herein:

The term "cellular localization" refers to a defined localization in the cellular context, including the extracellular space and any defined intracellular compartment, including, but not limited to, the nucleus, mitochondria, lysosomes, endoplasmatic reticulum (ER), Golgi, cytoplasm, cell membrane, endocytotic or exocytotic vesicles, cytoskeleton, peroxisomes. In microbes or plant cells, further cellular localizations may include the cell wall and chloroplast.

The term "control element" refers to a nucleic acid component capable of directing expression of an operatively associated nucleic acid encoding a polypeptide. Generally, a "control element" comprises regulatory sequences required for transcription and/or translation of genetic information. The control element further comprises a component which promotes, under certain conditions or circumstances, selective expression of the operatively linked nucleic acid, while expression of endogenous host proteins is suppressed. Optionally, the "control element" may further comprise components facilitating packaging of the operatively associated nucleic acid.

The term "exogenous protein" refers to a protein which is encoded by a recombinant nucleic acid. If the "exogenous protein" is expressed in a cell, it is encoded by a recombinant nucleic acid which has been introduced into the cell or its progenitors. In the expression systems of the invention, the nucleic acid encoding the exogenous protein is operatively linked to a control element. In some circumstances, the exogenous protein can be the same protein as one endogenously produced by the cell.

The term "virus" refers to a bio-entity capable of introducing genetic information into a cell. The genetic information may be introduced in the form of RNA, DNA, or derivatives thereof. The cell may be eukaryotic or prokaryotic.

VI. DETAILED DESCRIPTION OF THE INVENTION

A. General Overview Of The Invention

The present invention is directed to methods and expression systems allowing rapid identification, characterization and isolation of transcribed nucleic acid sequences encoding polypeptides having a predetermined property, including, but not limited to, cellular localization, structure, enzymatic function, or affinity to other molecules. The invention is based, in part, on the inventors' surprising discovery of materials and compositions that allow the discrimination between a unique exogenous protein of interest and all other "common" proteins present in the system, including endogenous cellular proteins and recombinant proteins which are perpetual part of the expression system. Generally, the methods of the invention employ eukaryotic host cell systems, into which the expression systems are introduced for any further characterization according to the invention. Preferably, the employed expression systems have an inherent feature which allows introduction of only one expression system per eukaroytic cell. Such systems have the advantage that they allow rapid one step cloning of individual expressed sequences.

The system which is described in more detail below offers a number of advantages. First, the system of this invention is an expression cloning system which allows the direct cloning of full-length cDNAs in one step. Second, it facilitates rapid expression of the protein of interest without further laborious handling such as subcloning and establishment of a production cell line. Third, as the products may be expressed in mammalian cells, the system may yield correctly folded, glycosylated and active material. Fourth, the system allows rapid purification of the material without explicit knowledge of the nature of the protein. Fifth, it allows labelling of the material facilitating rapid identification of sites of binding in any context including animals. Finally, the system directly provides vectors useful for gene transfer into cultured cells, tissues, or animals.

In one aspect, the invention discloses methods which allow the identification and isolation of novel and known proteins having a predetermined property, for example cellular localization. More specifically, within a plurality of expression systems encoding unique exogenous proteins, which are expressed in suitable host cell systems, the disclosed methods allow one to identify and isolate those expression systems which encode exogenous proteins located in a cellular compartment of interest. The method is based, in one of its aspects, on a unique feature of the employed expression system which allows, during a certain time window, high expression of the exogenous proteins while the synthesis of endogenous proteins is suppressed. If during this time window the expressed exogenous proteins are treated in a certain detectable way, for example by radioactive labelling, they may be identified easily within a chosen cellular fraction. Alternatively, all proteins expressed prior to the time window in which synthesis of endogenous protein is suppressed may be treated in an identifiable way; in this scenario the exogenous proteins which are expressed after such treatment, while expression of endogenous proteins is inhibited may be identified by not exhibiting the feature caused by the treatment.

In one aspect, the methods of the invention may be used to identify and isolate individual expression systems encoding secreted proteins. During a time window in which expression of the endogenous proteins of the host cell system is suppressed, the exogenous proteins are labelled, for example by incubation with radioactive amino acids. Subsequently, all secreted proteins are separated from the host cells comprising the individual expression systems. This separation is performed in a manner which allows one to correlate the secreted protein fractions with the host cell/expression system from which it derived. For example, the host cells comprising the individual expression systems may be grown in semisolid medium, such as soft agar at a density which allows physical separation of individual clones or colonies. If the secreted proteins are separated from the cells by a vertical diffusion process on, for example, a nitrocellulose filter, which may be achieved by placing the filter on top of the semisolid medium, the secreted proteins are bound on the filter in a pattern which exactly mirrors the physical distribution pattern of the corresponding host cells in the semisolid medium. Those host cells/expression systems which comprise exogenous secreted proteins can thus easily be identified by presence of the label in the fraction of secreted proteins.

Likewise, the methods may be applied to identify and isolate membrane associated proteins, nuclear proteins, mitochondrial proteins, lysosomal proteins, Golgi apparatus proteins, ER proteins, etc., as described in more detail within the body of this application. In short, the above principle may, with modifications, be applied to identify and isolate exogenous proteins localized in any other predetermined cellular localization of interest. Furthermore, the methods and expression systems of the invention may be applied to identify and isolate nucleic acids encoding exogenous proteins having a particular enzymatic activity, binding affinity to a binding partner, or structure of interest.

In a second general aspect, the invention provides methods which allow expression cloning of nucleic acids encoding exogenous proteins for which a predetermined binding molecule and substrate (ligand) is available. For example, to identify an unknown secreted ligand for a known receptor, receptor protein may be immobilized on a filter, e.g., a nitrocellulose filter, in a manner that the filter is saturated with protein, i.e., does not bind any further protein molecules. A plurality of expression systems is provided that has been prepared using expressed nucleic acids from a source known to express the receptor's ligand, which can be determined using standard methods. The expression systems are again introduced and expressed in suitable host cells in a manner that host cells comprising individual expression systems are physically separable in an identifiable way, e.g., by growing the cells in semisolid medium. Similarly, as described for the identification of expression systems comprising secreted proteins, the exogenous proteins are labelled within the time window in which endogenous protein expression is suppressed. Subsequently, the secreted proteins are transferred on the nitrocellulose filter which is saturated with the receptor protein. Since all binding positions on the filter are saturated with protein, see, supra, only a ligand binding to the receptor may adhere to the filter. Exogenous protein corresponding to the receptor's ligand may be identified due to its label, and correlated to the expression system it is derived from. Accordingly, if a receptor for a predetermined ligand is to be cloned, and binding of said labelled ligand to the host cells is detected, labelled ligand is subjected to host cells comprising a plurality of expression systems and detecting binding of said labelled ligand to the host cells. Individual expression systems giving rise to ligand binding may be isolated.

One advantage provided by the expression systems provided by the present invention is that they may be introduced and expressed in a wide variety of host cells. The expression cloning of receptors and ligands can therefore be performed in a host cell system of the same or related species as the receptor and ligand are derived. This is a valuable feature in particular in view of the significance of the glycosylation pattern which is known to be species dependent and might influence receptor ligand binding.

B. The Process For Identification And Isolation Of Proteins Having A Predetermined Property 1. The Expression System One important component for the methods provided by the present invention is an expression system having a number of features. To practice the methods of the invention, one or a plurality of unique expression systems is generated and introduced in eukaroytic host cells leading to a population of host cells, with generally each cell containing one unique type of expression system. It will be understood, however that the population of host cells can contain some cells having the same expression system.

Generally, the expression system provided by the present invention is a nucleic acid molecule comprising two critical elements. First, it comprises a control element; secondly, it comprises a heterologous nucleic acid encoding a recombinant protein, referred to as "exogenous protein", which is operatively linked to the control element.

The Control Element. In its most basic version, the control element comprises components which facilitate transcription and translation of the exogenous protein. Preferably, the control element also is or contains a component which promotes, under certain circumstances, selective expression of the exogenous protein while expression of endogenous proteins in a host is suppressed. The control element may further comprise additional components, as detailed below.

A control element useful for the practice of the invention may be derived from a number of sources. Most typically, the control element is derived from a virus. A variety of viral control elements have been described that are capable of directing expression in eukaryotic cells. Particularly preferred control elements are further capable of promoting, under certain circumstances, expression of nucleic acids in eukaryotic cells while expression of endogenous proteins is inhibited. Such viral control elements both already described and yet to be discovered are within the scope of the invention.

Viruses of the group of RNA viruses are preferred vectors for the present invention. Most preferably viruses of the group of alpha virus are used as viral vectors, because they themselves have the ability to block host protein synthesis. Examples of suitable alpha viruses are Sindbis virus, Semliki forest virus or Venezuelan equine encephalitis virus. A variety of alpha virus derived control elements has been described. See, among other places, Liljeström and Garoff, 1991, *Biotechnology* 9:356–361; Hahn et al., 1992, *Proc. Natl. Acad Sci. USA* 89:2679–2683; Bredenbeek, 1993, *J. Virol.* 67:6439–6446.

Alpha Viruses are positive-strand RNA viruses of the family of Togaviridae. Strauss et al., 1994, *Microbiological Reviews* pp. 491–562. Alpha viruses can function in a broad range of host cells, including mammalian avian, amphibian, reptilian and insect cells. The genome of alpha viruses comprises elements capable of directing the expression of proteins encoded by nucleic acids of said viral genome in large amounts.

The expression of proteins encoded by the alpha viral genome is independent of expression of proteins encoded by the genome of the host cell. Transcription of cellular genes may be arrested while the expression of virally encoded nucleic acids is not noticeably affected. Moreover, the expression of the viral genome of alpha viruses in a cell was found to result in the inhibition of translation of cellular messenger RNA molecules. Frolov et al., 1994, *J. Virol.* 68:1721–1727. This feature of alpha virus mediated expression of proteins in cells is particularly useful for the practice of the invention.

A number of, e.g. the double subgenomic vectors of the alpha virus group are provided, in which a recombinant nucleic acid may be inserted at a site in the genome downstream of a second subgenomic promoter or another genetic element leading to expression of the exogenous nucleic acid. Hahn et al., *PNAS*, 89:2679–2683. It is well known that for example internal ribosome entry sites are functional in a Sindbis virus background. An RNA molecule containing a viral internal ribosome entry site upstream of a resistance gene, e.g., a neomycine resistance gene, in the cytoplasma is sufficient to survive the selection with G418. Therefore, the viral internal ribosome entry site is sufficient for translation. Also, many sites within the genome are functional for expression of the exogenous nucleic acid. Sindbis virus vectors have been engineered which contain the second subgenomic promoter/expression cassette upstream or downstream of the structural genes. Frolov et al., 1996, *PNAS*, 93:11371–11377. Additionally, for increased cloning capacity and increased safety of the vectors, the structural proteins can be supplied by helper functions provided either by a packaging cell line or a helper virus particle. Bredenbeek et al., 1993, *J. Virol.*, pp. 6433–6446. Removing the structural proteins from the replicon increases the cloning capacity of the vector used, which is advantageous for cloning of large secreted proteins and glycoproteins. See, infra. As pointed out with these examples many modifications of the genetic arrangements are possible within the scope of the invention.

Although alpha viral control elements are most preferred, a number of other viral control elements may be employed which fulfill the criterion that synthesis of proteins under viral regulation can occur when protein synthesis of the host cell is arrested. According to the present invention, a variety of methods can be applied to uncouple viral protein synthesis from host cell protein synthesis. For example, all eukaroytic genes which encode proteins are transcribed by RNA polymerase II. Thus, if a control element is used which does not use RNA polymerase II for transcription, the host protein synthesis may selectively be inhibited using an RNA polymerase II inhibitor; inhibition of transcription leads consequently also to inhibition of translation.

A variety of other RNA polymerase II specific inhibitors have been described and are useful for the practice of this embodiment of the invention. The skilled artisan would readily know which RNA polymerase II specific inhibitor to use. For example, antibiotics have been demonstrated as useful for such inhibition. Such antibiotics are, for example, Actinomycin D, Aflatoxin B1, Amatoxin, which are useful for the practice of this embodiment of the invention.

In another embodiment of the invention, the control element may be derived from a prokaryotic cell. In that case, the expression system would also include the gene encoding bacterial RNA polymerase. Again, host transcription could then be selectively inhibited using a RNA polymerase II inhibitor, such as Actinomycin D, Aflatoxin B1, Amatoxin. The skilled artisan would readily know which control element to use in the practice of the invention.

In still another embodiment of the invention, control elements derived from eukaroytic systems may be used in the expression systems of the invention. For example, one may use a promoter or enhancer element specific for RNA polymerase I or III as control element. This would render the expression of the nucleic acid encoding the exogenous protein dependent upon RNA polymerase I or III, but not on RNA polymerase II. As in eukaryotic host cells genes encoding proteins have been demonstrated to be transcribed by RNA polymerase II, and it is believed in the art that RNA polymerase II is solely responsible for such transcription. Therefore, in the practice of this embodiment, one may, for example, inhibit RNA polymerase II dependent transcription by adding an RNA polymerase II specific inhibitor, thus inhibiting the expression of endogenous proteins without such an effect on the expression of the exogenous protein.

The Nucleic Acid Encoding An Exogenous Protein. As set forth above, the expression system of the invention comprises in addition to a control element a recombinant nucleic acid encoding an exogenous protein which is operatively linked to the control element. The recombinant nucleic acid may be derived from any source, i.e., any organism, tissue or cell type, disease state, etc. In one embodiment of the invention, a plurality of different nucleic acids is inserted into a plurality of expression systems, so that a plurality of expression systems is generated each encoding a unique exogenous protein. Alternatively, one known or unknown nucleic acid of interest encoding one particular exogenous protein to be characterized may be inserted into the expression system.

In one embodiment of the invention, the nucleic acid component encoding an exogenous protein may be derived from a nucleic acid library. This embodiment is particularly preferred if the objective is to identify and isolate nucleic acids encoding exogenous proteins with a predetermined property of interest. The library may be obtained from a tissue or cell type of interest. This library may be a cDNA library, a genomic library, an RNA library, a heterologous RNA library, or any other kind of library comprising transcribed nucleic acid from any kind of organism, tissue, or cell type known to the skilled artisan. In preferred embodiments, the library is derived from a mammalian source, in most preferred embodiments form a human source; however, it may be also derived from reptilian, amphibian, avian, insect, plant, fungi, bacterial cells, etc. In some instances, the recombinant nucleic acid will be derived from a subtractive library, for example a library which comprises cDNAs differentially expressed in a disease state when compared to the corresponding healthy tissue. A nucleic acid library typically comprises a number of different nucleic acid species, each species having a distinct nucleic acid sequence when compared to other species in the library. The number of nucleic acid species, or complexity, of a library may vary widely, depending on a number of parameters. For instance, in case of a cDNA library, the complexity of the library depends on the complexity of the RNA pool used to generate the cDNA library. Suitable nucleic acid libraries may be generated using standard methods, see, among other places, Sambrook et al., *Molecular Cloning: A Laboratory Manual, 2nd Ed.*, Cold Spring Harbor (1989). Alternatively, a suitable library may be obtained from numerous commercial sources, including, but not limited to, Clontech, Palo Alto, Calif.; and Stratagene, La Jolla, Calif.

Optionally, the genetic library may be propagated in *E. coli*, phages, yeast or the like.

Alternatively, the nucleic acid encoding the exogenous protein may be derived from mRNA isolated from a tissue or cell type of interest. In this case, the mRNA is reverse transcribed into cDNA. Starting with cellular RNA or, preferably, mRNA, many methods are known for the preparation of cDNA. Most preferably directed cDNA is produced which can be inserted into the viral vector such that the clones carry the inserts in sense orientation. Stratagene, e.g., offers several kits for the generation of directed cDNA (lambda ZAP cDNA kit). Further, standard protocols for the generation of cDNA are available, and can be found, among other places, in Sambrook et al., *Molecular Cloning: A Laboratory Manual, 2nd Ed.*, Cold Spring Harbor (1989).

In another embodiment of the invention, the nucleic acid encoding an exogenous protein is a particular and specific nucleic acid of interest. The so generated expression system is particularly useful for characterization of a particular nucleic acid or protein of interest as it conveniently allows to determine where a protein encoded by a nucleic acid molecule is located in the cell, thereby revealing important information to the skilled artisan as to the function of that protein.

The nucleic acid of interest may be DNA or RNA. Whether the nucleic acid is available as DNA or RNA, it can easily be used with a control element as part of the expression system of the invention. Once the artisan has chosen a control element useful for the method of the invention, it will require only routine experimentation to use the nucleic acid of interest with that control element.

For example, if the nucleic acid of interest is available in the form of RNA and the control element of choice is available in the form of DNA, the nucleic acid of interest can be converted into DNA using routine reverse transcriptase assays. Also, the control element could be converted into RNA by using routine transcription assays. Following either conversion, the resulting two DNA or RNA molecules can be ligated together using routine DNA ligase assays or RNA ligase assays. Finally, the resulting expression system comprising the nucleic acid of interest and the control element combined, can then be used in the invention. Similar to the above example, if the nucleic acid of interest is available in the form of DNA and the control element in the form of RNA, either routine conversion method can be applied followed by the appropriate routine ligase method. The skilled artisan would readily know which procedure for transcription, reverse transcription, or ligation to follow in order to practice the invention.

Alternatively, the nucleic acid of interest may be DNA of any kind. This includes, but is not limited to, complementary DNA ("cDNA"), genomic DNA, cDNA that was manipulated to include additional nucleic acids, or any other kind of DNA. Any kind of DNA can be used in the method of the invention. Any kind of DNA can be linked to the control element molecule by using routine ligation assays. The expression of genomic DNA is well within the scope of the invention as the use of eukaryotic cell types facilitates the necessary processing of heterogenous RNA molecules that are created through transcription of genomic DNA, to yield messenger RNA useful for cellular protein synthesis.

The nucleic acid encoding the exogenous protein, if derived from a cDNA library or from RNA or from any other source may be integrated into the expression system using tandard procedure. Such integration may be facilitated by, for example, DNA ligation or RNA ligation procedures to connect a nucleic acid molecule of the library with a control element molecule.

Additionally, different methods of assembly of the cDNA or RNA and the viral vector are available. Standard ligation of the nucleic acids as DNA are the preferred way to carry out the assembly step. Other methods are of course feasible, e.g., RNA molecules can be ligated using the enzyme T4 RNA ligase. Numerous standard methods are available and described, for example, in Sambrook et al., *Molecular Cloning: A Laboratory Manual, 2nd Ed.*, Cold Spring Harbor (1989).

Viral Propagation. When using a virally derived control element in the practice of the invention, one may want to propagate the virus in order to have the expression system available for future experimentation. The propagation of a virus requires the availability of certain molecular components to facilitate the assembly of viral particles. Some molecular components, in the case of proteins, typically have to be encoded by nucleic acids of the viral genome, depending on the particular virus. However, one cannot add unlimited numbers of nucleic acids to the genome of a virus while maintaining the ability of the resulting derivative of the viral genome to become packaged into viral particles.

Therefore, when trying to maximize the size of a nucleic acid of interest that can be incorporated into a viral genome for characterization in the method of the invention, it is necessary to delete nucleic acids found in the wild type viral genome from that genome. However, such deletion may render the resulting expression system incapable of propagation of the virus the control element is derived from.

This problem may, however, be overcome by using a helper function that provides for the necessary components for viral propagation. In one embodiment of the invention, such a helper function may be provided by use of a helper nucleic acid. A helper nucleic acid may be, for example, a defective helper RNA, as used for alpha virus based expression systems, to facilitate the propagation of the alpha virus.

In another embodiment of the invention, such a helper function may be provided through a packaging cell line. A packaging cell line encodes in its genome the components necessary for viral propagation usually encoded by the viral genome, but deleted for purposes of cloning utility. These components will therefore be expressed in the cell line used in the method of the invention and propagation of the virus will be facilitated.

The generation of such a packaging cell line is well within the knowledge of the skilled artisan by using routine experimentation. For example, depending on the virus chosen for the practice of the invention, one may take the exact same nucleotide sequence deleted from the viral genome, link it to a control element known to facilitate high level expression of nucleic acids in the chosen cell line, and transfect the resulting nucleic acid into the cell line. An example of such a vector is provided below. Specifically, the vector 987 BBneo (SEQ ID NO:2) can be transfected into BHK 21 cells with the Ca-phosphate method and subsequently selected with 200 mg/l G418 according to known methods. This can be further facilitated by, for example, using standard screening procedures for the establishment of cell lines with new properties, like, for example, the screen for the presence of a marker providing resistance to a certain toxin. Such a marker, like, for example, the neomycin resistance gene which renders cells resistant to neomycin selection, may be included in the expression system comprising the nucleic acids encoding components necessary for virus propagation and the control element specific for the chosen cell line.

2. Introduction Of The Expression System In Host Cells

The expression system, or typically a plurality of unique expression systems comprising library inserts encoding exogenous proteins, are introduced into suitable eukaryotic host cells. In this manner, a plurality of eukaryotic host cells can be provided, wherein each host cell has an expression system comprising a different member. Of course, in this population there may be multiple host cells that contain the same member. The host cells can be derived from any kind of organism, depending on the compatibility of the expression system. Preferably, the host cell is identical with or related to the cellular source of the recombinant nucleic acids encoding the exogenous protein, which, in preferred embodiments is mammal.

Introduction of the expression systems into eukaryotic host cells can be carried out using a number of different well known procedures. Transfection with $CaPO_4$, polyethylenimine, lipofection, electroporation, are only a number of available techniques to introduce nucleic acids into animal cells. An RNA molecule containing a viral internal ribosome entry site upstream of a resistance gene, e.g., a neomycine resistance gene, in the cytoplasma is sufficient to survive the selection with G418. Therefore, the viral internal ribosome entry site is sufficient for translation. An advantage of the alpha viruses is their broad host range; infection of mammalian, insect, avian, amphibian, and reptilian cells from various different tissues and different degree of transformation have been reported. Cells containing exogenous viral nucleic acids can be used to produce viral particles which can be collected from the supernatant or by cell lysis. Alternatively the cells containing the exogenous nucleic acids can be used to induce plaque formation in a feeder culture.

3. The Screening Process For The Identification And Isolation Of Exogenous Proteins Having A Predetermined Property In order to facilitate screening for individual exogenous proteins, a cell culture is provided which allows physical separation of different viral clones and physical separation of viral particles and/or viral proteins from exogenous novel secreted proteins or glycoproteins of interest.

According to the present invention, the detection of clones secreting novel radioactive labelled proteins or glycoproteins can be performed in various ways. Physical separation of the viral clones can be achieved for example by plaque formation in semisolid medium consisting of normal growth medium containing agarose or carboxymethylcellulose (similar to phage screening). Alternatively single virus particles (isolated by limited dilution) or plaque purified clones can be inoculated into wells of, e.g., a 96 well plate containing animal cells. Addition of single cells to a feeder layer in 96 well plates will infect the cells with a single clone. Other methods of physical separation of viral clones are possible without leaving the scope of the invention.

Blocking Of Residual Host Protein Synthesis. Where selective labelling of virally encoded exogenous proteins is desired, host cellular protein synthesis has to be silent. According to the present invention several methods can be used to suppress cellular protein synthesis. Using viruses of the alpha virus group addresses this problem, since the virus shuts down cellular protein synthesis entirely, see, supra. Alternatively, depending on the control element employed, see, supra, if other viruses are used host cell directed RNA polymerase II transcription and translation can be suppressed specifically by addition of agents such as Actinomycin D, Aflatoxin B1, Amatoxin. Also in cases where not all cells are subject to viral replication the remaining fraction of cells can be transcriptionally/translationally be arrested with this substance. Condreay et al., 1988, *J. Virol*, 62:2629–2635.

The Labelling Step. In a preferred embodiment of the invention, the exogenous protein expressed by the expression system is rendered distinguishable from the endogenous proteins of the host cell system by specific labelling during a time window in which endogenous protein expression is suppressed while the exogenous protein is expressed. For example, a pulse of radioactively labelled amino acids of suitable length and intensity is applied such that sufficient radioactive protein can be recovered from the clone for detection. The system may be varied in at least three dimensions, i.e., (1) pulse length, (2) pulse intensity, and (3) site of plaques.

At a suitable time after infection when sufficient cells undergo viral replication and express virally encoded proteins and when suppression of RNA polymerase II transcription and/or translation are complete, a pulse of radioactive amino acids is added to the culture. Of course, many different combinations of pulse and chase times, at different plaque sizes, choice of isotopes, mode of autoradiography (X-Ray film vs. Phosphoimager) etc. are suitable. Examples of suitable combinations of labelling times, isotopes, concentrations etc. are given in the examples. The application of radioactive amino acids can be carried out as a pulse with a subsequent chase period. Other schemes are suitable, e.g., a continuous incorporation of radioactive amino acids. Monomeric amino acids are not precipitable under certain conditions at which proteins are precipitable and can therefore be subtracted. Suitable isotopes are $^{35}S$, $^{3}H$, $^{14}C$, in any of the twenty (20) natural amino acids. Alternatively endogenous proteins can be treated in a way to allow discrimination with newly synthesized exogenous proteins. Treatments of the present invention are: 1) removal of sialic acid residues from the cell surface by sialidase. New membrane proteins being synthesized from the exogenous expression system display sialic acid residues on the cell surface allowing detection; 2) proteolytic digestion of endogenous proteins (e.g., on the cell surface). Other methods are possible and within the scope at the present invention.

Soluble Viral Proteins. When using an expression system with a control element derived from a virus comprising viral proteins, one may encounter the problem of soluble viral proteins that are expressed when the exogenous protein is expressed. This problem may be of varying significance° For example, when using the semisolid medium, e.g., soft-agar-plate, based screening method, such soluble viral proteins could bind the membrane designed to bind the exogenous protein.

In one embodiment of the invention, such soluble viral proteins are kept from interfering with the screen for desired exogenous proteins by using a filter that can bind or stop the flow of such soluble viral proteins. In another embodiment, antibodies specific to the soluble viral proteins are attached to such filter papers so to bind the soluble viral proteins. A variety of filter papers useful to bind or stop the flow of soluble viral proteins has been described. The skilled artisan would readily know which filter to use for the practice of the invention. It is also well within the knowledge of the skilled artisan to attach antibodies specific for soluble viral proteins to such filters. In another embodiment of the invention, antibodies are crosslinked to the semisolid medium (e.g., NuFix Agarose, FMC Bioproducts Rockland USA, which prevents interfering of the viral proteins with the screen.

In another embodiment of the invention, the generation of soluble viral protein is reduced by using serum containing medium. Any amount of reduction is desirable, preferably to levels that allow detection of secreted proteins of interest in the background of viral proteins. Yet another way of reducing the generation of soluble viral proteins is by using a protease inhibitor or inhibitors. An example of using protease inhibitors to reduce the amounts of soluble viral proteins is illustrated below by way of a working example. Any one or number of protease inhibitors can be used and are well known to those of ordinary skill in the art.

In another embodiment of the invention, the generation of soluble viral protein is educed by using an expression system containing a control element that is based on a mutant virus. A variety of mutant virus strains has been described which are useful for this embodiment of the invention.

The skilled artisan would readily know which mutant viral strain to use for this embodiment. For example, mutant viral strains of the genus alpha virus have been described that are useful for the practice of this embodiment of the invention. A mutant Sindbis Virus strain useful for the practice of this embodiment of the invention having the genotypes, for example, ts20, ts10, and ts23. Lindquist et al., 1986, Virology, 151:10–20; Arias et al., 1983, J. Mol. Biol., 168:87–102; Carleton and Brown, 1996, J. Virol, 70:952–959. Such temperature-sensitive virus mutants are defective in cleavage of PE2 (ts20) and defective in folding of E1 (ts10; ts23). As a consequence, the viral proteins do not reach the cell surface at the nonpermissive temperature. Leakage of soluble proteins is reduced by use of these mutants.

In another embodiment of the invention, the generation of soluble viral proteins is reduced using a cell line deficient in the proteolysis of viral proteins in the method of the invention. A variety of cell lines deficient in the proteolysis of viral proteins has been described. Watson et al., 1991, J. Virol. 65:2332–2339.

The skilled artisan would readily know which cell line deficient in proteolysis of viral proteins would be useful for the practice of the invention. A cell line useful for the practice of this embodiment of the invention would be deficient in the proteolytic cleavage of proteins of the virus used in the method of the invention. For example, when using an Alpha Virus in the practice of the invention, cell lines described that are deficient in the cleavage of the viral proteins PE2 to E2 and E3 may be useful.

More particular screening processes of the invention are exemplified below.

Compartment Screening. In one embodiment of the invention, host cells comprising unique expression systems encoding exogenous proteins may be screened by placing them into separate compartments. For example, individual cells may be picked physically and placed into a separate compartment, for example, a well in a 96 well plate. Of course, if desired, a number of cells may be placed into a compartment or well, to facilitate the screening of cells in groups. Alternatively, viral particles are diluted to 1 pfu per compartment leading to monoclones.

Semisolid Medium Screening. In another embodiment of the invention, cells used in the method of the invention may be separated by growing them in soft agar. For example, cells can be transfected with the nucleic acids of the expression system and then spread out onto plates in a semisolid medium, i.e., soft agar. This soft agar, or semisolid medium may consist of, for example, normal growth medium containing agarose or carboxymethylcellulose. Alternatively, a confluent layer of cells is infected with virus, e.g., alphavirus at an MOI that allows plagues to grow to a size of 1–3 mm. Three hours postinfection the virus solution is removed and replaced by semi-solid medium. This semisolid medium inhibits diffusion of virus particles and allows plaque formation. Other methods of maintaining cells in a semi solid medium known to the skilled artisan are also within the scope of the invention.

Once plated out in the soft agar, or semisolid, medium, the host cells can then be screened. This allows one to reduce lateral diffusion of substances on the plate and therefore reduces cross contamination of the various cells or viruses that contain expression systems expressing different exogenous proteins. In addition, this experimental setup allows the flow of proteins secreted by the cells, for example, extracellular proteins encoded by the nucleic acid of interest, from the cells to a filter that can bind such proteins. Filters useful for the binding of proteins are, for example, nitrocellulose filters and PVDF or nylon membranes.

Once exogenous proteins are bound to a filter, they may be screened by different methods known to the skilled artisan. In one embodiment of the invention, exogenous proteins are selectively labelled, see supra, to determine their location on the filter. For example, by exposing the filter to a film, the film, once developed, will have a dark spot in the place where it was juxtaposed to a spot of the filter that had bound labelled exogenous protein. When using proper markings, one may correlate each spot on the film to a particular area on the soft agar plate. Thus, one may locate the cells that express the exogenous protein which gave rise to a spot on the film. Therefore, one may also locate the particular expression system that contains the nucleic acid encoding the exogenous protein that was secreted and gave rise to the spot on the film.

In another embodiment of the invention, one may screen filters with bound exogenous protein by exposing the filters to a ligand. For example, one method of choice may be to expose the filter with the bound exogenous proteins to a labelled lectin, thereby screening for secreted glycoproteins. Or, for example, one may screen the filter with an antibody specific to a particular post-translational modification such as, for example, a sugar moiety. Also, one may use antibodies that are specific to a particular protein of interest.

Furthermore, this system facilitates the easy separation of viral particles from the exogenous proteins. Separation can be accomplished by, for example, using a different filter paper, i.e., one that binds or stops the flow of viral particles but not the exogenous protein. This additional filter paper may be placed underneath the filter that binds the exogenous protein. Therefore, the viral particles would not reach the filter paper that binds the exogenous protein.

Filters can be rendered more effective by, for example, attaching antibodies against the soluble viral proteins to the filter which bind the soluble viral proteins but not the exogenous protein.

Detection And Isolation Of Secreted Proteins. In a preferred embodiment of the invention, samples are prepared for detection of secreted radioactive protein and detecting radioactivity versus background.

According to the method of physical separation of the clones chosen, different modes of detection of the secreted protein or glycoprotein can be applied. For example, in cases where single clones were inoculated in microtiterplates, precipitation of the secreted radioactive protein or glycoprotein in.the supernatant can be carried out with, e.g., the TCA method. (Ma et al., 1994, *Cancer Chemother. Pharmacol.* 38(4):391–394). If physical separation of the clones was achieved using semisolid growth medium, then the membrane capturing the secreted radioactive protein or glycoprotein is washed and prepared for autoradiography. Many different commercially available membranes or filters are useful as tracer membranes. Protein captured at the membrane has to be bound such that the clones secreting radioactive protein can be detected. Several different washing procedures can be applied to link precipitable protein to the membrane and remove unincorporated radioactive amino acids. Several methods are suitable for autoradiography including exposure with or without intensifying agents to an X-Ray film and Phosphoimaging.

Ligand Selection. In another embodiment of the invention, cells containing expression systems expressing different exogenous proteins may be separated by ligand recognition. For example, when screening for nucleic acids of interest encoding receptor molecules of the cellular membrane, a ligand capable of recognizing such receptors may be used to screen for cells that express such receptors. That screen may be carried out by, for example, attaching the ligand to a solid support and exposing cells expressing the protein of interest to the ligand on the solid support. By binding cells that express membrane receptor molecules of interest, the cells expressing such receptors may be separated from cells not expressing such receptors.

In one embodiment of the invention, the ligand may be a protein. In another embodiment, the ligand may be an antibody. In yet another embodiment, the ligand may be a lectin. In a further embodiment, the ligand may be a non-protein. The choice of the ligand is dependent upon the protein that is to be selected for. A large number of ligands capable of binding proteins based on the peptide backbone, a post-translational modification, or other criteria have been described. The skilled artisan would readily know which ligand is useful for the practice of this embodiment of the invention.

In another embodiment of the invention, the ligand is attached to a solid support. A variety of solid supports useful for the practice of this embodiment have been described. For example, one may attach the ligand to a plate to which one would add the cells expressing exogenous protein. Once on the plate to which the ligand is bound, cells will bind to the ligand if they express a membrane protein which recognizes the ligand. Cells bound to the ligand will therefore remain on the plate when a washing solution is added for the removal of cells that do not bind to the ligand. This way, cells expressing a membrane receptor which binds the ligand will be removed from cells that do not. Consequently, this is a fast and simple way to identify membrane receptors and the nucleic acids that encode them. As membrane receptors are main targets for drug development, this embodiment of the invention will be highly useful for pharmaceutical research and drug discovery.

Membrane Protein Selection. In another embodiment of the invention, one may select for cells expressing an exogenous protein based on the exogenous protein being a membrane protein with an extracellular domain. For example, one may express exogenous proteins in cells while expression of endogenous proteins is inhibited or while using an expression system the operation of which inhibits the expression of endogenous proteins, see, supra.

Using this setup, one may, for example, treat the cells with proteases after inhibition of expression of endogenous proteins has set in, but while expression of exogenous protein is still continuing. After the cell surface has been deprived of extracellular proteinaceous protrusions, i.e., cellular membrane receptors and so on, the expression of the exogenous protein may replenish such protrusions. However, such replenishment will only occur if the exogenous protein expressed in a particular cell is a membrane receptor molecule.

Therefore, at this step, only cells containing an expression system that encodes a membrane receptor molecule will have extracellular proteinaceous protrusions. Such protrusions may be used to bind the cell to any structure that binds proteins, regardless of whether such binding occurs specifically or nonspecifically with regard to the structure of the protein that is bound. Cells bound to such a protein binding structure, may then, for example be further analyzed as to the sequence of the nucleic acid encoding the exogenous protein. A variety of structures that bind proteins have been described and are well known to the skilled artisan. For example, nitrocellulose, PVPF or nylon, filters may be used in this embodiment as a protein binding structure. Other structures, known to the skilled artisan, that bind proteins are also within the scope of the invention.

Membrane Glycoprotein Screening. In one embodiment of the invention, cell membrane glycoproteins are identified using the method of the invention. To facilitate the identification of cell membrane glycoproteins, a variety of method have been described that are useful for the practice of this embodiment of the invention. For example, one may alter the chemical reactivity of cell surface sugar residues and thereby facilitate the specific recognition and identification of such sugar residues. One method useful for such alteration of chemical reactivity is, for example, the introduction of reactive ketone groups into cell surface oligosaccharides. Mahal et al., 1997, *Science* 276:1125–1128. In this method one introduces new chemically reactive groups into cell surface glycoproteins. When this method is applied under conditions where the exogenous protein is expressed in the method of the invention while the expression of endogenous proteins is inhibited, the exogenous protein will preferably incorporate the reactive group, thereby facilitating the recognition of the exogenous protein. Other methods known to the skilled artisan useful for the practice of this embodiment of the invention and are also within the scope of the invention.

In another embodiment of the invention, membrane glycoproteins are identified using the method of the invention through selective glycosylation of such membrane glycoproteins. A variety of methods are known to selectively glycosylate membrane proteins and are within the scope of the invention. For example, one may first remove all cell surface sialic acid residues by using an enzyme exhibiting sialidase activity. After such removal, one may, using the method of the invention, express the exogenous protein in cells while the expression of endogenous proteins is inhibited. Thereby, the exogenous protein will be preferably transported in sialiated form to the cell surface which facilitates its improved identification.

Screening For Proteins Located In Other Cellular Fractions Of Interest. In one embodiment, the present invention provides a general approach with which expression systems comprising a nucleic acid encoding an exogenous protein located in any cellular location of interest may be identified. Host cells harboring expression system, comprising a unique nucleic acid encoding an exogenous protein are provided in a manner that physical separation of each host cell comprising an individual expression system is possible. Preferably, the expression systems comprise viral control elements. Most preferably, the host cell/expression system allows that viral particles comprising the expression system be released from the host cells.

For example, host cells may be plated in semisolid medium. At first, filter which is capable of binding viral particles is placed in the semisolid medium under conditions and for a duration which allow to captive viral particles on the filter. The skilled artisan will readily know what filters may be useful for production of this embodiment of the invention. For example, the filter may be a nitrocellose filter. The first filter having the virus particles attended to it is treated in a way which facilitates recovery of infectious virus particles comprising an expression system. Subsequently, the host cells in the semisolid medium are exposed to a composition which allows labelling of the expressed exogenous protein which expression of endogenous proteins is inhibited. For example, the exogenous proteins may be labelled with radioactive amino acids while endogenous protein expression is suppressed. In a next step, host cells in the semisolid medium are and/or conditions which allow recovery of the cellular fraction/compartment of interest. The skilled artisan will know what conditions would be appropriate depending on the cellular compartment/fraction under consideration. In a next step, a second filter having attached to it, e.g., antibodies against certain structures comprised within the cellular fraction of interest is placed on the semisolid medium. It is critical that the filter is saturated, i.e., does not allow for any further molecules to bind to its surface. The second filter is placed under conditions and for a duration which allows the predetermined cellular compartment of interest to adhere. If, for example, the cellular component of interest is in the nucleus, antibodies to nuclear membrane surface proteins would be attached to the filter. For other compartments, corresponding methods would be used. The second filter thus constitutes a "replica" of the first filter, where the first filter has attached to it the recoverable expression system, while the second filter has attached to it proteins derived from the cellular component of interest. Those individual clones of host cells which comprise an expression system comprising a nucleic acid encoding an exogenous protein located within the cellular fraction/component of interest may be identified through presence of the label. Additionally, cellular compartments can be physically separated using classical methods well-known in the art (e.g., differential centrifugation).

Identification Of Unknown Ligands Of Known Receptors. In one embodiment, the invention allows for the identification of unknown secreted ligands of known receptor of interest. Host cells comprising expression system comprising unique recombinant nucleic acids encoding exogenous proteins are cultured in a way that they are a physically separable. For example, for this purpose the host cells may be cultured in semisolid medium. The cells are incubated with compositions which allow labelling of expressed exogenous proteins while expression of endogenous proteins is inhibited. A filter coated with the receptor protein of interest whereby all binding sites are saturated (either by the receptor protein or by any other neutral protein) is placed on the semisolid medium under conditions and for a duration which allows all secreted proteins to move to the filter. Since all protein binding sites on the filter are saturated, only secreted proteins binding to the receptor of interest may adhere to the filter. Those exogenous proteins may be identified by means of their label. As the filters represent a replica, i.e., a mirror image of the original plate, colonies harboring the expression system comprising a nucleic acid encoding a ligand of the receptor of interest may be easily identified.

Identification of Unknown Receptors Of Known Ligands. In one embodiment, the invention allows for the identification of unknown receptors for a known ligand. Host cells comprising expression system comprising unique recombinant nucleic acids encoding exogenous proteins are cultured in a way that they are physically separable. For example, a confluent layer of cells can be infected with a low MOI of an infectious virus carrying the plurality of expression systems. After infection, the cells are incubated at 34° C. in semisolid medium with a melting point around 37° C. (e.g., low melting agarose). After plaques of sufficient size are produced, a filter is placed on top long enough to capture viral particles which serves as a replica of the plate. Subsequently, the agarose is melted by heating the plates to 39° C. After removal of the agarose and washing, the cells are incubated with the labelled ligand of choice. After washing of the cells, the binding of the ligand can be detected by autoradiography. Viral particles containing the expression system (and nucleic acid) of interest can then be recovered from the replica filter.

4. Recovery Of Viral Particles Comprising Exogenous Proteins Of Interest

In a next step, those viral particles from the samples or area where increased radioactivity was observed are identified and recovered. The identity of the well or the position of the plaques where exogenous protein of interest was detected can be traced back using the developed film and viral particles can be recovered. At this point, recombinant virus particles containing a nucleic acid sequence giving rise to expression of the protein of interest are collected. According to the invention the particles can be applied for, e.g., the one of the procedures described below.

C. Applications Of The Identified Expression Systems Encoding Proteins Of Predetermined Properties The pools of expression systems selected with the above screening methods having a predetermined property, e.g., cellular localization, structure, enzymatic function, or affinity to other molecules, may be used for further screening procedures. Alternatively, individual expression systems may be randomly picked and subjected to characterization and functional analysis. See, infra.

Additional Screening Rounds To Avoid Contamination. Individual clones may be picked and the procedure of steps 3 and 4 can be repeated to plaque purify the clones and to avoid contaminations.

Passaging The Viral Particles To Increase Their Number. The viral particles isolated and optionally amplified by passaging can be applied to one of the following procedures. Many useful application for viral particles containing exogenous nucleic acids encoding secreted proteins or glycoproteins are apparent, of which some are describe below. Therefore the present invention is not limited to the applications described above.

Infection Of A Cell Culture To Induce Production Of Novel Secreted Protein Or Glycoprotein, In Either Labelled Or Unlabelled Form Novel secreted proteins or glycoproteins can be produced at larger scale by infecting a substrate cell line growing in vessels such as T-flasks, spinner flask, roller bottles, bioreactors, perfusion reactors and the like with the isolated viral particles. Depending on the nature of the genetic construct chosen above, production will occur under slightly different conditions. When one way vectors are packaged in a packaging cell line the particles will induce only one round of infection (accordingly the MOI should be higher than one). Also a broad spectrum of host cell lines can be used for production of the novel secreted protein or glycoprotein. Labelling of the novel secreted protein or glycoprotein can be achieved by addition of radioactive amino acids as described above. This offers the advantage that product formation can easily be monitored by SDS polyacrylamide gel electrophoresis and subsequent autoradiography. In this way an unknown product can be easily detected for optimization of production parameters.

Application Of The So Produced Supernatant To Protein Purification Or Isolation Methods And Detecting Novel Secreted Protein Or Glycoprotein By Its Radioactive Label. The novel secreted protein or glycoprotein can easily be purified from the supernatant of the above step using standard protein purification techniques. The unique possibility to label the secreted protein during production, see supra, simplifies purification processes significantly. Eluent from chromatography columns or the like can automatically be collected using a sample collector. The samples containing the novel secreted protein can then easily be identified by detection of radioactivity. Enriched and purified material can be obtained in this way. Unlabelled material can be obtained by application of identical chromatography conditions to unlabelled cell culture supernatant.

D. Characterization And Functional Analysis Of Individual Identified Proteins Several procedures known in the art may be employed for further characterization and functional analysis of individual identified exogenous proteins.

1. Sequencing of The Nucleic Acid Encoding The Exogenous Protein

In one embodiment, the identity and the sequence of the exogenous nucleic acid in the recovered viral particles can be investigated by sequencing according to standard methods. Detailed description of suitable protocols can be found, for example, in Sambrook et al., *Molecular Cloning: A Laboratory Manual*, 2nd Ed., Cold Spring Harbor (1989).

Sequence comparisons with known polynucleotide sequences in data bases may reveal indications about the function of an identified and isolated exogenous protein.

2. Analysis Of The Expression Pattern Of The Identified Exogenous Protein

In one embodiment, the cDNA of the identified exogenous protein or fragments thereof are used as a probe to detect the expression of its mRNA. For example, sections of tissue samples may be prepared and examined by in situ hybridization with a suitable, labelled probe. Alternately, mRNA extracts may be prepared and analyzed in Northern blot analysis. Alternatively, synthetic oligonucleotides designed according to the identified protein's cDNA sequence may be generated and used as hybridization probes. Detailed description of suitable protocols can be found, for example, in Sambrook et al., *Molecular Cloning: A Laboratory Manual*, 2nd Ed., Cold Spring Harbor (1989).

In one embodiment, the level of the gene's expression is assayed by detecting and measuring its transcription. For example, RNA from a cell type or tissue known, or suspected to over- or under-express the gene, such as cancerous tissue, is isolated and tested utilizing hybridization or PCR techniques such as are described herein. The isolated cells can be derived from cell culture, from a patient, or from test animals. Such analyses may reveal both quantitative and qualitative aspects of the expression pattern of the gene encoding the identified exogenous protein, including activation or inactivation of its gene expression.

Hybridization probes for Northern blot, Southern blot, and in situ hybridization may be labelled by a variety of reporter groups, including radionuclides such as $^{32}P$, $^{35}S$, and $^3H$ (in the case of in situ hybridization), or enzymatic labels, such as alkaline phosphatase, coupled to the probe via avidin/biotin coupling systems, and the like. The labelled hybridization probes may be prepared by any method known in the art for the synthesis of DNA and RNA molecules. See, Section VI. H., infra. An additional use for nucleic acid hybridization probes involves their use as primers for polymerase chain reaction (PCR). PCR is described in detail in U.S. Pat. Nos. 4,965,188, 4,683,195, and 4,800,195.

DNA may be used in hybridization or amplification assays of biological samples to detect abnormalities involving gene structure, including point mutations, insertions, deletions and chromosomal rearrangements. Such assays include, but are not limited to, Southern analyses, single stranded conformational polymorphism analyses (SSCP), and PCR analyses.

Diagnostic methods for the detection of specific mutations of the gene encoding the identified exogenous protein can involve for example, contacting and incubating nucleic acids including recombinant DNA molecules, cloned genes or degenerate variants thereof, obtained from a sample, e.g., derived from a patient sample or other appropriate cellular source, with one or more labelled nucleic acid reagents including recombinant DNA molecules, cloned genes or degenerate variants thereof, under conditions favorable for the specific annealing of these reagents to their complementary sequences within the gene. Preferably, the lengths of these nucleic acid reagents are at least 15 to 30 nucleotides.

After incubation, all non-annealed nucleic acids are removed from the nucleic acid molecule hybrid. The presence of nucleic acids which have hybridized, if any, is then detected. Using such a detection system, the nucleic acid from the cell type or tissue of interest can be immobilized, for example, to a solid support such as a membrane, or a plastic surface such as that on a microtiter plate or polystyrene beads. In this case, after incubation, non-annealed, labelled nucleic acid reagents are easily removed. Detection of the remaining, annealed, labelled gene's nucleic acid reagents is accomplished using standard techniques well-known to those in the art. The sequences to which the nucleic acid reagents have annealed is compared to the annealing pattern expected from a normal gene sequence in order to determine whether a gene mutation is present.

Alternative methods for the detection of the gene's specific nucleic acid molecules, in patient samples or other appropriate cell sources, may involve their amplification, e.g., by PCR (the experimental embodiment set forth in Mullis, K. B., 1987, U.S. Pat. No. 4,683,202, see, supra), followed by the detection of the amplified molecules using techniques well known to those of skill in the art. If mutations are intended to be determined, the resulting amplified sequences can be compared to those which would be expected if the nucleic acid being amplified contained only normal copies of the gene in order to determine whether a gene mutation exists.

3. Detection Of The Identified Exogenous Protein Using Antibodies

Antibodies directed against the identified exogenous protein of interest or conserved variants or peptide fragments thereof, may also be used to gain more insight of its expression pattern in vivo. Antibodies may also be used to detect abnormalities in the level of the gene's expression, or abnormalities in the structure and/or temporal, tissue, cellular, or subcellular location of its gene product, and may be performed in vivo or in vitro, such as, for example, on biopsy tissue.

The analysis may be performed on any tissue or cell type, or, with labelled antibodies, even in vivo in a test animal. Alternatively, the tissue or cell type to be analyzed may include those which are known, or suspected, to aberrantly express the identified exogenous protein of interest, such as, for example, cancerous tissue.

The protein isolation methods employed herein may, for example, be such as those described in Harlow and Lane (Harlow, E. and Lane, D., 1988, "*Antibodies: A Laboratory Manual*", Cold Spring Harbor Laboratory Press, Cold Spring Harbor, N.Y.). The isolated cells can be derived from cell culture, a laboratory animal, or a patient.

For example, antibodies, or fragments of antibodies useful in the present invention may be used to quantitatively or qualitatively detect the presence of the identified exogenous protein of interest or conserved variants or peptide fragments thereof. This can be accomplished, for example, by immunofluorescence techniques employing a fluorescently labelled antibody (see, this Section, infra) coupled with light microscopic, flow cytometric, or fluorimetric detection.

The antibodies (or fragments thereof) or fusion or conjugated proteins useful in the present invention may, additionally, be employed histologically, as in immunofluorescence, immunoelectron microscopy or non-immuno assays, for in situ detection of the identified exogenous protein of interest or conserved variants or peptide fragments thereof, or for catalytic subunit binding (in the case of labelled catalytic subunit fusion protein).

In situ detection may be accomplished by removing a histological specimen from a patient, and applying thereto a labelled antibody or fusion protein of the present invention. The antibody (or fragment) or fusion protein is preferably applied by overlaying the labelled antibody (or fragment) onto a biological sample. Through the use of such a procedure, it is possible to determine not only the presence of the identified exogenous protein of interest, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for identified exogenous protein of interest or conserved variants or peptide fragments thereof will typically comprise incubating a sample, such as a biological fluid, a tissue extract, freshly harvested cells, or lysates of cells which have been incubated in cell culture, in the presence of a detectably labelled antibody capable of identifying the identified exogenous protein of interest or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labelled antibody or fusion protein. The solid phase support may then be washed with the buffer a second time to remove unbound antibody or fusion protein. The amount of bound label on solid support is then detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to readily ascertain the same.

The binding activity of a given lot of antibody or fusion protein is determined according to well known methods. Those skilled in the art will be able to readily determine operative and optimal assay conditions.

With respect to antibodies, one of the ways in which the antibody can be detectably labelled is by linking the same to an enzyme and use in an enzyme immunoassay (EIA) (Voller, 1978, *Diagnostic Horizons* 2:1–7, Microbiological Associates Quarterly Publication, Walkersville, Md.); Voller et al., 1978, *J. Clin. Pathol.* 31:507–520; Butler, 1981, *Meth. Enzymol.* 73:482–523; Maggio, E. (ed.), 1980, *Enzyme Immunoassay*, CRC Press, Boca Raton, Fla.,; Ishikawa et al., (eds.), 1981, *Enzyme Immunoassay*, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labelling the antibodies or antibody fragments, it is possible to detect the identified exogenous protein of interest through the use of a radioimmunoassay (RIA) (see, for example, Weintraub, B., *Principles of Radioimmunoassays*, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labelled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labelled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labelled by coupling it to a chemiluminescent compound. The presence of the chemiluminescent-tagged antibody is then determined by detecting the presence of luminescence that arises during the course of a chemical reaction. Examples of particularly useful chemiluminescent labelling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labelling are luciferin, luciferase and aequorin.

Infection Of Animals Tissues Or Cells. The viral particles obtained by the procedure described above can be used as gene transfer vectors to deliver the gene of interest to a tissue or animal. This approach is useful for the investigation of the nature of the protein of interest or could be used, e.g., for the production of antibodies against the novel protein as a result of its expression at the host.

E. Uses Of Proteins Having A Predetermined Property

The nucleic acids which are identified, characterized and isolated using the methods and expression systems of this invention, and, more importantly, proteins encoded by same, may be useful for a number of applications. First, in many instances they will be useful for research applications and laboratory use, for example the discovery and isolation of new growth factors, cytokines, or hormones may facilitate the growth of cells in culture which could not be cultured before. The discovery and isolation of membrane receptors, cytoplasmic, and nuclear proteins will be useful to gain more insight in important cellular signal transduction and control processes. The discovery and isolation of organelle proteins may provide more insight into metabolic, anabolic, and processing functions.

However, some of the genes and gene products identified and isolated by the present invention may directly be used as therapeutic agents or, alternatively, as therapeutic targets.

1. Use As Therapeutic Agents

Proteins, in particular the secreted proteins, identified and isolated with the expression systems of the present invention may be useful as therapeutic agents. In fact, a number of the already known secreted proteins, including cytokines and peptide hormones, are manufactured and used as therapeutic agents. Many severe diseases are caused by lack or insufficient amounts of certain secreted proteins which serve as intercellular communicators, for example in response to environmental changes or other physiological needs. A well known example is diabetes mellitus, which most frequently is caused by deficiencies in the production of the peptide hormone insulin. Many other examples are known. In light of the fact that only a small percentage of all secreted proteins have been identified, isolated and characterized thus far, it can be expected that many of the novel secreted proteins uncovered by the present invention will be useful as therapeutic compounds for the treatment of diseases, including, but not limited to, diseases relating to aberrant cell proliferation, metabolic signals, or certain other incapabilities of cells to communicate properly.

In addition, proteins which are derived from other cellular localizations may be useful as therapeutic agents. For example, a number of proteins expressed in the nucleus, including apoptosis-inducing proteins or tumor suppressors, are prone to be used as agents to treat, e.g., cancer.

The skilled artisan will be able to determine which proteins identified using the methods and expression systems of the invention may be useful as therapeutic targets. For example, in vivo assays using inhibitory antibodies or antisense strategies may be employed to elucidate the function of a protein. Further, purified forms of the protein may be used for cellular assays and tests in animal disease models to determine their value as therapeutic compound.

2. Use As Therapeutic Targets

Another important aspect of the invention is to provide proteins which serve as specific therapeutic targets for the treatment pathological disorders. While many diseases relating to inappropriate function or abundance of secreted proteins may be treated by administration of the respective protein (or an equivalent thereof), the situation is often different for proteins located within the cell. Deficiencies in the production of hormones or cytokines may frequently be remedied by their administration to reinstate a physiological response. In contrast, many other cellular fractions, in particular the cell membrane and the nucleus, are known to include numerous proteins which, if they function improperly, may be the cause of severe diseases, including cancer and other proliferative disorders, and a variety of metabolic diseases. For example, breast cancer is, in 30% of all occurrences, thought to be caused by overexpression of a cell surface receptor, i.e., the receptor tyrosine kinase HER2. Slamon, 1989, supra. It is believed that this type of breast cancer may be treated by administration of HER2 inhibitors to the appropriate target site. As an example of a metabolic disease, type II diabetes mellitus (Non-lnsulin-Dependent-Diabetes Mellitus, NIDDM) may be caused by aberrant expression or defective insulin receptors. Taira, 1989, supra. Type II diabetes could be treated with a therapeutic compound which surpasses the receptor and activates a molecule downstream of the insulin receptor's signal transduction pathway's. Alternatively, type II diabetes could be treated with compounds which are able to activate the defective insulin receptor.

In the case of many diseases, both diseases related to inappropriate cell proliferation and diseases relating to metabolic defects, the biological cause is not yet identified, but is thought to be due to inappropriate function or abundance of cellular proteins. Proteins identified by the methods of the present invention will be useful for the development of targeted therapeutic approaches, including drug development and gene therapy, or as diagnostics/reagents.

If a protein identified by the methods of the invention is used as therapeutic target, it may be subjected to suitable assays for the identification and isolation of compounds modulating its activity.

F. Generation And Use Of Antibodies Directed Against Proteins Identified By The Methods Of The Invention Various procedures known in the art may be used for the production of antibodies to epitopes of the recombinantly produced proteins identified and isolated employing the methods of the present invention. Such antibodies include but are not limited to polyclonal, monoclonal, chimeric, single chain, Fab fragments and fragments produced by an Fab expression library.

In one embodiment of the invention, such antibodies are used as tools for the investigation of expression pattern, abundance, function and other characteristics of the proteins identified by the methods of the invention. For example, cells or tissue sections may be exposed to antibodies, allowing to characterize expression specificity and abundance of the identified proteins of the invention. Various types of antibodies, including monoclonal, polyclonal and single chain antibodies may be used for such experiments determining cell and tissue specific expression pattern of the identified protein. Numerous techniques are well-established which allow detection of antibody binding to the expressed proteins in the cell or tissue section.

Furthermore, labelled antibodies, e.g., radiolabelled antibodies may be used to determine the expression patterns and abundance of the identified protein in vivo. See, supra. For example, the labelled antibody may be injected into a test subject, and its binding sites monitored in order to determine in which cell and/or tissue types the identified protein is located. To the extent that the originally identified and isolated protein of interest is the product of a species different from the test animal, the use of polyclonal antibodies is preferred. Thus, for example, if the identified protein used to generate the antibody is human, and the test subject is not human, polyclonal antibodies, with exceptions, will be preferred.

Furthermore, antibodies may be employed to analyze the physiological function of the protein identified with the methods and expression systems of the invention. For example, inhibitory antibodies, i.e., antibodies binding to certain functional epitopes of the identified protein of interest may identified, rationally or empirically, and injected into test cells or laboratory animals. Effects on the cells, certain tissues or physiological functions may be identified, allowing to elucidate the biological role of the identified protein and its potential involvement in aberrant or pathological conditions. Once the biological function and role in disease development is identified, development and design of targeted treatment strategies may be initiated. One of such strategies is the identification and isolation of compounds favorably modulating the function of a target protein, which is discussed in more detail below.

In other embodiments, antibodies are useful, e.g., as diagnostic or therapeutic agents. As therapeutic agents, neutralizing antibodies, i.e., those which compete for binding with a ligand, substrate or adapter molecule, or interfering with the proteins of the invention, where the proteins are used as therapeutic targets, are of especially preferred interest.

For use as diagnostic agents, monoclonal antibodies that bind to the identified protein are radioactively labelled allowing detection of their location and distribution in the body after injection. Radioactivity tagged antibodies may be used as a non-invasive diagnostic tool for imaging in vivo the presence of a tumors and metastases associated with the expression of the identified protein of the invention.

Immunotoxins may also be designed which target cytotoxic agents to specific sites in the body. For example, high affinity monoclonal antibodies may be covalently complexed to bacterial or plant toxins, such as diphtheria toxin, abrin, or ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate cells expressing the protein identified by the methods of the invention.

For the production of antibodies, various host animals are immunized by injection with the identified protein of interest including, but not limited to, rabbits, mice, rats, etc. Various adjuvants may be used to increase the immunological response, depending on the host species, including but not limited to Freund's adjuvance (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Monoclonal antibodies to the proteins of the invention may be prepared using any technique which provides for the production of antibody molecules by continuous cell lines in culture. These include, but are not limited to, the hybridoma technique originally described by Kohler and Milstein, 1975, *Nature* 256:495–497, the human B-cell hybridoma technique (Kosbor et al., 1983, *Immunology Today* 4:72; Cote et al., 1983, *Proc. Natl. Acad Sci. U.S.A.* 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, *Proc. Natl. Acad. Sci. U.S.A.* 81:6851–6855; Neubergeretal., 1984, *Nature* 312:604–608; Takeda et al., 1985, *Nature* 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce single chain antibodies specific for the proteins of the invention.

Antibody fragments which contain specific binding sites of the cell proliferation gene may be generated by known techniques. For example, such fragments include, but are not limited to, F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, *Science* 246:1275–1281) to allow rapid and easy identification of monoclonal Fab fragments with the desired specificity to the protein of the invention.

G. Use Of The Identified Nucleic Acids Encoding A Target Protein Of Interest For Development Of Antisense Approaches And Ribozymes The development and the use of oligonucleotide or oligoribonucleotide sequences comprising antisense DNA or RNA molecules or ribozymes that function to inhibit the translation of the cell proliferation gene mRNA may fulfill either of two purposes. First, such approaches may be used to investigate the function of novel proteins identified with the methods of the present invention. Second, these approaches may serve as actual treatment methods once the function of a protein and its involvement in pathological conditions is established. For example, antisense DNA or RNA molecules act to directly block the translation of targeted gene by binding to the targeted mRNA and thus preventing protein translation.

Ribozymes are enzymatic RNA molecules capable of catalyzing the specific cleavage of RNA. The mechanism of ribozyme action appears to involve site specific hybridization of the ribozyme molecule to complementary sequences of the target RNA, followed by endonucleolytic cleavage. In one embodiment of the invention, ribozyme molecules are engineered that specifically catalyze endonucleolytic cleavage of mRNA of the genes identified with the methods of the invention.

Suitable target sites for ribozyme activity are identified by first scanning the target molecule for potential ribozyme cleavage motifs, second by evaluating the structural features of the about 15 to 25 amino acids corresponding to the region of the target molecule containing the identified cleavage recognition site. Further, the suitability of the candidate targets may also be evaluated by testing their accessibility to hybridization with complementary oligonucleotides, using ribonuclease protection assays. Bordonaro et al., 1994, *Biotechniques* 16:428–430.

The labelled hybridization probes antisense DNA and RNA oligonucleotides and ribozymes of the subject invention are prepared by any method known in the art for the synthesis of DNA and RNA molecules. For example, oligonucleotides may be synthesized chemically using commercially available DNA or RNA synthesizers like machines sold by Applied Biosystems. Alternatively, RNA molecules may be generated by in vitro and in vivo transcription of DNA sequences encoding the antisense RNA molecule. Such DNA sequences may be incorporated into a wide variety of vectors which comprise suitable RNA polymerase promoters such as the T3, T7, or the SP6 polymerase promoters. Alternatively, antisense cDNA constructs that synthesize antisense RNA constitutively or inducibly, may be introduced stably into cell lines.

Various modifications to the DNA and RNA molecules may be introduced as a means of increasing the intracellular stability and half-life. For example, flanking sequences of ribo- or deoxyribo-nucleotides may be added to the 5' and/or 3' ends of the molecule, or phosphorothioate or 2'O-methyl rather than phosphodiester linkages may be used within the oligonucleotide backbone. Xu et al., 1996, *Nucleic Acid Res.* 24:1602–1607.

H. Generation Of Compounds Targeting The Identified, Isolated And Characterized Proteins 1. Identification Of Compounds For the identification and isolation of compounds modifying, inhibiting or enhancing the function of an identified and characterized protein according to the invention, suitable cellular systems expressing the identified protein may be employed. Alternatively, the proteins identified by the process of the invention may be isolated and used for in vitro or in vivo assays for the identification and isolation of compounds specifically interfering with their activity. Generally, the type of assay employed will largely depend on the nature and functional characteristics of the identified protein used as target, in the following referred to as "target protein". For example, if the target protein is a growth factor receptor, a cellular assay may be employed wherein the influence of compounds on proliferation is measured. If the target protein is a secreted protein, assays may be employed involving the effects of isolated secreted protein on suitable systems, e.g., receptor systems which allow one to measure the function of the secreted protein. If the target protein is a transcription factor, cellular systems may be employed which allow assaying the impact of compounds on expression of genes which are controlled by the transcription factor. If the target protein is an apoptosis regulator, cellular systems may be employed in which cell death (or survival) is driven by the respective target protein, and the impact of compounds may be assayed.

More specifically, cells in an appropriate assay system expressing the target protein may be exposed to chemical compounds or compound libraries to identify compounds having the desired modulating effects. Alternatively, the target protein may be expressed in suitable expression systems, designed to allow for high-throughput testing of compounds from any source, optionally isolated, to identify molecules binding to or having measurable inhibitory effects on the target protein.

Nucleotide sequences encoding the target protein identified and isolated using the methods of the invention may be used to produce the corresponding purified protein using well-known methods of recombinant DNA technology. Among the many publications that teach methods for the expression of genes after they have been isolated is *Gene Expression Technology Methods and Enzymology.* Vol.:185, edited by Goeddel, Academic Press, San Diego, Calif. (1990).

The protein of the invention chosen as target protein may be expressed in a variety of host cells, either prokaryotic or eukaryotic. In many cases, the host cells would be eukaryotic, more preferably host cells would be mammalian. Host cells may be from species either the same or different than the species from which the nucleic acid sequences encoding the protein identified with the methods of the invention are naturally present, i.e., endogenous. Advantages of producing the chosen target protein by recombinant DNA technology in cellular expression systems other than the expression systems primarily used see supra, for the original identification and isolation of the proteins according to their cellular localization include the development of optimized assay systems for the identification of modulating compounds. Generally, the expression systems of the invention have the advantage that they readily provide a system for the production of large amounts of recombinant proteins.

However, under certain circumstances which the skilled artisan will appreciate, alternative expression systems may, in some instances, also prove advantageous for obtaining highly enriched sources of the proteins for purification and the availability of simplified purification procedures. Methods for recombinant production of proteins are generally very well established in the art, and can be found, among other places in Sambrock et al., supra.

In an embodiment of the invention, cells transformed with expression vectors encoding the identified protein of the invention are cultured under conditions favoring expression of its gene sequence and the recovery of the recombinantly-produced protein from the cell culture. A target protein of interest produced by a recombinant cell may be secreted or may be contained intracellularly, depending on the nature of the gene and the particular genetic construction used. In general, it is more convenient to prepare recombinant proteins in secreted form. Purification steps will depend on the nature of the production and the particular protein produced. Purification methodologies are well established in the art; the skilled artisan will know how to optimize the purification conditions. General protocols of how to optimize the purification conditions for a particular protein can be found, among other places, in Scopes in: *Protein Purification: Principles and Practice*, 1982, Springer-Verlag New York, Heidelberg, Berlin.

In addition to recombinant production, peptide fragments may be produced by direct peptide synthesis using solid-phase techniques. See, Stewart et al., *Solid-Phase Peptide Synthesis* (1969), W. H. Freeman Co., San Francisco; and Merrifield, 1963, *J. Am. Chem. Soc.* 85:2149–2154.

In vitro polypeptide synthesis may be performed using manual techniques or by automation. Automated synthesis may be achieved, for example, using Applied Biosystems 431A Peptide Synthesizer (Foster City, Calif.) following the instructions provided in the instruction manual supplied by the manufacturer.

In an embodiment of the invention, the target protein and/or cell lines expressing the target protein are used to screen for antibodies, peptides, organic molecules or other ligands that act as agonist or antagonists of the cell proliferation gene activity. For example, antibodies capable of interfering with the activity, e.g., enzymatic activity of the target protein, or with its interaction with a ligand, adapter molecule, or substrate are used to inhibit the target protein's function. In cases where amplification of the target protein's function is desired, antibodies which mimic, e.g., a ligand, an adapter molecule or substrate of the corresponding the signal transduction pathway may be developed. Obviously, if desired, antibodies may be generated which modify the activity, function, or specificity of the target protein.

Alternatively, screening of peptide libraries or organic compounds with recombinantly expressed target protein or cell lines expressing the target protein may be useful for identification of therapeutic molecules that function by inhibiting, enhancing, or modifying its biological activity.

Synthetic compounds, natural products, and other sources of potentially biologically active materials can be screened in a number of ways. The ability of a test compound to inhibit, enhance or modulate the function of the target protein may be determined with suitable assays measuring the target protein's function. For example, responses such as its activity, e.g., enzymatic activity, or the target protein's ability to bind its ligand, adapter molecule or substrate may be determined in in vitro assays. Cellular assays can be developed to monitor a modulation of second messenger production, changes in cellular metabolism, or effects on cell proliferation. These assays may be performed using conventional techniques developed for these purposes. Finally, the ability of a test compound to inhibit, enhance or modulate the function of the target protein will be measured in suitable animal models in vivo. For example, mouse models will be used to monitor the ability of a compound to inhibit the development of solid tumors, or effect reduction of the solid tumor size.

In an embodiment of the invention, random peptide libraries consisting of all possible combinations of amino acids attached to a solid phase support are used to identify peptides that are able to interfere with the function of the target protein. For example, peptides may be identified binding to a ligand-, adapter molecule- or substrate binding site of a given target protein or other functional domains of the target protein, such as an enzymatic domain. Accordingly, the screening of peptide libraries may result in compounds having therapeutic value as they interfere with its activity.

Identification of molecules that are able to bind to the target protein may be accomplished by screening a peptide library with recombinant soluble target protein. Methods for expression and purification of the selected target protein and may be used to express recombinant full length target protein or fragments thereof, depending on the functional domains of interest.

In order to identify and isolate the peptide/solid phase support that interacts and forms a complex with the target protein, it is necessary to label or "tag" the target protein molecule or fragment thereof. For example, the target protein may be conjugated to enzymes such as alkaline phosphatase or horseradish peroxidase or to other reagents such as fluorescent labels which may include fluorescein isothyiocynate (FITC), phycoerythrin (PE) or rhodamine. Conjugation of any given label to the target protein may be performed using techniques that are routine in the art.

In addition to using soluble target protein molecules or fragments thereof, in another embodiment, peptides that bind to the target protein may be identified using intact cells. The use of intact cells is preferred in instances where the target protein which comprises cell surface receptors, which require the lipid domain of the cell membrane to be functional. Methods for generating cell lines expressing the target protein identified with the methods and expression systems of the invention. The cells used in this technique may be either live or fixed cells. The cells are incubated with the random peptide library and will bind to certain peptides in the library. The so formed complex between the target cells and the relevant solid phase support/peptide may be isolated by standard methods known in the art, including differential centrifugation.

In the case the target protein is a membrane bound receptor or a receptor that requires the lipid domain of the cell membrane to be functional, an alternative to whole cell assays is to reconstitute the receptor molecules into liposomes where a label or "tag" can be attached.

In another embodiment, cell lines that express the chosen target protein or, alternatively isolated target protein or fragments thereof, are used to screen for molecules that inhibit, enhance, or modulate the target protein's activity or, where applicable, signal transduction. Such molecules may include small organic or inorganic compounds, or other molecules that effect the target protein activity or that promote or prevent the complex formation with its ligand, adapter molecules, or substrates. Synthetic compounds, natural products, and other sources of potentially biologically active materials can be screened in a number of ways, which are generally known by the skilled artisan.

For example, the ability of a test molecule to interfere with the chosen target protein's function may be measured using standard biochemical techniques. Alternatively, cellular responses such as activation or suppression of a catalytic activity, phosphorylation, dephosphorylation, or other modification of other proteins, activation or modulation of second messenger production, changes in cellular ion levels, association, dissociation or translocation of signalling molecules, or transcription or translation of specific genes may also be monitored. These assays may be performed using conventional techniques developed for these purposes in the course of screening.

Further, effects on the target protein's function may, via signal transduction pathways, affect a variety of cellular processes. Cellular processes under the control of the its signalling pathway may include, but are not limited to, normal cellular functions, proliferation, differentiation, maintenance of cell shape, and adhesion, in addition to abnormal or potentially deleterious processes such as unregulated cell proliferation, loss of contact inhibition and, blocking of differentiation or cell death. The qualitative or quantitative observation and measurement of any of the described cellular processes by techniques known in the art may be advantageously used as a means of scoring for signal transduction in the course of screening.

Various technologies may be employed for the screening, identification, and evaluation of compounds which interact with the chosen target protein of the invention, which compounds may affect various cellular processes under the control of said target protein.

For example, the target protein or a functional derivative thereof, in pure or semi-pure form, in a membrane preparation, or in a whole live or fixed cell is incubated with the compound. Subsequently, under suitable conditions, the effect of the compound on the target protein's function is scrutinized, e.g., by measuring its activity, or its signal. transduction, and comparing the activity to that of the target protein, incubated under same conditions, without the compound, thereby determining whether the compound stimulates or inhibits the target protein's activity.

In addition to the use of whole cells expressing the chosen target protein for the screening of compounds, the invention also includes methods using soluble or immobilized target protein. For example, molecules capable of binding to the target protein may be identified within a biological or chemical preparation. For example, the target protein, or functional fragments thereof, e.g., fragments containing a specific domain of interest, is immobilized to a solid phase matrix, subsequently a chemical or biological preparation is contacted with the immobilized target protein for an interval sufficient to allow the compound to bind. Any unbound material is then washed away from the solid phase matrix, and the presence of the compound bound to the solid phase is detected, whereby the compound is identified. Suitable means are then employed to elute the binding compound.

2. Source Of Candidate Test Compounds

The test compounds employed for assays for the identification of modulators of a target protein's activity are obtained from any commercial source, including Aldrich (1001 West St. Paul Ave., Milwaukee, Wis. 53233), Sigma Chemical (P.O. Box 14508, St. Louis, Mo. 63178), Fluka Chemie AG (Industriestrasse 25, CH-9471 Buchs, Switzerland (Fluka Chemical Corp. 980 South 2nd Street, Ronkonkoma, N.Y. 11779)), Eastman Chemical Company, Fine Chemicals (P.O Box 431, Kingsport, Tenn. 37662), Boehringer Mannheim GmbH (Sandhofer Strasse 116, D-68298 Mannheim), Takasago (4 Volvo Drive, Rockleigh, N.J. 07647), SST Corporation (635 Brighton Road, Clifton, N.J. 07012), Ferro (111 West Irene Road, Zachary, La. 70791), Riedel-deHaen Aktiengesellschaft (P.O. Box D-30918, Seelze, Germany), PPG Industries Inc., Fine Chemicals (One PPG Place, 34th Floor, Pittsburgh, Pa. 15272); further any kind of natural products may be screened using the assay cascade of the invention, including microbial, fungal or plant extracts.

3. Indications For The Use Of Compounds Modulating The Activity Of Target Proteins Of The Invention According To Its Predetermined Property Depending on the nature and the function of the target protein, the compounds identified by the above exemplified assays and methods may be modulators of cell proliferation activity or modulators of certain metabolic functions. As such, the compounds produced by the processes and assays of the invention are useful for the treatment of disease related to aberrant, uncontrolled or inappropriate cell proliferation, including excess or diminished proliferation. Alternatively, the compounds may be useful for the treatment of diseases relating to aberrant metabolic functions.

A large number of disease states involve excess or diminished cell proliferation. Generally, many of these diseases may be treated with DNA sequences, proteins, or small molecules that influence cell proliferation. In some instances the goal is to stimulate proliferation; in others, to prevent or inhibit proliferation of cells. The list of diseases directly involving cell growth includes, but is not limited to, cancer, psoriasis, inflammatory diseases, such as rheumatoid arthritis, restenosis, immunological activation or suppression, including tissue rejection, neurodegeneration or expansion of neuronal cells and viral infection.

Numerous diseases involve aberrant metabolic functions, including, but not limited to, diabetes mellitus, fibrosis, cystic fibrosis. Further, pathological conditions relate both to aberrant cell proliferation and metabolic defects.

Accordingly, pharmaceutical compositions comprising a therapeutically effective amount of a compound identified by the methods described above will be useful for the treatment of diseases driven by unregulated or inappropriate cell proliferation, including cancer, such as glioma, melanoma, Kaposi's sarcoma, psoriasis, hemangioma and ovarian, breast, lung, pancreatic, prostate, colon and epidermoid cancer, rheumatoid arthritis, restenosis, immunological activation or suppression, including tissue rejection, neurodegeneration or expansion of neuronal cells; and diseases relating to metabolic dysfunction, including, but not limited to diabetes mellitus, fibrosis, cystic fibrosis.

I. Formulations/Route Of Administration

The present invention provides two forms of therapeutic compounds. First, the invention provides therapeutics which resemble a naturally occurring functional polypeptide or peptide, or functional fragment or derivative thereof. Such therapeutics are, for example, proteins which are secreted in their natural form; such proteins may be identified directly with the expression systems of the invention. This type of therapeutics includes, but are not limited to, cytokines, hormones, growth factors, etc. Second, the invention provides therapeutic compounds which modulate the function of target proteins identified using the methods and expression systems of the invention. Typically, these types of compounds are small organic molecules, but they also include peptide compounds and antibodies. The skilled artisan will appreciate that the following methods of administration, formulation and treatment methods will need to be adjected depending on the type of compound chosen, and the type of disease to be treated.

The identified therapeutic compound can be administered to a human patient alone or in pharmaceutical compositions where they are mixed with suitable carriers or excipient(s) at therapeutically effective doses to treat or ameliorate a variety of disorders. A therapeutically effective dose further refers to that amount of the compound sufficient to result in amelioration of symptoms as determined, for example, in a decrease or increase of cell proliferation, or in a restitution of metabolic functions. Techniques for formulation and administration of the compounds of the instant application may be found in "Remington's Pharmaceutical Sciences," Mack Publishing Co., Easton, Pa., latest edition.

1. Routes Of Administration.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer a compound of the invention in a local rather than systemic manner, for example, via injection of the compound directly into a solid tumor, often in a depot, or in a sustained release formulation.

Furthermore, one may administer the drug via a targeted drug delivery system, for example, in a liposome coated with tumor-specific antibody. The liposomes will be targeted to and taken up selectively by the tumor.

2. Composition/Formulation

The pharmaceutical compositions of the present invention may be manufactured by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active therapeutic compounds into preparations which can be used pharmaceutically. Proper formulation is dependent upon the route of administration chosen.

For injection, the agents of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the therapeutic compounds can be formulated readily by combining the active therapeutic compounds with pharmaceutically acceptable carriers well known in the art. Such carriers enable the therapeutic compounds of the invention to be formulated as tablets, pills, dragees, capsules, liquids, gels, syrups, slurries, suspensions and the like, for oral ingestion by a patient to be treated. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel,. polyethylene glycol, and/or titanium dioxide, lacquer solutions, and suitable organic solvents or solvent mixtures. Dyestuffs or pigments may be added to the tablets or dragee coatings for identification or to characterize different combinations of active therapeutic compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active therapeutic compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration,the compositions may take the form of tablets or lozenges formulated in conventional manner.

For administration by inhalation, the therapeutic compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an' inhaler or insufflator, may be formulated containing a powder mix of the therapeutic compound and a suitable powder base such as lactose or starch.

The therapeutic compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active therapeutic compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the therapeutic compounds to allow for the preparation of highly concentrated solutions.

Alternatively, the active ingredient may be in powder form for constitution with a suitable vehicle, such as sterile pyrogen-free water, before use.

The therapeutic compounds may also be formulated in rectal compositions such as suppositories or retention enemas, e.g., containing conventional suppository bases such as cocoa butter or other glycerides.

In addition to the formulations described previously, the therapeutic compounds may also be formulated as a depot preparation. Such long acting formulations may be administered by implantation (for example subcutaneously or intramuscularly) or by intramuscular injection. Thus, for example, the therapeutic compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical.carrier for the hydrophobic therapeutic compounds of the invention is a cosolvent system comprising benzyl alcohol, a nonpolar surfactant, a water-miscible organic polymer, and an aqueous phase.

The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic therapeutic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may be substituted for dextrose.

Alternatively, other delivery systems for hydrophobic pharmaceutical therapeutic compounds may be employed. Liposomes and emulsions are well known examples of delivery vehicles or carriers for hydrophobic drugs. Certain organic solvents such as dimethylsulfoxide also may be employed, although usually with a greater toxicity.

Additionally, the therapeutic compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the therapeutic compounds for a few weeks up to over 100 days.

Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the therapeutic compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

3. Effective Dosage.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any therapeutic compound used in the method of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test therapeutic compound which achieves a half-maximal inhibition or activation of the cell proliferation activity, or restitution of a metabolic function). Such information can be used to more accurately determine useful doses in humans.

A therapeutically effective dose refers to that amount of the therapeutic compound that results in amelioration of symptoms or a prolongation of survival in a patient. Toxicity and therapeutic efficacy of such therapeutic compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Therapeutic compounds which exhibit high therapeutic indices are preferred.

The data obtained from these cell culture assays and animal studies can be used in formulating a range of dosage for use in human. The dosage of such therapeutic compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1 p1).

Dosage amount and interval may be adjusted individually to provide plasma levels of the active moiety which are sufficient to maintain the kinase modulating effects, or minimal effective concentration (MEC). The MEC will vary for each therapeutic compound but can be estimated from in vitro data; e.g., the concentration necessary to achieve 50–90% inhibition of the kinase using the assays described herein. Dosages necessary to achieve the MEC will depend on individual characteristics and route of administration. However, HPLC assays or bioassays can be used to determine plasma concentrations.

Dosage intervals can also be determined using MEC value. Therapeutic compounds should be administered using a regimen which maintains plasma levels above the MEC for 10–90% of the time, preferably between 30–90% and most preferably between 50–90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

4. Packaging.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a therapeutic compound of the invention formulated in a compatible pharmaceutical carrier may also be prepared, placed in an appropriate container, and labelled for treatment of an indicated condition. Suitable conditions indicated on the label may include inhibition or activation of cell proliferation, restitution of a metabolic function, treatment of a tumor, treatment of arthritis, and the like.

The following examples for the generation and use of the selection systems of the invention are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VII. EXAMPLES

A. Materials And Methods

The following are experimental procedures and materials used for the Examples set forth below.

Construction Of cDNA Libraries Into The SinRep5 Vector. Total mRNA of any tissue or cell line is isolated by using the QuickPrep (Micro mRNA purification kit (Pharmacia, Pharmacia Biotech Europe GmbH, Duebendorf, Switzerland) according to supplier's recommendation. The first strand synthesis is carried out in the presence of 5-methyl-cytosine to protect, internal StuI restriction sites, using the Stratagene (Stratagene AG, Basel, Switzerland) ZAP cDNA synthesis kit according to supplier's instructions. After brief digestion with RNaseH, the second strand is synthesized using DNA polymerase I to produce 3' overhangs which can be recessed by T4 DNA polymerase (3' exonuclease activity). The double stranded DNA is finally ligated into the pSinRep5 vector (Invitrogen, NV Leek, Netherl; see FIG. 5 and Bredenbeek et al., 1993, *J. Virol.* 11:6439–6446). Subsequent digestion of the resulting DNA with StuI linearizes the plasmids for in vitro transcription.

The construction of cDNA libraries in the TE vectors (See FIG. 6 and Frolov et al., 1996, *PNAS* 93:11371–11377; the complete sequence of pTE5'2J is given in SEQ ID NO:1) is carried out essentially as described for the pSinRep5. The only exception is that during the second strand synthesis 5-methyl-adenosine is used to protect internal XbaI restriction sites to clone the resulting DNA fragment into the pTE plasmid pTE SEAP via XbaI/StuI or ApaI.

The plasmids used in this study are described in detail in Table I.

TABLE I

Description of the DNA construct:

| pSinRep5 construct: | |
| --- | --- |
| pSinRep5: | from Invitrogen Sindbis expression system European Headquarters: Invitrogen, NV Leek, Netherland Bredenbeek et al., Nov. 1993, J. Virology 67: 6439–6446. |
| SP6 promotor: | 9933–9951 |
| Non-structural genes: | 60–7598 |

TABLE I-continued

Description of the DNA construct:

| | |
| --- | --- |
| Subgenomic promotor: | 7580–7603 |
| Transcriptional start: | 7598 |
| Multiple cloning site: | 7647–7689 |
| polyA tail: | 7997–8033 |
| Amp resistance gene: | 8227–9085 |
| ColE1 origin: | 9232–9861 |
| pSinRep5 EPO: | pSinRep 5 digested with XbaI/SphI was ligated with a synthetic EPO sequence (XbaI/SphI) sequence of EPO see appendix: sequence I |
| pSinRep5 SEAP: | pSinRep5 digested with XbaI/StuI and ligated with NheI/ClaI fragment of pSEAP 2 Basic, Clontech Laboratories, Inc., Palo Alto, U.S.A. |
| pSinRep5 lacZ: | from Invitrogen Sindbis expression system. |
| pTE constructs: | |
| pTE 5'2J: | A general description of the related vectors pTE 3'2J is given in: Hahn et al., 1992, Proc. Natl. Acad. Sci. U.S.A. 89 2679–2683. Frolov et aL, 1996, Proc. Natl. Acad Sci. U.S.A. 93:11371–11377. The detailed sequence of TE 5'2J is given as SEQ ID NO: 1. |
| pTE 5'2J EPO: | pTE was digested with XbaI/ApaI was ligated with the XbaI/ApaI EPO fragment derived from pSinRep5. |
| pTE 5'2J SEAP: | pTE was digested with ApaI, the ends were treated with Klenow enzyme before digestion with XbaI. The vector was ligated with the NheI/ClaI fragment from pSEAP 2 Basic (Clontech Laboratories, Inc., Palo Alto U.S.A.). |
| pTE 5'2J CAT: | pTE 5'2J was digested with XbaI, the ends were filled according to standard procedures with Klenow enzyme CAT PCR fragment as shown in appendix: sequence 3, was ligated blunt into vector TE 5'2J. |
| Helper constructs: | |
| DHEB: | Bredenbeek et al., 1993, J Virology 67 : 6439–6446. |
| 987 BB neo: | (SEQ ID NO: 2). |

In Vitro Transcription Of Sindbis cDNA Libraries. The linearized vector DNA (pSinRep5 or pTE, linearized by NotI digestion; helper DNA DH-EB (Bredenbeek et al., 1993, *J. Virol.* 1: 6439–6446) linearized by EcoRI digestion) were made RNase-free by purification over QiaQuick PCR purification columns (QIAGEN AG, Basel, Switzerland) and elution with DEPC-H2O. Subsequent in vitro transcription was carried out using an SP6 in vitro transcription kit (Invitroscript CAP Kit, Invitrogen BV, NV Leek, The Netherlands) according to the manufacturer's recommendation. The resulting 5'-capped mRNA was analyzed on reducing and non-reducing agarose gels.

Generation OfSindbis Virus Particles. Two (2) to five (5) μg of in vitro transcribed mRNA was electroporated (for TE constructs) or co-electroporated (for PSinRep 5 and helper DH-EB) into BHK 21 cells (ATCC No. CCL 10) according to the Invitrogen's manual (Invitroscript CAP Kit, Invitrogen BV, NV Leek, The Netherlands). The 5'-capped mRNA of pSinRep5 encodes the viral non-structural proteins, which induce the viral replication steps. The co-electroporated helper mRNA (DH-EB) delivers the viral structural proteins. After incubation for eighteen (18) hours at 37° C., 5% $CO_2$ in Turbodoma HP-1 medium containing 1% FCS, the cell supernatant was harvested and the amount of released infectious virus particles was determined by plaque assays.

Plaque Assay. Dilution series of the harvested virus particles, see, supra, were carried out in 1 ml Turbodoma HP-1 (1:10$^4$, 1:5×104, 1:10$^5$, 1: 5×10$^5$, 1:10$^6$, 1:5×10$^6$) on 90% confluent BHK 21 cells in 6-well-plates. After two (2) hours incubation at 37° C. (in the case of the temperature-sensitive mutants from the complementation group C,D and E, the plates were incubated at the permissive temperature of 30° C. (Lindquist et al., 1986, *Virology* 151:10–20; Arias et al., *J. Mol. Biol.* 168:87–102; Carleton and Brown, 1996, *J. Virol.* 70:952–959) the medium was replaced with 2 ml 41° C. warm 0.8% agarose (Carl Roth GmbH, Karlsruhe, Germany) in Turbodoma HP-1 medium (Dr. F. Messi, Cell Culture Technologies, Zurich, CH). Plaques of 1 to 4 mm diameter had been formed after two (2) days of incubation at the permissive temperature. The plaques were counted and the corresponding numbers of plaque forming units ("pfu") per ml were calculated.

Agarose BlotAssay (ABA). 90% confluent BHK 21 cell layers in 60 mm dishes were incubated at the permissive temperature for two (2) hours with HP-1 medium containing approximately 800 to 1000 plaque forming units. The supernatant was replaced by overlaying the cells with 1.5 mm layer of 41° C. warm 0.8% agarose in 1×HP-1 and the cells were incubated for two (2) days at the permissive temperature. Secreted proteins were detected by $^{35}$S Met/Cys labeling of the infected cells. For this purpose, the medium was replaced for 30 minutes with 2 ml of RPMI 1640 (Met/Cys deficient medium) before 20 μCi $^{35}$S Met/Cys (Hartmann Analytic GmbH, Braunschweig, Germany) was added.

Release of viral proteins was inhibited by adding a protease inhibitor cocktail and/or crosslinked antibodies against the Sindbis Virus glycoproteins as described in the examples. The temperattire-sensitive Sindbis mutants were shifted to 40° C. for two (2) hours pre-labeling to inhibit virus particle release. The 20 μCi $^{35}$S Met/Cys were applied for 2 hours at 37° C., before the cells and the agarose layer were washed twice with 1 ml of RPMI 1640 (Met/Cys deficient medium). Afterwards pre-wetted nitrocellulose membranes were placed on top of the agarose for 4 to 20 hours. The membrane were removed and washed with buffers containing between 0.1% Triton X100 as described in the examples (Sigma, St. Louis, USA) and were exposed to X-ray films (Hyperfilm bmax, Amersham, Sweden) after drying. Black spots on the developed X-ray film indicated Sindbis Virus particles containing the cDNA for a secreted protein.

resulting supernatant contained about 104 to 106 pfu per ml, which corresponds to a total of about 10$^5$ to 10$^7$ pfu per T25 supernatant.

Sequencing Of The Selected Sindbis Virus Particles. The virus mRNA was isolated using a viral RNA isolation kit (High Pure Viral RNA Kit, Boehringer Mannheim, Mannheim, Germany) and RT-PCR was done with Superscript one-step RT-PCR according to Gibco (Gibco/BRL, Life Technologies AG, Basel, Switzerland) according to the recommedation of the manufactorer. The 3' primer for the RT-PCR was either the oligo GCGCGGGCCCT$_{20}$ (SEQ ID NO:9) (specific for the poly A tail) or the oligo GCGCGGGCCCCGCTG CGTGGCATTATGCACC (SEQ ID NO:10) specific for the 3° CIS sequence of the Sindbis Virus; the 5' primer was the oligo GCGCGGGCCCCGCT-GCGTGGCATTATGCACC. The RT-PCR product was digested with the restriction enzymes Bsp120I and EcoRI, gel-purified and ligated in pBluescript (digested with EcoRI and Bsp120I) and finally sequenced using the oligos "–40 forward and reverse primer" of the multiple cloning site.

Immunofluorescence Microscopy of Sindbis Virus Infected Cells. 60% confluent BHK 21 cells in 6 well plates were infected for 2 hours at the permissive temperature at a moi of 0.1 in 1 ml HP-1 medium with Sindbis virus particles containing a heterologous cDNA encoding a membrane protein (receptor). 20 hours post-infection, the cells were dissociated with cell dissociation solution (Sigma-Aldrich, Steinheim, Germany) and were washed twice at 4° C. with 1% BSA in HBSS. The resuspended cells were then incubated with ligand-flag fusion protein at concentrations between 100 ng/ml and 1 μg and with 5 μg/ml monoclonal antibody M2 for 15 min on ice. The cells were washed twice before being incubated for 30 min with 10 μg/ml FITC-conjugated secondary antibody in 1% BSA in HBSS at 4° C. After two (2) washing steps with 1% BSA in HBSS, the cells were analyzed with an immunfluorescence microscope (Leica DMIL, Leica, Heerburg, Switzerland) or the cells were analyzed and sorted with a FACS sorter.

Cloning Of ts2, ts20 And The Double Mutation ts2,20 In DH-EB. The mutations ts2, ts20 and the combination of these two mutations were inserted into DH-EB (Bredenbeek et al., 1993, *J. Virology* p. 6439–6446) by PCR using the following oligonucleotides:

```
pimers: oligo Aat II   GCACTTAAGTTGGAGGCCGAC       (SEQ ID NO:11)
        oligo BssH II  GGCACTCACGGCGCGCTTTACAGGC   (SEQ ID NO:12)
        oligo Hpa I.1  GCAATGTtAAcaGGTCTGTATCTAATTGG (SEQ ID NO:13)
        oligo Hpa I.2  CAGACCtgTTaACATTGCTCACCACCAGG (SEQ ID NO:14)
        oligo Pvu I.1  GACAGCGGTCGatCGATCATGGATAACTC (SEQ ID NO:15)
        oligo Pvu I.2  GAGTTATCCATGATCGatCGACCGCTGTC (SEQ ID NO:16)
```

Amplification Of Selected Virus Particles. Positive plaques were identified by superposition of the X-ray film with the agarose overlay. The corresponding plaques were picked with a 10 μl tip and eluted in 200 μl PBS overnight at 4° C. After pelleting the agarose, 60% confluent BHK 21 cells in a 12-well plate were infected at the permissive temperature with the eluted virus for two (2) hours in 0.5 ml Turbodoma HP-1 before the medium was replaced with 1ml Turbodoma HP-1 medium. After incubated for 20 hours at the permissive temperature the cell supernatant was harvested and a dilution of 1:20 in 2 ml Turbodoma HP-1 was incubated for two (2) hours in a T25 flask with 60% confluent BHK 21 cells, before the medium was replaced with 10 ml HP-1 medium. After 20 hours incubation the The restriction sites used for analysis are underlined, mutated nucleotides are indicated in small letters and bold. PCR reactions were performed using the following combinations:

PCR1: oligo Aat II—oligo Hpa I. 1 (for ts20)
PCR2: oligo BssH II—oligo Hpa I.2 (for ts20)
PCR3: oligo Aat II—oligo Pvu I1.1 (for ts2)
PCR4: oligo BssH II—oligo Pvu I1.2 (for ts2)

100 pmol of each oligo and 5 ng of the template DNA were used in the 100 μl reaction mixture, containing 4 units of Taq or Pwo polymerase, 0.1 μM dNTPs and 1.5 mM MgSO$_4$. The polymerase was added directly before starting the PCR reaction (starting point 95° C.). The temperature cycles were as following: 95° C. for 1.5 min, followed by 5 cycles of 95° C. (30 seconds), 54° C. (30 seconds), 72° C. (120 seconds) and followed by 25 cycles of 95° C. (30 seconds), 64° C. (30 seconds), 72° C. (120 seconds).

The four PCR (PCR 1 to 4) fragments were purified using Qia spin PCR kit (QIAGEN, Inc., Chatsworth, Calif. 91311, USA) and finally digested in the appropriate buffer using 10 units of DraIII and HpaI, HpaI and BssHII, DraIII and PvuI, or BssHII and PvuI respectively. The digestion was performed for 6 hours at 37° C., before the DNA fragments were gel-purified (gene-clean; Bio 101 Inc., Vista, Calif. 92083, USA). The purified PCR fragments 1 and 2 and the framents 3 and 4 were finally ligated into DraIII/BssHII digested and gel-purified pDH-EB (Bredenbeek et al, *J. Virology* November 1993, p. 6439–6446). The correct sequence of the obtained vectors was checked by restriction enzyme digestion and was verified by DNA sequencing using the following primers:

oligo seq ts2: TTCCAAGCCATCAGAGGGG (SEQ ID NO:17)

oligo seq ts20: AGATTAGCACCTCAGGACCG (SEQ ID NO:18)

The correct vectors DH-EB ts2 and DH-EB ts20 were digested for 4 hours at 37° C. with 10 units of Bsp68I and EcoRI in the appropriate buffer. The 4.5 kb DNA fragment of pDH-EB ts 2 and the 3.4 kb fragment of pDH-EB ts20 were gel-purified (as described above) and ligated to create DH-EB ts2,20. The correct sequence of the obtained vector was checked by restriction enzyme digestion and was verified by DNA sequencing using the primers oligo seq ts2 and oligo seq ts20 (described above).

Production Of Milligram Quantities Of Secreted Proteins. A batch of BHK 21 cells is infected with the virus supernatant containing the protein of interest. Subsequent purification will yield several milligrams of the pure protein.

B. Example 1

Figure 1B:
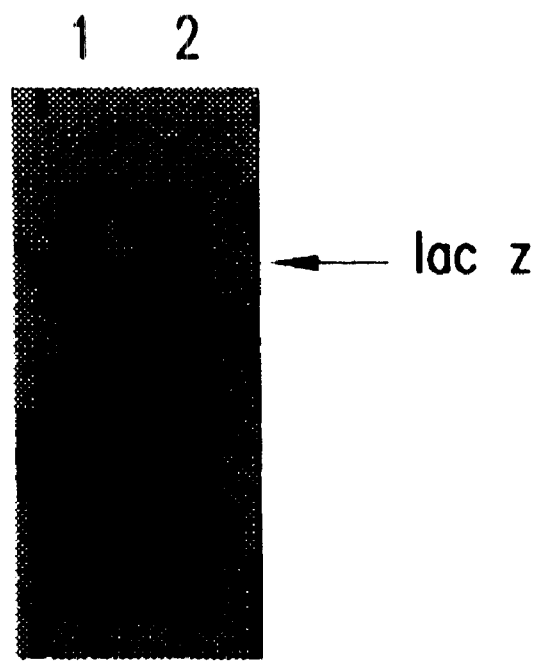

Compartment Screening and Identification of Nucleic Acids Encoding Proteins with a Predetermined Localization Confluent cultures of BHK cells were infected with viral particles containing two expression systems with two different nucleic acids (pSinRep5 EPO and pSinRep5 lacZ), both packaged with the helper construct DHBB. One culture was not infected as a negative control (Vial 1, lane 1 in FIG. 1A). Twenty-four hours postinfection, the cells were starved in starvation medium lacking Methionine and Cysteine for 30 minutes. A pulse of 10 $\mu$Ci 35S Met/Cys was added and replaced by fresh medium after 30 minutes. After an incubation of two hours, the cells and the supernatant were collected. The cells were resuspended in Laemmli buffer and boiled for 10 minutes. Five hundred $\mu$l supernatant was added to 600 $\mu$l methanol and 200 $\mu$l chloroform. The upper phase was discarded and precipitated protein was pelleted by adding 800 $\mu$l of methanol. Both the precipitated supernatant proteins and cell pellets were resuspended in 25 $\mu$l Laemmli buffer, and the proteins separated on a 15% SDS polyacrylamide gel. After drying, the gel was exposed overnight to an X-ray film. The labelled proteins found in the supernatant were run on the gel presented in FIG. 1A; FIG. 1B depicts labelled proteins found in the cell pellet corresponding to the supernatants in lanes 1 and 2 of FIG. 1A.

Identification of a nucleic acid encoding a secreted protein was possible by detection of a band on the X-ray film (FIG. 1A), which is the result of a unique labelled protein in the supernatant encoded by the exogenous expression system. FIG. 1A, lane 1 shows that uninfected cells (containing no exogenous expression system) secrete several unidentified proteins. The corresponding cell pellet is shown in FIG. 1B where any proteins were labelled and a multitude of bands is visible. The blank lane 2 in FIG. 1A indicates the presence of an expression system containing a nucleic acid encoding an intracellular protein in vial 2. Accordingly, lane 2 in FIG. 1B confirms this finding by the presence of a unique band which stems from a single labelled protein from the cell pellet. Expression of all other endogenous proteins was suppressed (compare with lane 1) allowing unique labelling and a clear identification of the nucleic acid of vial 2 as a nucleic acid coding for an intracellular protein (which confirms the published finding that lac Z is in fact an intracellular protein). A strong band resulting from a single radioactive protein in the supernatant in FIG. 1A, lane 6 indicates the presence of an expression system containing a nucleic acid encoding a secreted protein. Vial 6 (lane 6 in FIGS. 1A and 1B) was infected with the pSinRep5 EPO construct. This finding confirms that EPO is a secreted protein. Endogenous protein expression was again suppressed allowing unique labelling and a clear identification of the nucleic acid of vial 6 as a nucleic acid coding for a secreted protein. Lanes 3–5 show labelled secreted proteins from mixtures of the two expression systems. Increasing proportions of the EPO expression system with 10%, 50% and 90% give rise to a more uniquely labelled protein in the supernatant. These results demonstrate that compartment screening can identify nucleic acids which encode proteins of a predetermined cellular localization.

C. Example 2

Figure 2:
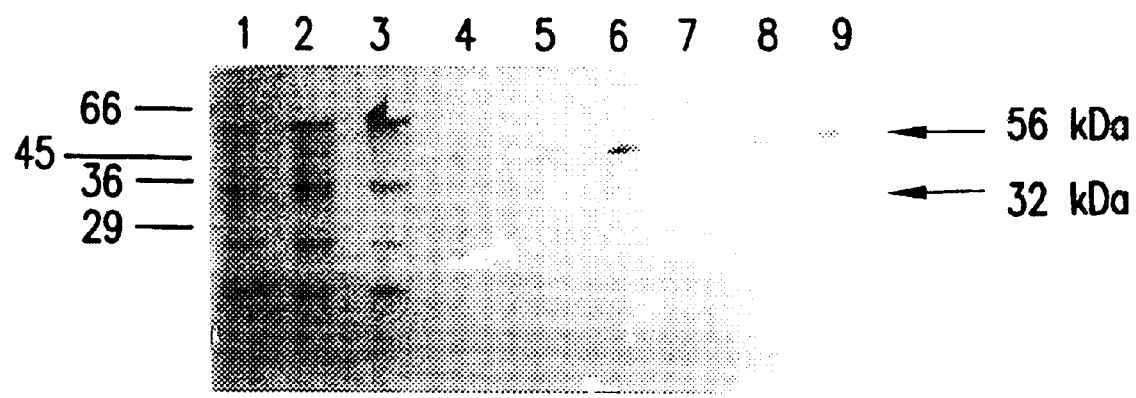

Separation of Labelled Viral Particles from Secreted Protein for Semisolid Medium Screening For optimal identification of expression systems encoding secreted proteins in semisolid medium, it is preferred that a) endogenous protein synthesis is suppressed; and b) labelled viral particles and other labelled soluble viral protein are prevented from interfering with the screen. Confluent layers of BHK 21 cells in 35 mm dishes were infected with pTEC5'2JCAT or pTE5'2JEPO double subgenomic infective viral particles at an MOI of 5. As a negative control, uninfected BHK 21 cells were used. Fourteen hours post infection, the medium was removed and the cells were overlaid with 4 mm of 0.8% agarose in RPMI 1640 medium containing 10 $\mu$Ci $^{35}$SMet/Cys per dish. After gelling, the cultures were overlaid with 1 ml of Cys/Met free RPMI, and the medium was collected after 2 hours, 4 hours and 8 hours. The protein was precipitated and separated on a 15% SDS gel. The gel was exposed to an X-ray film overnight. It could be demonstrated that endogenous protein synthesis was inhibited again and that labelling was specific (FIG. 2: compare lanes 1–3 with lanes 4–9). Moreover, diffusion of viral particles was also inhibited since the characteristic pattern of the three structural viral proteins (capsid, E1 and E2) could not be detected (lanes 4–9).

In both supernatants of the virally infected cultures, a labelled protein with a size of about 60 kD was present (lanes 4–9). It was speculated that this protein is a viral protein and that it might result from proteolytic cleavage of one of the glycoproteins of Sindbis virus. In the case of pTE5'2JEPO after 8 hours, an additional protein with the size of EPO was detected (lane 9) demonstrating the principal feasibility of semi-solid medium screening. This experiment demonstrates that labelled viral particles can be separated from secreted protein by limited diffusion in 0.8% agarose. However, without further measures, the release of soluble viral protein occurs. Such a release is undesirable because it may interfere with the phenotypic screen. Example 3 describes a method that inhibits the release of unwanted viral proteins.

D. Example 3

Inhibition of Release of Viral Soluble Proteins

Figure 3:
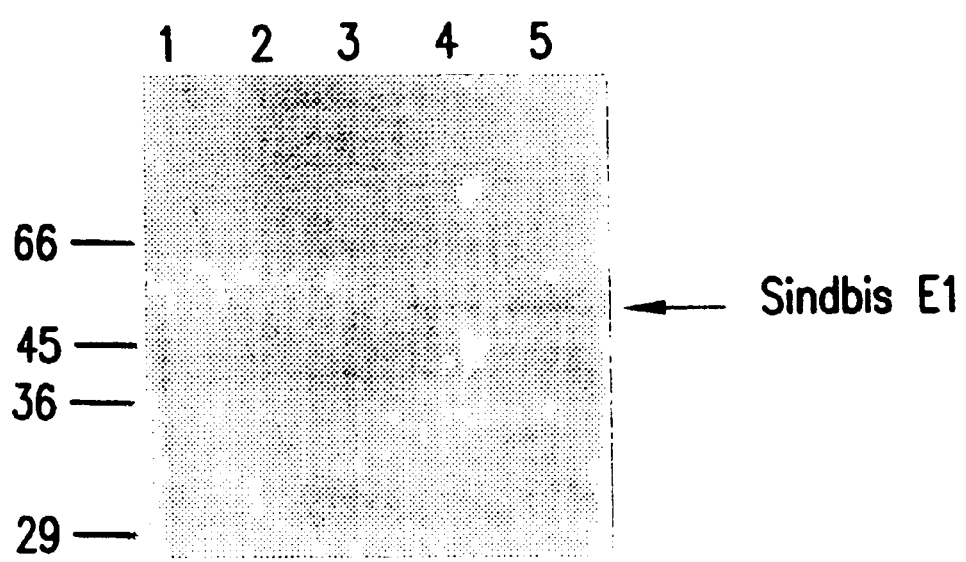
Figures 4A, 4B:
Figure 5A:
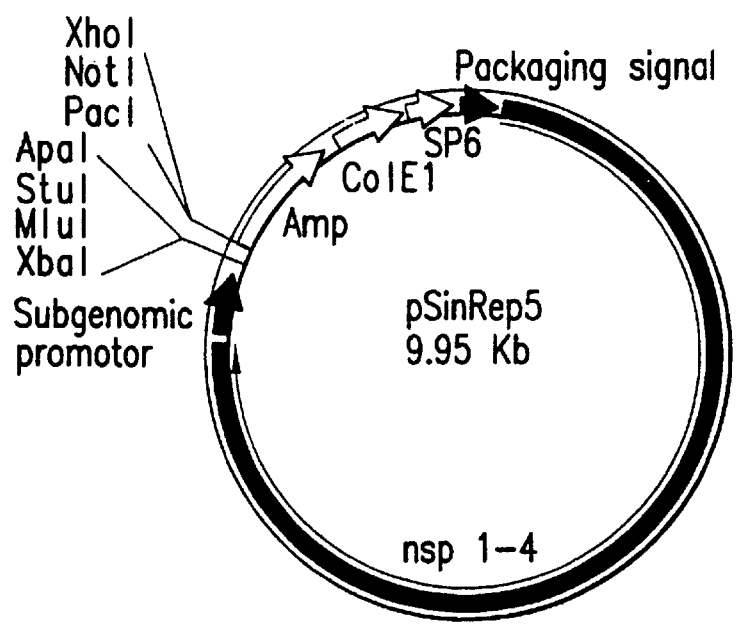
Figure 5B:
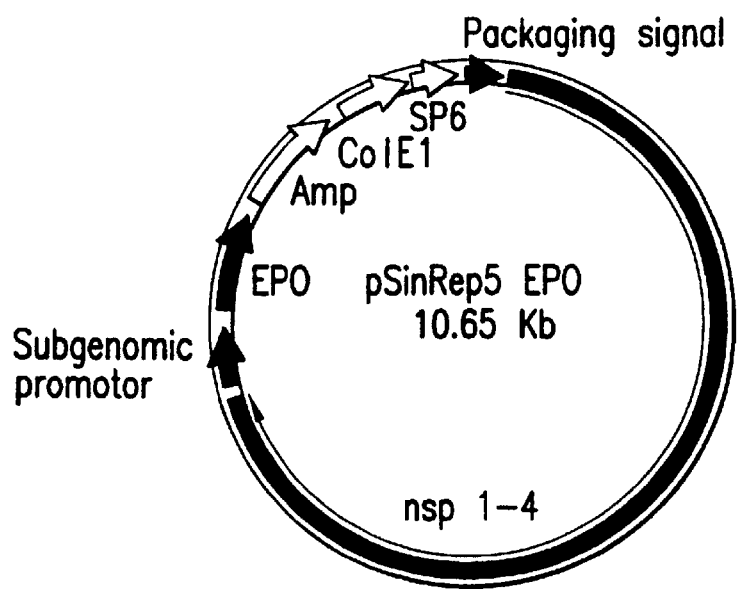
Figure 5C:
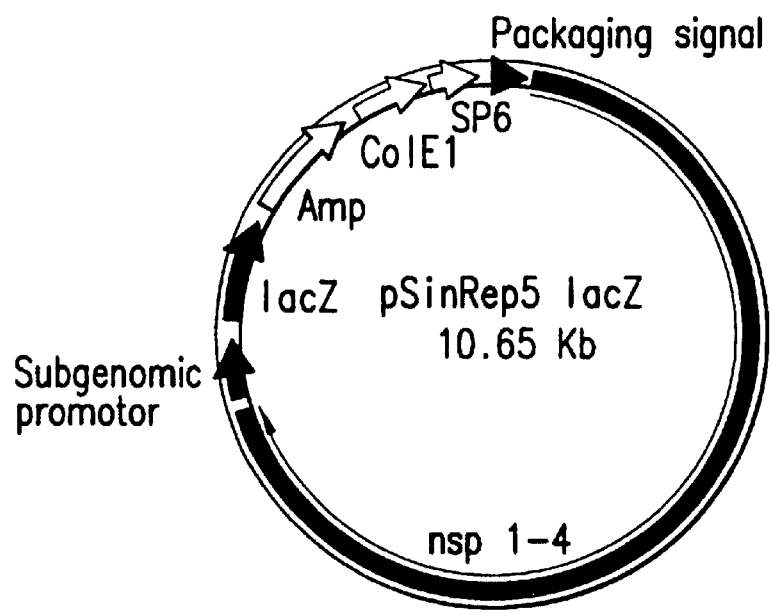
Figure 5D:
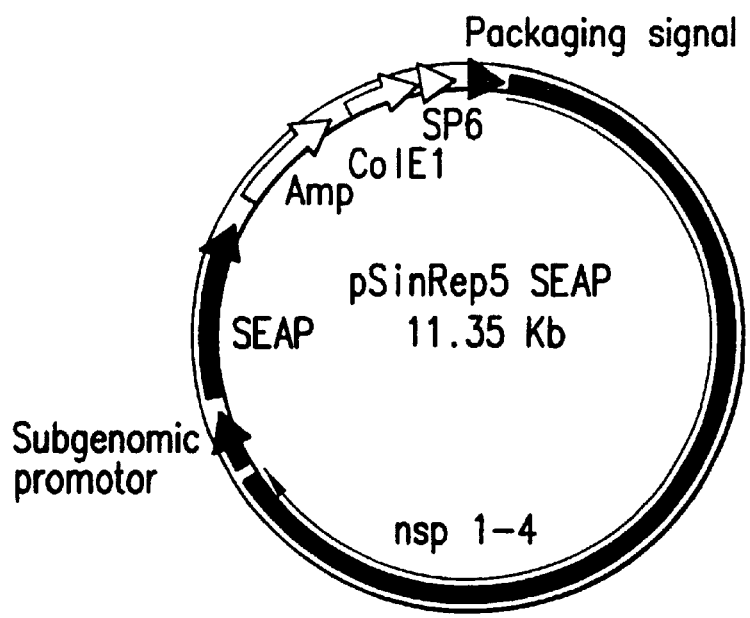
Figure 6A:
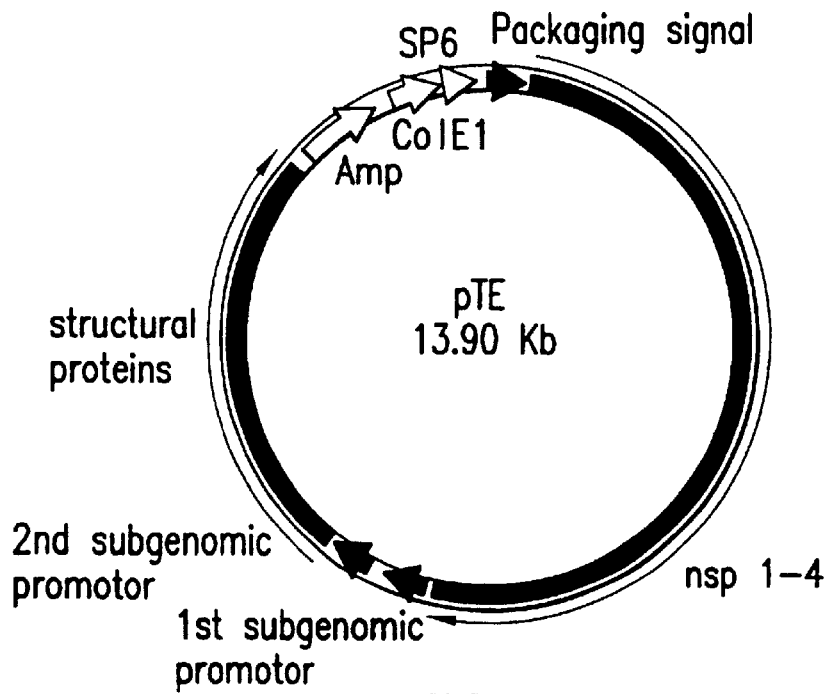
Figure 6B:
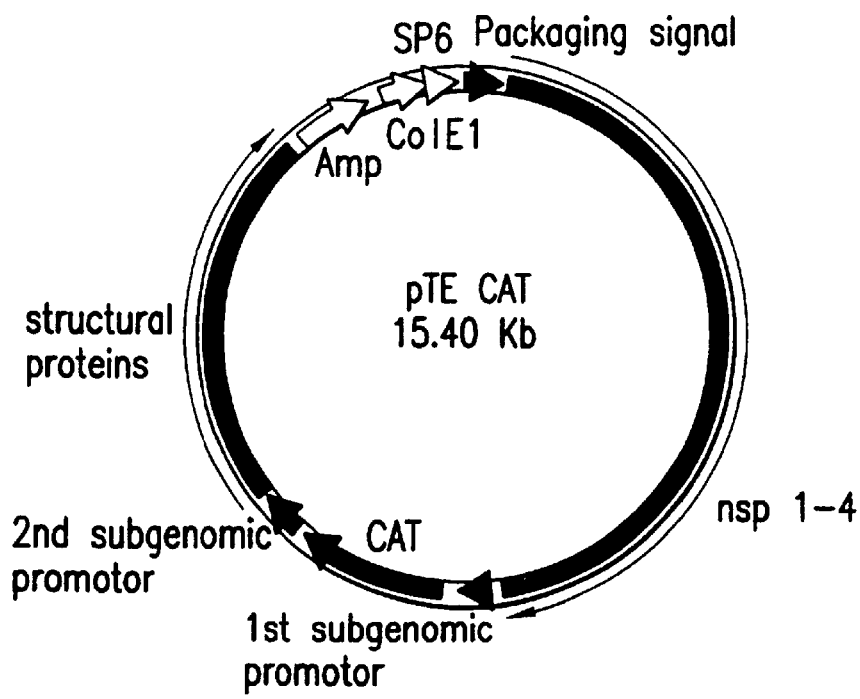
Figure 6C:
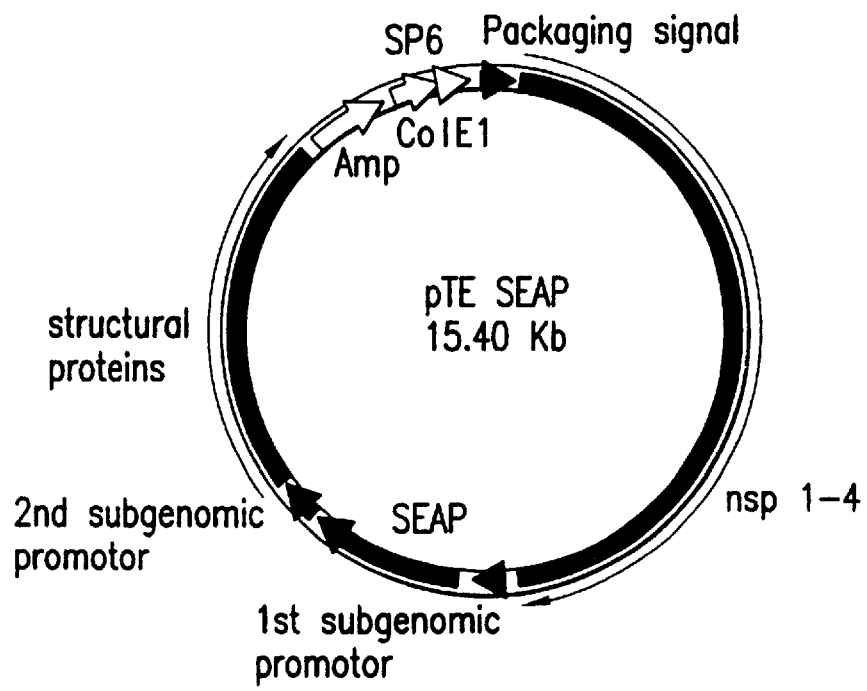
Figure 6D:
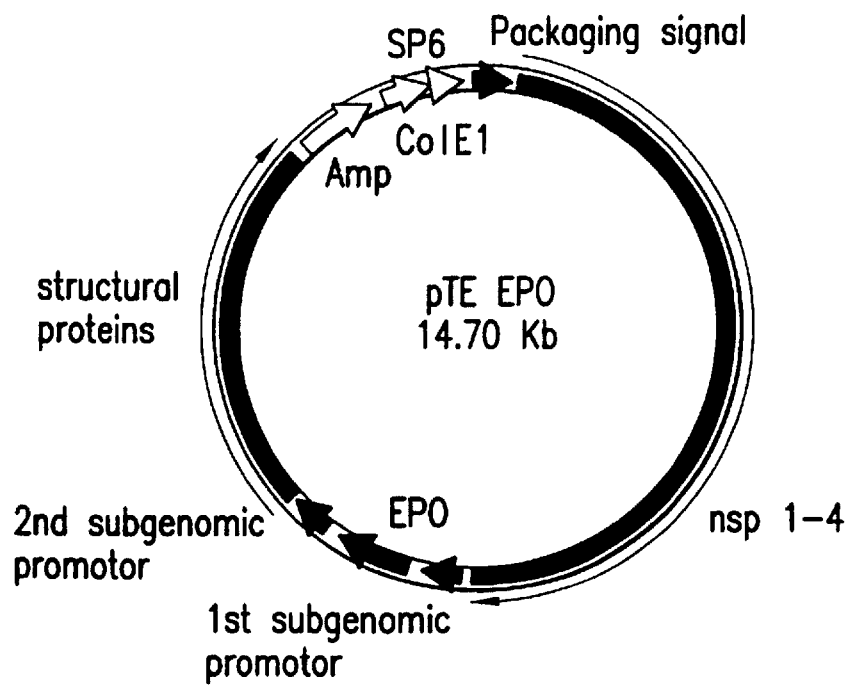

Confluent layers of BHK cells were infected with double subgenomic pTE5'2JCAT viral particles at an MOI of 5. Fourteen hours post infection, the medium was removed and the cells were overlaid with 4 mm of 0.8% agarose in RPMI 1640 medium containing 10 $\mu$Ci $^{35}$SMet/Cys per dish and varying amounts of Mini Protean protease inhibitor cocktail solution (seven times concentrated as described in the manual, Boehringer Mannheim, Rotkreuz, Switzerland). One hundred $\mu$l, 20 $\mu$l, 10 $\mu$l, 5 $\mu$l and 1 $\mu$l were used (see lanes 1–5 in FIG. 3). After gelling, the cultures were overlaid with 1 ml of Cys/Met free RPMI, and the medium was collected after 4 hours. The protein was precipitated and separated on a 15% SDS gel. The gel was exposed to an X-ray film overnight. The results (depicted in FIG. 3) demonstrated that release of viral protein was inhibited by addition of the protease inhibitor. At concentrations above 20 $\mu$l/ml (lanes 1 and 2), the release of soluble protein was inhibited showing that neither viral particles nor viral protein diffuses through the agarose layer, and that no endogenous or viral protein interfered with the screen.

E. Example 4

Identification of a Nucleic Acid Encoding a Protein with a Predetermined Enzymatic Activity in a Mixture of Nucleic Acids in Semi-Solid Medium Screening An expression system containing a nucleic acid encoding a protein with phosphatase activity was identified in a mixture of two expression systems. pSinRep5 lacZ and pSinRep5 SEAP were packaged individually with the helper DHEB, yielding infective particles. The two expression systems were mixed in a ratio of 10:1 (pSinRep5 lacZ: pSinRep5 SEAP). Confluent layers of BHK 21 cells in 35 mm dishes were infected with this mixture of expression systems and alternatively only with the pSinRep5 lacZ expression system. Two hours postinfection, the medium was removed and the cells were overlaid with 1.5 ml 0.8% agarose in 1×HP-1 medium Two days later, a nitrocellulose filter was placed on top of the agarose for 4 hours.

The filter was removed, washed in PBS and placed in a solution of 100 mM TrisHCl, 100 mM NaCl, 370 mg/nitroblue tetrazolium and 250 mg/l 5-bromo-4-chloro-3-indolylphosphate (all Sigma) to detect alkaline phosphatase activity.

In the sample containing 10% of the pSinRep5 SEAP expression system, two spatially distinct areas with alkaline phosphatase activity could be detected (FIG. 5). The two corresponding plaques that gave rise to the enzymatic conversion of the substrate and a negative control from an area that stained negative on the screen were isolated. The cell culture was then fixed in 0.5% glutaraldehyde in PBS and lac Z activity was detected in the cells by X-Gal staining as described in the instruction manual "Sindbis expression system" Invitrogen, San Diego, USA (not shown). About 20 to 30 plaques stained blue in this cell culture reflect the original distribution of expression systems.

Viruses from the positive alkaline phosphatase plaques and the negative control were eluted in PBS overnight by shaking at 4° C. The PBS was added to a fresh culture of confluent BHK cells in a 35 mm dish and SEAP activity was confirmed 2 days post infection by the following assay. Five hundred $\mu$l 2×SEAP buffer (2 mM L-homoarginine, 0.2 M diethanolamine, 0.1 mM MgCl$_2$ in H$_2$O) plus 100 $\mu$l substrate solution (120 mM nitrophenylphosphate in H$_2$O) were mixed with 400 $\mu$l of heat inactivated (10 minutes 60° C.) cell culture supernatant. SEAP activity was revealed by a color change from purple to yellow in the sample from the positive areas of the culture, whereas the negative controls did not give rise to a color change. This example demonstrates that an expression system containing a nucleic acid encoding a protein with a predetermined enzymatic activity can be isolated from a mixture of expression systems in semisolid medium screening.

F. Example 5

Stable Amplification of Expression Systems

The positive viral particles (containing the nucleic acid coding for SEAP) from Example 4 were amplified over three passages. One percent of the supernatant from the 35 mm dish of Example 4 was used to infect an 80% confluent T25 (25 cm$^2$) cell culture flash containing BHK 21. Twenty-four hours post infection, the supernatant was removed and assayed for SEAP activity. SEAP activity in this supernatant was proven by a fast color change in this sample. The particles were passaged in this way for a total of four times, thereby amplifying the expression system by a factor of $10^8$ within 5 days. This result demonstrates that the expression system can be amplified rapidly and efficiently to yield large amounts of a protein of interest. Moreover, this process yields substantial amounts of the expression system interest for further investigation of the protein's function and usefulness in any other mammalian system.

G. Example 6

Identification Of A Nucleic Acid Encoding A Secreted Protein In A Mixture Of Nucleic Acids In Semi-Solid Medium Screening An expression system containing a nucleic acid encoding a secreted protein with phosphatase activity was identified in a mixture of two expression systems. pSinRep5'LacZ and pSinRep5' SEAP were packaged individually with the helper DHEB, yielding infective particles. 90% confluent BHK 21 cell layers in 60 mm dishes (Easy Grip, Falcon 3004, Becton Dickinson and Company, England) were incubated at 37(C for 2 hours with 1 ml of 1×HP-1 medium containing approximately 780 plaque forming units ("pfu") of pSinRep5 LacZ and 20 pfu of pSinRep 5 SEAP (secreted alkaline phosphatase). After removal of the medium, the cells were overlaid with 3 ml 41° C. warm 0.8% agarose (Carl Roth GmbH, Karlsruhe, Germany) in HP-1 medium and were then incubated for 2 days at 37° C. in 5% CO$_2$.

The agarose was overlaid with 1 ml 1×RPMI 1640 Met$^-$/Cys$^-$ for 10 min before being replaced by 1 ml of fresh 1×RPMI 1640 Met$^-$/Cys$^-$. After 30 min starvation, the medium was replaced with 0.8 ml 1×RPMI 1640 Met$^-$/Cys$^-$ plus 20 $\mu$Ci of $^{35}$S Met/Cys. After labeling for 4 hour, the agarose overlay was washed 3 times for 10 min with 1 ml 1×HP-1, before the 54 mm pre-wetted nitrocellulose filter (0.45 μm membrane, BA85, Schleicher & Schuell, Germany) was applied for 16 to 18 hours.

Figure 7A:
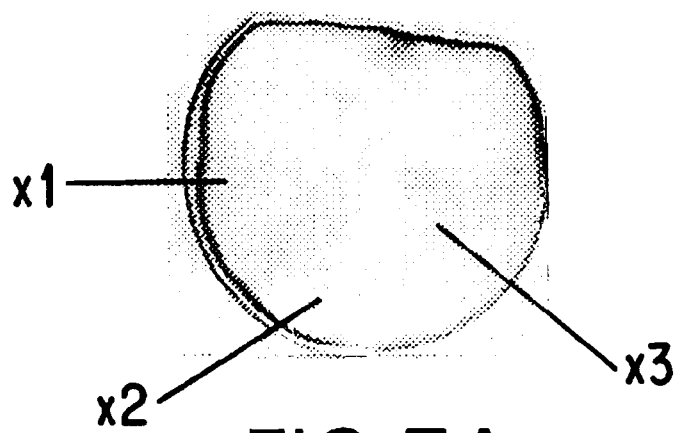
Figure 7B:
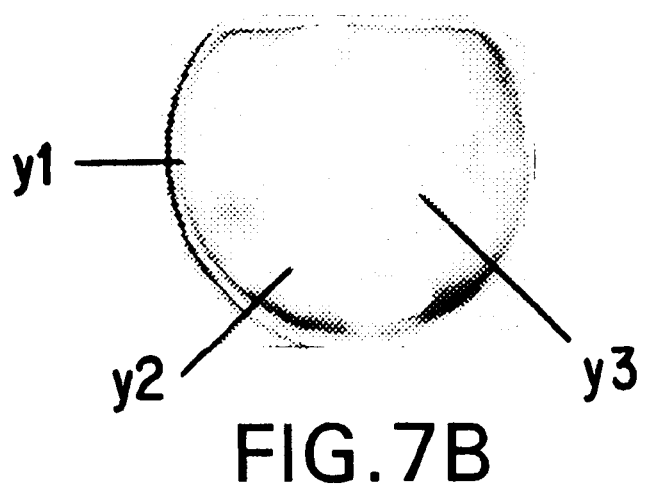

Diffusion blotting was proceeded during 18 hours, before SEAP activity was detected by AP staining (10 ml 100 mM TrisHCl, 100 mM NaCl, 370 mg nitroblue-tetrazolium and 250 mg/l 5-bromo-4chloro-3indolylphopshate (all Sigma)) resulting in violet spots (FIG. 7). The AP-developing was stopped by removal of the AP staining solution and with subsequent washing steps (3 times with TBS containing 0.1% Triton X-100). The nitrocellulose was then dried and exposed for at least 24 hours to an X-ray-film (Hyperfilm Pmax, Amersham, Sweden) before being developed with an AGFA Curix 60 (Schenk, Winterthur, Switzerland) machine (FIG. 7).

The coordinates of the radioactive spots were determined and the equivalent regions were picked from the agarose layer with a 10 μl tip. The eluted virus (as described above) was passaged in a 60% confluent BHK 21 12-well plate. Presence of a gene encoding SEAP in the insert of the eluted virus was determined by spotting 4 μl supernatant on a nitrocellulose membrane and by AP staining as described above.

The correspondance of the spots on the Secreted Alkaline Phosphatase stained filters with the spots on the X-ray film clearly demonstrated that nucleic acids encoding a secreted protein can be identified in a mixture of nucleic acids using semi-solid medium screening.

H. Example 7

Identification Of Nucleic Acids Encoding Secreted Proteins In A Sindbis Virus Library Representing A cDNA Library In Semi-Solid Medium Screening A directed cDNA library from ECV 304 cells (ATCC CRL-1998, human endothelial cell line) containing a Not I site at the 3' end and a 5' blunt end was ligated into Stu I, Bsp 120 L digested pSinRep 5 vector and $10^7$ primary clones were obtained after transformation of *E.coli* DH10b. After preparation of plasmid DNA and linearization with Not I, the library was transcribed in vitro as described before and packaged with the helper DHEB, yielding infective particles. 90% confluent BHK 21 cell layers in 60 mm dishes (Easy Grip, Falcon 3004, Becton Dickinson and Company, England) were incubated at 37° C. for 2 hours with 1 ml of 1×HP-1 medium containing approximately 800 pfu of pSin-Rep 5 ECV 304 library. After removal of the medium, the cells were overlaid with 3 ml 41° C. warm 0.8% agarose (Carl Roth GmbH, Karlsruhe, Germany) in HP-1 medium and were then incubated for 2 days at 37° C. in 5% CO2.

The agarose was overlaid with 1 ml 1×RPMI 1640 Met$^-$/Cys$^-$ for 10 min which was replaced by 1 ml of fresh 1×RPMI 1640 Met$^-$/Cys$^-$. After 30 min starvation, the medium was replaced with 0.8 ml 1×RPMI 1640 Met$^-$/Cys$^-$ containing 20 μCi of $^{35}$S Met/Cys. After 4 hour labeling, the agarose overlay was washed 3 times for 10 min with 1 ml 1×HP-1, before the 54 mm pre-wetted nitrocellulose filter (0.45 μm membrane, BA85, Schleicher & Schuell, Gremany) was applied.

Diffusion blotting was proceeded during 18 hours at 37° C., then the nitrocellulose was washed three (3) times 10 minutes with TBS containing 0.1% Triton X-100 before the membrane was dried and exposed for at least 24 hours to an X-ray film (Hyperfilm βmax, Amersham, Sweden), which was subsequently developed with an AGFA Curix 60 (Schenk, Winterthur, Switzerland) machine.

The coordinates of the radioactive spots were determined and the equivalent regions were picked from the agarose layer with a 10 μl tip. The virus was eluted as decribed before and was passaged on 60% confluent BHK 21 cells in 12-well plates. After reamplification of the virus particles on 60% confluent BHK 21 cells in 6-well plates, the viral RNA was isolated using the "high pure viral RNA kit" (Boehringer Mannheim, Mannheim, Germany). RT-PCR was carried out with the Superscript one-step RT-PCR kit according to the manufacturer (Gibco/BRL, Life Technologies AG, Basel, Switzerland) and the primers described before. The RT-PCR product was digested with the restriction enzymes Bsp120I and EcoRI, gel-purified and ligated in pBluescript (digested with EcoRI and Bsp120I) and finally sequenced using the oligos "–40 forward and reverse primer" of the multiple cloning site.

I. Example 8

Identification Of A Nucleic Acid Encoding A Secreted Protein In A Mixture Of Nucleic Acids In Semi-Solid Medium Screening Using Sindbis TS Mutants Recombinant SEAP Sindbis Virus Stocks. EcoRI-linearized DH-EB helper constructs (DH-EB, DH-EB ts2, DH-EB ts20, DH-EB ts2,20) and NotI-linearized pSinRep 5 SEAP and pSinRep5 LacZ DNA were made RNase-free by purification over QiaQuick PCR purification columns (QIAGEN AG, Basel, Switzerland) and elution with DEPC-H$_2$O. SP6 in vitro transcription was carried out according to the manufacturer Invitrogen (Invitroscript CAP Kit, Invitrogen BV, NV Leek, The Netherlands). 5 μg of SinRep 5' SEAP and 5 μg of the helper transcript were co-electroporated into BHK 21 cells according to Invitrogen (Invitroscript CAP Kit, Invitrogen BV, NV Leek, The Netherlands). The supernatants were harvested 30 hours post-electroporation (incubated at 30° C., 5% CO$_2$) and were assayed for SEAP activity. 4 μl of supernatant was spotted on nitrocellulose membrane (Schleicher & Schuell) and SEAP activity was detected by AP staining method as described above (FIG. 8).

First Passage Of ts Mutants. The recombinant virus stocks were passaged in a 60% confluent 6-well plate with BHK 21 cells. 100 μl of each. stock plus 900 μl of HP-1 were added for two (2) hours to the BHK cells at 30° C., then the virus supernatant was replaced with 2 ml HP-1. The cells were incubated for 24 hours either at the permissive temperature at 30° C. or at the nonpermissive temperature 37° C. before the supernatant was assayed for SEAP activity (as described before) (FIG. 8).

Plaque Assay For The ts Mutants. Dilution series of the harvested virus particles, see, supra, were carried out in 1 ml Turbodoma HP-1 ($1:10^4$, $1:5\times10^4$, $1:10^5$, $1:5\times10^5$, $1:10^6$, $1:5\times10^6$) on 90% confluent BHK 21 cells in 60 mm tissue culture dishes (Easy Grip, Falcon 3004, Becton Dickinson and Company, England). The cells were infected at 30° C. for 2 hours with the diluted virus at Dilution series of the harvested virus particles, see, supra, were carried out in 1 ml Turbodoma HP-1 ($1:10^4$, $1:5\times10^4$, $1:10^{5,}$ $1:5\times10^5$, $1:10^6$, $1:5\times10^6$). The supernatant was then replaced with 0.8% agarose in HP-1 and incubated for 2 days at 37° C. or 30° C. in 5% CO$_2$. The plaques were then counted.

Agarose BlotAssay With A Mixture Of pSinRep SEAPAndpSinRep LacZ An expression system containing a nucleic acid encoding a secreted protein was identified in a mixture of two expression systems. pSinRep5'LacZ and pSinRepS' SEAP were packaged individually with the ts mutant helpers DHEB (see TABLE I), yielding infective particles. 90% confluent BHK 21 cell layers in 60 mm dishes (Easy Grip, Falcon 3004, Becton Dickinson and Company, England) were incubated at 30° C. for 2 hours with 1 ml of 1×HP-1 medium containing approximately 780 plaque forming units ("pfu") of pSinRep 5 LacZ/DHEB ts and 20 pfu of pSinRep 5 SEAP (secreted alkaline phosphatase)/DHEB ts. After removal of the medium, the cells were overlaid with 3 ml 41° C. 0.8% agarose (Carl Roth GmbH, Karlsruhe, Germany) in HP-1 medium and were then incubated for 2 days at 30° C. in 5% $CO_2$.

Two (2) hours pre-starvation, the cells were shifted up to 40° C. in 5% $CO_2$. The agarose was overlaid with 1 ml 1×RPMI 1640 Met$^-$/Cys$^-$ for 10 min before the 1 ml RPMI medium was replaced with 1 ml of fresh 1×RPMI 1640 Met$^-$/Cys$^-$. After 30 min starvation at 40° C., the medium was replaced with 0.8 ml 1×RPMI 1640 Met$^-$/Cys$^-$ containing 20 μCi of $^{35}$S Met/Cys. After 4 hour labeling at 40° C., the agarose overlay was washed 3 times 10 min with 1 ml 1×HP-1, before a 54 mm pre-wetted nitrocellulose filter (0.45 μm membrane, BA85, Schleicher & Schuell, Gremany) was applied.

Figure 8A:
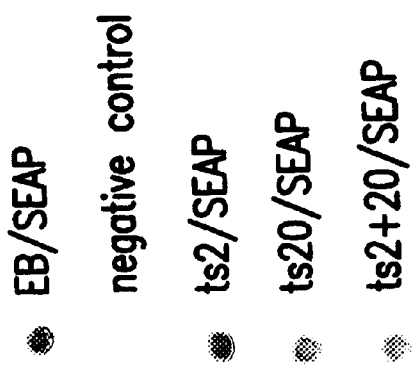
Figure 8B:
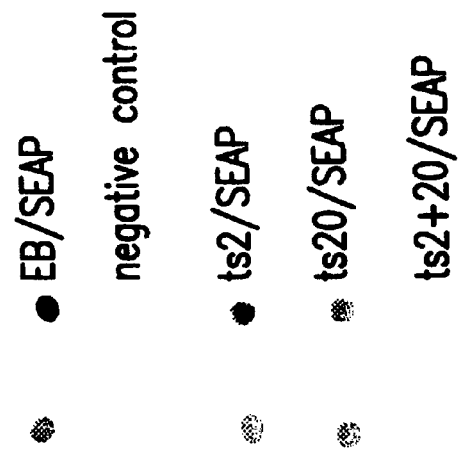
Figure 8C:
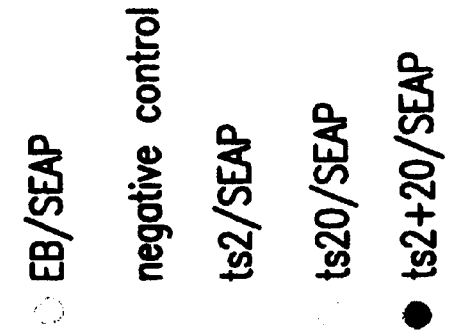
Figure 9A:
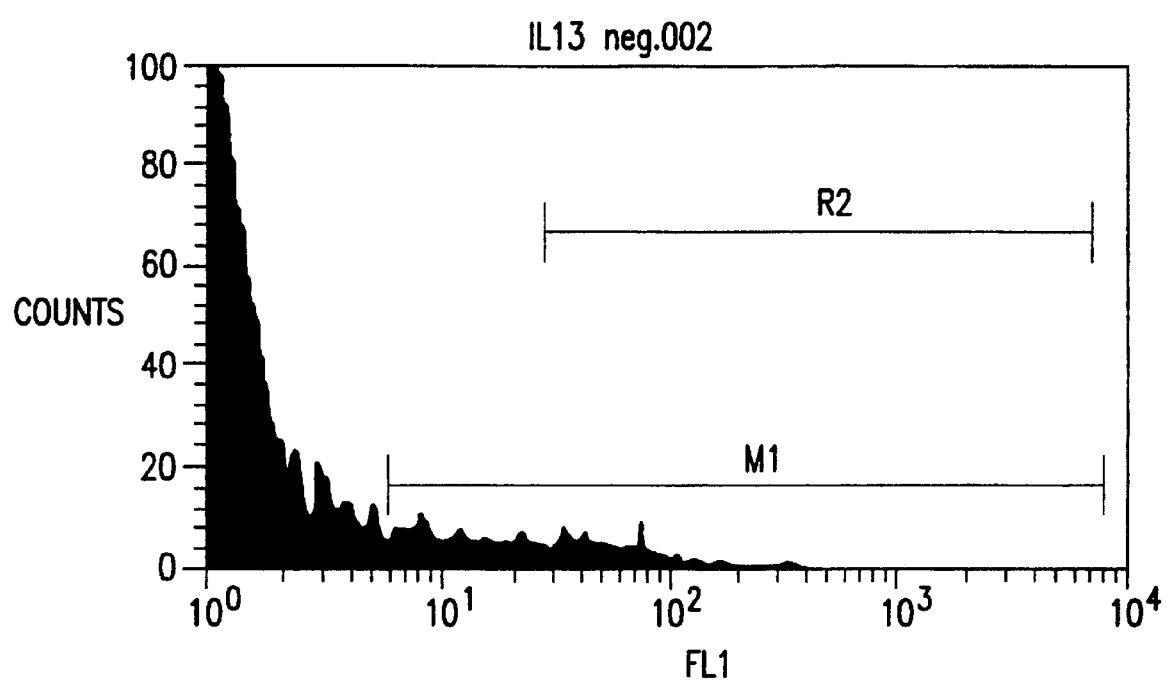
Figure 9B:
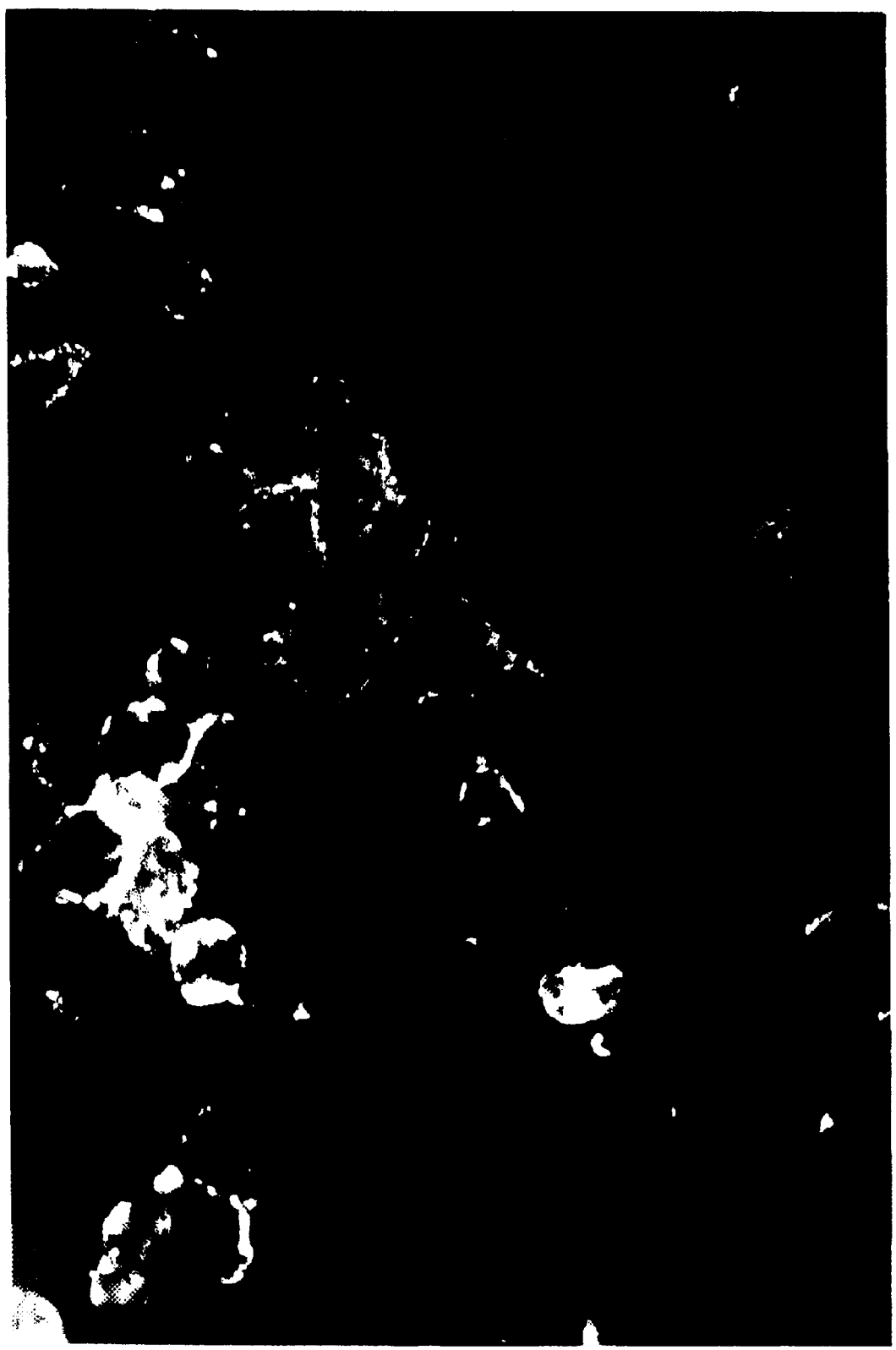
Figure 9C:
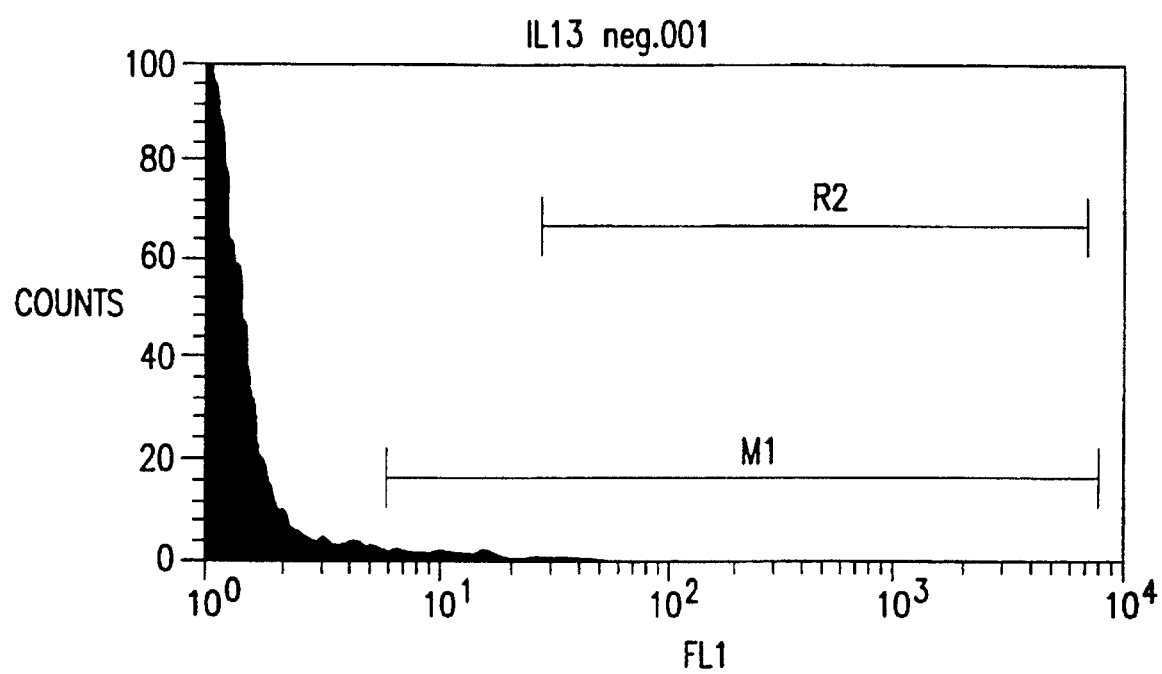
Figure 9D:
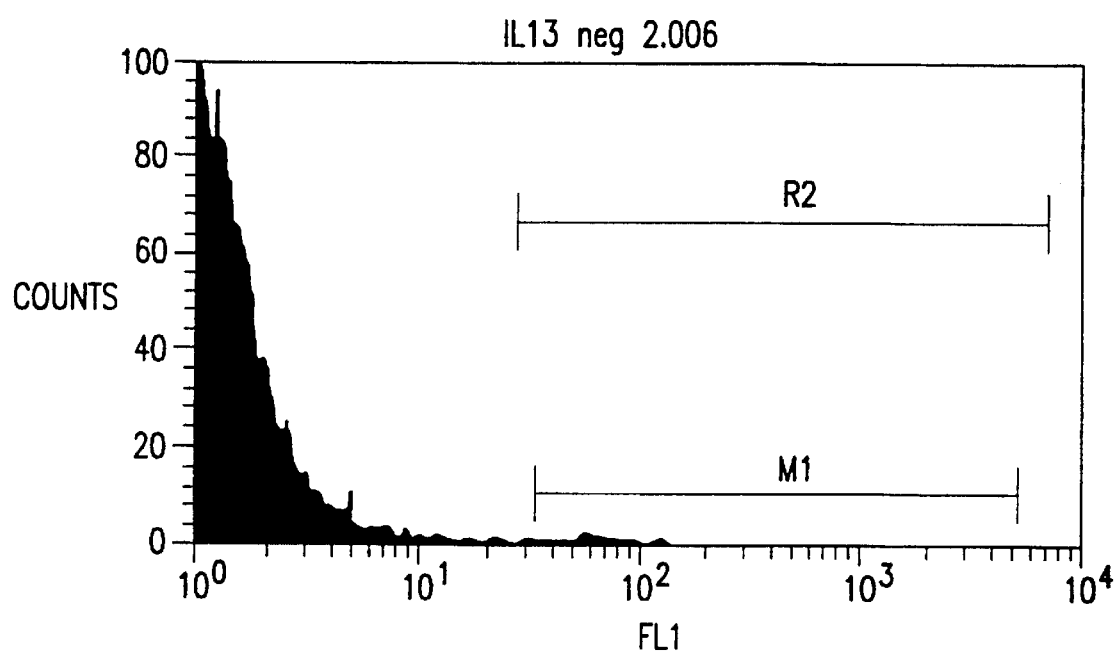

Diffusion blotting was proceeded at 40° C. during 18 hours, before SEAP activity was detected by AP staining (10 ml 100 mM Tris-HCl, 100 mM NaCl, 370 mg nitrobluetetrazolium and 250 mg/l 5-bromo-4chloro-3indolylphopshate (all Sigma)) resulting in violet spots (FIG. 8). The AP staining was stopped by removing the AP solution and by susequent washing steps (3 times TBS containing 0.1% Triton X100). The nitrocellulose was dried and exposed for at least 24 hours to an X-ray film (Hyperfilm bmax, Amersham, Sweden) before being developed with a AGFA Curix 60 (Schenk, Winterthur, Switzerland) machine.

The coordinates of the radioactive spots were determined and the equivalent regions were picked from the agarose layer with a 10 μl pipette tip.

J. Example 9

Identification Of A Nucleic Acid Encoding A Secreted Protein In A Mixture Of Nucleic Acids In Semi-Solid Medium Library Screening Using The TS Mutants pSinRep5' cDNA library ECV 304 was packaged with the mutant helpers DHEB, yielding infective particles. 90% confluent BHK 21 cell layers in 60 mm dishes (Easy Grip, Falcon 3004, Becton Dickinson and Company, England) were incubated at 30° C. for 2 hours with 1 ml of 1×HP-1 medium containing approximately 800 pfu of the pSinRep 5 cDNA library ECV 304. After removal of the medium, the cells were overlaid with 3 ml 0.8% agarose (Carl Roth GmbH, Karlsruhe, Germany) in HP-1 medium and were then incubated for 2 days at 30° C. in 5% $CO_2$.

Two (2) hours pre-starvation, the cells were shifted to 40° C. in 5% $CO_2$. The agarose was overlaid with 1 ml 1×RPMI 1640 Met$^-$/Cys$^{-31}$ for 10 min before being replaced by 1 ml of fresh 1×RPMI 1640 Met$^-$/Cys$^-$. After 30 min starvation, the medium was replaced with 0.8 ml 1×RPMI 1640 Met$^-$/Cys$^-$ plus 20 μCi of $^{35}$ Met/Cys. After 4 hour labeling, the agarose overlay was washed 3 times for 10 min with 1 ml 1×HP-1, before the 54 mm pre-wetted nitrocellulose filter (0.45 μm membrane, BA85, Schleicher & Schuell, Germany) was applied for 16 to 18 hours.

Diffusion blotting was proceeded during 18 hours, before the nitrocellulose was dried and exposed for at least 24 hours to an X-ray film(Hyperfilm βmax, Amersham, Sweden) and then developed with a AGFA Curix 60 (Schenk, Winterthur, Switzerland) machine. The coordinates of the radioactive spots were determined and the equivalent regions were picked from the agarose layer with a 10 μl tip.

K. Example 10

Expression Cloning Using Sindbis Virus: Cloning A Receptor For A Known Ligand By FACS Single Cell Sorting 60% confluent BHK 21 cultures in T150 flasks were infected at 37° C. for 2 hours at an moi of 0.1 in 1×HP-1 medium. Different dilutions of pSinRep 5 hIL 13 Ra (human Interleukin 13 Receptor, subunit alpha; hIL13 Ra digested from pDR2-hIL13Ra with XbaI and PvuII, cloned into pSinRep5 digested with XbaI and StuI)/DHEB with pSinRep 5 LacZ/DHEB (1:0/1:100/1:100'000) were used with a total moi of 0.1. The medium was then replaced with fresh 1×HP-1 medium and the cells were incubated at 37° C. in 5% $CO^2$ for 20 hours.

The cells were then resuspended with 5 ml cell dissociation solution (Sigma-Aldrich, Steinheim, Germany) followed by two additional washing steps in HBSS containing 1% BSA. 1 ml 1%BSA, 1 μg/ml IL13flag (according to IBR GmbH, Waengi, Switzerland) and 5 μg/ml mAb M2 (according to to IBR GmbH, Waengi, Switzerland) in HBSS were incubated with the cells at 4° C. for 15 min. The cells were washed twice with 1.5 ml 1% BSA/HBSS and incubated with 1 ml 1% BSA and 10 μg/ml FITC conjugated secondary antibody for 30 min at 4° C. The cells were washed twice with 4° C. 1% BSA in HBSS and resuspended in HBSS at a concentration of $3×10^6$/ml. Single cell sorting into 96-well plates was done for cells with FITC fluorescence intensity above background (see FIG. 9).

FIG. 9 shows that the Interleukin 13-Receptor alpha is transiently expressed and that single cells expressing the correct receptor for a chosen ligand can be sorted by FACS analysis.

L. Example 11

Expression Cloning Using Sindbis Viruses: Cloning A Ligand For A Known Receptor An infectious Sindbis Virus library is produced in double subgenomic Sindbis Virus vectors (pTE) or in pSinRep5 copackaged with the DH-EB helper as described supra. Confluent BHK 21 cells in 150 mm dishes are incubated for two (2) hours with HP-1 medium containing about 5,000 pfu of the infectious sindbis virus library. After removal of the medium, the cells are overlaid with 2 mm of 0.8% agarose in 1×HP-1 medium and are incubated for three days at 37° C. A nitrocellulose filter is placed on top of the agarose and incubated for at least three hours. The membrane is removed and subsequently washed with TBS. After agitating the filters for 15 minutes in TBS, the filter is blocked by incubation in 1% skim milk for one (1) hour. After three washing steps in TBS, the filters are incubated in TBS containing the radiolabelled solubilized receptor for at least one (1) hour. After several washing steps in TBS, the filters are dried and exposed to X-ray films. Dark spots indicate colonies expressing a binding partner of the chosen receptor of interest.

M. Example 12

Cloning A Cell Associated Protein For Which The Ligand Is Known

An infectious Sindbis Virus library is produced in double subgenomic Sindbis Virus vectors (pTE) or in pSinRep5 copackaged with the DH-EB helper as described in the Materials and Methods section, supra. BHK 21 cells are grown on nitrocellulose filters in 150 mm dishes to confluency. The cells are incubated for two hours with HP-1 medium containing about 5,000 pfu. After removal of the medium, the cells are overlaid with 2 mm of 0.8% low melting agarose in 1×HP-1 medium and are incubated for two days at 37° C. After this incubation, a nitrocellulose filter is placed on top of the agarose to capture viral particles. After 24 hours of incubation, the nitrocellulose filters are removed and placed in new 150 mm dishes where a new culture of BHK cells is added at a cell density of 400,000 cells per $cm^2$ in medium containing 10% FCS. After adhesion of the cells, this culture is again overlaid with 2 mm agarose and incubated at 37° C. This culture serves as a stock of virus particles for later isolation. The initial plate is heated to 40° C. to melt the agarose. After removal of the melted agarose, the cells are fixed to the membrane by known methods (0.5% glutaraldehyde in PBS, 3% paraformaldeyde, −20° C. methanol and the like) according to the expected localization (nucleus, cytoplasmic membrane, etc.) and nature of the protein that is to be cloned. After several washing steps in TBS, the filters are incubated in TBS containing the radioactive labelled ligand. After several washing steps, the filters are dried and exposed to X-ray films. Dark spots indicate colonies expressing a binding partner of the chosen ligand.

N. Example 13

Discovery And Expression Of Novel Membrane Proteins

A Sindbis Virus library in pSinRep5 as described in Example 6 is coelectroporated with the DHBB helper to produce one way virions described supra. After determination of the virus titer, confluent cultures of 987 BB neo cells (See Table I and SEQ ID NO:2 for a description of the vector by which BHK 21 cells were transfected to yield the 987BBneo cell line after selection in 200µg/ml G418). After removal of the medium, the cells are overlaid with 2 mm of agarose to allow plaque formation. After three days, a coated polyester mat as described in Motobu et al. (in E. C. Beuvery et al. (eds.) "Animal Cell Technology;. Developments towards the 21th century", pp. 811–815 (1995) Kluwer Academic Publishers) is placed on top of the agarose and BHK 21 cells are added on top at a cell density of 400,000 cells/$cm^2$ at a concentration of 1,000,000 cells/ml of medium. After adhesion of the cells, the same amount of fresh medium is added and the culture is incubated for an additional 12 hours. The liquid medium is removed and replaced by labelling medium (10 µCi of $^{35}S$ methionine/cysteine). After 12 hours of incorporation, the labelling medium is removed and the culture is washed by adding 10 ml of normal medium. This medium is replaced every 10 minutes for a total of two hours. After removal of all liquid medium, the cells are overlaid with a 2 mm layer of medium containing 0.8% agarose and 0.1% trypsin. After gelling of the agarose, a nitrocellulose membrane is placed on top of the agarose and the culture is incubated for an additional one to six (6) hours. Proteolytically released fragments of membrane proteins diffuse to the membrane and are captured on the nitrocellulose filter. Autoradiographing the filter indicates the clones coding for membrane proteins.

O. Example 14

Discovery And Expression Of Novel Organelle Specific Proteins

An infectious Sindbis Virus library is produced in double subgenomic Sindbis Virus vectors (pTE) or in pSinRepS copackaged with the DH-EB helper as described in Materials and Methods. BHK 21 cells are grown in 150 mm dishes to confluency. The cells are incubated for two hours with HP-1 medium containing about 5,000 pfu. After removal of the medium, the cells are overlaid with 2 mm of 0.8% low melting agarose in 1×HP-1 medium and are incubated for one to two days at 37° C. After this incubation, a nitrocellulose filter is placed on top of the agarose to capture viral particles. After at least 12 (twelve) hours of incubation, the nitrocellulose filters are removed and placed in new 150 mm dishes where a new culture of BHK cells is added at a cell density of 400,000 cells per $cm^2$ in medium containing 10% FCS. After adhesion of the cells, this culture is again overlaid with 2 mm agarose and incubated at 37° C. This culture serves as a stock of virus particles for later isolation.

The initial plate is overlaid with a second layer of 0.8% agarose in RPMI 1640 medium containing 40 µCi of $^{35}S$ labelled mix of methionine and cysteine. After two hours of labelling, the plates are heated to 40° C. to melt the agarose. After removal of the melted agarose, the cells are lysed by known methods to yield intact organelles. A blocked nitrocellulose filter with immobilized antibodies against a surface protein of the organelle to be captured is placed on top of the homogenate. After several washing steps, the filters are dried and exposed to X-ray films. Autoradiographing the filter indicates the clones coding for proteins localized in the desired organelle.

P. Example 15

Expression Cloning Using Sindbis Virus: Cloning A New Receptor For A Known Ligand By FACS Single Cell Sorting 60% confluent BHK 21 cells in T150 flask are infected for 2 hours with pSinRep ECV cDNA library at an moi of 0.1 in 20 ml Turbodoma HP-1 medium. The medium is then replaced with 40 ml fresh 1×HP-1 medium and the cells are incubated at 37° C. in 5% $CO_2$ for 20 hours.

The cells are then resuspended with 5 ml cell dissociation solution (Sigma-Aldrich, Steinheim, Germany) and washed twice in HBSS containing 1% BSA. The cells are incubated in 1 ml HBSS in the presence of 1% BSA, 1 µg/ml ligand-flag fusion protein and 5 µg/ml mAb M2 at 4° C. for 15 min and washed twice with 1.5 ml 1%BSA/HBSS before subsequent incubation with 1 ml 1% BSA and 10 µl/ml antiM2 FITC for 30 min at 4° C. The cells are washed twice with 1% BSA in HBSS before resuspension in HBSS at a concentration of $3×10^6$/ml. Single cell sorting into 96-well plates is done for cells with FITC activity above background.

The supernatant of the 96-well plates are used for a plaque assay in 6-well plates with 90% confluent BHK 21 cells. Plaques are picked with 10 µl pipette tips and the eluted as described before. The eluted virus is passaged in a 60% confluent BHK 21 12-well plate in 1 ml Turbodoma HP-1 at the permissive temperature. The insert of the eluted virus is determined by reamplification of the virus particles in 2 ml Turbodoma HP-1 medium in a 6-well plate containing 60% BHK 21 cell layers. Viral RNA is isolated using a "high pure viral RNA kit" (Boehringer Mannheim, Mannheim, Germany) and RT-PCR is done with the Superscript one-step RT-PCR kit according to the manufacturer (Gibco/BRL, Life Technologies AG, Basel, Switzerland) and the primers as described before. The RT-PCR product ligation into pBluescript and the sequence determination are done as described above.

Q: Example 16

Expression Cloning Of A Ligand For A Known Binding Partner pSinRep5' EPO and pSinRep 5 LacZ were packaged with the helper DHEB, yielding infective particles. 90% confluent BHK 21 cell layers in 60 mm dishes (Easy Grip, Falcon 3004, Becton Dickinson and Company, England) were incubated at 37° C. for two (2) hours with 1 ml of 1×HP-1 medium containing approximately 25 to 30 pfu of pSinRep EPO/DH-EB and approximately 180 to 200 pfu of pSinRep 5 LacZ/DH-EB. After removal of the medium, the cells were overlaid with 3 ml 41° C. warm 0.8% agarose (Carl Roth GmbH, Karlsruhe, Germany) in HP-1 medium and the plates were incubated for two (2) days at 37° C. in 5% $CO_2$.

A pre-wetted 54 mm nitrocellulose filter (0.45 μm membrane, BA85, Schleicher & Schuell, Germany) was applied for sixteen (16) hours, before the nitrocellulose was blocked with 1% BSA in TBS for two (2) hours. The first antibody (anti-EPO, polyclonal, Research Diagnostics, Inc., USA) specific for the screened secreted protein was incubated for one (1) hour at the dilution of 1:3000 in TBS (according to the manufacturer). The membrane was then washed three (3) times with TBS 0.05% Tween before the second antibody (AP conjugated anti-rabbit IgG, Jackson ImmunoResearch Laboratories, Inc., USA) was incubated with the filter at a dilution of 1:4000 in TBS 1% BSA. After washing the membrane with TBS 0.05% Tween, AP staining was carried out as described above.

The plaques corresponding to the AP positive spots (see FIG. 10) were picked from the agarose layer with a 10 μl pipette tip. Elution of the virus was done as described. The virus was passaged in a 60% confluent BHK 21 12-well plate. The insert of the eluted virus was determined by reamplifying of the virus particles in a 60% BHK 21 6-well plate before a dot blot against EPO was done as described above.

Figure 10:
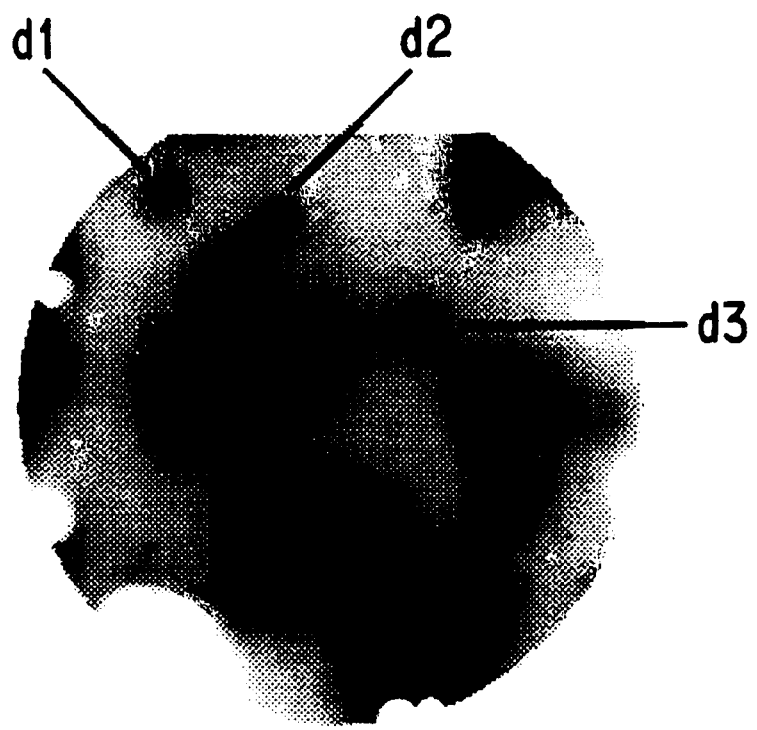

FIG. 10 shows, that a specific secreted ligand for a known binding partner (receptor, antibody) can be cloned successfully and that the system can be efficiently used to screen viruses representing cDNA libraries.

All references cited within the body of the instant specification are hereby incorporated by reference in their entirety.

What is claimed is:

1. A method for identifying a nucleic acid encoding an exogenous polypeptide which shares a property of interest with members of a class of polypeptides, the nucleic acid being present in a nucleic acid library encoding a plurality of distinct polypeptides, said method comprising:
   (a) providing a composition comprising a population of eukaryotic host cells, each of which contains an individual expression system, and wherein each individual eukaryotic host cell in substantially all of the population comprises at least one copy of one unique expression system;
   (b) culturing the population of eukaryotic host cells under conditions where the exogenous polypeptide is expressed; and
   (c) identifying the nucleic acid by detecting the property of interest,
wherein the individual expression systems comprise the individual nucleic acids of the nucleic acid library and wherein said individual expression system directs the generation of infectious viral particles from said eukaryotic host cell.

2. The method of claim 1, wherein the property of interest is a predetermined cellular localization.

3. The method of claim 2, wherein the predetermined cellular localization is the extracellular space.

4. The method of claim 2, wherein the predetermined cellular localization is the cell membrane.

5. The method of claim 2, wherein the predetermined cellular localization is selected from the group consisting of nucleus, lysosomes, mitochondria, endoplasmic reticulum, Golgi apparatus, peroxysomes, endosomes and cytoplasm.

6. The method of claim 1, wherein the property of interest is a binding affinity to a binding partner.

7. The method of claim 1, wherein the property of interest is an enzymatic activity.

8. The method of claim 1, wherein the property of interest is a structural property.

9. The method of claim 1, wherein the exogenous polypeptide is labeled while expression of endogenous host cell polypeptides is suppressed.

10. The method of claim 9, wherein the exogenous polypeptide is labeled with a marker selected from the group consisting of radioactive marker and spectroscopically detectable marker.

11. The method of claim 1, wherein the nucleic acid is operably linked to a control element derived from a virus.

12. The method of claim 11, wherein the control element is capable of directing expression of the exogenous polypeptide while expression of endogenous host cell polypeptides is suppressed.

13. The method of claim 12, further comprising the step of separating the infectious viral particles from the exogenous polypeptide.

14. The method of claim 13, wherein the infectious viral particles are separated from the exogenous polypeptide by filtration, chromatography or precipitation.

15. The method of claim 12, wherein expression of the endogenous host cell polypeptides is suppressed by the inhibition of transcription or translation of nucleic acids encoding the endogenous host cell polypeptides.

16. The method of claim 11, wherein the virus suppresses expression of endogenous host cell polypeptides.

17. The method of claim 11, wherein the virus is an alpha virus.

18. The method of claim 17, wherein the alpha virus is selected from the group consisting of Sindbis Virus, Semliki Forest Virus, and Venezuelan Equine Encephalitis Virus.

19. The method of claim 1, wherein the infectious viral particles produce solubilized viral polypeptide, and wherein production of the solubilized viral polypeptide is reduced.

20. The method of claim 19, wherein production of solubilized polypeptide is reduced through use of a protease inhibitor.

21. The method of claim 19, wherein production of solubilized polypeptide is reduced through use of a mutant virus strain.

22. The method of claim 21, wherein the mutant virus strain is selected from the group consisting of the temperature sensitive Sindbis mutants ts20, ts10, and ts23.

23. The method of claim 19, wherein production of solubilized polypeptide is reduced through use of a cell line deficient in cleavage of a polypeptide of the virus.

24. The method of claim 23, wherein the cell line is deficient in cleavage of polypeptide PE2 to E2 and E3.

25. The method of claim 1, wherein the nucleic acid library is screened using physical separation of individual members of the population of eukaryotic host cells.

26. The method of claim 25, wherein the physical separation is achieved by separating the eukaryotic host cells in a semi-solid medium.

27. The method of claim 25, wherein the physical separation is achieved by placing eukaryotic host cells in separate compartments, wherein substantially all of the host cells in each compartment contain identical expression systems.

28. A method for identifying a nucleic acid encoding an exogenous polypeptide which shares a property of interest with members of a class of polypeptides, the nucleic acid being present in a nucleic acid library encoding a plurality of distinct polypeptides, said method comprising:
(a) providing a composition comprising a population of eukaryotic host cells which contain the individual expression systems;
(b) culturing the population of eukaryotic host cells under conditions where the exogenous polypeptide is expressed while expression of endogenous host cell polypeptides of the population of eukaryotic host cells is suppressed; and
(c) identifying the nucleic acid by detecting the property of interest,
wherein the individual expression systems comprise a control element derived from a virus operably linked to the individual nucleic acids of the nucleic acid library, wherein said individual expression system directs the generation of infectious viral particles from said eukaryotic host cell and wherein each individual eukaryotic host cell in substantially all of the population comprises at least one copy of one unique expression system.

29. The method of claim 28, wherein the property of interest is a binding affinity to a binding partner.

30. The method of claim 28, wherein the property of interest is an enzymatic activity.

31. The method of claim 28, wherein the virus is an alpha virus.

32. The method of claim 28, wherein the expression system directs the generation of viral particles.

33. The method of claim 32, further comprising the step of separating the viral particles from the exogenous polypeptide.

34. A method for screening a nucleic acid library to identify a nucleic acid which encodes a polypeptide having an identifiable property, said method comprising:
(a) generating a population of eukaryotic host cells which contain the nucleic acid in operable linkage with a viral control element, wherein each individual eukaryotic host cell in substantially all of the population comprises at least one copy of one unique nucleic acid;
(b) culturing the population of eukaryotic host cells;
(c) screening to identify cells which express the encoded polypeptide by detecting the identifiable property; and
(d) recovering infectious viral particles from the cells identified in step (c).

35. The method of claim 34, wherein the property of interest is a binding affinity to a binding partner.

36. The method of claim 34, wherein the property ofinterest is an enzymatic activity.

37. The method of claim 34, wherein the property of interest is a structural property.

38. The method of claim 34, wherein the individual eukaryotic host cells in the population comprise a virus which suppresses expression of endogenous host cell polypeptides.

39. The method of claim 38, wherein expression of the endogenous host cell polypeptides is suppressed by inhibiting transcription or translation of nucleic acids encoding the endogenous host cell polypeptides.

40. The method of claim 34, wherein the viral control element is derived from an alpha virus.

41. The method of claim 40, wherein the alpha virus is selected from the group consisting of Sindbis Virus, Semliki Forest Virus, and Venezuelan Equine Encephalitis Virus.

42. The method of claim 34, wherein the viral control element is capable of directing expression of the exogenous polypeptide while expression of endogenous host cell polypeptides is suppressed.

43. The method of claim 42, further comprising the step of separating the infectious viral particles from the exogenous polypeptide.

44. The method of claim 34, wherein the nucleic acid library is screened using physical separation of individual members of the population of eukaryotic host cells.

45. The method of claim 44, wherein the physical separation is achieved by separating the eukaryotic host cells in a semi-solid medium.

46. The method of claim 44, wherein the physical separation is achieved by placing eukaryotic host cells in separate compartments, wherein substantially all ofthe host cells in each compartment contain identical nucleic acids.

47. A method for identifying a nucleic acid which is present in a nucleic acid library and encodes an exogenous polypeptide having a property of interest, said method comprising:
(a) providing a composition comprising a population of eukaryotic host cells which contain the nucleic acids of the library operably linked to a control element derived from a virus;
(b) culturing the population of eukaryotic host cells under conditions where the exogenous polypeptide is expressed while expression to endogenous host cell polypeptides of the population of eukaryotic host cells is suppressed; and
(c) identifying the nucleic acid by detecting the property of interest;
wherein said individual expression system directs the generation of infectious viral particles from said eukaryotic host cell and wherein each individual eukaryotic host cell in substantially all of the population comprises at least one copy of one unique nucleic acid.

48. The method of claim 47, wherein the property of interest is a binding affinity to a binding partner.

49. The method of claim 47, wherein the property of interest is an enzymatic activity.

50. The method of claim 47, wherein the virus is an alpha virus.

51. The method of claim 50, wherein the alpha virus is selected from the group consisting of Sindbis Virus, Semliki Forest Virus, and Venezuelan Equine Encephalitis Virus.

52. The method of claim 47, further comprising the step of separating the viral particles from the exogenous polypeptide.

53. A method for identifying a nucleic acid which is present in a nucleic acid library and encodes an exogenous polypeptide having a property of interest, said method comprising:
(a) providing a composition comprising a population of eukaryotic host cells which contain expression systems comprising the nucleic acids of the library operably linked to a subgenomic promoter;
(b) culturing the population of eukaryotic host cells under conditions where the exogenous polypeptide is expressed; and (c) identifying the nucleic acid by detecting the property of interest;

wherein each individual expression system directs the generation of infectious viral particles from said eukaryotic host cells and wherein each individual eukaryotic host cell in substantially all of the population comprises at least one copy of one unique expression system.

54. The method of claim 53, wherein the subgenomic promoter is derived from an alpha virus.

55. The method of claim 54, wherein the alpha virus is selected from the group consisting of Sindbis Virus, Semliki Forest Virus, and Venezuelan Equine Encephalitis Virus.

56. The method of claim 53, further comprising the step of separating the viral particles from the exogenous polypeptide.

57. A population of eukaryotic host cells, each of which contains an individual expression system, each individual expression system comprising:
(a) a nucleic acid which encodes an exogenous polypeptide; and
(b) a control element of a virus which directs the expression of the exogenous polypeptide while expression of endogenous host cell polypeptides of the eukaryotic host cells is suppressed;

wherein said individual expression system directs the generation of infectious viral particles from said eukaryotic host cell, and wherein each individual eukaryotic host cell in substantially all of the population of eukaryotic host cells comprises at least one copy of one unique expression system.

58. The population of eukaryotic host cells of claim 57, wherein the control element is derived from an alpha virus.

59. The population of eukaryotic host cells of claim 58, wherein the alpha virus is selected from the group consisting of Sindbis Virus, Semliki Forest Virus, and Venezuelan Equine Encephalitis Virus.

60. The method of claim 1, wherein said method further comprises recovering said infectious viral particles.

61. The method of claim 28, wherein said method further comprises recovering said infectious viral particles.

62. The method of claim 47, wherein said method further comprises recovering said infectious viral particles.

63. The method of claim 53, wherein said method further comprises recovering said infectious viral particles.

* * * * *

UNITED STATES PATENT AND TRADEMARK OFFICE
CERTIFICATE OF CORRECTION

PATENT NO. : 6,524,792 B1
DATED : February 25, 2003
INVENTOR(S) : Renner et al.

It is certified that error appears in the above-identified patent and that said Letters Patent is hereby corrected as shown below:

Column 115,
Line 45, please delete "," and insert -- ; --.
Line 46, please insert -- : (i) -- after "comprise".
Line 47, please insert -- , and (ii) a nucleic acid encoding one or more molecular component that facilitates the assembly of infectious viral particles in said eukaryotic host cell; -- after "library".

Column 117,
Line 19, please delete "the" after "contain".
Line 28, please insert -- : (i) -- after "comprise".
Line 30, please insert -- and (ii) a nucleic acid encoding one or more molecular component that facilitates the assembly of infectious viral particles in said eukaryotic host cell; -- after "library,".
Line 51, please insert -- individual expression systems, wherein said individual expression systems comprise: (i) -- after "contain".
Line 52, please insert -- ; and (ii) a nucleic acid encoding one or more molecular component that facilitates the assembly of infectious viral particles in said eukaryotic host cell; -- after "element".
Line 59, please delete "step" after "in".
Line 67, please delete "eukaryotic host cells in the population" and insert
-- expression systems --.

Column 118,
Line 32, please insert -- individual expression systems, wherein said individual expression systems comprise: (i) -- after "contain".
Line 34, please insert -- and (ii) a nucleic acid encoding one or more molecular component that facilitates the assembly of infectious viral particles in said eukaryotic host cell; -- after "virus;".
Line 65, please insert -- : (i) -- after "comprising".
Line 66, please insert -- and (ii) a nucleic acid encoding one or more molecular component that facilitates the assembly of infectious viral particles in said eukaryotic host cell; -- after "promoter;".

UNITED STATES PATENT AND TRADEMARK OFFICE
CERTIFICATE OF CORRECTION

PATENT NO. : 6,524,792 B1
DATED : February 25, 2003
INVENTOR(S) : Renner et al.

It is certified that error appears in the above-identified patent and that said Letters Patent is hereby corrected as shown below:

Column 119,
Line 21, please delete "which" and insert -- , wherein said control element comprises a nucleic acid encoding one or more molecular component that facilitates the assembly of infectious viral particles in said eukaryotic host cell, and wherein said control element --.

Signed and Sealed this

Sixteenth Day of December, 2003

JAMES E. ROGAN
*Director of the United States Patent and Trademark Office*